(12) United States Patent
Henriques Normark et al.

(10) Patent No.: US 11,844,829 B2
(45) Date of Patent: Dec. 19, 2023

(54) **MICROPARTICLES FROM *STREPTOCOCCUS PNEUMONIAE* AS VACCINE ANTIGENS**

(71) Applicant: ZalVac AB, Stockholm (SE)

(72) Inventors: Birgitta Henriques Normark, Stockholm (SE); Mario Codemo, Stockholm (SE); Federico Iovino, Bromma (SE); Sandra Muschiol, Solna (SE); Staffan Normark, Stockholm (SE); Sun Nyunt Wai, Umea (SE)

(73) Assignee: ZalVac AB, Stockholm (SE)

( * ) Notice: Subject to any disclaimer, the term of this patent is extended or adjusted under 35 U.S.C. 154(b) by 0 days.

(21) Appl. No.: 16/474,940

(22) PCT Filed: Dec. 21, 2017

(86) PCT No.: PCT/SE2017/051323
§ 371 (c)(1),
(2) Date: Jun. 28, 2019

(87) PCT Pub. No.: WO2018/124959
PCT Pub. Date: Jul. 5, 2018

(65) Prior Publication Data
US 2019/0328861 A1 Oct. 31, 2019

(30) Foreign Application Priority Data
Dec. 28, 2016 (SE) .................................. 1651746-8

(51) Int. Cl.
| | | |
|---|---|---|
| *A61K 39/09* | (2006.01) | |
| *C07K 14/315* | (2006.01) | |
| *A61K 39/00* | (2006.01) | |
| *C07K 16/12* | (2006.01) | |

(52) U.S. Cl.
CPC ........ *A61K 39/092* (2013.01); *C07K 14/3156* (2013.01); *C07K 16/1275* (2013.01); *A61K 2039/55555* (2013.01)

(58) Field of Classification Search
CPC ........ A61K 39/00; A61K 39/02; A61K 39/09; A61K 39/092; A61K 2039/55555; C07K 14/3156
USPC .................. 424/9.1, 9.2, 184.1, 234.1, 237.1
See application file for complete search history.

(56) References Cited

U.S. PATENT DOCUMENTS

| | | | | |
|---|---|---|---|---|
| 2011/0275132 A1* | 11/2011 | Covacci | ............ | C07K 16/1275 435/259 |
| 2014/0072622 A1* | 3/2014 | Denoel | .................... | A61P 31/00 424/244.1 |
| 2015/0118263 A1 | 4/2015 | Feldman | | |

FOREIGN PATENT DOCUMENTS

| | | |
|---|---|---|
| CA | 2776413 | 4/2011 |
| KR | 20150067058 | 6/2015 |
| WO | WO 1998021337 | 5/1998 |
| WO | WO 2002/022168 | 3/2002 |
| WO | WO 2002101026 | 12/2002 |
| WO | WO 2007071710 | 6/2007 |
| WO | WO 2010120921 | 10/2010 |
| WO | WO 2011110241 | 9/2011 |
| WO | WO 2011151760 | 12/2011 |
| WO | WO 2015110942 | 7/2015 |
| WO | WO 2016081839 | 5/2016 |

OTHER PUBLICATIONS

Olaya-Abril et al., "Characterization of protective extracellular membrane-derived vesicles produced by *Streptococcus pneumoniae*," J. Proteomics, 106:46-60, Jun. 2014 (Year: 2014).*
Swedish Search Report in SE Appln. No. 1651746-8, dated Jul. 18, 2017, 4 pages.
Rounioja, et al., "Defense of zebrafish embryo against *Streptococcus pneumoniae* infection is dependent on the phagocytic activity of leukocytes," Developmental and Comparative Immunology, 2012, 36:342-348.
Gingles, et al.. "Role of genetic resistance in invasive pneuomococcal infection: Identification and study of susceptibility and resistance in inbred mouse strains," Infection and Immunity, 2001, 69(1):426-434.
Barocchi et al.,"A pneumococcal pilus influences virulence and host inflammatory responses," Proc. Natl. Acad. Sci. USA., 103(8):2857-62, Feb. 2006.
Bergmann and Hammerschmidt, "Versatility of pneumococcal surface proteins," Microbio., 152(2):295-303, Feb. 2006.
Bersch et al., "New insights into histidine triad proteins: solution structure of a *Streptococcus pneumoniae* PhtD domain and zinc transfer to AdcAII," PLoS one, 8(11):e81168, Nov. 2013.
Bielig et al., "NOD-like receptor activation by outer membrane vesicles from Vibrio cholerae non-O1 non-O139 strains is modulated by the quorum-sensing regulator HapR," Infect. Immun., 79(4):1418-27, 2011.

(Continued)

*Primary Examiner* — Gary B Nickol
*Assistant Examiner* — Amelia Nicole Dickens
(74) *Attorney, Agent, or Firm* — Fish & Richardson P.C.

(57) ABSTRACT

An isolated *Streptococcus pneumoniae* membrane vesicle microparticle (MP), wherein said MP comprises: the protein Ply at the level of ≥0.070 µg/µg total protein in the MP; and/or the protein LytA at the level of ≥0.070 µg/µg total protein in the MP; and/or the protein PspC at the level of ≥0.130 µg/µg total protein in the MP; and/or the protein RrgB at the level of ≥0.020 µg/µg total protein in the MP. Compositions comprising such MPs. Uses thereof in particular in immunization, as well as methods of manufacture thereof.

21 Claims, 24 Drawing Sheets
Specification includes a Sequence Listing.

(56) References Cited

OTHER PUBLICATIONS

Brooks-Walter et al., "The pspC gene of *Streptococcus pneumoniae* encodes a polymorphic protein, PspC, which elicits cross-reactive antibodies to PspA and provides immunity to pneumococcal bacteremia," Infect. Immun., 67(12):6533-42, Dec. 1999.
Ellis et al., "Naturally produced outer membrane vesicles from Pseudomonas aeruginosa elicit a potent innate immune response via combined sensing of both lipopolysaccharide and protein components," Infect Immun., 78(9):3822-31, 2010.
Fernebro et al., "Capsular expression in *Streptococcus pneumoniae* negatively affects spontaneous and antibiotic-induced lysis and contributes to antibiotic tolerance," J. Infect. Dis., 189(2):328-38, Jan. 2004.
Gosink et al., "Role of novel choline binding proteins in virulence of *Streptococcus pneumoniae*," Infect. Immun., 68(10):5690-5, Oct. 2000.
Gurung et al., "*Staphylococcus aureus* produces membrane-derived vesicles that induce host cell death," PLoS one, 6(11):e27958, Nov. 2011.
Iannelli et al., "Allelic variation in the highly polymorphic locus pspC of *Streptococcus pneumoniae*," Gene, 284(1-2):63-71, Feb. 2002.
Iovino et al., ""Pneumococcal meningitis is promoted by single cocci expressing pilus adhesin RrgA,"" J. Clin. Invest., 126(8):2821-6, Jun. 2016.
Johnston et al., "Lipoprotein PsaA in virulence of *Streptococcus pneumoniae*: surface accessibility and role in protection from superoxide," Infect. Immun., 72(10):5858-67, Oct. 2004.
Kilian et al., Pathogenic species of the genus *Haemophilus* and *Streptococcus pneumoniae* produce immunoglobulin A1 protease. Infect. Immun., 26(1):143-9, Oct. 1979.
Littmann et al., "*Streptococcus pneumoniae* evades human dendritic cell surveillance by pneumolysin expression," EMBO Mol. Med., 1(4):211-22, 2009.
Mellroth et al., "LytA, major autolysin of *Streptococcus pneumoniae*, requires access to nascent peptidoglycan," J. Biol. Chem., 287(14):11018-29, Feb. 2012.
Mitchell and Dalziel, "The biology of pneumolysin," Subcell Biochem., 80:145-60, 2014.
Nelson et al., "RrgA is a pilus-associated adhesin in *Streptococcus pneumoniae*," Mol. Microbiol., 66(2):329-40, Sep. 2007.
Olaya-Abril et al., "Characterization of protective extracellular membrane-derived vesicles produced by *Streptococcus pneumoniae*," J. Proteomics, 106:46-60, Jun. 2014.
Paterson and Mitchell, "The role of *Streptococcus pneumoniae* sortase A in colonisation and pathogenesis," Microbes Infect, 8(1):145-53, 2006.
PCT International Preliminary Report on Patentability in PCT Appln. No. PCT/SE2017/051323, dated Jul. 2, 2019, 6 pages.
PCT International Search Report and Written Opinion in PCT Appln. No. PCT/SE2017/051323, dated Jun. 28, 2018, 10 pages.
Singh et al., "Unravelling the multiple functions of the architecturally intricate *Streptococcus pneumoniae* beta-galactosidase, BgaA," PLoS Pathog., 10(9):e1004364, Sep. 2014.
Terrasse et al., "*Streptococcus pneumoniae* GAPDH Is Released by Cell Lysis and Interacts with Peptidoglycan," PloS one, 10(4):e0125377, Apr. 2015.
Tettelin et al., "Complete genome sequence of a virulent isolate of *Streptococcus pneumoniae*," Science, 293(5529):498-506, Jul. 2001.
Thay et al., "*Staphylococcus aureus* alpha-toxin-dependent induction of host cell death by membrane-derived vesicles," PLoS one, 8(1):e54661, Jan. 2013.
Zhou et al., "LocateP: genome-scale subcellular-location predictor for bacterial proteins," BMC Bioinformatics, 9(1):173, Mar. 2008.

* cited by examiner

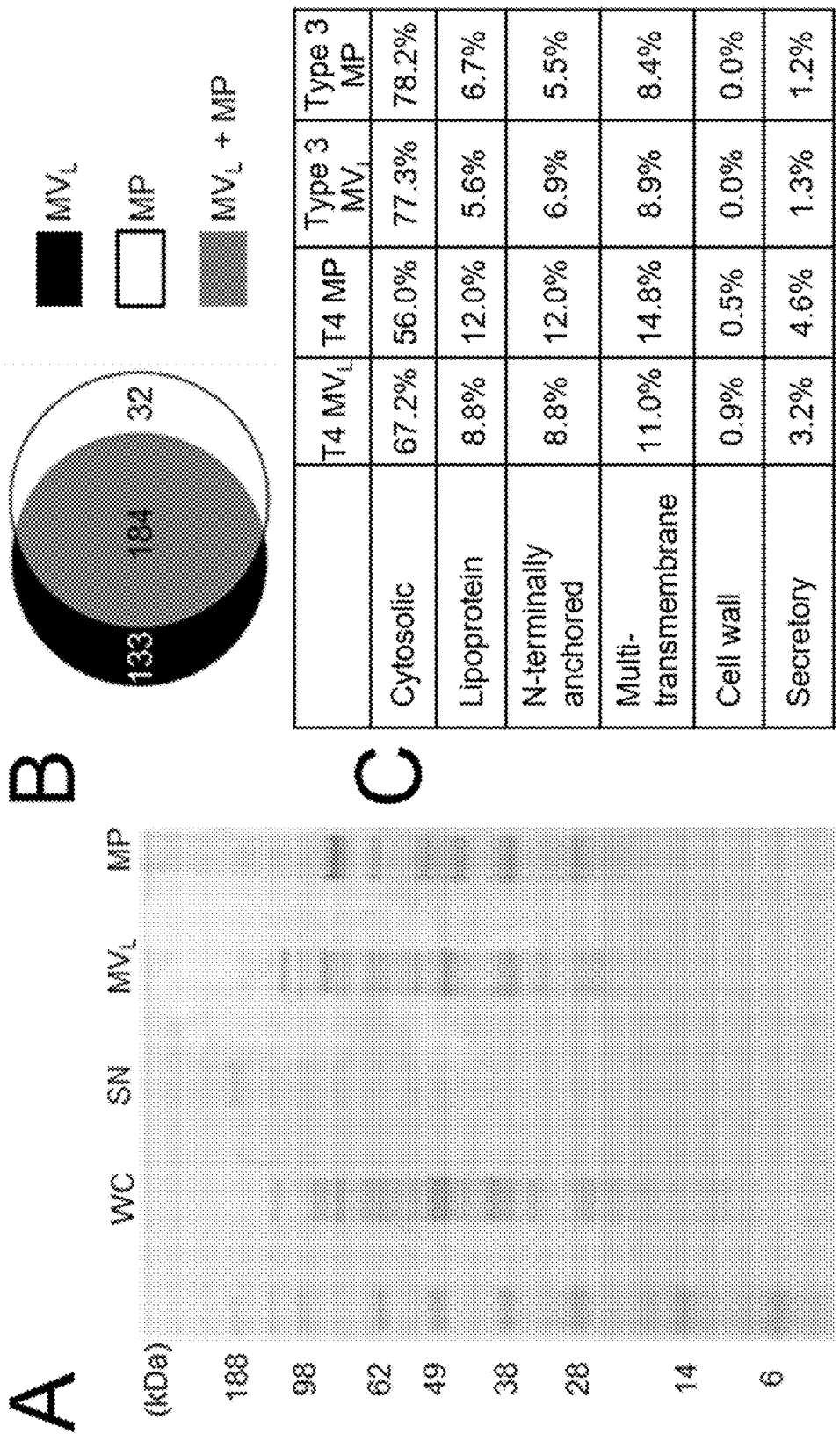
Fig 2A-C

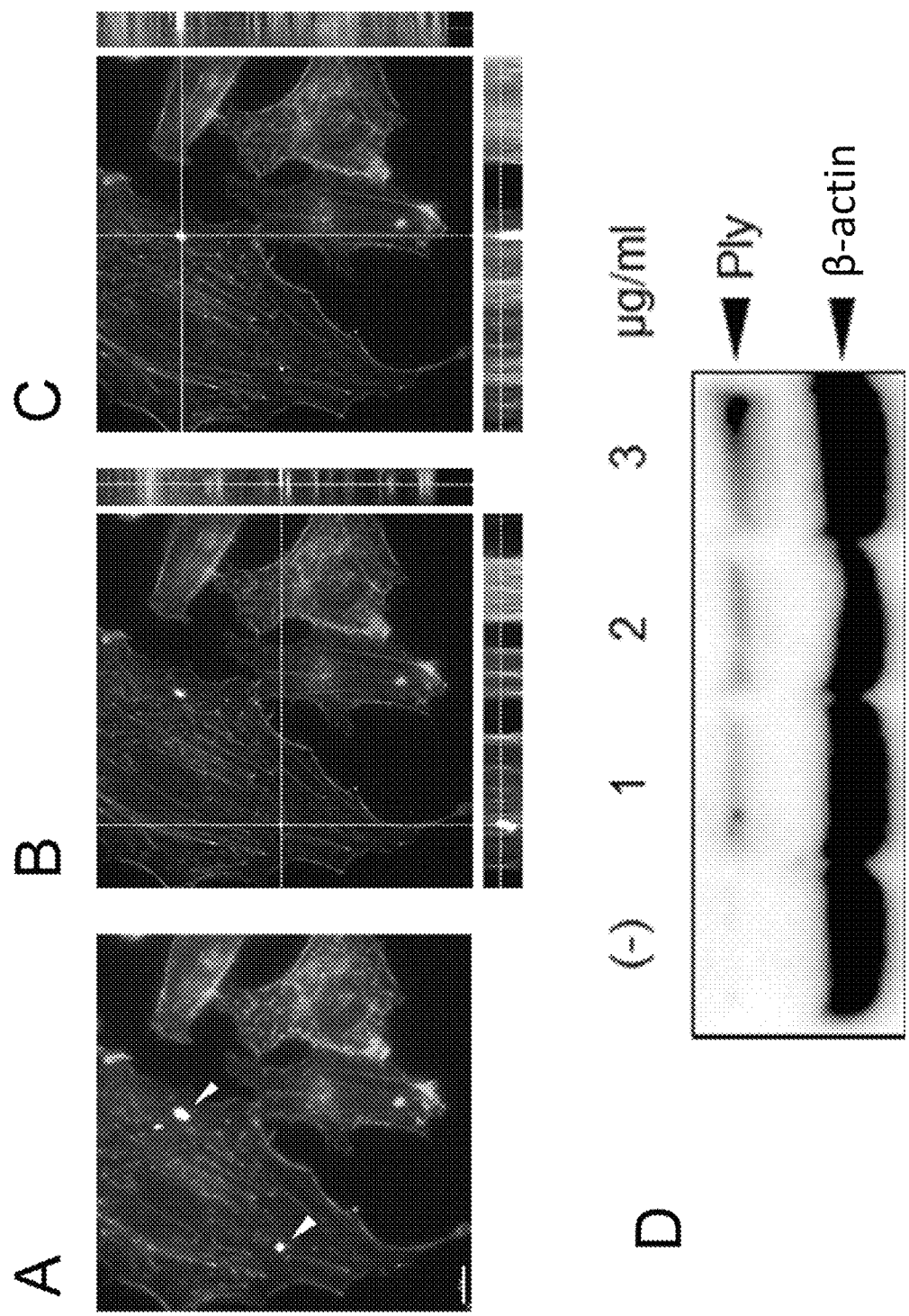

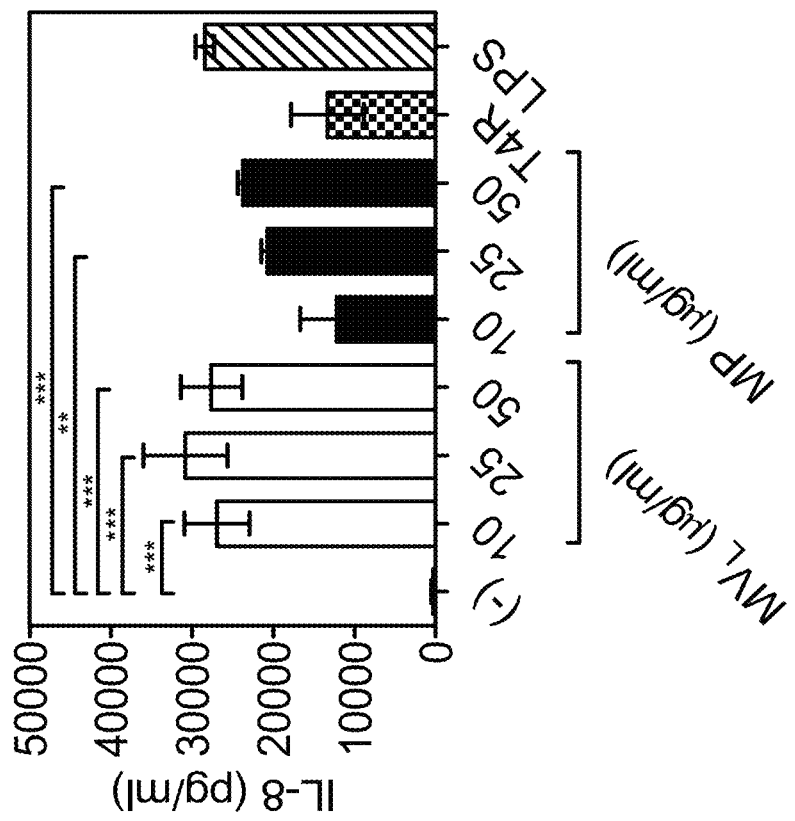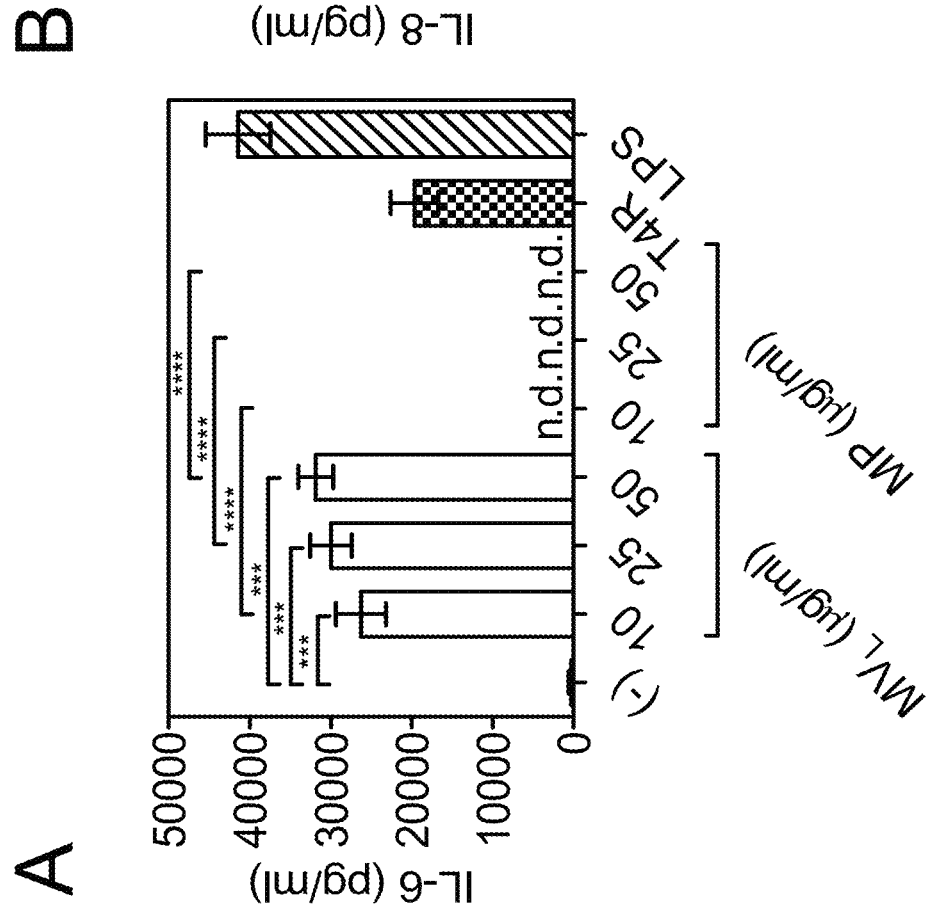
Fig 6A-B

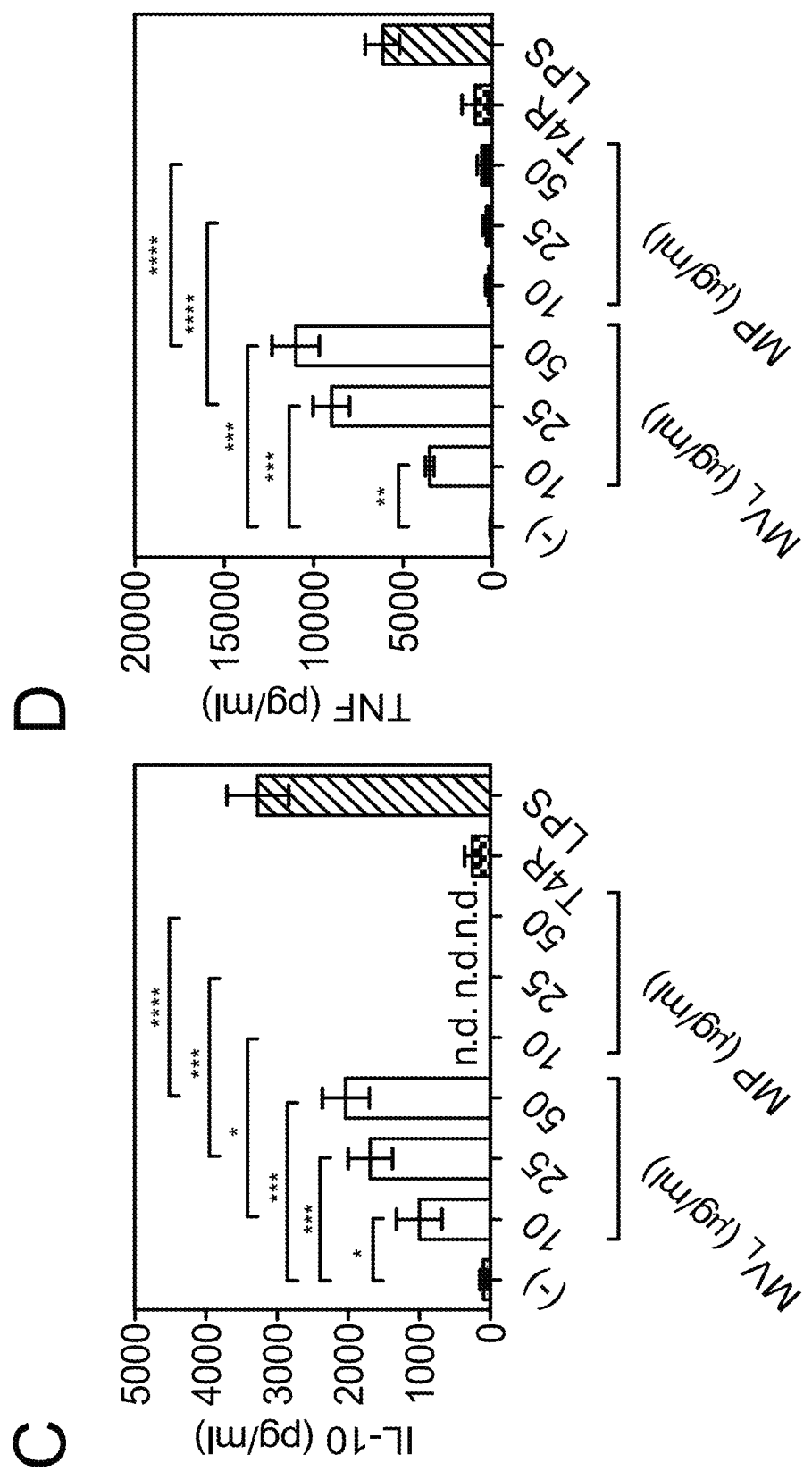
Fig 6C-D

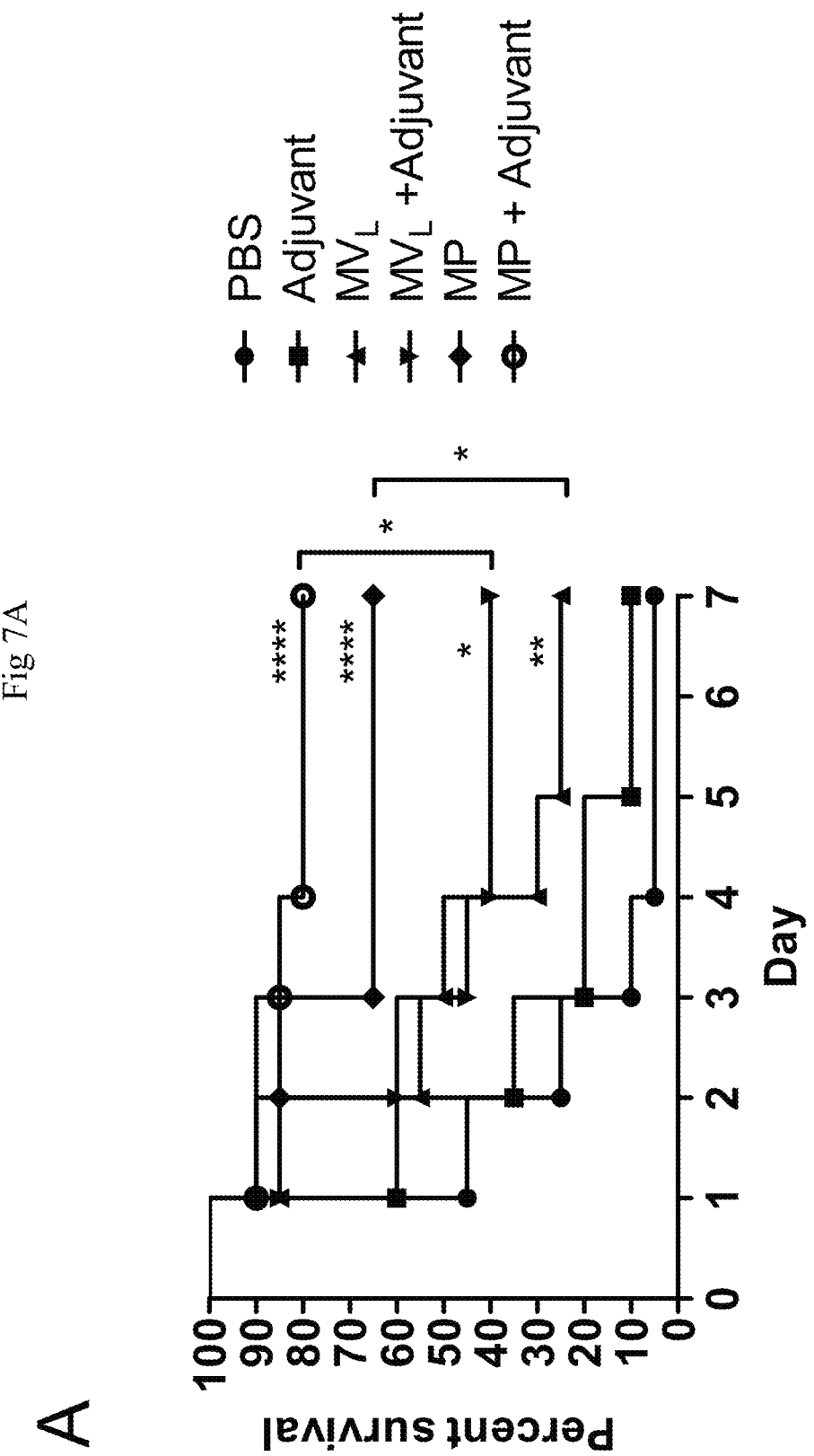

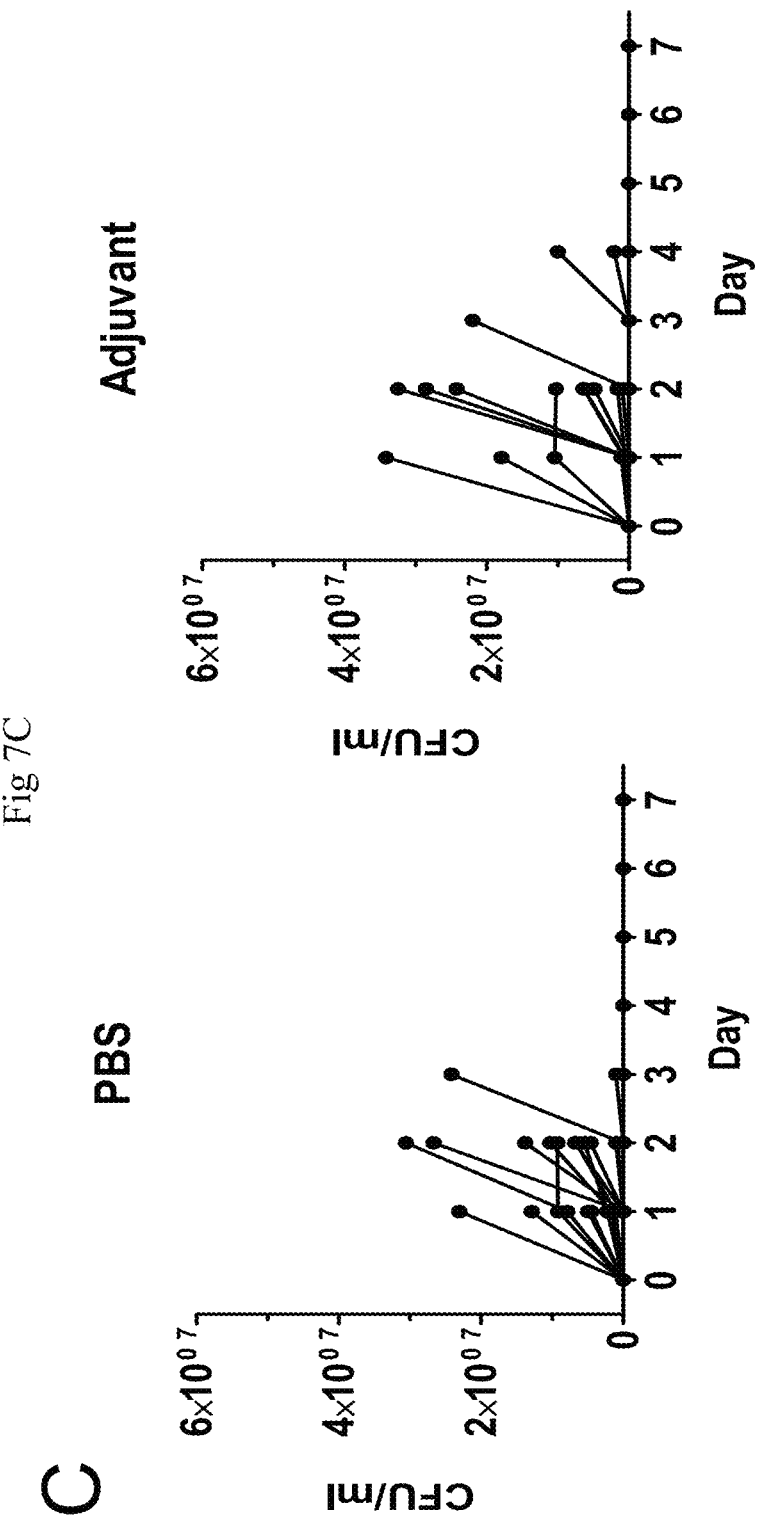

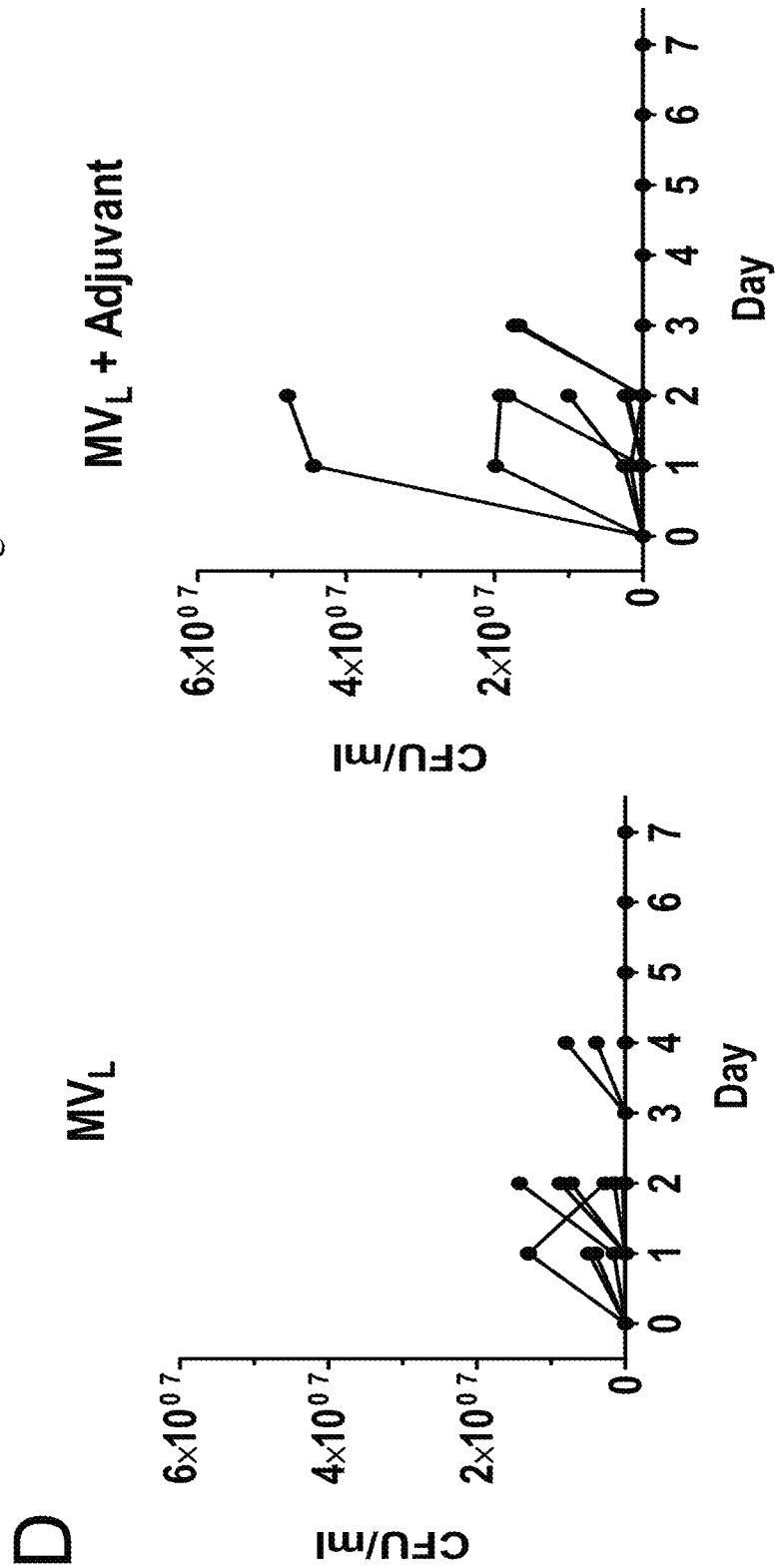

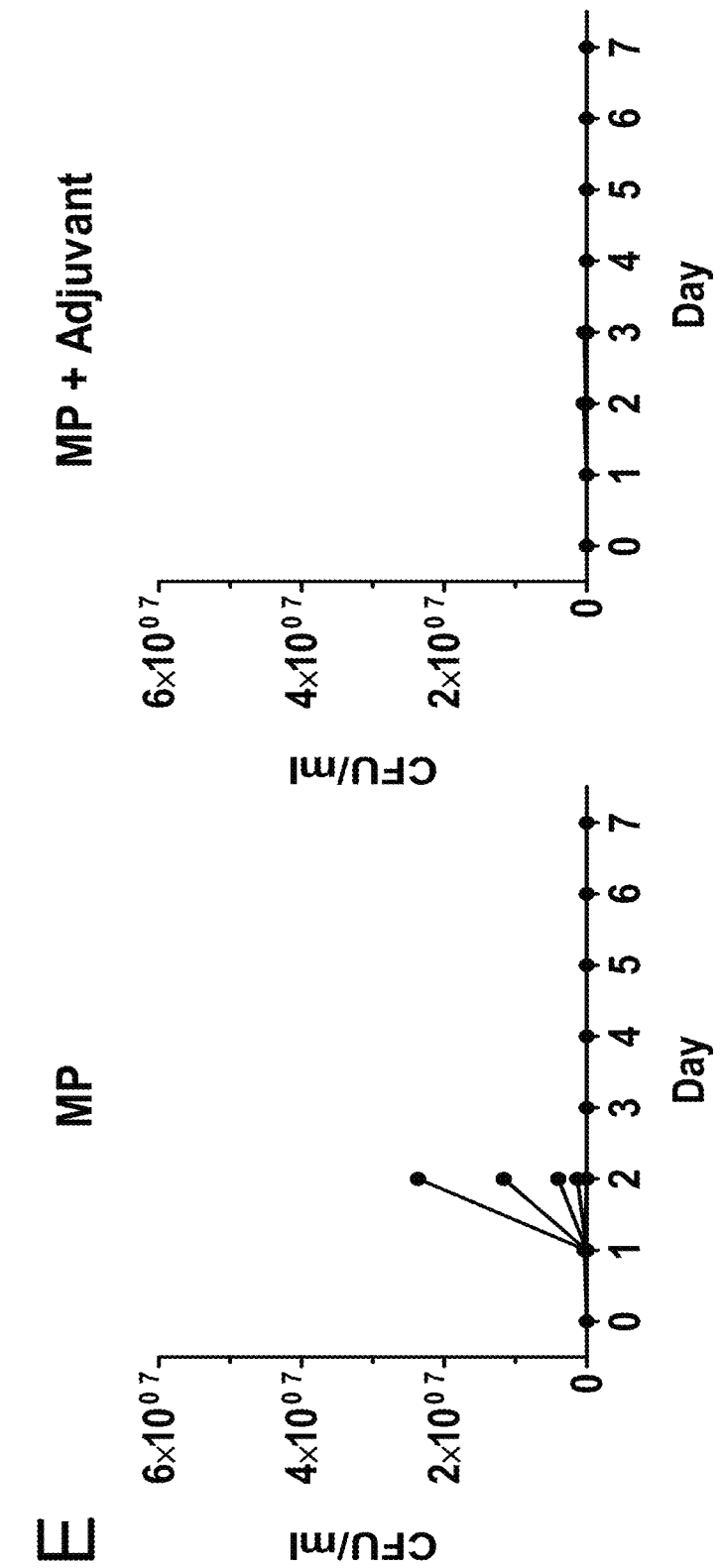

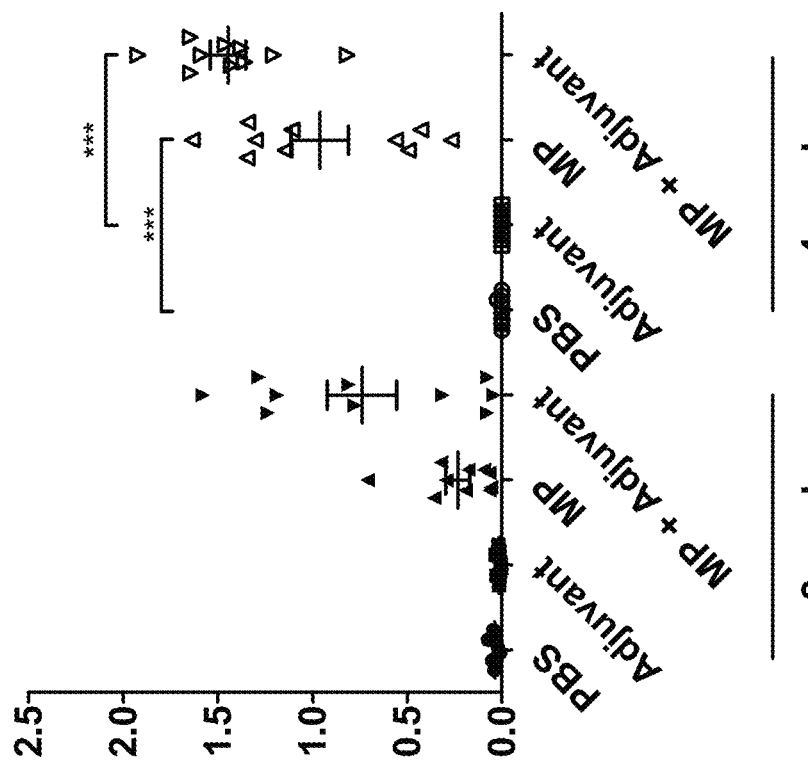
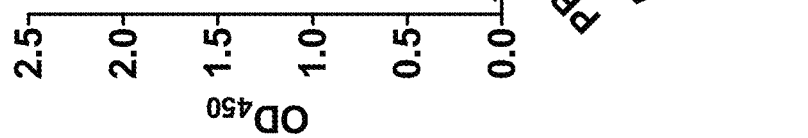
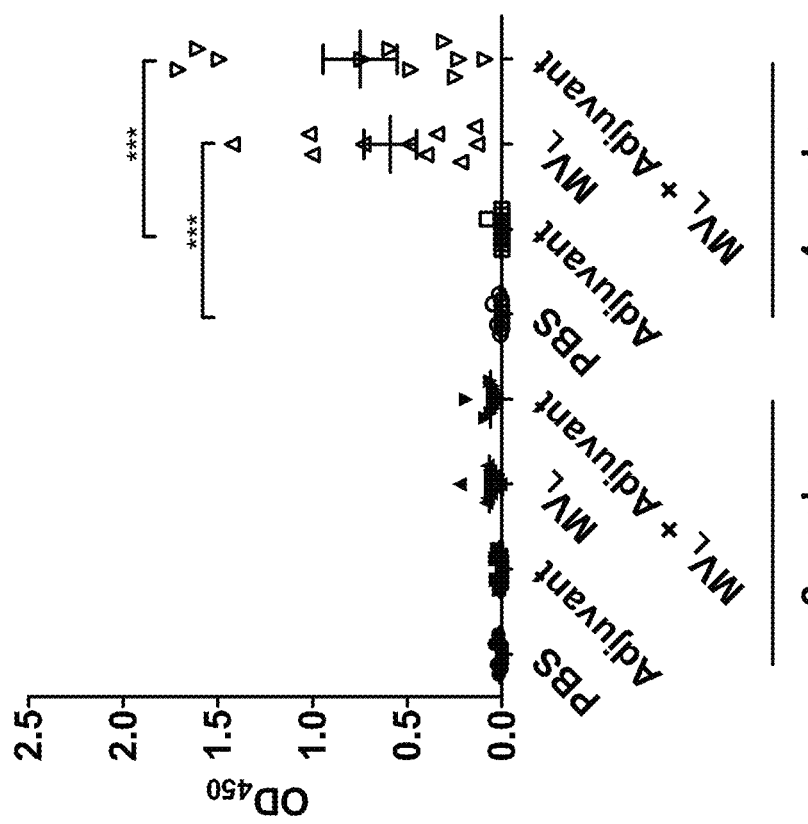
Fig 8A-B

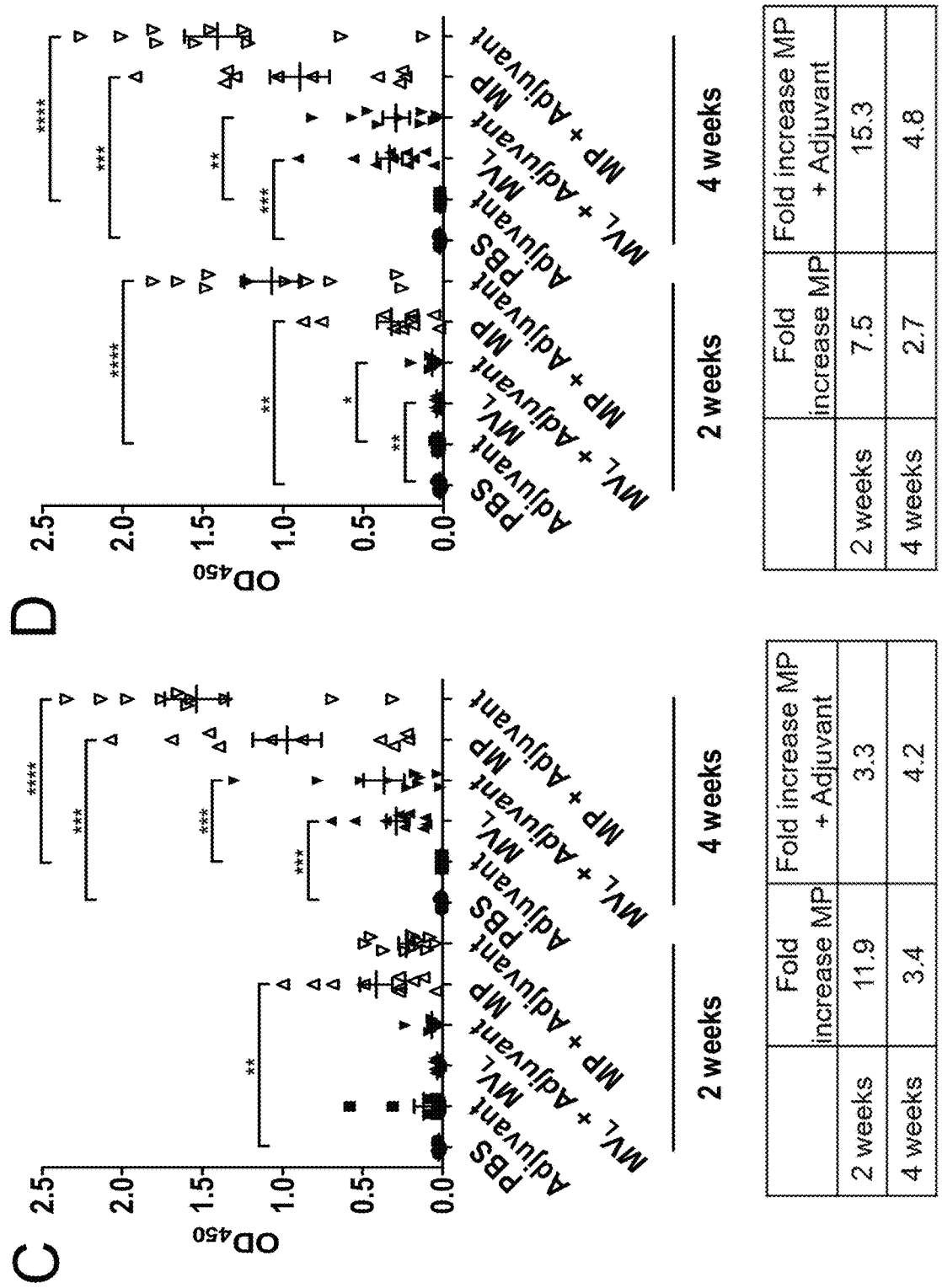
Fig 8C-D

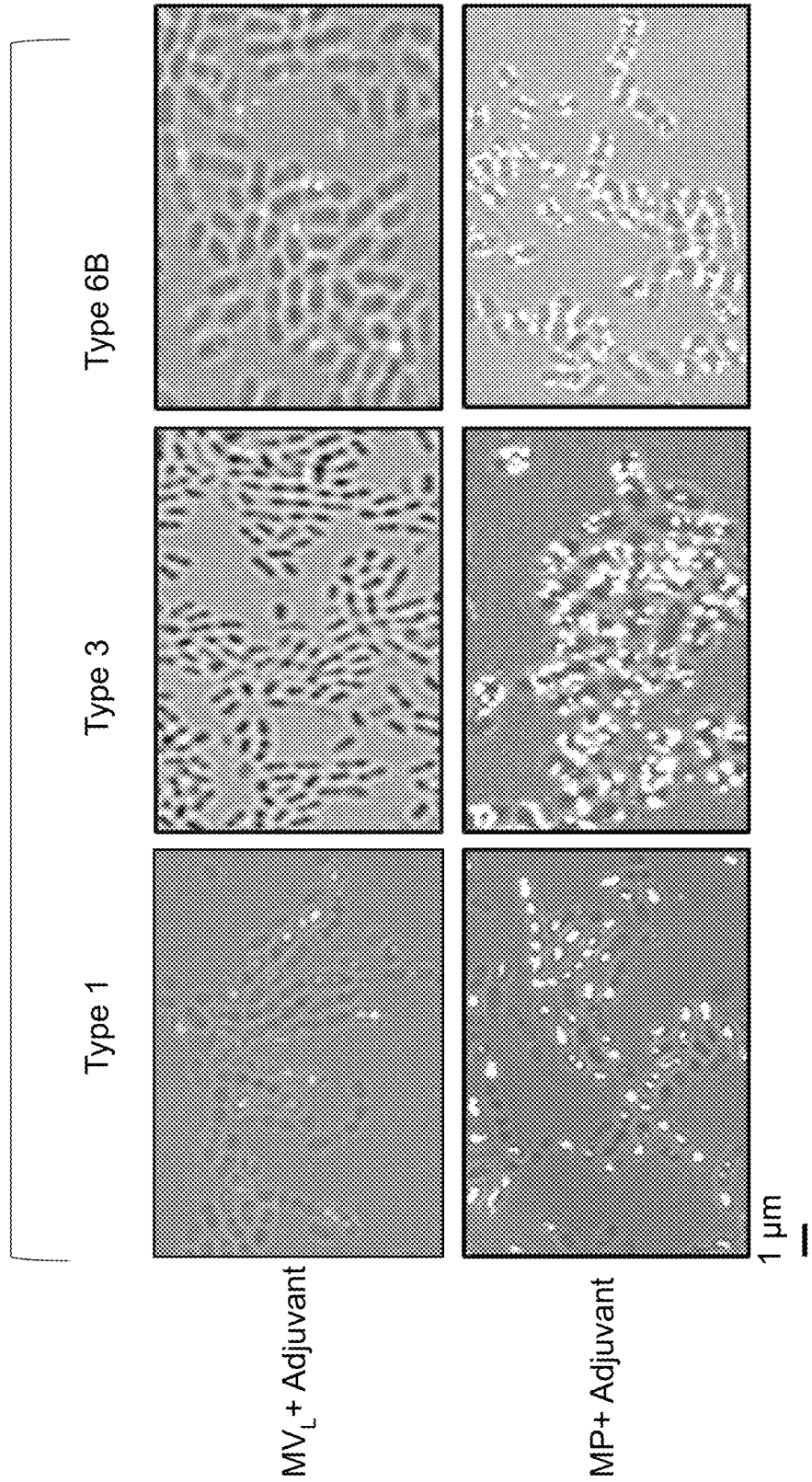

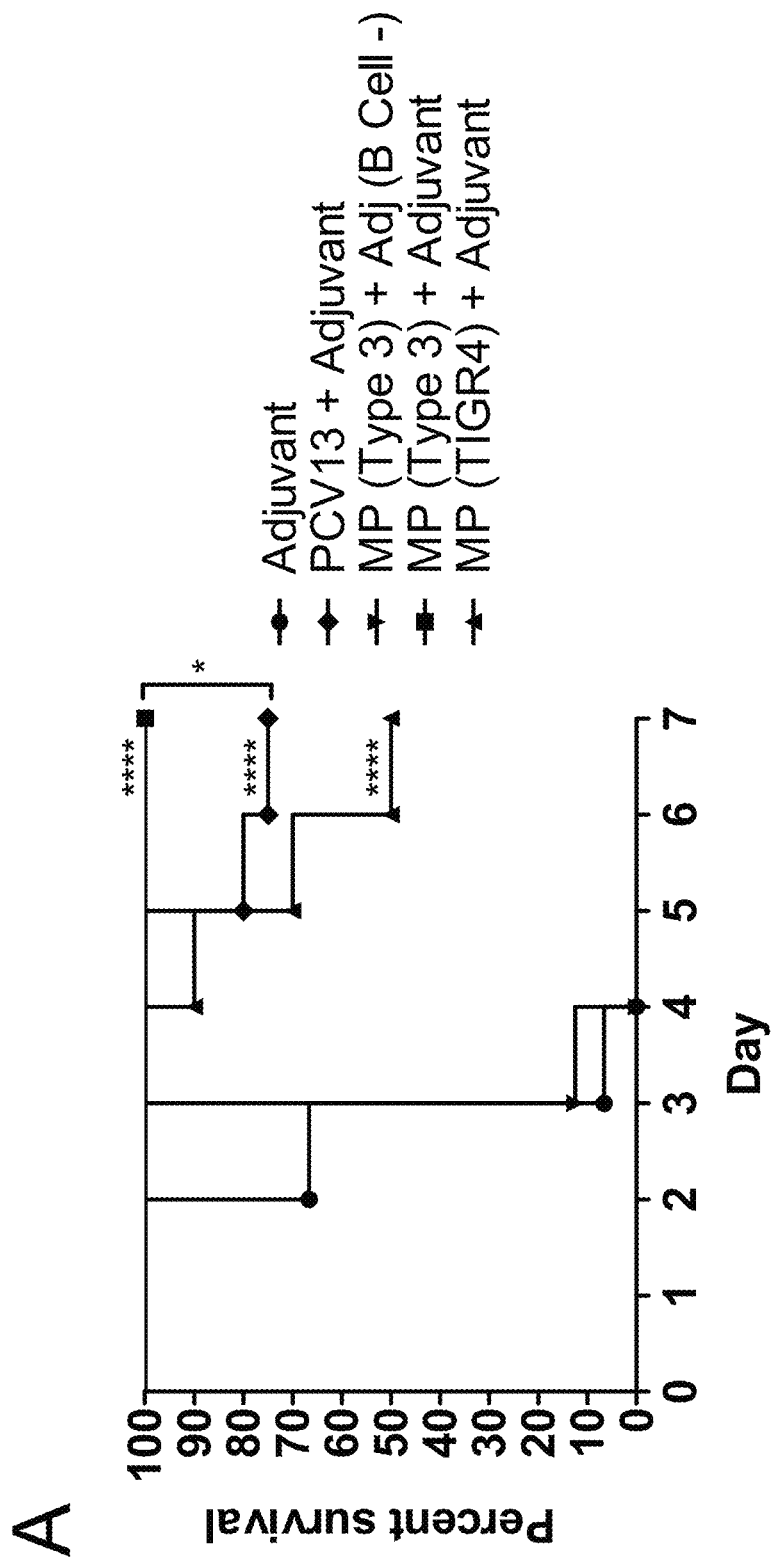

MICROPARTICLES FROM *STREPTOCOCCUS PNEUMONIAE* AS VACCINE ANTIGENS

This application is a National Stage application under 35 U.S.C. § 371 of International Application No. PCT/SE2017/051323, having an International Filing Date of Dec. 21, 2017, which claims the benefit of SE Application No. 1651746-8 filed Dec. 28, 2016, each of which is incorporated herein by reference in its entirety.

TECHNICAL FIELD

The present invention relates to the field of vaccines against *Streptococcus pneumoniae*.

BACKGROUND TO THE INVENTION

*Streptococcus pneumoniae* is a Gram-positive bacterium that is a major contributor to morbidity and mortality worldwide causing about 2 million deaths annually, i e the same range as for tuberculosis. Pneumococci are the major cause of common infections such as sinusitis, otitis, and community-acquired pneumonia (CAP), but also a common cause of severe invasive diseases (IPD) such as sepsis and meningitis. Young children and the elderly are the most susceptible age groups to acquire pneumococcal infections, but other factors such as underlying diseases, splenectomy, immunosuppression (including HIV), diabetes and a prior influenza-virus infection also sensitize for a pneumococcal infection. Pneumococcal infections such as CAP also predispose for cardiovascular diseases such as cardiac infarction, and meningitis patients may get neurological sequelae such as hearing loss and cognitive impairments.

Pneumococci have the human upper airways as their normal ecological niche, and up to 60% of preschool children may be colonized at any given time without symptoms. It is believed that most transmission events to the elderly come from young colonized children. *S. pneumoniae* is a highly genetically diverse species due to an efficient DNA exchange system resulting in a multitude of clonal lineages that may differ from one another in the presence and absence of genes and gene clusters, as well as in variations in individual genes. Variations in the capsular locus, the major virulence factor and vaccine target of pneumococci, have resulted in at least 97 known capsular serotypes with different potential of causing disease.

Pneumococcal conjugate vaccines (PCVs), targeting a limited number (7, 10 or 13 in PCV7, PCV10 and PCV13 respectively) of the known 97 capsular serotypes, have been introduced in the childhood vaccination program in many countries. Vaccine introduction has led to a decrease in IPD caused by vaccine-types in vaccinated children, however, non-vaccine type pneumococci have rapidly expanded and replaced vaccine-types in child-hood carriage and in IPD, but also in non-vaccinated population such as the elderly. Furthermore, protection against vaccine types differ, and for serotype 3, a serotype included in PCV13 and with a high mortality rate, there is more or less no evidence for protection against IPD so far. Data from Sweden, where both PCV10 and PCV 13 are used, show that serotype 3 was a dominaiting serotype among IPD cases during 2016, also in counties using only PCV13. Hence, novel vaccine approaches are needed.

In Sweden the total number of patients with IPD has remained almost the same after vaccine introduction. Moreover, in a recent study we found that pneumococcal carriage rates remained around 30% in the youngest children 8 years after vaccine introduction in Stockholm, and non-vaccine types were found in over 90% of the isolates. Antibiotic resistance is emerging among clinical pneumococcal isolates and according to reports from the European Centre for Disease prevention and Control (ECDC), and the European Antimicrobial Resistance Surveillance Network (EARS-Net), reduced susceptibility to penicillin has increased during the last years in Sweden and now exceeds 5% among IPD cases. In addition, the need for multiple antigens covering various capsular serotypes lead to high production costs for the known vaccines.

Opsonophagocytosis is the primary mechanism for clearance of pneumococci from the host, and the measurement of opsonophagocytic antibodies appears to correlate with vaccine-induced protection. However, it has proven difficult to design vaccines that elicit an efficient response in form of opsonophagocytic antibodies.

Taken together, the above issues stress the need for novel vaccine approaches. Thus, an object of the present invention is the provision of improved pneumococcal antigens able to confer serotype-independent immunological responses and/or improved response in terms of opsonophagocitic antibodies and protection in experimental models.

Background for Pneumococcal Microparticles

Spherical membranous blebs, so called outer membrane vesicles (OMVs), are produced by Gram-negative bacteria. OMVs range in size from 10 to 300 nm and they have been shown to be formed by budding from the bacterial outer membrane, and to have many functions, such as influencing virulence by different mechanisms. In Gram-negative bacteria OMVs have been suggested to act as vehicle to deliver virulence factors to host cells. Only recently, membrane vesicles ($MV_L$) were discovered also in Gram-positive bacteria and their formation and function is poorly understood compared to OMVs. Gram-positive bacteria do not contrain an outer membrane and the the cell wall differs from Gram-negative bacteria.

For *Streptococcus pneumoniae* $MV_L$ (membrane vesicle) were isolated from pneumococci belonging to different serotypes (2, 6B, 8 and 23F) grown in liquid culture medium (1). $MV_L$ from serotype 8 were shown to be protective against pneumococcal challenge with the same serotype in mice. Importantly, no cross protection was shown to pneumococci of other serotypes.

DEFINITIONS

The pneumococcal capsule. The pneumococcal capsule, consisting of polysaccharide, exists in at least 97 different variants, so called capsular serotypes. The pneumococcal capsule is a major virulence determinant of pneumococci, affecting phagocytosis of the bacteria by host cells, and influence bacterial interactions with the innate immune response.

Pneumolysin (termed Ply herein) is a 53 kDa cholesterol dependent cytolysin released by *Streptococcus pneumoniae* upon lysis. It is one of the major virulence factors of this bacterium. It forms pores in all eukaryotic cells that have cholesterol in their membranes. The formation of pores by Ply frequently results in host cell death as membrane integrity is destroyed. Ply plays a central role in protecting the pneumococcus from complement attack and aiding its spread to other tissues/organs. Ply is able to activate the classical complement pathway, even in the absence of Ply specific antibody (2). A reference sequence from strain TIGR4 is presented in HQ ID NO: 1.

LytA is the major autolysin of *Streptococcus pneumoniae*. Lysis is caused by cleaving the lactyl-amide bond between the stem peptides and the glycan strands of peptidoglycan, resulting in hydrolysis of the cell wall. The contribution of LytA to pneumococcal virulence is still unclear. It is possible that LytA-mediated lysis releases other virulence factors such as pneumolysin. LytA could also be released to lyse neighboring non-competent pneumococcal cells in a fratricidal manner. This would potentially facilitate genetic exchange between naturally competent pneumococcal populations that easily take up and incorporate DNA by homologous recombination. A third possibility is that LytA mediates lysis to release proteins involved in immune evasion or cell wall components that may interfere with the host immune response (3). A reference sequence from strain TIGR4 is presented in SEQ ID NO: 2.

PspC/CbpA (choline binding protein A) is a protein that binds the phosphocholine present in the teichoic acid and the lipoteichoic acid of the cell membrane and the cell wall. It is a major pneumococcal adhesin. It promotes pneumococcal adherence via a human-specific interaction with the ectodomain of the polymeric Ig receptor. It also prevents activation of C3b and complement-mediated opsonophagocytosis of pneumococci (4). The pspC locus is highly polymorphic and 11 major groups of this protein have been identified. Single PspC proteins are identified by sequential numbers separated from the group number by a dot (5) as follows: PspC1.1, PspC2.1, PspC2.2, PspC3.1, PspC3.4, PspC4.2/PspC10.1, PspC5.1, PspC6.1/PspC9.1, PspC7.1, PspC8.1, PspC11.1 and PspC11.4 (SEQ ID NOs: 3-14, respectively).

RrgB is the major subunit and stalk protein of the pneumococcal pilus. *S. pneumoniae* pilus 1 is encoded by a genetic islet (PI-1) present in 30 to 50% of the pneumococcal strains and is implicated in adhesion to epithelial cells, lung infection, and virulence. Pilus 1 is composed of the backbone subunit RrgB, the minor pilin subunits RrgA, and RrgC (6). A reference sequence from strain TIGR4 is presented in SEQ ID NO: 15.

RrgA is a minor pilin subunit of the pneumococcal pilus. RrgA is the tip protein of the pilus and has been shown to mediate adhesion to epithelial cells (6, 7). Recently, RrgA was shown to promote meningitis development in mice (8). A reference sequence is presented in SEQ ID NO: 16.

PhtD is a polyhistidine triad protein of *S. pneumoniae*. Polyhistidine triad (Pht) proteins are streptococcal surface proteins that contain multiple copies of a characteristic HxxHxH sequence, designed as histidine triads, which were predicted to bind divalent metal cations. Despite the increasing amount of biochemical, structural and physiological data, the functional role of PhtD and the other Pht proteins remains unclear. PhtD could be involved in zinc uptake. Alternatively, Pht proteins could play a role in protecting the pneumococcus from toxic effects of high $Zn^{2+}$ concentrations by scavenging, storing or trapping $Zn^{2+}$ ions (9). A reference sequence from strain TIGR4 is presented in SEQ ID NO: 17.

IgA refers to Immunoglobulin A1 protease of *S. pneumoniae* (10). Said IgA1-protease is a highly specific enzyme that cleaves amino acid sequences of certain proteins. The natural substrate of the IgA protease is immunoglobulin A1, hence its name. The enzyme is in fact capable of cleavage of proteins with the amino acid sequence N—X-Z-Pro-Pro/-Y-Pro-C, where the X in the sequence is preferably a Proline or Serine; the Y=Threonine, Serine or Alanine; and Z preferably is Arginine or Threonine. Thus, the IgA1 protease acts by cleaving the proline-rich hinge region of the heavy chain of IgA1. Release of the IgA1 protease by the pathogen allows adherence to mucous membranes by degrading host immunoglobulin A. A reference sequence from strain TIGR4 is presented in SEQ ID NO: 18.

The term protective immunity in the present context refers to immunization measures resulting in any degree of reduction in the likelihood of developing the condition for which the protective immunity is relevant, including a minor, substantial or major reduction in likelihood of developing the condition as well as total prevention. Preferably, the degree of likelihood reduction is at least a minor reduction.

The term sequence identity expressed in percentage is defined as the value determined by comparing two optimally aligned sequences over a comparison window, wherein a portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Unless indicated otherwise, the comparison window is the entire length of the sequence being referred to. In this context, optimal alignment is the alignment produced by the BLASTP algorithm as implemented online by the US National Center for Biotechnology Information (see The NCBI Handbook [Internet], Chapter 16), with the following input parameters: Word length=3, Matrix=BLOSUM62, Gap cost=11, Gap extension cost=1.

Figure 1:
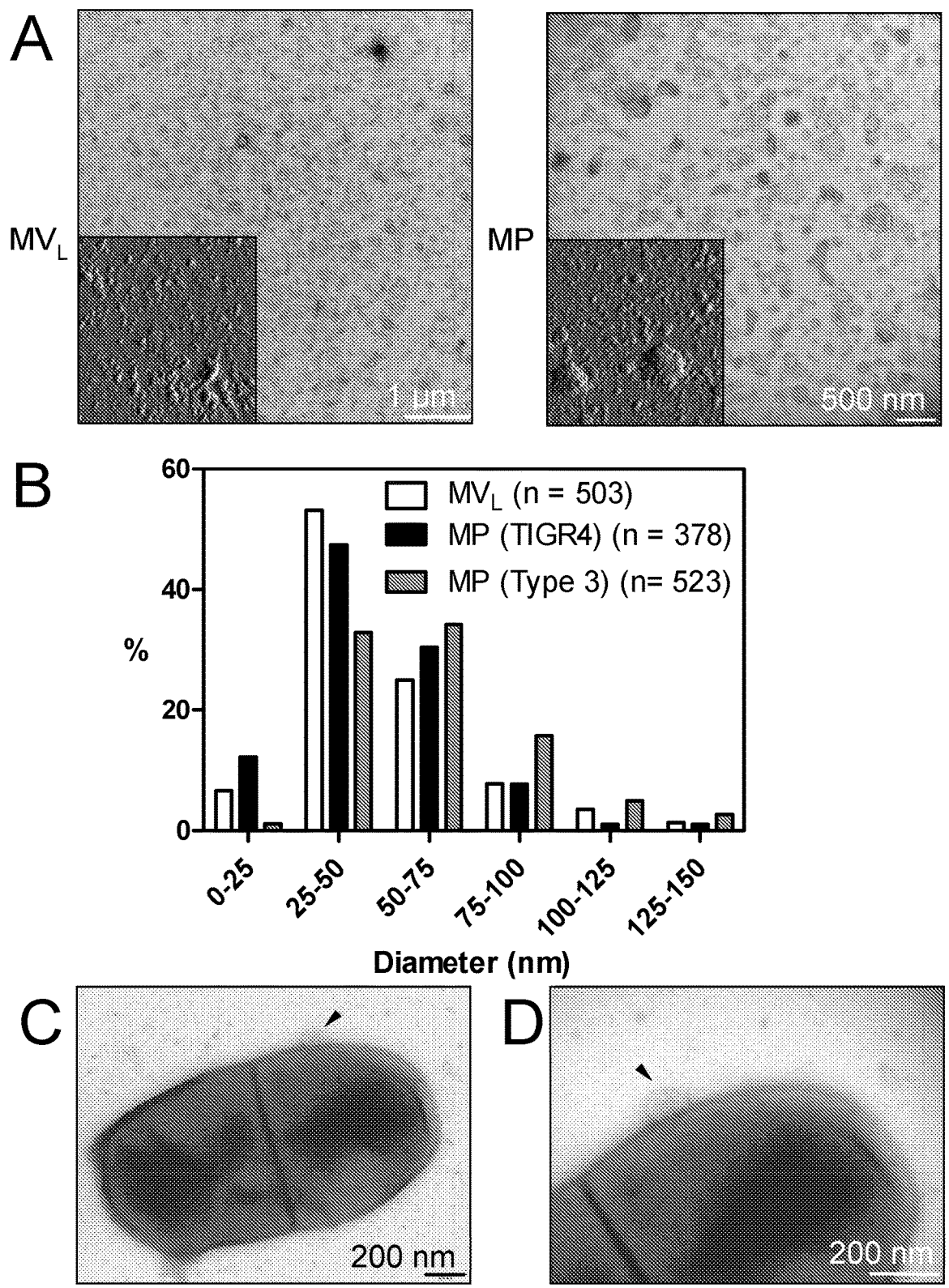
FIG. 1: Membrane-derived vesicles and microparticles produced by *S. pneumoniae* TIGR4 (T4). (A) Electron micrographs and atomic force micrographs (insets) of membrane vesicles and microparticles after isolation and density gradient purification from liquid culture ($MV_L$) and microparticles from plate-grown (MP) bacteria. (B) Size distribution of $MV_L$, MPs from TIGR4 and MPs from serotype 3. (C) Electron micrograph of a membrane budding from *S. pneumoniae* T4R and (D) the same electron micrograph in larger magnification. Released particle is indicated by arrow.

(A, B and C) Immunofluorescence pictures of A549 cells treated with MP (10 μg/ml) for 24 hours. Cells were stained for F-actin, MP are detected with anti-pneumolysin and LytA antibodies. (A) Z-stack image (nr. stacks=21) of MP-treated cells. Internalized MP are indicated by arrows. (B and C) Orthogonal views of the same picture, taken at stack nr. 11, for the two indicated MP, further showing their intracellular localization.

(D) Immunoblot detection of anti-Ply, and anti-β-actin as loading control, in A549 cell lysates after incubation with increasing concentrations (1, 2, 3 μg/ml) of MP. As control treatment, A549 cells were incubated with PBS (−). (E) Viability of A549 cells examined by flow cytometry of fixable viability dye (FVD) positive cells after 24 hours of incubation with $MV_L$ or MP. As control treatment, A549 cells were incubated with PBS (−) or 0.02% NP40 in PBS. Data are represented as means +/−SEM of three independent experiments.

FIG. 5: $MV_L$ and microparticles (MP) activate human monocyte-derived dendritic cells (DCs). (A) Percentages of FVD and Annexin V-positive cells analyzed by flow cytometry. Cells were incubated for 24 hours with different concentrations (10, 25, 50 μg/ml) of $MV_1$, MP, PBS (−) or the unencapsulated mutant of TIGR4 (T4R). Data are represented as means+/−SEM of three independent experiments. *=P<0.05. (B) Immunoblot detection of anti-Ply, and anti-3-actin as loading control, in cell lysates after incubation of DCs with MP (4 μg/ml) in presence or absence of the inhibitors Cytochalasin D and Wortmannin (C/W), to block active phagocytosis, or methyl-β-cyclodextrin (MβCD), to block lipid rafts and membrane fusion. Numbers represent the relative intensity of bands corresponding to Ply, adjusted to the loading control bands, in three independent experiments. (C) DC activation measured by flow cytometry of MHCII and CD86-positive cells after 24 hours incubation with different concentrations (2.5, 5 μg/ml) of $MV_L$, MP, PBS (−) or LPS (1 μg/ml). Data are represented as means+/−SEM of three independent experiments. *=P<0.05; ***=P<0.001.

FIG. 6: Cytokine release by human monocyte-derived dendritic cells upon incubation with $MV_L$ or MP. (A) IL-6, (B) IL-8, (C) IL-10 and (D) TNF released by dendritic cells after 24 hours of incubation with different concentrations (10, 25, 50 μg/ml) of $MV_L$ or MP. Control treatments include PBS (−), the unencapsulated mutant of TIGR4 (T4R) and LPS (1 μg/ml). Not detectable (n.d.) amounts of cytokines are indicated. Data are represented as means+/−SEM of three independent experiments. *=P<0.05; =P<0.01; *=P<0.001; ****=P<0.0001.

FIG. 7: Intranasal immunization of C57BL/6 mice with $MV_1$ or MP of *S. pneumoniae* TIGR4 increase survival against intranasal infection with serotype 1.

(A) Percentage of mice survived after challenge. 20 mice per group. *=P<0.05; =P<0.01; =P<0.0001. (B) CFUs in lungs of mice after sacrifice. Each dot represents one mouse. =P<0.01; ***=P<0.001. (C-E) CFUs in blood of mice. Each line represents one mouse.

FIG. 8: Intranasal immunization of mice with MV or MPs stimulate the production of pneumoccal-specific IgG. Detection of MW-reactive (A), MP-reactive (B), T4-reactive (C) and T4R-reactive (D) mouse IgG in immunized mice sera using ELISA assay. Each dot represents one mouse serum. *=P<0.05; =P<0.01; *=P<0.001; ****=P<0.0001.

FIG. 9: Staining of serotypes 1, 3 and 6B using antibodies raised against MP from a serotype 4 strain. (A) Immunofluorescence pictures of pneumococcal strains belonging to serotypes 1, 3 and 6B stained using sera, as primary antibodies, from mice immunized either with $MV_L$+adjuvant or MP+adjuvant. The white spots on the bacterial surface indicates the presence of specific antibodies against pneumococci in the sera of the immunized mice. (B) Quantification of the signal (white spots) detected on the bacteria; the signal ratio was calculated by dividing the area of the signal detected on the bacteria (white spots) by the total area detected occupied by the bacteria. The area covered by the bacteria and the area covered by the signal detected on the bacteria after staining with sera were selected, defined and measured using the functions Image>Adjust>Threshold and Analyze>Measure of ImageJ. *=P<0.05; =P<0.01; *=P<0.001.

Figure 10:
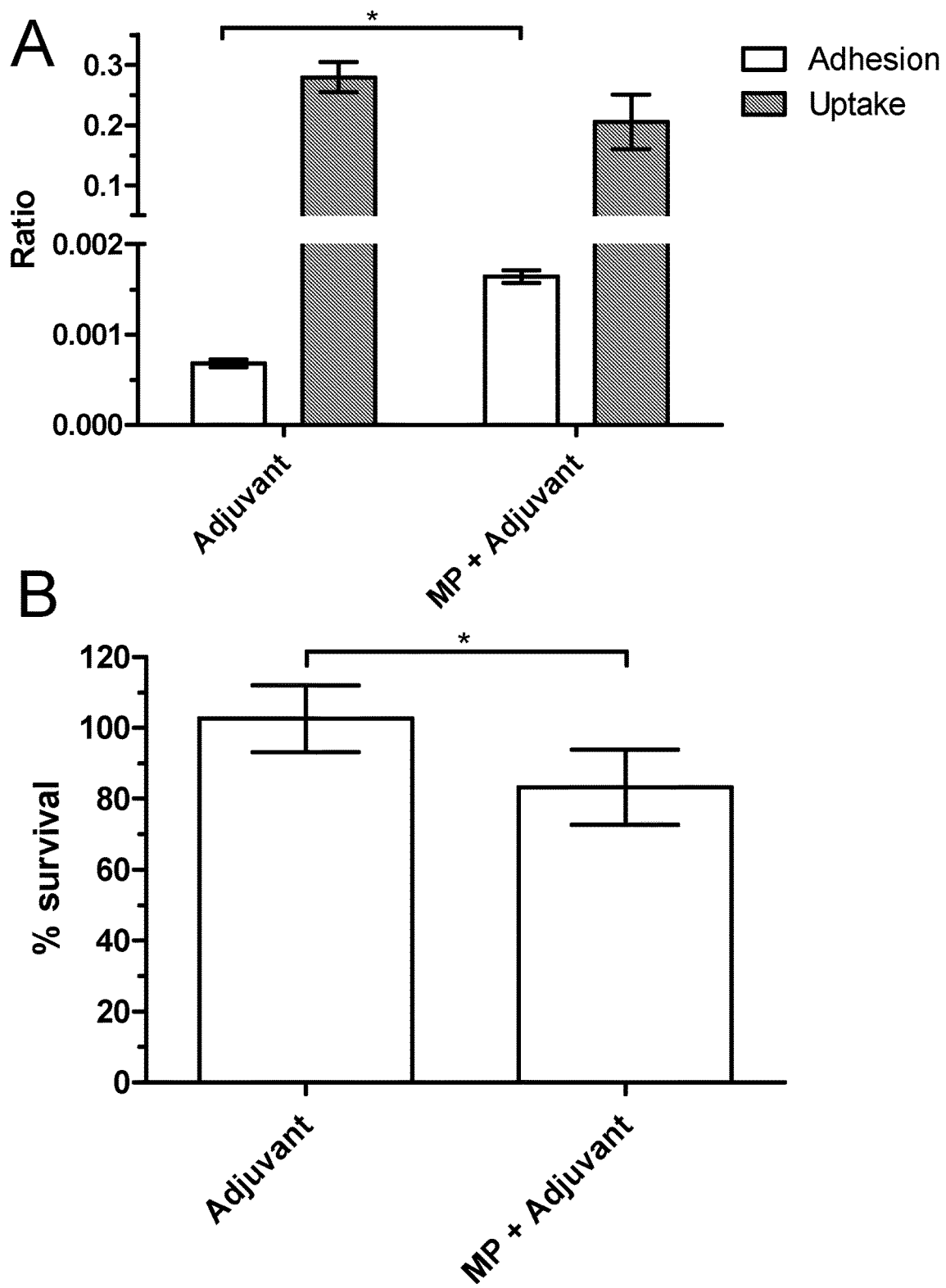
Figure 11B:
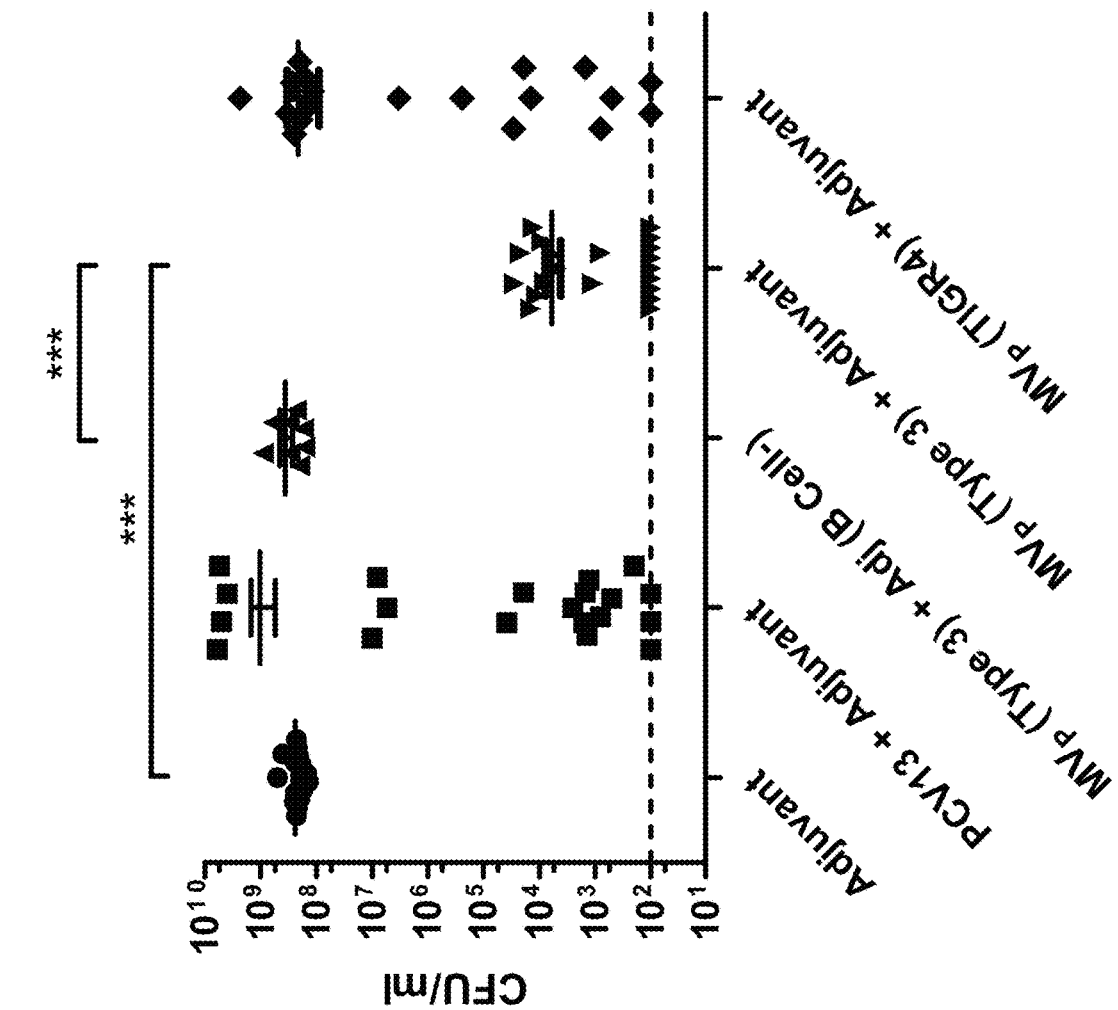
Figure 11C:
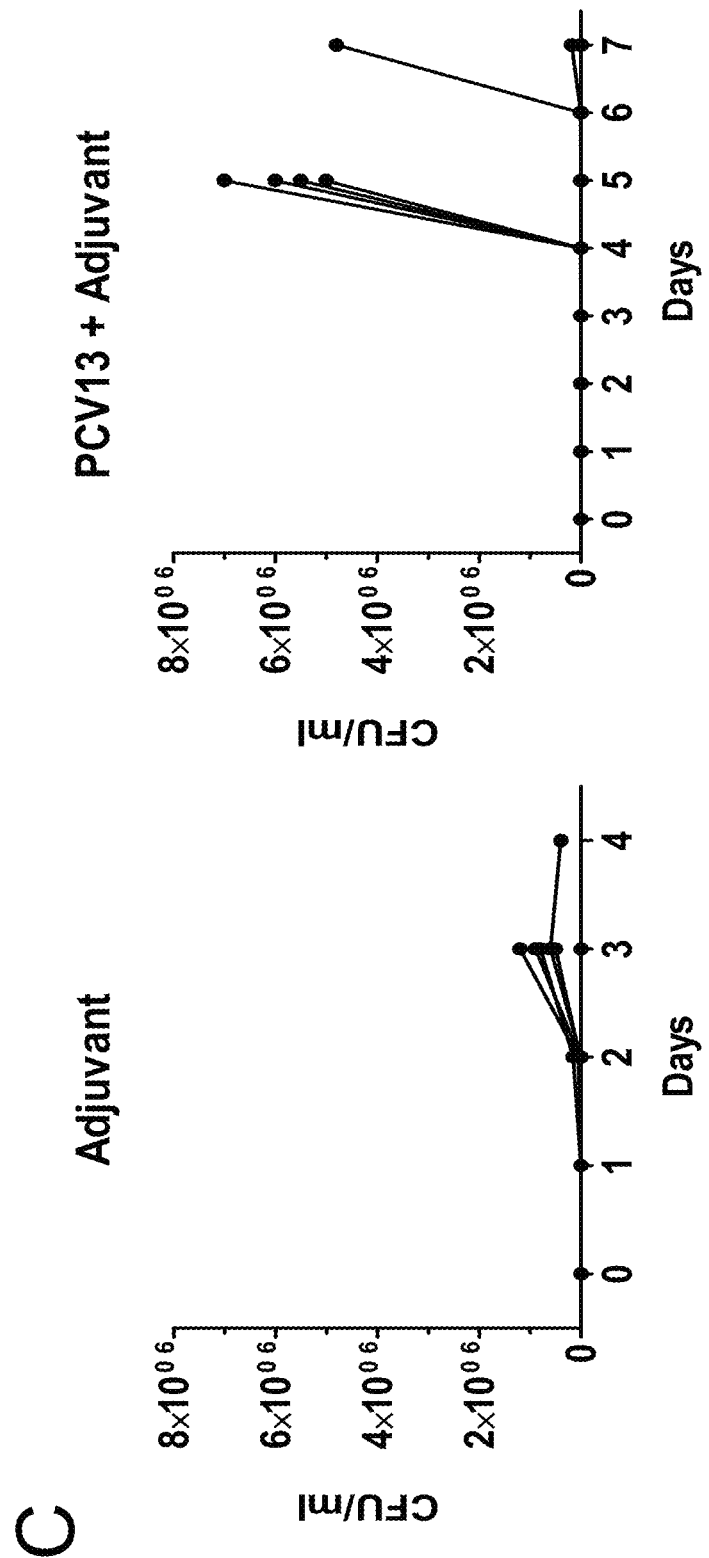
Figure 11D:
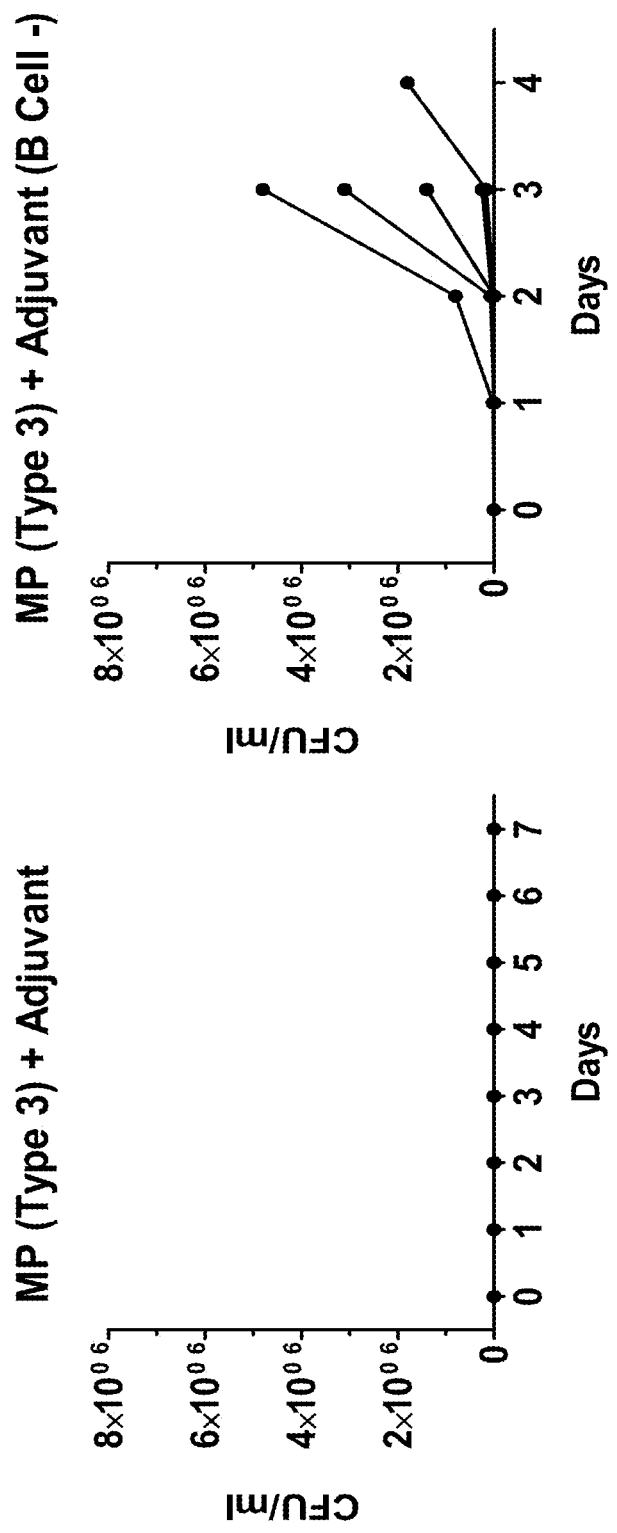
Figure 11E:
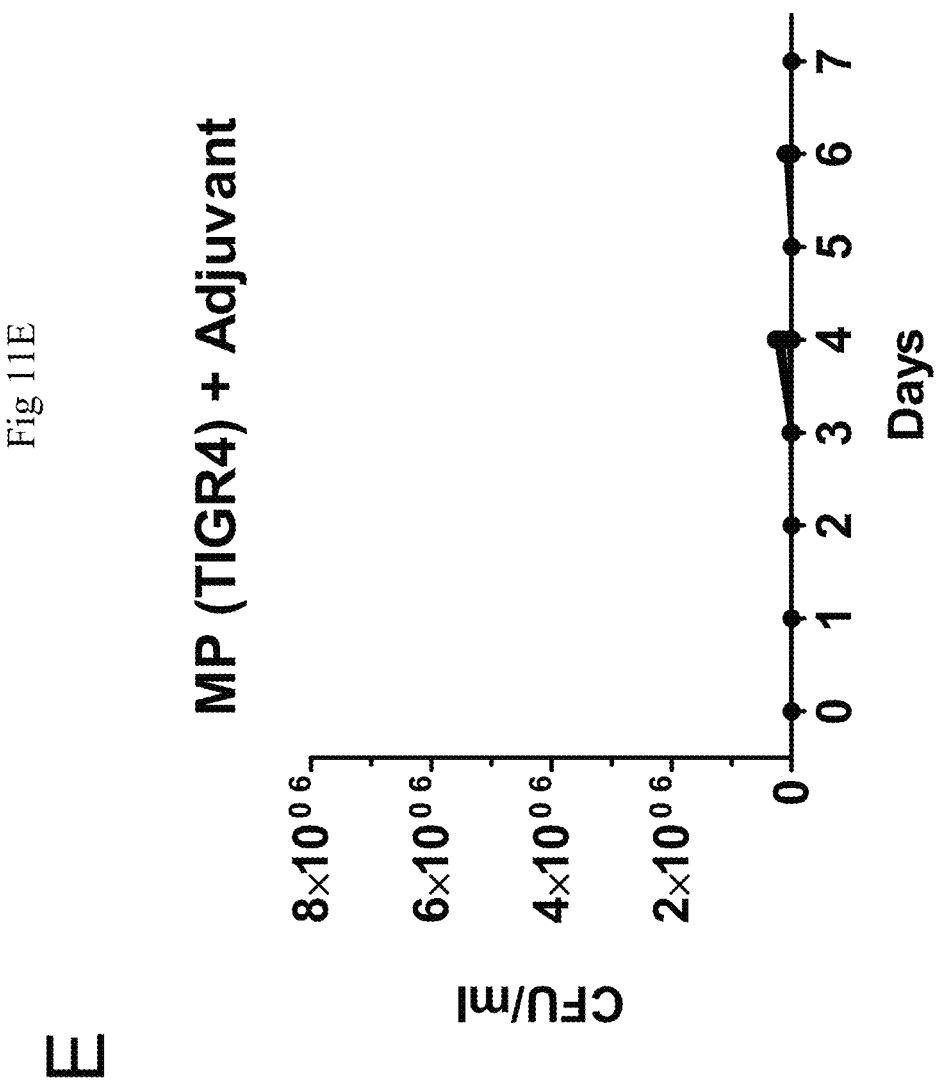

FIG. 10: Opsonophagocytic activity of antibodies in mice sera. (A) RAW mouse macrophages were incubated with *Streptococcus pneumoniae* type 1, pre-incubated with mouse sera from the adjuvant or MP+adjuvant groups. Indicated are the ratios of adherence of bacteria to cells, or uptake of bacteria inside cells. Data are represented as means+/−SEM of three independent experiments. *=P<0.05. (B) RAW mouse macrophages have been incubated with *Streptococcus pneumoniae* type 1, pre-incubated with mouse sera from the adjuvant or MP+adjuvant groups. Indicated is the percentage of taken up bacteria surviving inside the cells after 1 hour. Data are represented as means+/−SEM of three independent experiments. *=P<0.05.

FIG. 11: Intranasal immunization of C57BL/6 mice with MP of *S. pneumoniae* increases survival against intranasal infection with serotype 3. In particular, immunization with MPs of serotype 3 confers 100% protection against serotype 3 infection in comparison to PCV13 immunization, which confers 75% protection. B-cell deficient mice immunized with MPs of serotype 3 are not protected against intranasal infection with serotype 3, strongly suggesting that protection provided by MPs is antibody-dependent.

(A) Percentage of mice that survived after pneumococcal challenge. 10 mice in the group of "B Cell—(deficient mice)", 10 mice in the group "Adjuvant", 20 mice per all other groups. *=P<0.05; **=P<0.0001. (B) CFUs in lungs of mice after sacrifice. Each dot represents one mouse. *=P<0.001. (C-E) CFUs in blood of mice. Each line represents one mouse.

SUMMARY OF THE INVENTION

The present invention relates to the following items. The subject matter disclosed in the items below should be regarded disclosed in the same manner as if the subject matter were disclosed in patent claims.

1. An isolated *Streptococcus pneumoniae* membrane vesicle microparticle (MP), wherein said MP comprises:
   i. the protein Ply at the level of ≥0.70 μg/μg total protein in the MP;

ii. the protein LytA at the level of ≥0.70 μg/μg total protein in the MP;

iii. the protein PspC at the level of ≥0.130 μg/μg total protein in the MP; or iv. the protein RrgB at the level of ≥0.020 μg/μg total protein in the MP.

2. The microparticle according to item 1, further comprising a capsular polysaccharide of a capsular serotype of *Streptococcus pneumoniae*, preferably at a level of ≥0.001, more preferably ≥1.01, most preferably ≥0.1 μg/μg total protein in the MP.

3. The microparticle according to any of the preceding items, comprising the protein Ply at the level of ≥0.70 μg/μg total protein in the MP.

4. The microparticle according to any of the preceding items, comprising the protein Ply at the level of ≥0.15, preferably more ≥0.2, preferably most preferably ≥0.35 μg/μg total protein in the MP.

5. The microparticle according to any of the preceding items, comprising the protein LytA at the level of ≥0.70 μg/μg total protein in the MP.

6. The microparticle according to any of the preceding items, comprising the protein LytA at the level of ≥0.08, preferably ≥0.09, yet more preferably ≥0.10, most preferably ≥0.20 μg/μg total protein in the MP.

7. The microparticle according to any of the preceding items, comprising the protein PspC at the level of ≥0.130 μg/μg total protein in the MP.

8. The microparticle according to any of the preceding items, comprising the protein PspC at the level of ≥0.15, preferably ≥0.18, more preferably ≥0.20, most preferably ≥0.3 μg/μg total protein in the MP.

9. The microparticle according to any of the preceding items, comprising the protein RrgB at the level of ≥0.20 μg/μg total protein in the MP.

10. The microparticle according to any of the preceding items, comprising the protein RgrB at the level of ≥0.22, preferably ≥0.025, most preferably ≥0.028 μg/μg total protein in the MP.

11. The microparticle according to any of the preceding items, further comprising the protein PhtD.

12. The microparticle according to any of the preceding items, comprising the protein PhtD at a level being at least 2-fold, more preferably at least 2.5-fold compared to *Streptococcus pneumoniae* membrane vesicles obtained in liquid culture in terms of μg/μg total protein in the particle or the vesicle, respectively.

13. The microparticle according to any of the preceding items, further comprising the protein RrgA.

14. The microparticle according to any of the preceding items, comprising the protein RrgA at the level of ≥0.02, preferably ≥0.05, more preferably ≥0.10, most preferably ≥0.2 μg/μg total protein in the MP.

15. The microparticle according to any of the preceding items, comprising the protein IgA.

16. The microparticle according to any of the preceding items, comprising the protein IgA at the level of ≥0.02, preferably ≥0.05, more preferably ≥0.10, most preferably ≥0.2 μg/μg total protein in the MP.

17. The microparticle according to any of the preceding items, wherein the protein Ply comprises a sequence having at least 80%, preferably 85%, more preferably 90%, yet more preferably 95%, most preferably 100% sequence identity to SEQ ID NO: 1.

18. The microparticle according to any of the preceding items, wherein the protein LytA comprises a sequence having at least 80%, preferably 85%, more preferably 90%, yet more preferably 95%, most preferably 100% sequence identity to SEQ ID NO: 2.

19. The microparticle according to any of the preceding items, wherein the protein PspC comprises a sequence having at least 40%, preferably 80%, more preferably 85%, yet more preferably 90%, still more preferably 95%, most preferably 100% sequence identity to SEQ ID NOs: 3.

20. The microparticle according to any of the preceding items, wherein the protein PspC comprises a sequence having at least 80%, preferably 85%, more preferably 90%, yet more preferably 95%, most preferably 100% sequence identity to any one of SEQ ID NOs: 3-14.

21. The microparticle according to any of the preceding items, wherein the protein RgrB comprises a sequence having at least 80%, preferably 85%, more preferably 90%, yet more preferably 95%, most preferably 100% sequence identity to SEQ ID NO: 15.

22. The microparticle according to any of the preceding items, wherein the protein PhtD comprises a sequence having at least 80%, preferably 85%, more preferably 90%, yet more preferably 95%, most preferably 100% sequence identity to SEQ ID NO: 16.

23. The microparticle according to any of the preceding items, comprising the protein RgrA, wherein the protein RgrA comprises a sequence having at least 80%, preferably 85%, more preferably 90%, yet more preferably 95%, most preferably 100% sequence identity to SEQ ID NO: 17.

24. The microparticle according to any of the preceding items, comprising the protein IgA, wherein the protein IgA comprises a sequence having at least 80%, preferably 85%, more preferably 90%, yet more preferably 95%, most preferably 100% sequence identity to SEQ ID NO: 18.

25. The microparticle according to any of the preceding items, wherein the MP is 5-300 nm in diameter, preferably 15-175 nm.

26. The microparticle according to any of the preceding items, wherein the MP is 10-125 nm in diameter.

27. The microparticle according to any of the preceding items, wherein the MP is derived from a *Streptococcus pneumoniae* strain selected from any serotype 1 strain, any serotype 3 strain, TIGR4, P1031 and A66, preferably TIGR4.

28. The microparticle according to any of the preceding items, obtainable by:
 a. Culturing host cells of a *Streptococcus pneumoniae* strain on blood agar plates;
 b. harvesting the cultured host cells;
 c. centrifuging the harvested host cells at 17,000 g for 30 minutes at +4C;
 d. subjecting the supernatant to filtration through a 0.22 μm filter;
 e. centrifuging the filtered supernatant at 120,000 g for 2 h at +4C;
 f. washing the pellets from e) twice in phosphate-buffered saline with sedimentations at 120,000 g for 2 h at +4C;
 g. resuspending the pellet in 1 ml phosphate-buffered saline;
 h. adjusting the resuspended pellet to 50% (w/v) Optiprep™ density gradient medium in a total volume of 2 ml and overlaying with one fraction of 30% (w/v) Optiprep™ (9 ml) followed by a fraction of 5% (w/v) Optiprep™ (3 ml);

i. centrifuging the gradients at 250,000×g for 3 hours at 4° C.;
j. collecting the 4 ml top fraction, containing the membrane microparticle; and
k. washing the microparticle three times phosphate-buffered saline with sedimentations of 250,000×g for 2 hours at +4° C.

29. A composition comprising a microparticle according to any of items 1-28.
30. The composition according to item 29, wherein the composition is devoid of whole *Streptococcus pneumoniae* cells.
31. The composition according to any of items 29-30, further comprising capsular polysaccharides from *Streptococcus pneumoniae*.
32. The composition according to any of items 29-31, comprising MPs in an amount of 1 µg/ml, preferably 5 µg/ml, more preferably 10 µg/ml, most preferably 100 µg/ml.
33. The composition according to any of items 29-32, further comprising an adjuvant.
34. The composition according to any of items 29-33, further comprising an adjuvant comprising aluminium hydroxide.
35. The composition according to any of items 29-34, being an immunogenic composition.
36. The composition according to any of items 29-35, being an immunogenic composition capable of eliciting opsonophagocitic antibodies against *Streptococcus pneumoniae* when administered to a mammalian host.
37. The composition according to any of items 29-36, being an immunogenic composition is capable of eliciting serotype independent antibodies against *Streptococcus pneumoniae* when administered to a mammalian host.
38. The composition according to any of items 29-37, being an immunogenic composition is capable of eliciting antibodies against *Streptococcus pneumoniae* serotype 3 when administered to a mammalian host.
39. The composition according to any of items 29-38, further comprising capsular polysaccharides of a capsular serotype of *Streptococcus pneumoniae*.
40. The composition according to any of items 29-39, being a vaccine.
41. The composition according to any of items 29-40, for use in a method for inducing protective immunity against *Streptococcus pneumoniae* in a subject.
42. The composition according to item 41, for use according to item 41, wherein the immunity is protective against a condition selected from pneumococcal sinusitis, pneumococcal otitis, pneumococcal pneumonia and invasive pneumococcal disease including but not limited to pneumococcal sepsis and pneumococcal meningitis, preferably invasive pneumococcal disease.
43. A use of a microparticle according to any of items 1-28 in an immunogenic composition.
44. The use according to item 43, wherein the immunogenic composition is a vaccine.
45. A use of a microparticle according to any of items 1-28 in the manufacture of a vaccine.
46. A method for manufacturing a vaccine, comprising:
a. Providing a microparticle according to any of items 1-28;
b. Providing an adjuvant;
c. Mixing the microparticle and the adjuvant in a suitable vehicle in order to produce a vaccine.
47. A method for producing an isolated *Streptococcus pneumoniae* microparticle according to any of items 1-28, comprising:
a. providing a *Streptococcus pneumoniae* host cell;
b. culturing said host cell under conditions allowing the production of a microparticle according to any of items 1-28 by the host cell; and
c. isolating the microparticle thus produced.
48. The method according to item 47, wherein the host cell is of a strain selected from any serotype 1 strain, any serotype 3 strain, TIGR4, P1031 and A66, preferably TIGR4.
49. The method according to any of items 47-48, wherein the culturing is carried out in solid phase.
50. The method according to any of items 47-49, wherein the culturing is carried out in solid phase on blood agar.
51. The method according to any of items 47-50, wherein isolating the microparticle comprises density gradient centrifugation.

DETAILED DESCRIPTION

The inventors isolated membrane vesicles ($MV_L$) from *S. pneumoniae* of serotype 4 grown in liquid cultures as previously described in the literature (1). They also isolated a novel type of membrane particles termed microparticles (MP) using a method involving growth of the bacteria overnight on blood agar plates. FIG. 1 shows the appearance of the $MV_L$ and MP using electron microscopy and atomic force microscopy as well as their size distribution. Microparticles from *S. pneumoniae* TIGR4 grown on plates (MP) were smaller in size on average than $MV_L$ coming from liquid media ($MV_L$). However, MP from *S.pneumoniae* serotype 3 display a different size distribution, containing less of the smallest particles and more of the largest ones.

Figure 2D:
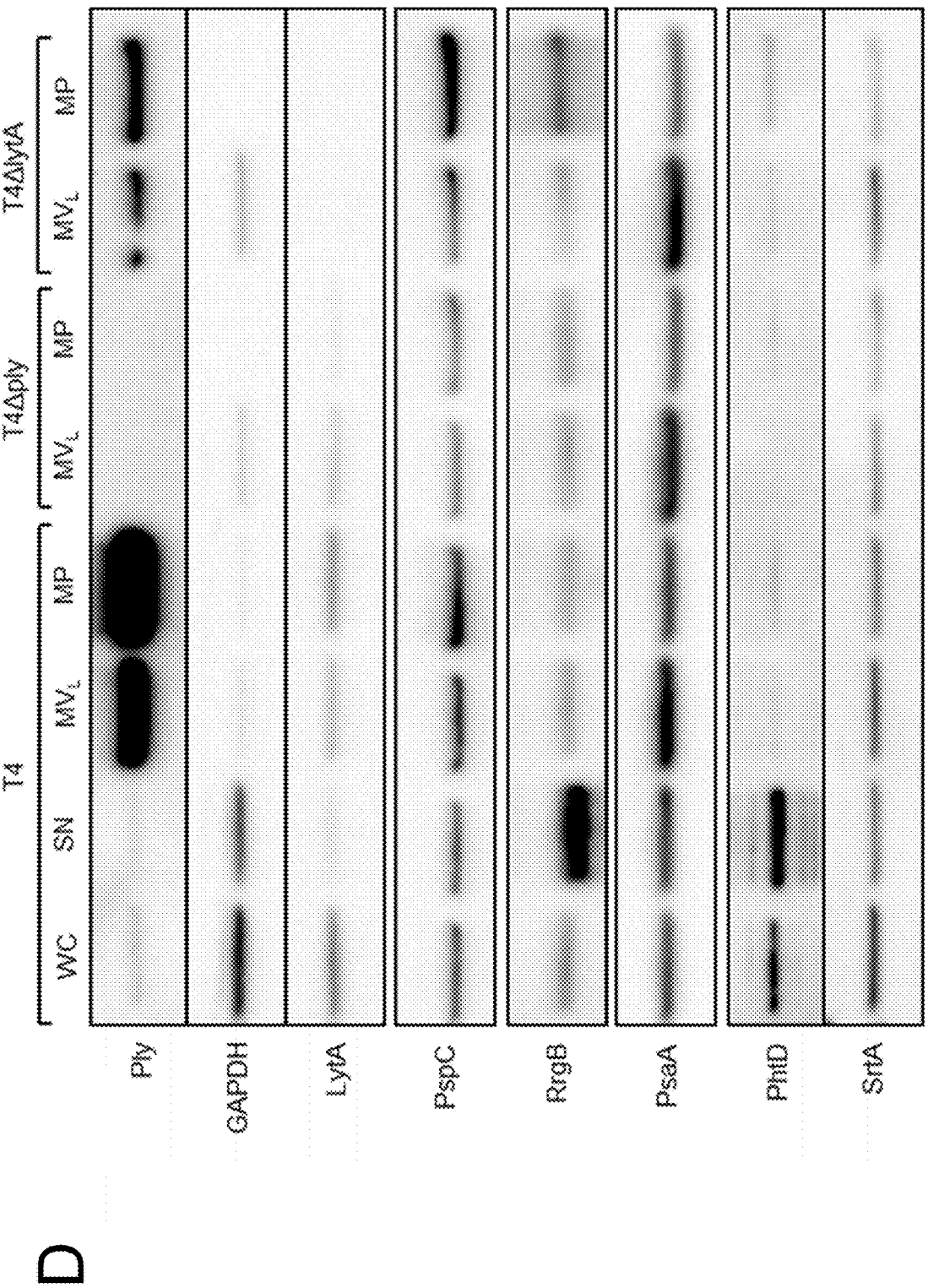
FIG. 2: Identification of proteins present in pneumococcal $MV_L$ and MP. (A) Preparations of $MV_L$ and MP were separated by SDS-PAGE and proteins visualized by coomassie staining. In comparison, proteins present in a whole cell lysate (WC) and supernatant (SN) of a liquid bacterial culture were visualized. (B) Venn diagram displaying the number of proteins identified by mass spectrometry (repeated twice) exclusively found in $MV_L$ and MP preparations and common to both. (C) Mass spectrometry identification of proteins from $MV_L$ and MP. Numbers indicate percentages of proteins based on their subcellular localization, defined as cytosolic proteins, membrane-associated proteins (lipoproteins), proteins with one transmembrane domain (N-terminally anchored), transmembrane proteins, cell wall associated proteins and secreted proteins. (D) Immunoblot detection of pneumococcal proteins and virulence factors present in $MV_L$ and MP isolated from *S. pneumoniae* T4 WT, pneumolysin-(T4Δply) and LytA-deficient (T4ΔdlytA) strains.

Biochemical comparison of $MV_L$ and MP preparations from TIGR4 revealed different properties for the MP and $MV_L$. MP isolated from plates carried certain pneumococcal proteins to a higher extent than liquid grown $MV_L$. They were particularly enriched in pneumolysin, the major pore-forming toxin in *S. pneumoniae*, as shown in FIG. 2D.

Figure 3:
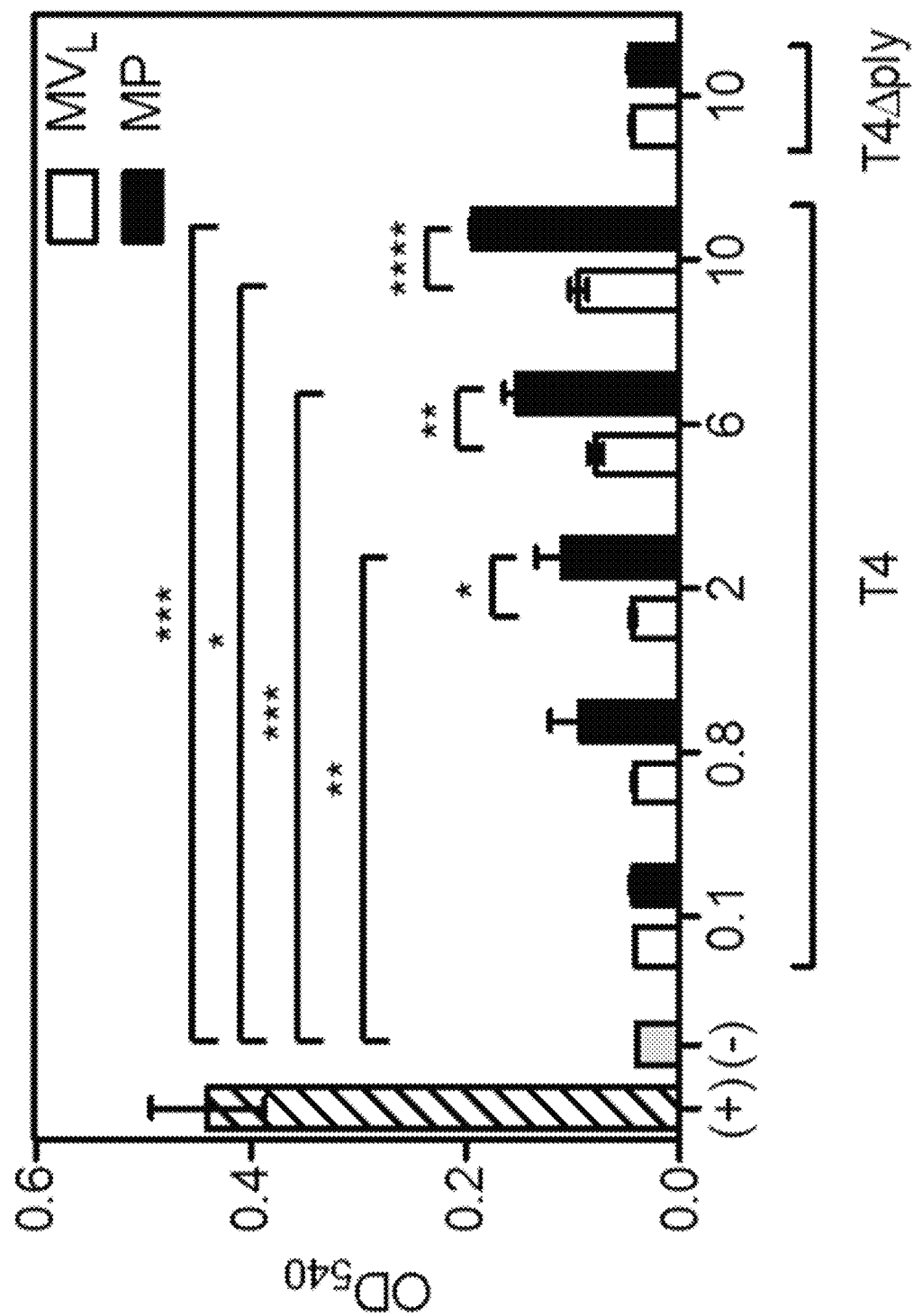
FIG. 3: Pneumolysin associated with pneumococcal $MV_L$ and MP is biologically active. Quantification of in vitro hemolytic activity of purified $MV_L$ and MP isolated from *S. pneumoniae* T4 and T4Δply. Erythrocytes from buffy coat blood were incubated for 60 minutes with different concentrations (0.1, 0.8, 2, 6 and 10 μg protein) of $MV_L$ and MP. As control treatments, erythrocytes were incubated with PBS (−) or 1% Triton X-100 (+). Data are represented as means +/−SEM of three independent experiments. *=P<0.05; =P<0.01; *=P<0.001.
Figure 4E:
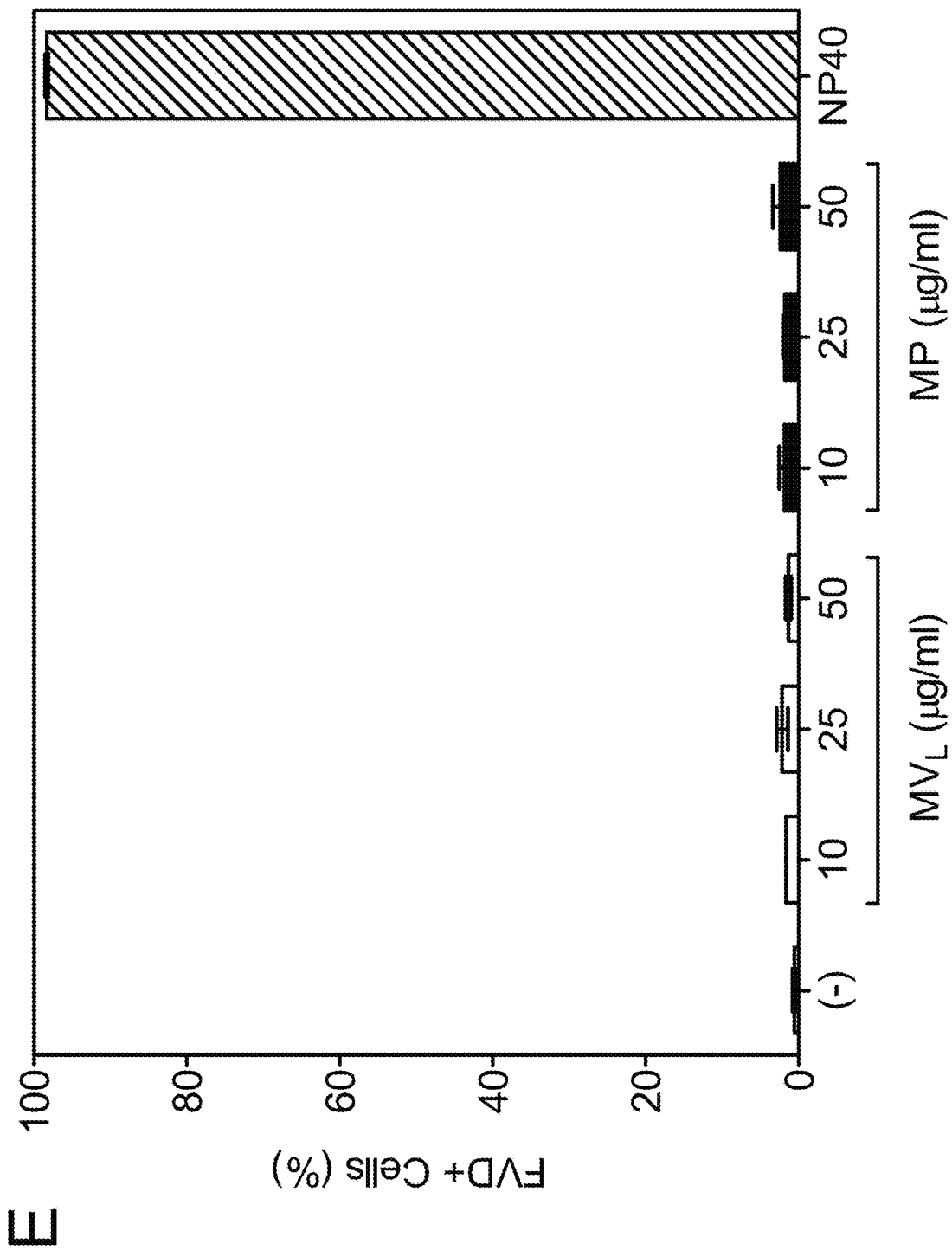
FIG. 4: Microparticles (MP) are internalized by A549 epithelial cells.

The novel MP were characterized using in vitro cell assays, and it was shown that consistent with the quantitated levels, the MP contain more biological pneumolysin activity than the $MV_L$ (FIG. 3). It was further shown that the MP are taken up by epithelial cells (FIG. 4A-D) but are not cytotoxic (FIG. 4E). Using human monocyte-derived dendritic cells it was shown that both MP and $MV_L$ are internalized into DCs, induce maturation of DCs (FIG. 5), and elicit differential cytokine responses (FIG. 6).

Next, the inventors investigated the potential of MP to protect mice using experimental models of pneumonia and invasive disease (FIGS. 7-11). The results showed that 80% of mice (wild type C57BL/6 mice) immunized with MP from serotype 4 (combined with aluminium hydroxide as adjuvant) survived after an intranasal pneumococcal infection caused by serotype 1 (heterologous challenge, cross protection). ELISA analysis showed that mice immunized with MP had a significantly higher MP-specific IgG response in comparison to control mice (treated only with the adjuvant) (FIG. 8). Immunization with serotype 3 and then challenge with serotype 3 led to a 100% protection (FIG. 11). Immunization with serotype 4 MP and then challenge with serotype 3 (a serotype that has been problematic in current vaccines) gave a protection of ca 50% (FIG. 11). Furthermore, immunofluorescence stainings showed that sera from mice immunized with MP from serotype 4 contained antibodies specific against multiple other serotypes, such as serotypes 1, 3 and 6B (FIG. 9).

In conclusion, it was found that MP protect mice against pneumococcal infection, and, most importantly, such protection is serotype-independent to a significant degree, in contrast to the protection conferred by currently available vaccines (polysaccharide or conjugated vaccines) that are, as mentioned in the background section, strictly serotype-dependent. The MP immunisation furthermore elicited protection against serotype 3 which is a challenge for current vaccines. Indeed, immunization with the currently clinically used vaccine PCV13 provided significantly less protection to mice than MP isolated from serotype 3 (FIG. 11).

Moreover, for protein based vaccines that are under development today, there is a problem in obtaining opsonophagocytic capability. Importantly, the present data show that using MP as a vaccine affects opsonophagocytosis (Example 3, FIG. 10). Last but not least, available pneumococcal vaccines (PCVs) are extremely important to fight pneumococcal diseases in developing countries. However, the costs to produce current vaccines are very high. An important benefit with the present approach is a drop in production costs since isolation of microparticles does not require high-cost preparations with conjugations, instead the method of the present invention is more simple based on bacterial growth combined with high speed-centrifugation.

Isolated *Streptococcus pneumoniae* Membrane Vesicles and Microparticles

As discussed in the Background section, a few types of *Streptococcus pneumoniae* membrane vesicles have been obtained in liquid culture (1). The solid phase culture method used by the inventors resulted in a novel type of particles termed microparticles having different and advantageous properties as discussed above and shown in the Examples. As shown in Table 1, the microparticles differ from the known membrane vesicles, MVS in terms of relative protein expression.

TABLE 1

Quantification of proteins present in membrane vesicles, $MV_L$, from serotype 4 strain TIGR4 and microparticles, MP, from serotype 4 and 3. Percentage sequence identities of protein homologues in reference strains for serotype 1 (P1031) and serotype 3 (A66) are shown. The amounts are indicated in μg/μg total protein or relative amount in percentage.

| Protein | $MV_L$ | MP (TIGR4) | MP (Type 3) | Homology in P1031* | Homology in A66** |
|---|---|---|---|---|---|
| Ply | 0.055 μg | 0.406 μg | 0.314 μg | 99% | 99% |
| LytA | 0.050 μg | 0.100 μg | 0.266 μg | 99% | 100% |
| PspC (PspC3.4) | 0.118 μg | 0.300 μg | Not determined* | 85% (PspC 2.1) | 45% (PspC 11.4) |
| RrgB | 0.016 μg | 0.028 μg | Absent | Absent | Absent |
| PhtD | 100% | 266% | 5793% | 95% | 87% |

*Because of the high genetic diversity of the pspC gene among pneumococcal serotypes it was not possible to use the anti TIGR4 PspC antibody (which was specific for the TIGR4 strain) to detect the serotype 3 PspC Thus, in a first aspect of the present invention, there is provided isolated *Streptococcus pneumoniae* microparticle (MP) (a novel type of pneumococcal membrane vesicle particle), wherein said MP comprise either one, two, three or four of the following proteins at the designated levels:
  i. the protein Ply at the level of ≥0.070 μg/μg total protein in the MP;
  ii. the protein LytA at the level of ≥0.070 μg/μg total protein in the MP;
  iii. the protein PspC at the level of ≥0.130 μg/μg total protein in the MP; and/or
  iv. the protein RrgB at the level of ≥0.020 μg/μg total protein in the MP.

The microparticles may further comprise capsular polysaccharides of a capsular serotype of *Streptococcus pneumoniae*, preferably at a level of ≥0.001, more preferably ≥0.01, most preferably ≥0.1 μg/μg total protein in the MP.

The microparticle may comprise the protein Ply at the level of ≥0.070 μg/μg total protein in the MP. The microparticle may comprise the protein Ply at the level of ≥0.15, preferably ≥0.2, more preferably ≥0.3, most preferably ≥0.35 μg/μg total protein in the MP.

The microparticle may comprise the protein LytA at the level of ≥0.070 μg/μg total protein in the MP. The microparticle may comprise the protein LytA at the level of ≥0.08, preferably ≥0.09, yet more preferably ≥0.1 μg/μg, most preferably ≥0.2 μg/μg total protein in the MP.

The microparticle, MP, may comprise the protein PspC at the level of ≥0.130 μg/μg total protein in the MP. The microparticle may comprise comprising the protein PspC at the level of ≥0.15, preferably ≥0.18, more preferably ≥0.2, most preferably ≥0.3 μg/μg total protein in the MP.

The microparticle may comprise the protein RrgB at the level of ≥0.02 μg/μg total protein in the MP. The microparticle may comprise the protein RgrB at the level of ≥0.022, preferably ≥0.025, most preferably ≥0.028 μg/μg total protein in the MP.

The microparticle may further comprise the protein PhtD. The protein PhtD may be present at a level being at least 2-fold, more preferably at least 2.5-fold compared to *Streptococcus pneumoniae* membrane vesicles obtained in liquid culture in terms of μg/μg total protein in the particle or the vesicle, respectively.

The microparticle may further comprise the protein RrgA. The protein RrgA may be present at the level of ≥0.02, preferably ≥0.05, more preferably ≥0.10, most preferably ≥0.2 μg/μg total protein in the MP.

The microparticle may further comprise the *Streptococcus pneumoniae* protein IgA. The protein IgA may be present at the level of ≥0.02, preferably ≥0.05, more preferably ≥0.10, most preferably ≥0.2 μg/μg total protein in the MP.

The protein Ply may comprise a sequence having at least 70%, preferably 80%, more preferably 85%, yet more preferably 90%, still more preferably 95%, most preferably 100% sequence identity to SEQ ID NO: 1.

The protein LytA may comprise a sequence having at least 70%, preferably 80%, more preferably 85%, yet more preferably 90%, still more preferably 95%, most preferably 100% sequence identity to SEQ ID NO: 2.

The protein PspC may comprise a sequence having at least 40% or 70%, preferably 80%, more preferably 85%, yet more preferably 90%, still more preferably 95%, most preferably 100% sequence identity to SEQ ID NOs: 3.

The protein PspC may comprise a sequence having at least 70%, preferably 80%, more preferably 85%, yet more preferably 90%, still more preferably 95%, most preferably 100% sequence identity to any one of SEQ ID NOs: 3-14.

The protein RgrB may comprise a sequence having at least 70%, preferably 80%, more preferably 85%, yet more preferably 90%, still more preferably 95%, most preferably 100% sequence identity to SEQ ID NO: 15.

The protein PhtD may comprise a sequence having at least 70%, preferably 80%, more preferably 85%, yet more preferably 90%, still more preferably 95%, most preferably 100% sequence identity to SEQ ID NO: 16.

The protein RgrA may comprise a sequence having at least 70%, preferably 80%, more preferably 85%, yet more preferably 90%, still more preferably 95%, most preferably 100% sequence identity to SEQ ID NO: 17.

The protein IgA may comprise a sequence having at least 70%, preferably 80%, more preferably 85%, yet more preferably 90%, still more preferably 95%, most preferably 100% sequence identity to SEQ ID NO: 18.

Thus, the first aspect encompasses (but is not limited to) embodiments disclosed in Table 2 below.

TABLE 2

Minimum levels of designated proteins in various embodiments of the first aspect. A blank cell indicates that the protein is optional i.e. may be absent or present at any level.

| Embodiment# | Ply | LytA | PspC | PhtD | RgrB |
|---|---|---|---|---|---|
| 1 | 0.070 | | | | |
| 2 | 0.070 | 0.070 | | | |
| 3 | 0.070 | | 0.130 | | |
| 4 | 0.070 | | | 2-FOLD | |
| 5 | 0.070 | 0.070 | 0.130 | | |
| 6 | 0.070 | 0.070 | | 2-FOLD | |
| 7 | 0.070 | 0.070 | 0.130 | 2-FOLD | |
| 8 | 0.070 | | 0.130 | 2-FOLD | |
| 9 | | 0.070 | | | |
| 10 | | | 0.130 | | |
| 11 | | | | 2-FOLD | |
| 12 | | 0.070 | 0.130 | | |
| 13 | | 0.070 | | 2-FOLD | |
| 14 | | 0.070 | 0.130 | 2-FOLD | |
| 15 | | | 0.130 | 2-FOLD | |
| 16 | 0.070 | | | | 0.020 |
| 17 | 0.070 | 0.070 | | | 0.020 |
| 18 | 0.070 | | 0.130 | | 0.020 |
| 19 | 0.070 | | | 2-FOLD | 0.020 |
| 20 | 0.070 | 0.070 | 0.130 | | 0.020 |
| 21 | 0.070 | 0.070 | | 2-FOLD | 0.020 |
| 22 | 0.070 | 0.070 | 0.130 | 2-FOLD | 0.020 |
| 23 | 0.070 | | 0.130 | 2-FOLD | 0.020 |
| 24 | | 0.070 | | | 0.020 |
| 25 | | | 0.130 | | 0.020 |
| 26 | | | | 2-FOLD | 0.020 |
| 27 | | 0.070 | 0.130 | | 0.020 |
| 28 | | 0.070 | | 2-FOLD | 0.020 |
| 29 | | 0.070 | 0.130 | 2-FOLD | 0.020 |
| 30 | | | 0.130 | 2-FOLD | 0.020 |
| 31 | 0.070 | | | | |
| 32 | 0.070 | 0.070 | | | |
| 33 | 0.070 | | 0.130 | | |
| 34 | 0.070 | | | 2-FOLD | |
| 35 | 0.070 | 0.070 | 0.130 | | |
| 36 | 0.070 | 0.070 | | 2-FOLD | |
| 37 | 0.070 | 0.070 | 0.130 | 2-FOLD | |
| 38 | 0.070 | | 0.130 | 2-FOLD | |
| 39 | | 0.070 | | | |
| 40 | | | 0.130 | | |
| 41 | | | | 2-FOLD | |
| 42 | | 0.070 | 0.130 | | |
| 43 | | 0.070 | | 2-FOLD | |
| 44 | | 0.070 | 0.130 | 2-FOLD | |
| 45 | | | 0.130 | 2-FOLD | |
| 46 | 0.070 | | | | 0.020 |
| 47 | 0.070 | 0.070 | | | 0.020 |
| 48 | 0.070 | | 0.130 | | 0.020 |
| 49 | 0.070 | | | 2-FOLD | 0.020 |
| 50 | 0.070 | 0.070 | 0.130 | | 0.020 |
| 51 | 0.070 | 0.070 | | 2-FOLD | 0.020 |
| 52 | 0.070 | 0.070 | 0.130 | 2-FOLD | 0.020 |
| 53 | 0.070 | | 0.130 | 2-FOLD | 0.020 |
| 54 | | 0.070 | | | 0.020 |
| 55 | | | 0.130 | | 0.020 |
| 56 | | | | 2-FOLD | 0.020 |
| 57 | | 0.070 | 0.130 | | 0.020 |
| 58 | | 0.070 | | 2-FOLD | 0.020 |
| 59 | | 0.070 | 0.130 | 2-FOLD | 0.020 |
| 60 | | | 0.130 | 2-FOLD | 0.020 |

Units: µg/µg total protein, except for PhtD, where the amount is in comparing to *Streptococcus pneumoniae* membrane vesicles obtained in liquid culture in terms of µg/µg total protein in the particle or the vesicle, respectively.

The microparticles may be 5-300 nm in diameter, preferably 10-125 nm in diameter.

The microparticles may be derived from any *Streptococcus pneumoniae* strain, but is preferably selected from a group consisting of all serotype 3 strains, all serotype 1 strains, TIGR4, P1031 and A66, most preferably TIGR4.

The microparticles according to the first aspect may be obtainable by:
a. culturing host cells of a *Streptococcus pneumoniae* strain on blood agar plates or other plates;
b. harvesting the cultured host cells;
c. centrifuging the harvested host cells at 17,000 g for 30 minutes at +4° C.;
d. subjecting the supernatant to filtration through a 0.22 µm filter;
e. centrifuging the filtered supernatant at 120,000 g for 2 h at +4° C.;
f. washing the pellets from e) twice in phosphate-buffered saline with sedimentations at 120,000 g for 2 h at +4° C.;
g. resuspending the pellet in 1 ml phosphate-buffered saline;
h. adjusting the resuspended pellet to 50% (w/v) Optiprep™ density gradient medium in a total volume of 2 ml and overlaying with one fraction of 30% (w/v) Optiprep™ (9 ml) followed by a fraction of 5% (w/v) Optiprep™ (3 ml);
i. centrifuging the gradients at 250,000×g for 3 hours at 4° C.;
j. collecting the 4 ml top fraction, containing the membrane microparticles;
k. washing the microparticles three times phosphate-buffered saline with sedimentations of 250,000×g for 2 hours at +4° C.

Compositions and Uses

In a second aspect of the present invention, there is provided a composition comprising a microparticle according to the first aspect. The composition may be devoid of whole *Streptococcus pneumoniae* cells. The composition may optionally comprise capsular polysaccharides from *Streptococcus pneumoniae*.

The composition according to the second aspect may comprise MP in an amount of 1 µg/ml, preferably 5 µg/ml, more preferably 10 µg/ml, most preferably 100 µg/ml (the concentrations refer to the total protein content of MP per ml).

The composition may further comprise an adjuvant. The adjuvant preferably comprises aluminium hydroxide.

The composition may be an immunogenic composition. Preferably, the immunogenic composition is capable of eliciting opsonophagocitic antibodies against *Streptococcus pneumoniae* when administered to a mammalian host. Preferably, the immunogenic composition is capable of eliciting serotype independent antibodies against *Streptococcus* pneumoniae when administered to a mammalian host. Preferably, the immunogenic composition is capable of eliciting antibodies against *Streptococcus pneumoniae* serotype 3 when administered to a mammalian host.

The composition may be formulated as a vaccine.

In a third aspect of the present invention, there is provided a composition according to the second aspect, for use in a method for inducing protective immunity against *Streptococcus pneumoniae* in a subject. The third aspect also encompasses a method for inducing protective immunity against *Streptococcus pneumoniae* in a subject in need thereof, comprising administering an effective amount of the composition according to the second aspect to the subject. The third aspect also encompasses the use of a composition according to the second aspect in the manufacture of a vaccine for immunization against *Streptococcus pneumoniae*.

The protective immunity may be an immunity reducing the likelihood of a condition selected from pneumococcal sinusitis, pneumococcal otitis, pneumococcal pneumonia and invasive pneumococcal disease including but not limited to pneumococcal sepsis and pneumococcal meningitis, preferably invasive pneumococcal disease. Preferably, the subject to be immunized is a young child (e.g. less than 7 years of age) or an elderly person (e.g. over 65 years of age), but also other age groups could be targeted.

For immunization, the composition may be administered to the subject in various manners known in the art, including but not limited to by way of injection (e.g. intramuscular, intracutaneous, subcutaneous, intravenous), buccal, oral and intranasal administration as well as inhalation.

In a fourth aspect there is provided a use of a microparticle according to the first aspect in an immunogenic composition. The immunogenic composition may be a vaccine.

In a fifth aspect, there is provided a use of a microparticle according to the first aspect in the manufacture of a vaccine.

In a sixth aspect, there is provided a method for manufacturing a vaccine, comprising:
  a. Providing a microparticle according to the first aspect
  b. Providing an adjuvant, such as aluminium hydroxide;
  c. Mixing the microparticle and the adjuvant in a suitable vehicle in order to produce a vaccine.

Methods for Producing *Streptococcus pneumoniae* Microparticles

In a sixth aspect of the present invention there is provided a method for producing an isolated *Streptococcus pneumoniae* microparticle according to the first aspect, comprising:
  a. providing a *Streptococcus pneumoniae* bacterial cell;
  b. culturing said bacterial cell under conditions allowing the production of a microparticle according to the first aspect by the bacterial cell; and
  c. isolating the microparticle thus produced.

The bacterial cell may be from any pneumococcal strain, but is preferably TIGR4, a serotype 1 and/or a serotype 3 strain.

The culturing may be carried out using plates or liquid culture. Preferably, the culturing is carried out in solid phase, most preferably on blood agar or other plates. Isolating the microparticles may comprise a density gradient centrifugation step.

General Aspects Relating to the Present Disclosure

The term "comprising" is to be interpreted as including, but not being limited to. All references are hereby incorporated by reference. The arrangement of the present disclosure into sections with headings and subheadings is merely to improve legibility and is not to be interpreted limiting in any way, in particular, the division does not in any way preclude or limit combining features under different headings and subheadings with each other.

EXAMPLES

The following examples are not to be regarded as limiting. For further information on the experimental details, the skilled reader is directed to a separate section titled Materials and Methods.

Example 1: Isolation and In Vitro Characterization of Novel Pneumococcal Microparticles

*S. pneumoniae* TIGR4 Produces Microparticles that Differ Depending on Bacterial Growth Conditions.

Membrane vesicles were isolated and purified from *Streptococcus pneumoniae* serotype 4 strain TIGR4 grown in liquid medium ($MV_L$). Microparticels (MP) were isolated from pneumococci grown on blood agar plates. Preparations were analyzed by transmission electron microscopy (TEM) and atomic force microscopy, and revealed spherical bodies surrounded by membranous structures (FIG. 1A). The distribution of the size varied between $MV_L$, MP from TIGR4 and MP from serotype 3 (FIG. 1B). In total 503 $MV_L$, 378 MP from TIGR4 and 523 MP from serotype 3 were analyzed. As a control we also studied an isogenic pneumolysin mutant strain (TIGR4Δply) and found a similar size distribution. To reveal shedding of $MV_L$ or MP from the surface of bacteria by TEM we then used an isogenic unencapsulated mutant in TIGR4 (T4R) grown in liquid culture. In the absence of the thick bacterial capsule, $MV_L$ were clearly visible, emanating from the plasma membrane of *S. pneumoniae* into the extracellular milieu (FIG. 1C-D).

Proteomic Analysis Revealed Differences in Protein Content Between $MV_L$ from Liquid Culture or MP from Plates To analyze the protein content of both pneumococcal preparations, purified $MV_L$ and MP were subjected to SDS-PAGE analysis. Distinct protein patterns in $MV_L$ and MPs as compared with proteins present in whole cell lysates or bacterial supernatants (FIG. 2A), were identified. Interestingly, the proteomic content in $MV_L$ and MP fractions differed, suggesting a differential enrichment of proteins in the different types of particles. We further conducted proteomic analysis using tandem mass spectrometry. In total, in TIGR4, we identified 317 proteins in $MV_L$ (Table 3), and 216 in MP (Table 4), of which 184 proteins were found in both preparations. 133 proteins were unique to $MV_L$ and 32 to MP (FIG. 2B). In serotype 3 we identified 462 proteins in $MV_L$ (Table 5) and 344 in MP (Table 6). All detected proteins were further classified according to their subcellular localization based on the combination of LocateP and GO annotation (FIG. 2C) (11). A majority of the proteins identified in $MV_L$ and MP were cytosolic proteins, followed by multi-transmembrane proteins, lipoproteins, N-terminally anchored proteins, secretory proteins and cell wall-associated proteins. While $MV_L$ appeared to be more enriched in cytosolic protein and cell wall-associated proteins than MP from TIGR4, the latter harbored a higher percentage of multi-transmembrane proteins, lipoproteins, N-terminally anchored proteins and secretory proteins.

We further analyzed the mass spectrometry data in order to determine the presence of 30 known pneumococcal virulence factors in the particles. Both types of particles contained approximately half of these virulence factors present in TIGR4. Just two were unique to $MV_L$, CbpD (12) and BgaA (13), and one to MP, IgA (10).

Based on the proteomic results, we next performed immunoblot analysis on specific pneumococcal proteins and virulence factors (FIG. 2D). Among cytosolic proteins we investigated the presence of the cytotoxin pneumolysin (Ply), which is a pore-forming toxin and one of the most important virulence factors in pneumococcal pathogenesis (2), GAPDH as a cytosolic marker (14), and LytA, the major autolysin of Streptococcus pneumoniae (3).

The most striking observation was the high enrichment of Ply especially in MP, which also contained more LytA than $MV_L$. Smaller differences were also observed in the enrichment of virulence factors belonging to other subcellular localizations. While $MV_L$ displayed a higher amount of Pneumococcal surface antigen A (PsaA) (15) and Sortase A (SrtA) (16) than MP, the latter contained more Pneumococcal surface protein C (PspC) (17) and Polyhistidine triad protein D (PhtD) (9) (FIG. 2D). The major component of the pneumococcal pilus, RrgB (6), was equally found in both particle preparations.

These findings suggest the presence of a still uncharacterized mechanism for the selective secretion and enrichment of specific proteins and virulence factors of Streptococcus pneumoniae in these particle preparations.

A Biologically Active Pneumolysin was Found in Membrane Microparticles

The enrichment of Ply in both $MV_L$ and MP prompted us to determine whether particle-associated Ply was functional and able to lyse erythrocytes in a hemolytic assay. For both types of particles we observed a dose dependent hemolysis (FIG. 3), however, Ply from MP showed higher activity than from $MV_L$, which is consistent with the observation that MP contain more Ply. Notably, hemolysis seemed to be entirely caused by Ply, and particles prepared from a TIGR4 mutant lacking Ply (TIGR4Δply) exhibited no hemolytic activity.

MP are Taken Up by A549 Epithelial Cells, but are not Cytotoxic.

MV in other Gram-positive bacteria have been described to function as vehicle to deliver vesicle-associated proteins to human cells (18) (19). To test whether pneumococcal MP can deliver pneumococcal proteins, we incubated MP from TIGR4 with A549 lung epithelial cells for 24 hours and visualized Ply and LytA by immunofluorescence staining (FIG. 4A-C). By analyzing orthogonal views of A549 cells treated with MP, we showed by immunofluorescence that MP can be taken up, with Ply and LytA detectable inside the cells (FIG. 4B-C).

To confirm our observation we further analyzed lysates of A549 cells treated with MP by immunoblotting with anti-Ply antibody (FIG. 4D). In order to minimize extracellular associated particles, treated cells were excessively washed before lysates were made. Consistent with our immunofluorescence results, western blotting revealed a dose dependent increase in Ply further suggesting that MP can be internalized.

Next we asked whether proteins associated with $MV_L$ or MP, and in particular Ply, may contribute to cytotoxic effects on cultured human cells. To assess toxicity, A549 cells were treated with different concentrations of $MV_L$ and MP for 24 hours, stained with fixable viability dye and analyzed by flow cytometry (FIG. 4E). The difference in cell death between samples incubated with $MV_L$ or MPs and the negative control sample was not statistically significant, suggesting that Ply is not cytotoxic to the cells at concentrations present in $MV_L$ or MP.

$MV_L$ and MP are Internalized by Human Monocyte-Derived Dendritic Cells (DCs) and Induce their Maturation.

Figure 5A:
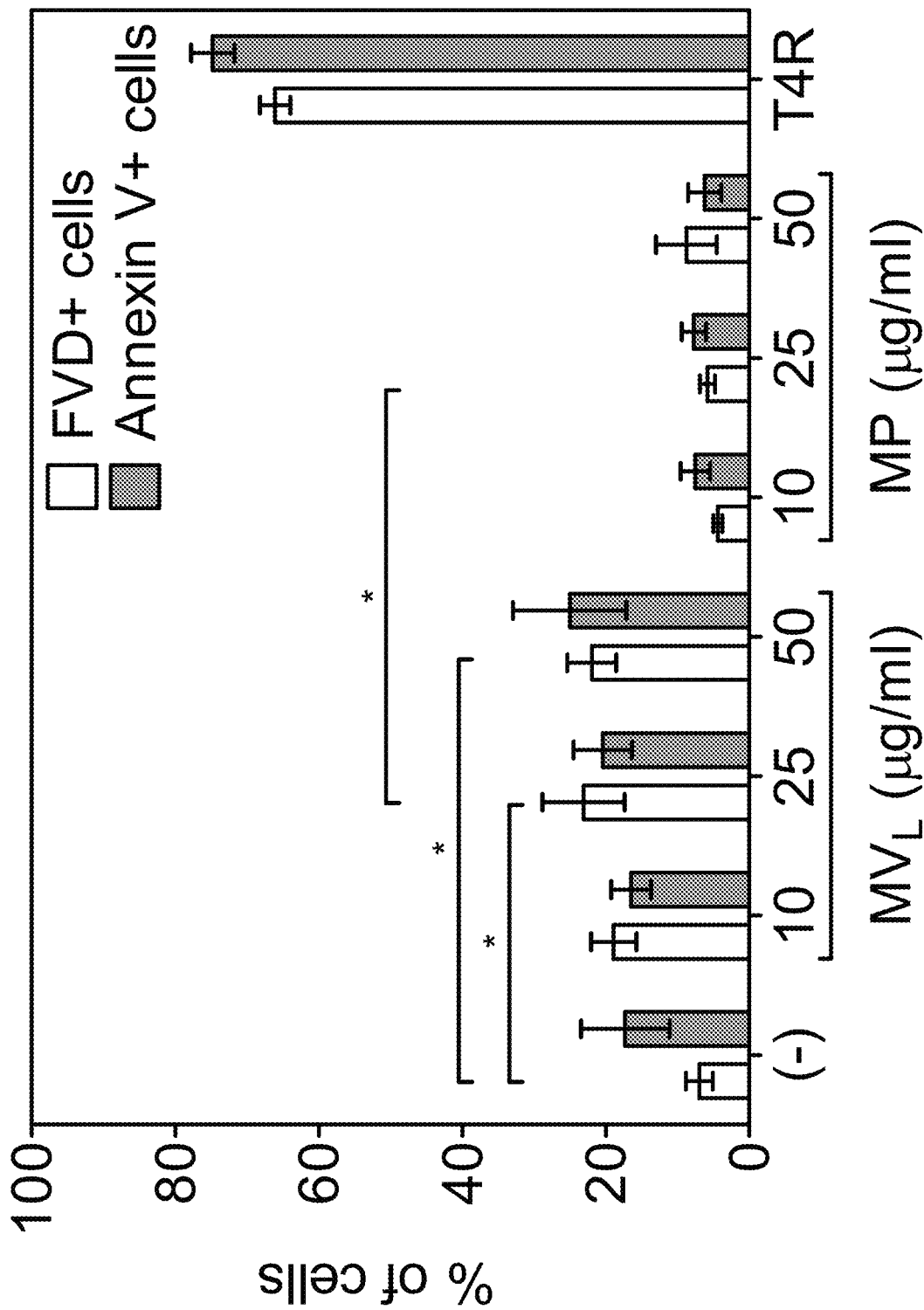

Since we found that MP can be internalized by epithelial cells, we then studied potential interactions of $MV_L$ or MP with innate immune cells, focusing on DCs. First we assessed cytotoxicity by incubating DCs with $MV_L$ or MP, stained with fixable viability dye and Annexin V, and then analyzed using flow cytometry (FIG. 5A). No significant increase in cytotoxicity was detected in samples incubated with MP, while addition of $MV_L$ displayed cytotoxic effects at the two highest concentrations used. While both preparations were considerably less cytotoxic than live bacteria, with 70-80% cytotoxic cells after 24 hours of incubation, more studies are needed to assess the mechanism behind the increased cytotoxicity of $MV_L$ from liquid cultures. Moreover, the percentage of apoptotic cells did not change after incubation with either of the particle preparations.

Then we investigated uptake of MP by DCs. First we incubated DCs with MP for 1 hour, lysed the cells and performed SDS-PAGE and immunoblotting on cell lysates to check for presence of Ply. Indeed, Ply was found in the cell lysates (FIG. 5B), suggesting that DCs internalize MP. Next, DCs were challenged for 30 minutes with inhibitors of actin polymerization and phosphatidylinositol 3-kinase (PI3K), cytochalasin and wortmannin, to block active phagocytosis, or with an inhibitor of lipid rafts, methyl-β-cyclodextrin, to block fusion of membranes. Subsequently, cells were incubated with MP for 1 hour, lysed, and the same protocol for immunoblotting was followed. Interestingly, blocking active phagocytosis or membrane fusion resulted in less Ply. However, when all inhibitors were used together, Ply still remained present in the lysates, suggesting either that the particles adhered to the cells or were internalized by another mechanism, not investigated in this study.

Taken together these data suggest that MP can function as a vehicle to deliver bacterial components to host cells. Since DCs are professional antigen presenting cells, we then assessed whether $MV_L$ or MP could influence DC maturation. Cells were incubated for 24 hours with $MV_L$ or MP, and then stained for MHCII and the co-stimulatory molecule CD86, and analyzed by flow cytometry (FIG. 5C). A dose-dependent increase in the presence of both markers on the surface of DCs was detected when cells were incubated with the particles. $MV_L$ appeared to induce more maturation than MP, and similar levels of maturation were obtained with LPS.

$MV_L$ and MP Induce Pro-Inflammatory Cytokine Responses in DCs

Since OMVs from Gram-negative have been shown to trigger a potent innate immune response (20) (21), we studied whether also pneumococcal $MV_L$ or MP could affect pro-inflammatory cytokine responses. DCs we incubated with $MV_L$ or MP for 24 hours, and ELISA assays were used on supernatants to determine concentrations of IL-6 (FIG. 6A), IL-8 (FIG. 6B), IL-10 (FIG. 6C) and TNF (FIG. 6D). MP induced release of IL-8 and low levels of TNF, while no induction was seen for IL-6 and IL-10. In contrast, $MV_L$ induced all four cytokines tested to levels higher than live bacteria. None of the particles induced IL-10 or IL-12 (data not shown).

TABLE 3

Proteins identified in MV$_L$ from TIGR4. The accession numbers refer to SwissProt on the date of filing.

| Accession | Coverage | # Peptides | #AAs | Score | Desription | Localization |
|---|---|---|---|---|---|---|
| Q97RH0 | 76.86 | 47 | 350 | 2615.53 | Lipoprotein OS = Streptococcus pneumoniae serotype 4 (strain ATCC BAA-334/TIGR4) GN = SP_0845 PE = 4 SV = 1 – [Q97RH0_STRPN] | Lipid anchored |
| Q2MGF6 | 82.45 | 59 | 490 | 1620.74 | Lysozyme OS = Streptococcus pneumoniae serotype 4 (strain ATCC BAA-334/TIGR4) GN = lytC PE = 4 SV = 1 – [Q2MGF6_STRPN] | Secretory (released) (with CS) |
| Q97NK0 | 73.39 | 64 | 883 | 1364.43 | Aldehyde-alcohol dehydrogenase OS = Streptococcus pneumoniae serotype 4 (strain ATCC BAA-334/TIGR4) GN = SP_2026 PE = 3 SV = 1 – [Q97NK0_STRPN] | Intracellular |
| P18791 | 72.99 | 48 | 659 | 1307.17 | Oligopeptide-binding protein AmiA OS = Streptococcus pneumoniae serotype 4 (strain ATCC BAA-334/TIGR4) GN = amiA PE = 1 SV = 3 – [AMIA_STRPN] | Lipid anchored |
| Q9L7Q2 | 55.82 | 91 | 1906 | 1166.89 | Zinc metalloprotease ZmpB OS = Streptococcus pneumoniae serotype 4 (strain ATCC BAA-334/TIGR4) GN = zmpB PE = 3 SV = 2 – [ZMPB_STRPN] | Multi-trans-membrane |
| Q97T80 | 58.3 | 87 | 1856 | 1012.57 | Zinc metalloprotease ZmpC OS = Streptococcus pneumoniae serotype 4 (strain ATCC BAA-334/TIGR4) GN = zmpC PE = 3 SV = 1 – [ZMPC_STRPN] | LPxTG Cell-wall anchored |
| Q97NQ8 | 59.59 | 75 | 1225 | 936.07 | DNA-directed RNA polymerase subunit beta' OS = Streptococcus pneumoniae serotype 4 (strain ATCC BAA-334/TIGR4) GN = rpoC PE = 3 SV = 1 – [RPOC_STRPN] | Intracellular |
| P59213 | 74.47 | 48 | 423 | 838.2 | Maltose/maltodextrin-binding protein OS = Streptococcus pneumoniae serotype 4 (strain ATCC BAA-334/TIGR4) GN = malX PE = 1 SV = 1 – [MALX_STRPN] | Lipid anchored |
| P64022 | 75.61 | 46 | 693 | 803.77 | Elongation factor G OS = Streptococcus pneumoniae serotype 4 (strain ATCC BAA-334/TIGR4) GN = fusA PE = 3 SV = 1 – [EFG_STRPN] | Intracellular |
| P0C2J9 | 92.99 | 46 | 471 | 753.38 | Pneumolysin OS = Streptococcus pneumoniae serotype 4 (strain ATCC BAA-334/TIGR4) GN = ply PE = 3 SV = 1 – [TACY_STRPN] | Intracellular |
| Q97N55 | 75 | 27 | 392 | 729.12 | Secreted 45 kd protein OS = Streptococcus pneumoniae serotype 4 (strain ATCC BAA-334/TIGR4) GN = usp45 PE = 4 SV = 1 – [Q97N55_STRPN] | Secretory (released) (with CS) |
| Q97RY6 | 42.1 | 73 | 2140 | 715.85 | Serine protease, subtilase family OS = Streptococcus pneumoniae serotype 4 (strain ATCC BAA-334/TIGR4) GN = SP_0641 PE = 4 SV = 1 – [Q97RY6_STRPN] | LPxTG Cell-wall anchored |
| P64030 | 68.84 | 32 | 398 | 684.61 | Elongation factor Tu OS = Streptococcus pneumoniae serotype 4 (strain ATCC BAA-334/TIGR4) GN = tuf PE = 3 SV = 1 – [EFTU_STRPN] | Intracellular |
| Q97NQ7 | 66.42 | 61 | 1203 | 683.01 | DNA-directed RNA polymerase subunit beta OS = Streptococcus pneumoniae serotype 4 (strain ATCC BAA-334/TIGR4) GN = rpoB PE = 3 SV = 1 – [RPOB_STRPN] | Intracellular |
| Q97PE6 | 77.38 | 35 | 442 | 645.41 | Sugar ABC transporter, sugar-binding protein OS = Streptococcus pneumoniae serotype 4 (strain ATCC BAA-334/TIGR4) GN = SP_1683 PE = 4 SV = 1 – [Q97PE6_STRPN] | Lipid anchored |

TABLE 3-continued

Proteins identified in MV$_L$ from TIGR4. The accession numbers refer to SwissProt on the date of filing.

| Accession | Coverage | # Peptides | #AAs | Score | Desription | Localization |
|---|---|---|---|---|---|---|
| Q97PT1 | 74.59 | 45 | 551 | 641.52 | Uncharacterized protein OS = *Streptococcus pneumoniae* serotype 4 (strain ATCC BAA-334/ TIGR4) GN = SP_1518 PE = 4 SV = 1 – [Q97PT1_STRPN] | Intracellular |
| Q97RQ0 | 81.35 | 26 | 386 | 599.79 | Branched-chain amino acid ABC transporter, amino acid-binding protein OS = *Streptococcus pneumoniae* serotype 4 (strain ATCC BAA-334/TIGR4) GN = livJ PE = 4 SV = 1 – [Q97RQ0_STRPN] | Lipid anchored |
| Q97SV2 | 62.45 | 19 | 277 | 575.15 | 50S ribosomal protein L2 OS = *Streptococcus pneumoniae* serotype 4 (strain ATCC BAA-334/ TIGR4) GN = rplB PE = 3 SV = 1 – [RL2_STRPN] | Intracellular |
| Q97R51 | 74.12 | 32 | 313 | 574.61 | Foldase protein PrsA OS = *Streptococcus pneumoniae* serotype 4 (strain ATCC BAA-334/ TIGR4) GN = prsA PE = 3 SV = 1 – [PRSA_STRPN] | Lipid anchored |
| Q97SV5 | 59.62 | 17 | 208 | 571.92 | 50S ribosomal protein L3 OS = *Streptococcus pneumoniae* serotype 4 (strain ATCC BAA-334/ TIGR4) GN = rplC PE = 3 SV = 1 – [RL3_STRPN] | Intracellular |
| Q04707 | 64.12 | 38 | 719 | 564.47 | Penicillin-binding protein 1A OS = *Streptococcus pneumoniae* serotype 4 (strain ATCC BAA-334/ TIGR4) GN = ponA PE = 1 SV = 2 – [PBPA_STRPN] | N-terminally anchored (No CS) |
| Q97NL1 | 88.36 | 26 | 335 | 546.25 | Glyceraldehyde-3-phosphate dehydrogenase OS = *Streptococcus pneumoniae* serotype 4 (strain ATCC BAA-334/TIGR4) GN = gap PE = 3 SV = 1 – [Q97NU_STRPN] | Intracellular |
| Q97PD6 | 64.87 | 46 | 837 | 501.57 | Protein translocase subunit SecA 1 OS = *Streptococcus pneumoniae* serotype 4 (strain ATCC BAA-334/ TIGR4) GN = secA1 PE = 3 SV = 1 – [SECA1_STRPN] | Intracellular |
| P35592 | 75.61 | 44 | 660 | 500.22 | Oligopeptide-binding protein AliA OS = *Streptococcus pneumoniae* serotype 4 (strain ATCC BAA-334/ TIGR4) GN = aliA PE = 3 SV = 4 – [ALIA_STRPN] | Lipid anchored |
| P0A4G2 | 72.49 | 21 | 309 | 482.72 | Manganese ABC transporter substrate-binding lipoprotein OS = *Streptococcus pneumoniae* serotype 4 (strain ATCC BAA-334/ TIGR4) GN = psaA PE = 1 SV = 1 – [MTSA_STRPN] | Lipid anchored |
| Q54970 | 61.59 | 38 | 591 | 482.11 | Pyruvate oxidase OS = *Streptococcus pneumoniae* serotype 4 (strain ATCC BAA-334/TIGR4) GN = spxB PE = 3 SV = 2 – [PDXB_STRPN] | Intracellular |
| Q97R09 | 68.62 | 21 | 341 | 442.02 | Iron-compound ABC transporter, iron compound-binding protein OS = *Streptococcus pneumoniae* serotype 4 (strain ATCC BAA-334/ TIGR4) GN = SP_1032 PE = 1 SV = 1 – [Q97R09_STRPN] | Lipid anchored |
| Q97PU3 | 67.63 | 31 | 278 | 434.28 | Amino acid ABC transporter, amino acid-binding protein OS = *Streptococcus pneumoniae* serotype 4 (strain ATCC BAA-334/ TIGR4) GN = aatB PE = 4 SV = 1 – [Q97PU3_STRPN] | Lipid anchored |
| P0A4C3 | 72.35 | 20 | 217 | 427.97 | 30S ribosomal protein S3 OS = *Streptococcus pneumoniae* serotype 4 (strain ATCC BAA-334/ TIGR4) GN = rpsC PE = 3 SV = 1 – [RS3_STRPN] | Intracellular |

TABLE 3-continued

Proteins identified in MV$_L$ from TIGR4. The accession numbers refer to SwissProt on the date of filing.

| Accession | Coverage | # Peptides | #AAs | Score | Desription | Localization |
|---|---|---|---|---|---|---|
| Q97T39 | 36.42 | 28 | 744 | 407.46 | Pneumococcal surface protein A OS = Streptococcus pneumoniae serotype 4 (strain ATCC BAA-334/ TIGR4) GN = pspA PE = 4 SV = 1 – [Q97T39_STRPN] | N-terminally anchored (with CS) |
| I6L8V7 | 41.79 | 28 | 627 | 381.01 | Choline binding protein E OS = Streptococcus pneumoniae serotype 4 (strain ATCC BAA-334/ TIGR4) GN = cbpE PE = 4 SV = 1 – [I6L8V7_STRPN] | Secretory (released) (with CS) |
| P0A475 | 54.74 | 11 | 137 | 354.71 | 50S ribosomal protein L16 OS = Streptococcus pneumoniae serotype 4 (strain ATCC BAA-334/ TIGR4) GN = rplP PE = 1 SV = 1 – [RL16_STRPN] | Intracellular |
| P66112 | 51.26 | 9 | 119 | 346.49 | 50S ribosomal protein L20 OS = Streptococcus pneumoniae serotype 4 (strain ATCC BAA-334/ TIGR4) GN = rplT PE = 3 SV = 1 – [RL20_STRPN] | Intracellular |
| Q97SV4 | 56.04 | 14 | 207 | 345.01 | 50S ribosomal protein L4 OS = Streptococcus pneumoniae serotype 4 (strain ATCC BAA-334/ TIGR4) GN = rplD PE = 3 SV = 1 – [RL4_STRPN] | Intracellular |
| Q97T12 | 78.99 | 26 | 276 | 332.96 | ABC transporter, substrate-binding protein OS = Streptococcus pneumoniae serotype 4 (strain ATCC BAA-334/TIGR4) GN = SP_0148 PE = 4 SV = 1 – [Q97T12_STRPN] | Lipid anchored |
| Q97N74 | 47.47 | 31 | 693 | 320.12 | Choline binding protein A OS = Streptococcus pneumoniae serotype 4 (strain ATCC BAA-334/ TIGR4) GN = cbpA PE = 1 SV = 1 – [Q97N74_STRPN] | N-terminally anchored (with CS) |
| Q97QS2 | 58.06 | 22 | 434 | 315.73 | Enolase OS = Streptococcus pneumoniae serotype 4 (strain ATCC BAA-334/TIGR4) GN = eno PE = 1 SV = 1 – [ENO_STRPN] | Intracellular |
| Q97S57 | 49.58 | 34 | 958 | 315.37 | Translation initiation factor IF-2 OS = Streptococcus pneumoniae serotype 4 (strain ATCC BAA-334/ TIGR4) GN = infB PE = 3 SV = 1 – [IF2_STRPN] | Intracellular |
| Q97T11 | 75 | 27 | 284 | 313.6 | Lipoprotein OS = Streptococcus pneumoniae serotype 4 (strain ATCC BAA-334/TIGR4) GN = SP_0149 PE = 3 SV = 1 – [Q97T11_STRPN] | Lipid anchored |
| P66359 | 55.12 | 10 | 127 | 299.97 | 30S ribosomal protein S11 OS = Streptococcus pneumoniae serotype 4 (strain ATCC BAA-334/ TIGR4) GN = rpsK PE = 3 SV = 1 – [RS11_STRPN] | Intracellular |
| Q97PT6 | 68.8 | 24 | 468 | 285.18 | ATP synthase subunit beta OS = Streptococcus pneumoniae serotype 4 (strain ATCC BAA-334/ TIGR4) GN = atpD PE = 3 SV = 1 – [ATPB_STRPN] | Intracellular |
| Q97SP2 | 60.24 | 18 | 332 | 279.63 | PTS system, mannose-specific IIAB components OS = Streptococcus pneumoniae serotype 4 (strain ATCC BAA-334/TIGR4) GN = manL PE = 4 SV = 1 – [Q97SP2_STRPN] | Intracellular |
| Q97RZ7 | 60.08 | 15 | 238 | 278.06 | Uncharacterized protein OS = Streptococcus pneumoniae serotype 4 (strain ATCC BAA-334/ TIGR4) GN = SP_0629 PE = 1 SV = 1 – [Q97RZ7_STRPN] | Lipid anchored |
| Q97NL3 | 55.13 | 34 | 731 | 275.05 | Penicillin-binding protein 2A OS = Streptococcus pneumoniae serotype 4 (strain ATCC BAA-334/ TIGR4) GN = pbp2A PE = 4 SV = 1 – [Q97NL3_STRPN] | N-terminally anchored (No CS) |

TABLE 3-continued

Proteins identified in MV$_L$ from TIGR4. The accession numbers refer to SwissProt on the date of filing.

| Accession | Coverage | # Peptides | #AAs | Score | Desription | Localization |
|---|---|---|---|---|---|---|
| Q97PE1 | 62.92 | 29 | 445 | 269.34 | ABC transporter, substrate-binding protein OS = *Streptococcus pneumoniae* serotype 4 (strain ATCC BAA-334/TIGR4) GN = SP_1690 PE = 4 SV = 1 − [Q97PE1_STRPN] | Lipid anchored |
| Q97SX2 | 81.48 | 19 | 189 | 268.65 | Uncharacterized protein OS = *Streptococcus pneumoniae* serotype 4 (strain ATCC BAA-334/TIGR4) GN = SP_0191 PE = 1 SV = 1 − [Q97SX2_STRPN] | Lipid anchored |
| Q97RN2 | 67.79 | 15 | 267 | 248.33 | Peptidyl-prolyl cis-trans isomerase, cyclophilin-type OS = *Streptococcus pneumoniae* serotype 4 (strain ATCC BAA-334/TIGR4) GN = SP_0771 PE = 3 SV = 1 − [Q97RN2_STRPN] | Lipid anchored |
| P65887 | 62.62 | 25 | 428 | 243.93 | Adenylosuccinate synthetase OS = *Streptococcus pneumoniae* serotype 4 (strain ATCC BAA-334/TIGR4) GN = purA PE = 1 SV = 1 − [PURA_STRPN] | Intracellular |
| Q97QH2 | 33.7 | 23 | 721 | 242.51 | Amino acid ABC transporter, amino acid-binding protein/permease protein OS = *Streptococcus pneumoniae* serotype 4 (strain ATCC BAA-334/TIGR4) GN = SP_1241 PE = 1 SV = 1 − [Q97QH2_STRPN] | Multi-trans-membrane |
| O69076 | 50.46 | 25 | 652 | 240.51 | ATP-dependent zinc metalloprotease FtsH OS = *Streptococcus pneumoniae* serotype 4 (strain ATCC BAA-334/TIGR4) GN = ftsH PE = 3 SV = 3 − [FTSH_STRPN] | Multi-trans-membrane |
| Q97N37 | 62.6 | 22 | 393 | 236.55 | Serine protease OS = *Streptococcus pneumoniae* serotype 4 (strain ATCC BAA-334/TIGR4) GN = SP_2239 PE = 1 SV = 1 − [Q97N37_STRPN] | N-terminally anchored (No CS) |
| Q97T63 | 60.29 | 26 | 491 | 232.33 | ABC transporter, substrate-binding protein OS = *Streptococcus pneumoniae* serotype 4 (strain ATCC BAA-334/TIGR4) GN = SP_0092 PE = 4 SV = 1 − [Q97T63_STRPN] | Lipid anchored |
| Q97NQ0 | 68.79 | 19 | 330 | 230.07 | Aspartate-ammonia ligase OS = *Streptococcus pneumoniae* serotype 4 (strain ATCC BAA-334/TIGR4) GN = asnA PE = 3 SV = 1 − [ASNA_STRPN] | Intracellular |
| Q97SV1 | 86.67 | 12 | 180 | 229.35 | 50S ribosomal protein L5 OS = *Streptococcus pneumoniae* serotype 4 (strain ATCC BAA-334/TIGR4) GN = rplE PE = 3 SV = 1 − [RL5_STRPN] | Intracellular |
| Q97Q37 | 69.37 | 18 | 271 | 227.84 | Amino acid ABC transporter, amino acid-binding protein OS = *Streptococcus pneumoniae* serotype 4 (strain ATCC BAA-334/TIGR4) GN = SP_1394 PE = 4 SV = 1 − [Q97Q37_STRPN] | Lipid anchored |
| P66907 | 42.63 | 9 | 380 | 223.83 | Queuine tRNA-ribosyltransferase OS = *Streptococcus pneumoniae* serotype 4 (strain ATCC BAA-334/TIGR4) GN = tgt PE = 3 SV = 1 − [TGT_STRPN] | Intracellular |
| P59205 | 43.77 | 20 | 658 | 217.64 | Putative endo-beta-N-acetylglucosaminidase OS = *Streptococcus pneumoniae* serotype 4 (strain ATCC BAA-334/TIGR4) GN = lytB PE = 1 SV = 1 − [LYTB_STRPN] | Secretory (released) (with CS) |
| Q97SC6 | 49.35 | 27 | 774 | 216.35 | Formate acetyltransferase OS = *Streptococcus pneumoniae* serotype 4 (strain ATCC BAA-334/TIGR4) GN = pfl PE = 4 SV = 1 − [Q97SC6_STRPN] | Intracellular |

TABLE 3-continued

Proteins identified in MV$_L$ from TIGR4. The accession numbers refer to SwissProt on the date of filing.

| Accession | Coverage | # Peptides | #AAs | Score | Desription | Localization |
|---|---|---|---|---|---|---|
| Q97NB5 | 42.19 | 22 | 621 | 215.44 | Choline binding protein PcpA OS = *Streptococcus pneumoniae* serotype 4 (strain ATCC BAA-334/TIGR4) GN = pcpA PE = 1 SV = 1 – [Q97NB5_STRPN] | Secretory (released) (with CS) |
| P0A2U8 | 49.58 | 19 | 355 | 215.01 | Oligopeptide transport ATP-binding protein AmiE OS = *Streptococcus pneumoniae* serotype 4 (strain ATCC BAA-334/TIGR4) GN = amiE PE = 3 SV = 1 – [AMIE_STRPN] | Intracellular |
| Q97PA9 | 39 | 21 | 659 | 212.01 | Serine/threonine-protein kinase StkP OS = *Streptococcus pneumoniae* serotype 4 (strain ATCC BAA-334/TIGR4) GN = stkP PE = 1 SV = 1 – [STKP2_STRPN] | Intracellular/TMH start AFTER 60 |
| Q97RF9 | 56.25 | 22 | 400 | 204.01 | Ribosomal protein S1 OS = *Streptococcus pneumoniae* serotype 4 (strain ATCC BAA-334/TIGR4) GN = rpsA PE = 4 SV = 1 – [Q97RF9_STRPN] | Intracellular |
| Q97SP4 | 43.89 | 12 | 303 | 202.88 | PTS system, mannose-specific IID component OS = *Streptococcus pneumoniae* serotype 4 (strain ATCC BAA-334/TIGR4) GN = SP_0282 PE = 4 SV = 1 – [Q97SP4_STRPN] | Multi-trans-membrane |
| P0A4A7 | 58.39 | 11 | 137 | 202.86 | 30S ribosomal protein S12 OS = *Streptococcus pneumoniae* serotype 4 (strain ATCC BAA-334/TIGR4) GN = rpsL PE = 3 SV = 1 – [RS12_STRPN] | Intracellular |
| Q97Q31 | 55.82 | 13 | 292 | 202.43 | Phosphate-binding protein PstS 1 OS = *Streptococcus pneumoniae* serotype 4 (strain ATCC BAA-334/TIGR4) GN = pstS1 PE = 1 SV = 1 – [PSTS1_STRPN] | Lipid anchored |
| Q97N56 | 69.11 | 20 | 259 | 201.44 | 30S ribosomal protein S2 OS = *Streptococcus pneumoniae* serotype 4 (strain ATCC BAA-334/TIGR4) GN = rpsB PE = 3 SV = 1 – [RS2_STRPN] | Intracellular |
| Q97RC6 | 48.66 | 14 | 335 | 201.21 | ATP-dependent 6-phosphofructokinase OS = *Streptococcus pneumoniae* serotype 4 (strain ATCC BAA-334/TIGR4) GN = pfkA PE = 3 SV = 1 – [PFKA_STRPN] | Intracellular |
| Q97QX5 | 68.02 | 15 | 344 | 200.45 | Uncharacterized protein OS = *Streptococcus pneumoniae* serotype 4 (strain ATCC BAA-334/TIGR4) GN = SP_1069 PE = 1 SV = 1 – [Q97QX5_STRPN] | Secretory (released) (with CS) |
| Q97NM6 | 60.64 | 17 | 404 | 197.5 | Aminotransferase, class I OS = *Streptococcus pneumoniae* serotype 4 (strain ATCC BAA-334/TIGR4) GN = SP_1994 PE = 4 SV = 1 – [Q97NM6_STRPN] | Intracellular |
| Q97N69 | 65.37 | 19 | 335 | 194.36 | Putative ABC transporter, substrate-binding protein OS = *Streptococcus pneumoniae* serotype 4 (strain ATCC BAA-334/TIGR4) GN = SP_2197 PE = 4 SV = 1 – [Q97N69_STRPN] | Lipid anchored |
| Q97NS5 | 60.95 | 16 | 338 | 193.02 | Putative transcriptional regulator OS = *Streptococcus pneumoniae* serotype 4 (strain ATCC BAA-334/TIGR4) GN = SP_1942 PE = 4 SV = 1 – [Q97NS5_STRPN] | Secretory (released) (with CS) |
| P0A4M7 | 38.35 | 20 | 498 | 189.98 | Oligopeptide transport system permease protein AmiC OS = *Streptococcus pneumoniae* serotype 4 (strain ATCC BAA-334/TIGR4) GN = amiC PE = 3 SV = 1 – [AMIC_STRPN] | Multi-transmembrane |

TABLE 3-continued

Proteins identified in MV$_L$ from TIGR4. The accession numbers refer to SwissProt on the date of filing.

| Accession | Coverage | # Peptides | #AAs | Score | Desription | Localization |
|---|---|---|---|---|---|---|
| Q97QD2 | 56.41 | 20 | 523 | 188.15 | Signal recognition particle protein OS = *Streptococcus pneumoniae* serotype 4 (strain ATCC BAA-334/ TIGR4) GN = ffh PE = 1 SV = 1 – [Q97QD2_STRPN] | Intracellular |
| P14677 | 49.87 | 26 | 750 | 185.33 | Penicillin-binding protein 2 × OS = *Streptococcus pneumoniae* serotype 4 (strain ATCC BAA-334/ TIGR4) GN = pbpX PE = 1 SV = 2 – [PBPX_STRPN] | N-terminally anchored (No CS) |
| Q97NQ3 | 51.88 | 14 | 345 | 183.26 | Uncharacterized protein OS = *Streptococcus pneumoniae* serotype 4 (strain ATCC BAA-334/ TIGR4) GN = SP_1967 PE = 4 SV = 1 – [Q97NQ3_STRPN] | N-terminally anchored (No CS) |
| Q97RW9 | 59.34 | 16 | 332 | 182.68 | Putative pneumococcal surface protein OS = *Streptococcus pneumoniae* serotype 4 (strain ATCC BAA-334/TIGR4) GN = SP_0667 PE = 1 SV = 1 – [Q97RW9_STRPN] | Lipid anchored |
| Q97RL9 | 66.17 | 16 | 399 | 180.86 | Uncharacterized protein OS = *Streptococcus pneumoniae* serotype 4 (strain ATCC BAA-334/ TIGR4) GN = SP_0785 PE = 4 SV = 1 – [Q97RL9_STRPN] | N-terminally anchored (No CS) |
| P0A3M9 | 47.26 | 14 | 328 | 180.34 | L-lactate dehydrogenase OS = *Streptococcus pneumoniae* serotype 4 (strain ATCC BAA-334/ TIGR4) GN = ldh PE = 3 SV = 2 – [LDH_STRPN] | Intracellular |
| Q97PT4 | 39.72 | 17 | 501 | 180.17 | ATP synthase subunit alpha OS = *Streptococcus pneumoniae* serotype 4 (strain ATCC BAA-334/ TIGR4) GN = atpA PE = 3 SV = 1 – [ATPA_STRPN] | Multi-trans-membrane |
| Q97QH1 | 67.48 | 9 | 246 | 175.25 | Amino acid ABC transporter, ATP-binding protein OS = *Streptococcus pneumoniae* serotype 4 (strain ATCC BAA-334/TIGR4) GN = SP_1242 PE = 3 SV = 1 – [Q97QH1_STRPN] | Intracellular |
| Q97NX9 | 72.9 | 19 | 321 | 174.95 | Iron-compound ABC transporter, iron-compound-binding protein OS = *Streptococcus pneumoniae* serotype 4 (strain ATCC BAA-334/ TIGR4) GN = SP_1872 PE = 4 SV = 1 – [Q97NX9_STRPN] | Lipid anchored |
| Q97QC6 | 66.09 | 14 | 115 | 173.94 | 50S ribosomal protein L19 OS = *Streptococcus pneumoniae* serotype 4 (strain ATCC BAA-334/ TIGR4) GN = rplS PE = 3 SV = 1 – [RL19_STRPN] | Intracellular |
| Q97N99 | 63.14 | 18 | 274 | 172.57 | SPFH domain/Band 7 family OS = *Streptococcus pneumoniae* serotype 4 (strain ATCC BAA-334/ TIGR4) GN = SP_2156 PE = 4 SV = 1 – [Q97N99_STRPN] | Intracellular |
| Q97PW1 | 50.97 | 17 | 463 | 169.74 | Peptidoglycan N-acetylglucosamine deacetylase A OS = *Streptococcus pneumoniae* serotype 4 (strain ATCC BAA-334/TIGR4) GN = pgdA PE = 4 SV = 1 – [Q97PW1_STRPN] | N-terminally anchored (No CS) |
| Q97SE1 | 36.4 | 14 | 555 | 169.45 | Uncharacterized protein OS = *Streptococcus pneumoniae* serotype 4 (strain ATCC BAA-334/ TIGR4) GN = SP_0443 PE = 1 SV = 1 – [Q97SE1_STRPN] | Intracellular |
| Q97PM5 | 59.04 | 16 | 376 | 168.92 | Sugar ABC transporter, ATP-binding protein OS = *Streptococcus pneumoniae* serotype 4 (strain ATCC BAA-334/TIGR4) GN = msmK PE = 4 SV = 1 – [Q97PM5_STRPN] | Intracellular |

TABLE 3-continued

Proteins identified in MV$_L$ from TIGR4. The accession numbers refer to SwissProt on the date of filing.

| Accession | Coverage | # Peptides | #AAs | Score | Desription | Localization |
|---|---|---|---|---|---|---|
| Q97SN5 | 85.81 | 15 | 148 | 165.86 | 50S ribosomal protein L13 OS = *Streptococcus pneumoniae* serotype 4 (strain ATCC BAA-334/ TIGR4) GN = rplM PE = 3 SV = 1 – [Q97SN5_STRPN] | Intracellular |
| Q97PQ2 | 28.88 | 18 | 914 | 162.85 | Cation-transporting ATPase, E1-E2 family OS = *Streptococcus pneumoniae* serotype 4 (strain ATCC BAA-334/ TIGR4) GN = SP_1551 PE = 3 SV = 1 – [Q97PQ2_STRPN] | Multi-trans-membrane |
| Q97NE4 | 32.16 | 21 | 821 | 161.61 | Penicillin-binding protein 1B OS = *Streptococcus pneumoniae* serotype 4 (strain ATCC BAA-334/ TIGR4) GN = pbp1B PE = 4 SV = 1 – [Q97NE4_STRPN] | N-terminally anchored (No CS) |
| Q97Q62 | 54.48 | 20 | 424 | 161.35 | Psr protein OS = *Streptococcus pneumoniae* serotype 4 (strain ATCC BAA-334/TIGR4) GN = SP_1368 PE = 4 SV = 1 – [Q97Q62_STRPN] | Intracellular/ TMH start AFTER 60 |
| P18766 | 50 | 13 | 308 | 160.11 | Oligopeptide transport ATP-binding protein AmiF OS = *Streptococcus pneumoniae* serotype 4 (strain ATCC BAA-334/TIGR4) GN = amiF PE = 3 SV = 2 – [AMIF_STRPN] | Intracellular |
| I6L8U0 | 42.39 | 16 | 394 | 155.34 | UDP-N-acetylglucosamine 2-epimerase OS = *Streptococcus pneumoniae* serotype 4 (strain ATCC BAA-334/TIGR4) GN = cps4L PE = 3 SV = 1 – [I6L8U0_STRPN] | Intracellular |
| P0CC08 | 55.21 | 15 | 288 | 154.74 | Acetyl-coenzyme A carboxylase carboxyl transferase subunit beta OS = *Streptococcus pneumoniae* serotype 4 (strain ATCC BAA-334/ TIGR4) GN = accD PE = 1 SV = 1 – [ACCD_STRPN] | Intracellular |
| Q97RG9 | 51.27 | 21 | 511 | 154.04 | Sugar ABC transporter, ATP-binding protein OS = *Streptococcus pneumoniae* serotype 4 (strain ATCC BAA-334/TIGR4) GN = SP_0846 PE = 3 SV = 1 – [Q97RG9_STRPN] | Intracellular |
| Q97SJ4 | 50.28 | 17 | 360 | 153.5 | Uncharacterized protein OS = *Streptococcus pneumoniae* serotype 4 (strain ATCC BAA-334/ TIGR4) GN = SP_0355 PE = 4 SV = 1 – [Q975J4_STRPN] | Intracellular |
| P72524 | 33.82 | 22 | 822 | 148.92 | DNA gyrase subunit A OS = *Streptococcus pneumoniae* serotype 4 (strain ATCC BAA-334/ TIGR4) GN = gyrA PE = 3 SV = 3 – [GYRA_STRPN] | Intracellular |
| P66565 | 56.16 | 17 | 203 | 148.91 | 30S ribosomal protein S4 OS = *Streptococcus pneumoniae* serotype 4 (strain ATCC BAA-334/ TIGR4) GN = rpsD PE = 3 SV = 1 – [RS4_STRPN] | Intracellular |
| P0A4G0 | 41.1 | 20 | 652 | 146.87 | Oligopeptide-binding protein AliB OS = *Streptococcus pneumoniae* serotype 4 (strain ATCC BAA-334/ TIGR4) GN = aliB PE = 3 SV = 1 – [ALIB_STRPN] | Lipid anchored |
| Q97SG0 | 57.78 | 18 | 424 | 144.79 | Serine-tRNA ligase OS = *Streptococcus pneumoniae* serotype 4 (strain ATCC BAA-334/TIGR4) GN = serS PE = 3 SV = 1 – [SYS_STRPN] | Intracellular |
| Q97PF9 | 51.79 | 20 | 419 | 144.46 | Cell division protein FtsZ OS = *Streptococcus pneumoniae* serotype 4 (strain ATCC BAA-334/ TIGR4) GN = ftsZ PE = 3 SV = 1 – [Q97PF9_STRPN] | Intracellular |
| Q97Q34 | 64.04 | 17 | 267 | 144.16 | Phosphate import ATP-binding protein PstB 2 OS = *Streptococcus pneumoniae* serotype 4 (strain ATCC BAA-334/ TIGR4) GN = pstB2 PE = 3 SV = 1 – [PSTB2_STRPN] | Intracellular |

TABLE 3-continued

Proteins identified in MV$_L$ from TIGR4. The accession numbers refer to SwissProt on the date of filing.

| Accession | Coverage | # Peptides | #AAs | Score | Desription | Localization |
|---|---|---|---|---|---|---|
| I6L8N1 | 47.25 | 14 | 455 | 141.81 | Acetyl-CoA carboxylase, biotin carboxylase OS = *Streptococcus pneumoniae* serotype 4 (strain ATCC BAA-334/TIGR4) GN = accC PE = 4 SV = 1 – [I6L8N1_STRPN] | Intracellular |
| Q97SR1 | 45.54 | 19 | 617 | 140.84 | Proline-tRNA ligase OS = *Streptococcus pneumoniae* serotype 4 (strain ATCC BAA-334/TIGR4) GN = proS PE = 3 SV = 1 – [SYP_STRPN] | Intracellular |
| Q97SI4 | 40.88 | 11 | 340 | 140.1 | Choline binding protein C OS = *Streptococcus pneumoniae* serotype 4 (strain ATCC BAA-334/TIGR4) GN = cbpC PE = 4 SV = 1 – [Q97SI4_STRPN] | N-terminally anchored (with CS) |
| P0A4D7 | 40.84 | 17 | 524 | 138.63 | DEAD-box ATP-dependent RNA helicase CshA OS = *Streptococcus pneumoniae* serotype 4 (strain ATCC BAA-334/TIGR4) GN = cshA PE = 3 SV = 1 – [CSHA_STRPN] | Intracellular |
| Q97RN3 | 44.44 | 17 | 513 | 136.66 | ABC transporter, ATP-binding protein OS = *Streptococcus pneumoniae* serotype 4 (strain ATCC BAA-334/TIGR4) GN = SP_0770 PE = 1 SV = 1 – [Q97RN3_STRPN] | Intracellular |
| Q97PR0 | 43.62 | 17 | 447 | 136.28 | Asparagine-tRNA ligase OS = *Streptococcus pneumoniae* serotype 4 (strain ATCC BAA-334/TIGR4) GN = asnS PE = 1 SV = 1 – [SYN_STRPN] | Intracellular |
| P22976 | 40.73 | 18 | 658 | 132.04 | Probable transketolase OS = *Streptococcus pneumoniae* serotype 4 (strain ATCC BAA-334/TIGR4) GN = tkt PE = 3 SV = 2 – [TKT_STRPN] | Intracellular |
| Q97PX1 | 34.2 | 16 | 459 | 132 | NADH oxidase OS = *Streptococcus pneumoniae* serotype 4 (strain ATCC BAA-334/TIGR4) GN = nox PE = 4 SV = 1 – [Q97PX1_STRPN] | Intracellular |
| O05703 | 50.5 | 17 | 501 | 129.61 | Zinc-binding lipoprotein AdcA OS = *Streptococcus pneumoniae* serotype 4 (strain ATCC BAA-334/TIGR4) GN = adcA PE = 3 SV = 4 – [ADCA_STRPN] | Lipid anchored |
| P66095 | 52.4 | 12 | 229 | 128.44 | 50S ribosomal protein L1 OS = *Streptococcus pneumoniae* serotype 4 (strain ATCC BAA-334/TIGR4) GN = rplA PE = 3 SV = 1 – [RL1_STRPN] | Intracellular |
| Q97RP4 | 55.65 | 12 | 230 | 127.75 | Cell division ABC transporter, ATP-binding protein FtsE OS = *Streptococcus pneumoniae* serotype 4 (strain ATCC BAA-334/TIGR4) GN = ftsE PE = 3 SV = 1 – [Q97RP4_STRPN] | Intracellular |
| Q97RP3 | 37.66 | 12 | 308 | 126.99 | Cell division protein FtsX OS = *Streptococcus pneumoniae* serotype 4 (strain ATCC BAA-334/TIGR4) GN = ftsX PE = 3 SV = 1 – [Q97RP3_STRPN] | Multi-trans-membrane |
| Q97N72 | 38.4 | 23 | 810 | 122.4 | ATP-dependent Clp protease, ATP-binding subunit OS = *Streptococcus pneumoniae* serotype 4 (strain ATCC BAA-334/TIGR4) GN = SP_2194 PE = 3 SV = 1 – [Q97N72_STRPN] | Intracellular |
| Q97Q67 | 43.9 | 14 | 344 | 121.11 | Conserved domain protein OS = *Streptococcus pneumoniae* serotype 4 (strain ATCC BAA-334/TIGR4) GN = SP_1363 PE = 4 SV = 1 – [Q97Q67_STRPN] | Multi-trans-membrane |
| P95830 | 50.79 | 15 | 378 | 120.38 | Chaperone protein DnaJ OS = *Streptococcus pneumoniae* serotype 4 (strain ATCC BAA-334/TIGR4) GN = dnaJ PE = 1 SV = 2 – [DNAJ_STRPN] | Intracellular |

TABLE 3-continued

Proteins identified in $MV_L$ from TIGR4. The accession numbers refer to SwissProt on the date of filing.

| Accession | Coverage | # Peptides | #AAs | Score | Desription | Localization |
|---|---|---|---|---|---|---|
| Q97SJ6 | 53.04 | 8 | 230 | 119.51 | Capsular polysaccharide biosynthesis protein CpsC OS = *Streptococcus pneumoniae* serotype 4 (strain ATCC BAA-334/TIGR4) GN = cpsC PE = 3 SV = 1 − [CPSC_STRPN] | Multi-trans-membrane |
| P63373 | 71.03 | 13 | 252 | 116.79 | Phosphate import ATP-binding protein PstB 1 OS = *Streptococcus pneumoniae* serotype 4 (strain ATCC BAA-334/TIGR4) GN = pstB1 PE = 3 SV = 1 − [PSTB1_STRPN] | Intracellular |
| I6L8Q3 | 32.35 | 12 | 340 | 114.44 | Choline binding protein F OS = *Streptococcus pneumoniae* serotype 4 (strain ATCC BAA-334/TIGR4) GN = cbpF PE = 4 SV = 1 − [I6L8Q3_STRPN] | N-terminally anchored (with CS) |
| Q97RS8 | 62.96 | 16 | 378 | 110.09 | Lactate oxidase OS = *Streptococcus pneumoniae* serotype 4 (strain ATCC BAA-334/TIGR4) GN = lctO-2 PE = 4 SV = 1 − [Q97RS8_STRPN] | Intracellular |
| Q97N53 | 70.96 | 11 | 272 | 109.3 | Cell shape-determining protein MreC OS = *Streptococcus pneumoniae* serotype 4 (strain ATCC BAA-334/TIGR4) GN = mreC PE = 3 SV = 1 − [Q97N53_STRPN] | N-terminally anchored (No CS) |
| P0A3M5 | 41.32 | 18 | 680 | 109.25 | Penicillin-binding protein 2B OS = *Streptococcus pneumoniae* serotype 4 (strain ATCC BAA-334/TIGR4) GN = penA PE = 3 SV = 1 − [PBP2_STRPN] | N-terminally anchored (No CS) |
| P0A4S1 | 49.15 | 9 | 293 | 109 | Fructose-bisphosphate aldolase OS = *Streptococcus pneumoniae* serotype 4 (strain ATCC BAA-334/TIGR4) GN = fba PE = 3 SV = 1 − [ALF_STRPN] | Intracellular |
| Q97RK0 | 29.57 | 13 | 575 | 107.28 | Septation ring formation regulator EzrA OS = *Streptococcus pneumoniae* serotype 4 (strain ATCC BAA-334/TIGR4) GN = ezrA PE = 3 SV = 1 − [EZRA_STRPN] | N-terminally anchored (No CS) |
| Q97SI9 | 60.55 | 7 | 109 | 107.21 | Cell cycle protein GpsB OS = *Streptococcus pneumoniae* serotype 4 (strain ATCC BAA-334/TIGR4) GN = gpsB PE = 3 SV = 1 − [GPSB_STRPN] | Intracellular |
| P63413 | 36.36 | 12 | 396 | 106.75 | Acetate kinase OS = *Streptococcus pneumoniae* serotype 4 (strain ATCC BAA-334/TIGR4) GN = ackA PE = 3 SV = 1 − [ACKA_STRPN] | Intracellular |
| P0A2Z2 | 59.76 | 10 | 164 | 105.18 | ATP synthase subunit b OS = *Streptococcus pneumoniae* serotype 4 (strain ATCC BAA-334/TIGR4) GN = atpF PE = 3 SV = 1 − [ATPF_STRPN] | Intracellular |
| Q97SQ4 | 39.74 | 8 | 156 | 103.23 | 30S ribosomal protein S7 OS = *Streptococcus pneumoniae* serotype 4 (strain ATCC BAA-334/TIGR4) GN = rpsG PE = 3 SV = 1 − [RS7_STRPN] | Intracellular |
| Q97QK5 | 48.6 | 19 | 607 | 101.3 | Elongation factor 4 OS = *Streptococcus pneumoniae* serotype 4 (strain ATCC BAA-334/TIGR4) GN = lepA PE = 3 SV = 1 − [LEPA_STRPN] | Intracellular |
| P65239 | 39.75 | 11 | 322 | 100.54 | Ribose-phosphate pyrophosphokinase 1 OS = *Streptococcus pneumoniae* serotype 4 (strain ATCC BAA-334/TIGR4) GN = prs1 PE = 3 SV = 1 − [KPRS1_STRPN] | Intracellular |
| P95829 | 36.41 | 14 | 607 | 100.51 | Chaperone protein DnaK OS = *Streptococcus pneumoniae* serotype 4 (strain ATCC BAA-334/TIGR4) GN = dnaK PE = 3 SV = 2 − [DNAK_STRPN] | Intracellular |

TABLE 3-continued

Proteins identified in MV$_L$ from TIGR4. The accession numbers refer to SwissProt on the date of filing.

| Accession | Coverage | # Peptides | #AAs | Score | Desription | Localization |
|---|---|---|---|---|---|---|
| I6L8U5 | 55.47 | 11 | 411 | 100.01 | 3-oxoacyl-[acyl-carrier-protein] synthase 2 OS = *Streptococcus pneumoniae* serotype 4 (strain ATCC BAA-334/TIGR4) GN = fabF PE = 3 SV = 1 – [I6L8U5_STRPN] | Intracellular |
| Q97PV1 | 21.8 | 6 | 289 | 93.98 | Putative glycerol uptake facilitator protein OS = *Streptococcus pneumoniae* serotype 4 (strain ATCC BAA-334/TIGR4) GN = SP_1491 PE = 3 SV = 1 – [Q97PV1_STRPN] | Multi-trans-membrane |
| Q2MGH6 | 15.73 | 18 | 1767 | 93.68 | Endo-alpha-N-acetylgalactosaminidase OS = *Streptococcus pneumoniae* serotype 4 (strain ATCC BAA-334/TIGR4) GN = SP_0368 PE = 1 SV = 1 – [GH101_STRPN] | LPxTG Cell-wall anchored |
| Q97SQ9 | 36.05 | 13 | 602 | 92.56 | Glutamine-fructose-6-phosphate aminotransferase [isomerizing] OS = *Streptococcus pneumoniae* serotype 4 (strain ATCC BAA-334/TIGR4) GN = glmS PE = 3 SV = 3 – [GLMS_STRPN] | Intracellular |
| Q97P40 | 53.96 | 9 | 202 | 92.31 | Putative general stress protein 24 OS = *Streptococcus pneumoniae* serotype 4 (strain ATCC BAA-334/TIGR4) GN = SP_1804 PE = 4 SV = 1 – [Q97P40_STRPN] | Intracellular |
| Q97QE4 | 25.33 | 18 | 1058 | 90.95 | Carbamoyl-phosphate synthase large chain OS = *Streptococcus pneumoniae* serotype 4 (strain ATCC BAA-334/TIGR4) GN = carB PE = 3 SV = 1 – [CARB_STRPN] | Intracellular |
| I6L8Q9 | 40.04 | 11 | 457 | 90.76 | Cell division protein ftsA OS = *Streptococcus pneumoniae* serotype 4 (strain ATCC BAA-334/TIGR4) GN = ftsA PE = 3 SV = 1 – [I6L8Q9_STRPN] | Intracellular |
| I6L8S9 | 45.52 | 10 | 413 | 90.26 | D-alanyl-D-alanine carboxypeptidase OS = *Streptococcus pneumoniae* serotype 4 (strain ATCC BAA-334/TIGR4) GN = dacA PE = 3 SV = 1 – [I6L8S9_STRPN] | N-terminally anchored (with CS) |
| Q97Q48 | 27.52 | 18 | 872 | 89.81 | Alanine-tRNA ligase OS = *Streptococcus pneumoniae* serotype 4 (strain ATCC BAA-334/TIGR4) GN = alaS PE = 3 SV = 1 – [SYA_STRPN] | Intracellular |
| Q97QD5 | 64.52 | 12 | 186 | 89.81 | LemA protein OS = *Streptococcus pneumoniae* serotype 4 (strain ATCC BAA-334/TIGR4) GN = lemA PE = 1 SV = 1 – [Q97QD5_STRPN] | N-terminally anchored (No CS) |
| Q97NW2 | 48.69 | 13 | 419 | 88.69 | Sugar ABC transporter, sugar-binding protein OS = *Streptococcus pneumoniae* serotype 4 (strain ATCC BAA-334/TIGR4) GN = rafE PE = 1 SV = 1 – [Q97NW2_STRPN] | Lipid anchored |
| I6L8N0 | 43.01 | 14 | 365 | 88.6 | UDP-N-acetylglucosamine-2-epimerase OS = *Streptococcus pneumoniae* serotype 4 (strain ATCC BAA-334/TIGR4) GN = cps4I PE = 3 SV = 1 – [I6L8N0_STRPN] | Intracellular |
| Q97QW4 | 36.47 | 13 | 425 | 87.93 | Uncharacterized protein OS = *Streptococcus pneumoniae* serotype 4 (strain ATCC BAA-334/TIGR4) GN = SP_1083 PE = 4 SV = 1 – [Q97QW4_STRPN] | Intracellular |
| Q9FBB7 | 58.43 | 12 | 255 | 86.89 | Acetyl-coenzyme A carboxylase carboxyl transferase subunit alpha OS = *Streptococcus pneumoniae* serotype 4 (strain ATCC BAA-334/TIGR4) GN = accA PE = 1 SV = 1 – [ACCA_STRPN] | Intracellular |

TABLE 3-continued

Proteins identified in MV$_L$ from TIGR4. The accession numbers refer to SwissProt on the date of filing.

| Accession | Coverage | # Peptides | #AAs | Score | Desription | Localization |
|---|---|---|---|---|---|---|
| P67266 | 42.42 | 4 | 99 | 86.55 | Nucleoid-associated protein SP_1102 OS = Streptococcus pneumoniae serotype 4 (strain ATCC BAA-334/TIGR4) GN = SP_1102 PE = 1 SV = 1 – [Y1102_STRPN] | Intracellular |
| Q97QM4 | 24.06 | 13 | 719 | 86.48 | Ribonucleoside-diphosphate reductase OS = Streptococcus pneumoniae serotype 4 (strain ATCC BAA-334/TIGR4) GN = nrdE PE = 3 SV = 1 – [Q97QM4_STRPN] | Intracellular |
| Q97PF5 | 44.17 | 8 | 283 | 85.34 | Putative phosphosugar-binding transcriptional regulator OS = Streptococcus pneumoniae serotype 4 (strain ATCC BAA-334/TIGR4) GN = SP_1674 PE = 4 SV = 1 – [Q97PF5_STRPN] | Intracellular |
| P0A3Y3 | 50.87 | 10 | 230 | 84.95 | 2,3-bisphosphoglycerate-dependent phosphoglycerate mutase OS = Streptococcus pneumoniae serotype 4 (strain ATCC BAA-334/TIGR4) GN = gpmA PE = 3 SV = 1 – [GPMA_STRPN] | Intracellular |
| Q97NE1 | 40.78 | 4 | 103 | 84.35 | Uncharacterized protein OS = Streptococcus pneumoniae serotype 4 (strain ATCC BAA-334/TIGR4) GN = SP_2102 PE = 4 SV = 1 – [Q97NE1_STRPN] | Intracellular |
| P67282 | 35.58 | 16 | 534 | 83.04 | Ribonuclease Y OS = Streptococcus pneumoniae serotype 4 (strain ATCC BAA-334/TIGR4) GN = rny PE = 3 SV = 1 – [RNY_STRPN] | N-terminally anchored (No CS) |
| Q97QX6 | 22.61 | 14 | 898 | 82.38 | Phosphoenolpyruvate carboxylase OS = Streptococcus pneumoniae serotype 4 (strain ATCC BAA-334/TIGR4) GN = ppc PE = 3 SV = 1 – [CAPP_STRPN] | Intracellular |
| Q97SD1 | 32.63 | 12 | 521 | 81.72 | Amino acid ABC transporter, amino acid-binding protein/permease protein OS = Streptococcus pneumoniae serotype 4 (strain ATCC BAA-334/TIGR4) GN = SP_0453 PE = 4 SV = 1 – [Q97SD1_STRPN] | Multi-trans-membrane |
| P66419 | 50.56 | 8 | 89 | 78.12 | 30S ribosomal protein S14 OS = Streptococcus pneumoniae serotype 4 (strain ATCC BAA-334/TIGR4) GN = rpsN PE = 3 SV = 1 – [RS14_STRPN] | Intracellular |
| P61182 | 61.4 | 8 | 114 | 77.58 | 50S ribosomal protein L22 OS = Streptococcus pneumoniae serotype 4 (strain ATCC BAA-334/TIGR4) GN = rplV PE = 1 SV = 1 – [RL22_STRPN] | Intracellular |
| P66278 | 33.33 | 4 | 66 | 77.34 | 50S ribosomal protein L35 OS = Streptococcus pneumoniae serotype 4 (strain ATCC BAA-334/TIGR4) GN = rpmI PE = 3 SV = 1 – [RL35_STRPN] | Intracellular |
| Q97R14 | 34.57 | 10 | 324 | 76.27 | Uncharacterized protein OS = Streptococcus pneumoniae serotype 4 (strain ATCC BAA-334/TIGR4) GN = SP_1027 PE = 4 SV = 1 – [Q97R14_STRPN] | Secretory (released) (with CS) |
| Q97T52 | 22.4 | 12 | 616 | 70.86 | Putative capsular polysaccharide biosynthesis protein OS = Streptococcus pneumoniae serotype 4 (strain ATCC BAA-334/TIGR4) GN = SP_0103 PE = 4 SV = 1 – [Q97T52_STRPN] | Multi-trans-membrane |
| Q97SW2 | 26.53 | 13 | 735 | 70.68 | Anaerobic ribonucleoside-triphosphate reductase OS = Streptococcus pneumoniae serotype 4 (strain ATCC BAA-334/TIGR4) GN = nrdD PE = 4 SV = 1 – [Q97SW2_STRPN] | Intracellular |

TABLE 3-continued

Proteins identified in MV$_L$ from TIGR4. The accession numbers refer to SwissProt on the date of filing.

| Accession | Coverage | # Peptides | #AAs | Score | Desription | Localization |
|---|---|---|---|---|---|---|
| Q97SE4 | 32.3 | 12 | 514 | 70.62 | Peptide chain release factor 3 OS = Streptococcus pneumoniae serotype 4 (strain ATCC BAA-334/TIGR4) GN = prfC PE = 3 SV = 1 – [RF3_STRPN] | Intracellular |
| Q97PC4 | 27.24 | 9 | 492 | 68.5 | ABC transporter, ATP-binding protein OS = Streptococcus pneumoniae serotype 4 (strain ATCC BAA-334/TIGR4) GN = SP_1715 PE = 4 SV = 1 – [Q97PC4_STRPN] | Multi-trans-membrane |
| I6L8V8 | 47.33 | 7 | 243 | 68.48 | 3-oxoacyl-[acyl-carrier protein] reductase OS = Streptococcus pneumoniae serotype 4 (strain ATCC BAA-334/TIGR4) GN = fabG PE = 3 SV = 1 – [I6L8V8_STRPN] | Intracellular |
| Q97S28 | 21.17 | 11 | 737 | 68.26 | Polyribonucleotide nucleotidyltransferase OS = Streptococcus pneumoniae serotype 4 (strain ATCC BAA-334/TIGR4) GN = pnp PE = 3 SV = 1 – [PNP_STRPN] | Intracellular |
| Q97RC4 | 41.38 | 9 | 290 | 67.69 | Uncharacterized protein OS = Streptococcus pneumoniae serotype 4 (strain ATCC BAA-334/TIGR4) GN = SP_0899 PE = 4 SV = 1 – [Q97RC4_STRPN] | Lipid anchored |
| Q97S86 | 21.65 | 7 | 448 | 65.38 | Glutamine synthetase, type I OS = Streptococcus pneumoniae serotype 4 (strain ATCC BAA-334/TIGR4) GN = glnA PE = 3 SV = 1 – [Q97S86_STRPN] | Intracellular |
| Q97NH4 | 41.48 | 9 | 352 | 65.13 | Alcohol dehydrogenase, zinc-containing OS = Streptococcus pneumoniae serotype 4 (strain ATCC BAA-334/TIGR4) GN = SP_2055 PE = 3 SV = 1 – [Q97NH4_STRPN] | Intracellular |
| P0A495 | 65.79 | 3 | 38 | 64.65 | 50S ribosomal protein L36 OS = Streptococcus pneumoniae serotype 4 (strain ATCC BAA-334/TIGR4) GN = rpmJ PE = 3 SV = 1 – [RL36_STRPN] | Intracellular |
| Q97ND6 | 25.72 | 13 | 587 | 64.48 | Aspartate-tRNA ligase OS = Streptococcus pneumoniae serotype 4 (strain ATCC BAA-334/TIGR4) GN = aspS PE = 3 SV = 1 – [SYD_STRPN] | Intracellular |
| P72525 | 18.1 | 10 | 823 | 63.42 | DNA topoisomerase 4 subunit A OS = Streptococcus pneumoniae serotype 4 (strain ATCC BAA-334/TIGR4) GN = parC PE = 1 SV = 3 – [PARC_STRPN] | Intracellular |
| Q97PH2 | 23.11 | 12 | 740 | 63.08 | GTP pyrophosphokinase OS = Streptococcus pneumoniae serotype 4 (strain ATCC BAA-334/TIGR4) GN = relA PE = 3 SV = 1 – [Q97PH2_STRPN] | Intracellular |
| Q97T46 | 32.63 | 4 | 95 | 63.06 | Putative bacteriocin OS = Streptococcus pneumoniae serotype 4 (strain ATCC BAA-334/TIGR4) GN = SP_0109 PE = 4 SV = 1 – [Q97T46_STRPN] | Secretory |
| I6L8V0 | 42.17 | 11 | 351 | 60.21 | Capsular polysaccharide biosynthesis protein Cps4J OS = Streptococcus pneumoniae serotype 4 (strain ATCC BAA-334/TIGR4) GN = cap4J PE = 4 SV = 1 – [I6L8V0_STRPN] | Intracellular |
| Q97RQ6 | 23.84 | 6 | 281 | 60.06 | DegV domain-containing protein SP_0742 OS = Streptococcus pneumoniae serotype 4 (strain ATCC BAA-334/TIGR4) GN = SP_0742 PE = 3 SV = 1 – [Y742_STRPN] | Intracellular |
| Q97SR2 | 35.08 | 9 | 419 | 60.03 | Putative zinc metalloprotease SP_0263 OS = Streptococcus pneumoniae serotype 4 (strain ATCC BAA-334/TIGR4) GN = SP_0263 PE = 3 SV = 1 – [Y263_STRPN] | Multi-trans-membrane |

TABLE 3-continued

Proteins identified in MV$_L$ from TIGR4. The accession numbers refer to SwissProt on the date of filing.

| Accession | Coverage | # Peptides | #AAs | Score | Desription | Localization |
|---|---|---|---|---|---|---|
| Q97PB8 | 15.63 | 8 | 627 | 59.73 | PTS system IIABC components OS = *Streptococcus pneumoniae* serotype 4 (strain ATCC BAA-334/TIGR4) GN = SP_1722 PE = 4 SV = 1 – [Q97PB8_STRPN] | Multi-trans-membrane |
| Q97QE6 | 41.47 | 9 | 340 | 58.95 | Alcohol dehydrogenase, zinc-containing OS = *Streptococcus pneumoniae* serotype 4 (strain ATCC BAA-334/TIGR4) GN = SP_1270 PE = 4 SV = 1 – [Q97QE6_STRPN] | Intracellular |
| Q97P07 | 34.56 | 10 | 408 | 58.93 | Putative capsular polysaccharide biosynthesis protein OS = *Streptococcus pneumoniae* serotype 4 (strain ATCC BAA-334/TIGR4) GN = SP_1837 PE = 3 SV = 1 – [Q97P07_STRPN] | Intracellular |
| Q97T09 | 40.23 | 9 | 353 | 57.99 | Methionine import ATP-binding protein MetN OS = *Streptococcus pneumoniae* serotype 4 (strain ATCC BAA-334/TIGR4) GN = metN PE = 3 SV = 1 – [METN_STRPN] | Intracellular |
| Q97NP5 | 18.83 | 7 | 308 | 57.43 | Membrane protein insertase YidC 1 OS = *Streptococcus pneumoniae* serotype 4 (strain ATCC BAA-334/TIGR4) GN = yidC1 PE = 3 SV = 1 – [YIDC1_STRPN] | Multi-trans-membrane |
| P0A451 | 41.49 | 12 | 388 | 57.14 | Protein RecA OS = *Streptococcus pneumoniae* serotype 4 (strain ATCC BAA-334/TIGR4) GN = recA PE = 2 SV = 1 – [RECA_STRPN] | Intracellular |
| Q97SU7 | 51.12 | 5 | 178 | 56.93 | 50S ribosomal protein L6 OS = *Streptococcus pneumoniae* serotype 4 (strain ATCC BAA-334/TIGR4) GN = rplF PE = 3 SV = 1 – [RL6_STRPN] | Intracellular |
| Q97NE2 | 18.49 | 9 | 687 | 56.54 | Cation-transporting ATPase, EI-E2 family OS = *Streptococcus pneumoniae* serotype 4 (strain ATCC BAA-334/TIGR4) GN = SP_2101 PE = 3 SV = 1 – [Q97NE2_STRPN] | Intracellular |
| Q97SN4 | 32.31 | 6 | 130 | 56.22 | 30S ribosomal protein S9 OS = *Streptococcus pneumoniae* serotype 4 (strain ATCC BAA-334/TIGR4) GN = rpsI PE = 3 SV = 1 – [RS9_STRPN] | Intracellular |
| P66392 | 51.24 | 7 | 121 | 56.15 | 30S ribosomal protein S13 OS = *Streptococcus pneumoniae* serotype 4 (strain ATCC BAA-334/TIGR4) GN = rpsM PE = 3 SV = 1 – [RS13_STRPN] | Intracellular |
| Q97S10 | 23.51 | 11 | 553 | 55.98 | Ribonuclease J OS = *Streptococcus pneumoniae* serotype 4 (strain ATCC BAA-334/TIGR4) GN = rnj PE = 3 SV = 1 – [Q97S10_STRPN] | Intracellular |
| Q97PG0 | 20.99 | 5 | 262 | 55.94 | Cell division protein DivIVA OS = *Streptococcus pneumoniae* serotype 4 (strain ATCC BAA-334/TIGR4) GN = divIVA PE = 4 SV = 1 – [Q97PG0_STRPN] | Intracellular |
| P35597 | 17.61 | 9 | 778 | 55.84 | Probable cation-transporting ATPase exp7 OS = *Streptococcus pneumoniae* serotype 4 (strain ATCC BAA-334/TIGR4) GN = exp7 PE = 3 SV = 2 – [EXP7_STRPN] | Multi-trans-membrane |
| Q97SJ2 | 43.52 | 12 | 409 | 55.75 | Capsular polysaccharide biosynthesis protein Cps4K OS = *Streptococcus pneumoniae* serotype 4 (strain ATCC BAA-334/TIGR4) GN = cps4K PE = 4 SV = 1 – [Q97SJ2_STRPN] | Intracellular |
| Q97PI4 | 29.98 | 12 | 647 | 55.52 | Threonine-tRNA ligase OS = *Streptococcus pneumoniae* serotype 4 (strain ATCC BAA-334/TIGR4) GN = thrS PE = 1 SV = 1 – [SYT_STRPN] | Intracellular |

TABLE 3-continued

Proteins identified in MV$_L$ from TIGR4. The accession numbers refer to SwissProt on the date of filing.

| Accession | Coverage | # Peptides | #AAs | Score | Desription | Localization |
|---|---|---|---|---|---|---|
| Q97QW8 | 25.81 | 8 | 434 | 55.41 | GTPase Obg OS = Streptococcus pneumoniae serotype 4 (strain ATCC BAA-334/TIGR4) GN = obg PE = 3 SV = 1 – [OBG_STRPN] | Intracellular |
| P67293 | 43.9 | 3 | 82 | 55.21 | UPF0154 protein SP_1882 OS = Streptococcus pneumoniae serotype 4 (strain ATCC BAA-334/TIGR4) GN = SP_1882 PE = 3 SV = 1 – [Y1882_STRPN] | N-terminally anchored (No CS) |
| P0A4L9 | 20.52 | 10 | 648 | 54.97 | DNA gyrase subunit B OS = Streptococcus pneumoniae serotype 4 (strain ATCC BAA-334/TIGR4) GN = gyrB PE = 3 SV = 1 – [GYRB_STRPN] | Intracellular |
| Q97SJ8 | 33.2 | 11 | 494 | 54.78 | UPF0371 protein SP_0341 OS = Streptococcus pneumoniae serotype 4 (strain ATCC BAA-334/TIGR4) GN = SP_0341 PE = 3 SV = 1 – [Y341_STRPN] | Intracellular |
| Q54869 | 24.16 | 10 | 563 | 54.43 | Arginine-tRNA ligase OS = Streptococcus pneumoniae serotype 4 (strain ATCC BAA-334/TIGR4) GN = argS PE = 1 SV = 2 – [SYR_STRPN] | Intracellular |
| P35595 | 14.88 | 7 | 726 | 53.64 | PTS system glucose-specific EIICBA component OS = Streptococcus pneumoniae serotype 4 (strain ATCC BAA-334/TIGR4) GN = exp5 PE = 3 SV = 2 – [PTG3C_STRPN] | Multi-trans-membrane |
| Q97SI7 | 22.41 | 7 | 464 | 53.36 | Mid-cell-anchored protein Z OS = Streptococcus pneumoniae serotype 4 (strain ATCC BAA-334/TIGR4) GN = mapZ PE = 1 SV = 1 – [Q97SI7_STRPN] | Intracellular |
| P0A4B5 | 55.91 | 7 | 93 | 52.72 | 30S ribosomal protein S19 OS = Streptococcus pneumoniae serotype 4 (strain ATCC BAA-334/TIGR4) GN = rpsS PE = 3 SV = 1 – [RS19_STRPN] | Intracellular |
| Q97SU3 | 23.29 | 4 | 146 | 52.09 | 50S ribosomal protein L15 OS = Streptococcus pneumoniae serotype 4 (strain ATCC BAA-334/TIGR4) GN = rplO PE = 3 SV = 1 – [RL15_STRPN] | Intracellular |
| Q97RV5 | 27.57 | 11 | 613 | 51.74 | Elongation factor Tu family protein OS = Streptococcus pneumoniae serotype 4 (strain ATCC BAA-334/TIGR4) GN = SP_0681 PE = 4 SV = 1 – [Q97RV5_STRPN] | Intracellular |
| Q97NW9 | 8.4 | 5 | 655 | 50.97 | Trehalose PTS system, IIABC components OS = Streptococcus pneumoniae serotype 4 (strain ATCC BAA-334/TIGR4) GN = SP_1884 PE = 4 SV = 1 – [Q97NW9_STRPN] | Multi-trans-membrane |
| Q97QE7 | 41.6 | 9 | 262 | 49.97 | Choline kinase OS = Streptococcus pneumoniae serotype 4 (strain ATCC BAA-334/TIGR4) GN = pck PE = 4 SV = 1 – [Q97QE7_STRPN] | Intracellular |
| P67595 | 31.96 | 8 | 341 | 48.09 | Tryptophan-tRNA ligase OS = Streptococcus pneumoniae serotype 4 (strain ATCC BAA-334/TIGR4) GN = trpS PE = 3 SV = 1 – [SYW_STRPN] | Intracellular |
| P66581 | 55.49 | 6 | 164 | 47.77 | 30S ribosomal protein S5 OS = Streptococcus pneumoniae serotype 4 (strain ATCC BAA-334/TIGR4) GN = rpsE PE = 3 SV = 1 – [RS5_STRPN] | Intracellular |
| Q97R57 | 16.33 | 10 | 784 | 47.19 | Ribonuclease R OS = Streptococcus pneumoniae serotype 4 (strain ATCC BAA-334/TIGR4) GN = rnr PE = 3 SV = 1 – [Q97R57_STRPN] | Intracellular |

TABLE 3-continued

Proteins identified in MV$_L$ from TIGR4. The accession numbers refer to SwissProt on the date of filing.

| Accession | Coverage | # Peptides | #AAs | Score | Desription | Localization |
|---|---|---|---|---|---|---|
| Q97RP0 | 21.03 | 7 | 447 | 46.86 | DEAD-box ATP-dependent RNA helicase CshB OS = *Streptococcus pneumoniae* serotype 4 (strain ATCC BAA-334/TIGR4) GN = cshB PE = 3 SV = 1 − [Q97RP0_STRPN] | Intracellular |
| P0A3R1 | 22.65 | 9 | 649 | 46.48 | DNA mismatch repair protein HexB OS = *Streptococcus pneumoniae* serotype 4 (strain ATCC BAA-334/TIGR4) GN = hexB PE = 3 SV = 1 − [HEXB_STRPN] | Intracellular |
| P0A3R3 | 18.48 | 11 | 844 | 45.87 | DNA mismatch repair protein HexA OS = *Streptococcus pneumoniae* serotype 4 (strain ATCC BAA-334/TIGR4) GN = hexA PE = 3 SV = 1 − [HEXA_STRPN] | Intracellular |
| Q97SF6 | 27.97 | 7 | 261 | 45.73 | Enoyl-CoA hydratase/isomerase family protein OS = *Streptococcus pneumoniae* serotype 4 (strain ATCC BAA-334/TIGR4) GN = SP_0415 PE = 4 SV = 1 − [Q97SF6_STRPN] | Intracellular |
| P66708 | 45.98 | 9 | 311 | 45.6 | DNA-directed RNA polymerase subunit alpha OS = *Streptococcus pneumoniae* serotype 4 (strain ATCC BAA-334/TIGR4) GN = rpoA PE = 3 SV = 1 − [RPOA_STRPN] | Intracellular |
| I6L8S8 | 28.69 | 9 | 481 | 45.33 | Capsular polysaccharide biosynthesis protein Cps4A OS = *Streptococcus pneumoniae* serotype 4 (strain ATCC BAA-334/TIGR4) GN = cps4A PE = 4 SV = 1 − [I6L8S8_STRPN] | Multi-trans-membrane |
| Q97N43 | 19.51 | 7 | 492 | 45.08 | Inosine-5'-monophosphate dehydrogenase OS = *Streptococcus pneumoniae* serotype 4 (strain ATCC BAA-334/TIGR4) GN = guaB PE = 3 SV = 1 − [Q97N43_STRPN] | Intracellular |
| I6L8W8 | 16.87 | 6 | 332 | 44.57 | Choline binding protein J OS = *Streptococcus pneumoniae* serotype 4 (strain ATCC BAA-334/TIGR4) GN = cbpJ PE = 4 SV = 1 − [I6L8W8_STRPN] | N-terminally anchored (with CS) |
| Q2MGG2 | 27.62 | 7 | 467 | 44.4 | Serine protease, subtilase family OS = *Streptococcus pneumoniae* serotype 4 (strain ATCC BAA-334/TIGR4) GN = SP_1954 PE = 4 SV = 1 − [Q2MGG2_STRPN] | Secretory (released) (with CS) |
| Q97SP0 | 42.22 | 7 | 270 | 44.36 | Cof family protein OS = *Streptococcus pneumoniae* serotype 4 (strain ATCC BAA-334/TIGR4) GN = SP_0286 PE = 4 SV = 1 − [Q97SP0_STRPN] | Intracellular |
| Q97PG9 | 38.75 | 7 | 240 | 44.16 | Manganese ABC transporter, ATP-binding protein OS = *Streptococcus pneumoniae* serotype 4 (strain ATCC BAA-334/TIGR4) GN = psaB PE = 3 SV = 1 − [Q97PG9_STRPN] | Intracellular |
| Q97T72 | 31.67 | 6 | 221 | 44.14 | Potassium uptake protein, Trk family OS = *Streptococcus pneumoniae* serotype 4 (strain ATCC BAA-334/TIGR4) GN = SP_0079 PE = 4 SV = 1 − [Q97T72_STRPN] | N-terminally anchored (No CS) |
| Q97RS9 | 21.98 | 7 | 496 | 44.07 | Lysine-tRNA ligase OS = *Streptococcus pneumoniae* serotype 4 (strain ATCC BAA-334/TIGR4) GN = lysS PE = 1 SV = 2 − [SYK_STRPN] | Intracellular |
| Q97PK5 | 27.22 | 2 | 158 | 43.99 | Uncharacterized protein OS = *Streptococcus pneumoniae* serotype 4 (strain ATCC BAA-334/TIGR4) GN = SP_1604 PE = 4 SV = 1 − [Q97PK5_STRPN] | N-terminally anchored (No CS) |
| Q97RV8 | 38.89 | 6 | 126 | 43.74 | Uncharacterized protein OS = *Streptococcus pneumoniae* serotype 4 (strain ATCC BAA-334/TIGR4) GN = SP_0678 PE = 4 SV = 1 − [Q97RV8_STRPN] | N-terminally anchored (No CS) |

TABLE 3-continued

Proteins identified in MV$_L$ from TIGR4. The accession numbers refer to SwissProt on the date of filing.

| Accession | Coverage | # Peptides | #AAs | Score | Desription | Localization |
|---|---|---|---|---|---|---|
| P06653 | 26.1 | 6 | 318 | 43.37 | Autolysin OS = *Streptococcus pneumoniae* serotype 4 (strain ATCC BAA-334/TIGR4) GN = lytA PE = 1 SV = 2 – [ALYS_STRPN] | Intracellular |
| P63791 | 27.8 | 8 | 410 | 42.54 | ATP-dependent Clp protease ATP-binding subunit ClpX OS = *Streptococcus pneumoniae* serotype 4 (strain ATCC BAA-334/TIGR4) GN = clpX PE = 3 SV = 1 – [CLPX_STRPN] | Intracellular |
| Q97Q36 | 37.33 | 7 | 217 | 42.45 | Phosphate-specific transport system accessory protein PhoU OS = *Streptococcus pneumoniae* serotype 4 (strain ATCC BAA-334/TIGR4) GN = SP_1395 PE = 3 SV = 1 – [Q97Q36_STRPN] | Intracellular |
| Q97R16 | 32.06 | 10 | 418 | 42.38 | Serine hydroxymethyltransferase OS = *Streptococcus pneumoniae* serotype 4 (strain ATCC BAA-334/TIGR4) GN = glyA PE = 3 SV = 1 – [GLYA_STRPN] | Intracellular |
| Q97NM1 | 38.99 | 9 | 336 | 42.33 | Catabolite control protein A OS = *Streptococcus pneumoniae* serotype 4 (strain ATCC BAA-334/TIGR4) GN = ccpA PE = 4 SV = 1 – [Q97NM1_STRPN] | Intracellular |
| Q97PQ8 | 42.66 | 6 | 143 | 40.36 | Uncharacterized protein OS = *Streptococcus pneumoniae* serotype 4 (strain ATCC BAA-334/TIGR4) GN = SP_1545 PE = 4 SV = 1 – [Q97PQ8_STRPN] | Intracellular |
| Q97SU6 | 59.32 | 7 | 118 | 40.13 | 50S ribosomal protein L18 OS = *Streptococcus pneumoniae* serotype 4 (strain ATCC BAA-334/TIGR4) GN = rplR PE = 3 SV = 1 – [RL18_STRPN] | Intracellular |
| Q97RC9 | 30.77 | 3 | 156 | 40.01 | Arginine repressor OS = *Streptococcus pneumoniae* serotype 4 (strain ATCC BAA-334/TIGR4) GN = argR PE = 3 SV = 1 – [Q97RC9_STRPN] | Intracellular |
| Q97RC5 | 25.15 | 8 | 501 | 39.74 | Pyruvate kinase OS = *Streptococcus pneumoniae* serotype 4 (strain ATCC BAA-334/TIGR4) GN = pyk PE = 3 SV = 1 – [Q97RC5_STRPN] | Intracellular |
| Q97PM1 | 45.04 | 7 | 262 | 38.81 | GTP-sensing transcriptional pleiotropic repressor CodY OS = *Streptococcus pneumoniae* serotype 4 (strain ATCC BAA-334/TIGR4) GN = codY PE = 1 SV = 1 – [CODY_STRPN] | Intracellular |
| I6L8N6 | 28.91 | 5 | 211 | 38.64 | Capsular polysaccharide biosynthesis protein Cps4E OS = *Streptococcus pneumoniae* serotype 4 (strain ATCC BAA-334/TIGR4) GN = cps4E PE = 4 SV = 1 – [I6L8N6_STRPN] | N-terminally anchored (No CS) |
| Q97R36 | 38.38 | 7 | 185 | 38.61 | Thioredoxin family protein OS = *Streptococcus pneumoniae* serotype 4 (strain ATCC BAA-334/TIGR4) GN = SP_1000 PE = 1 SV = 1 – [Q97R36_STRPN] | Lipid anchored |
| Q97S93 | 17.76 | 7 | 535 | 37.74 | CTP synthase OS = *Streptococcus pneumoniae* serotype 4 (strain ATCC BAA-334/TIGR4) GN = pyrG PE = 3 SV = 1 – [PYRG_STRPN] | Intracellular |
| Q97QW1 | 20.71 | 9 | 763 | 37.7 | DNA helicase OS = *Streptococcus pneumoniae* serotype 4 (strain ATCC BAA-334/TIGR4) GN = pcrA PE = 4 SV = 1 – [Q97QW1_STRPN] | Intracellular |
| P63544 | 51.76 | 6 | 170 | 37.59 | Adenine phosphoribosyltransferase OS = *Streptococcus pneumoniae* serotype 4 (strain ATCC BAA-334/TIGR4) GN = apt PE = 1 SV = 1 – [APT_STRPN] | Intracellular |

TABLE 3-continued

Proteins identified in MV$_L$ from TIGR4. The accession numbers refer to SwissProt on the date of filing.

| Accession | Coverage | # Peptides | #AAs | Score | Desription | Localization |
|---|---|---|---|---|---|---|
| P65241 | 18.18 | 5 | 319 | 37.57 | Ribose-phosphate pyrophosphokinase 2 OS = *Streptococcus pneumoniae* serotype 4 (strain ATCC BAA-334/TIGR4) GN = prs2 PE = 3 SV = 1 - [KPRS2_STRPN] | Intracellular |
| Q97RE5 | 17.08 | 6 | 650 | 37.17 | PTS system, fructose specific IIABC components OS = *Streptococcus pneumoniae* serotype 4 (strain ATCC BAA-334/TIGR4) GN = SP_0877 PE = 4 SV = 1 - [Q97RE5_STRPN] | Multi-trans-membrane |
| P35596 | 21.38 | 9 | 608 | 37.12 | Alpha-glycerophosphate oxidase OS = *Streptococcus pneumoniae* serotype 4 (strain ATCC BAA-334/TIGR4) GN = glpO PE = 3 SV = 2 - [GLPO_STRPN] | N-terminally anchored (No CS) |
| Q97R12 | 19.52 | 7 | 543 | 37.11 | Uncharacterized RNA methyltransferase SP_1029 OS = *Streptococcus pneumoniae* serotype 4 (strain ATCC BAA-334/TIGR4) GN = SP_1029 PE = 3 SV = 1 - [Y1029_STRPN] | Intracellular |
| P64166 | 12.91 | 7 | 767 | 36.81 | DNA translocase FtsK OS = *Streptococcus pneumoniae* serotype 4 (strain ATCC BAA-334/TIGR4) GN = ftsK PE = 3 SV = 1 - [FTSK_STRPN] | Multi-trans-membrane |
| P35594 | 17.15 | 10 | 752 | 36.7 | ATP-dependent Clp protease ATP-binding subunit ClpE OS = *Streptococcus pneumoniae* serotype 4 (strain ATCC BAA-334/TIGR4) GN = clpE PE = 3 SV = 2 - [CLPE_STRPN] | Intracellular |
| P64072 | 53.33 | 8 | 195 | 36.63 | Probable GTP-binding protein EngB OS = *Streptococcus pneumoniae* serotype 4 (strain ATCC BAA-334/TIGR4) GN = engB PE = 3 SV = 1 - [ENGB_STRPN] | Intracellular |
| Q97TC4 | 31.11 | 5 | 180 | 36.56 | Hypoxanthine-guanine phosphoribosyltransferase OS = *Streptococcus pneumoniae* serotype 4 (strain ATCC BAA-334/TIGR4) GN = hpt PE = 3 SV = 1 - [HPRT_STRPN] | Intracellular |
| Q97PU2 | 37.8 | 4 | 209 | 36.45 | Amino acid ABC transporter, ATP-binding protein OS = *Streptococcus pneumoniae* serotype 4 (strain ATCC BAA-334/TIGR4) GN = SP_1501 PE = 3 SV = 1 - [Q97PU2_STRPN] | Intracellular |
| P0A3S3 | 38.69 | 6 | 274 | 36.43 | DNA-entry nuclease OS = *Streptococcus pneumoniae* serotype 4 (strain ATCC BAA-334/TIGR4) GN = endA PE = 1 SV = 1 - [NUCE_STRPN] | N-terminally anchored (No CS) |
| I6L8N9 | 25.49 | 8 | 506 | 36.2 | Choline transporter OS = *Streptococcus pneumoniae* serotype 4 (strain ATCC BAA-334/TIGR4) GN = proWX PE = 3 SV = 1 - [I6L8N9_STRPN] | Multi-trans-membrane |
| Q97PQ5 | 25.99 | 8 | 531 | 36.19 | Uncharacterized protein OS = *Streptococcus pneumoniae* serotype 4 (strain ATCC BAA-334/TIGR4) GN = SP_1548 PE = 4 SV = 1 - [Q97PQ5_STRPN] | Multi-trans-membrane |
| Q97NI7 | 28.66 | 6 | 328 | 36.13 | Putative jag protein OS = *Streptococcus pneumoniae* serotype 4 (strain ATCC BAA-334/TIGR4) GN = SP_2040 PE = 4 SV = 1 - [Q97NI7_STRPN] | Intracellular |
| P63742 | 19.32 | 7 | 502 | 36.12 | Glycerol kinase OS = *Streptococcus pneumoniae* serotype 4 (strain ATCC BAA-334/TIGR4) GN = glpK PE = 3 SV = 1 - [GLPK_STRPN] | Intracellular |
| Q97NT7 | 32.91 | 4 | 158 | 36 | Uncharacterized protein OS = *Streptococcus pneumoniae* serotype 4 (strain ATCC BAA-334/TIGR4) GN = SP_1926 PE = 4 SV = 1 - [Q97NT7_STRPN] | Multi-trans-membrane |

TABLE 3-continued

Proteins identified in MV$_L$ from TIGR4. The accession numbers refer to SwissProt on the date of filing.

| Accession | Coverage | # Peptides | #AAs | Score | Desription | Localization |
|---|---|---|---|---|---|---|
| P64297 | 23.85 | 7 | 520 | 35.92 | GMP synthase [glutamine-hydrolyzing] OS = *Streptococcus pneumoniae* serotype 4 (strain ATCC BAA-334/ TIGR4) GN = guaA PE = 3 SV = 1 − [GUAA_STRPN] | Intracellular |
| Q97R84 | 28.38 | 7 | 444 | 35.81 | Methylenetetrahydrofolate-tRNA-(uracil-5-)-methyltransferase TrmFO OS = *Streptococcus pneumoniae* serotype 4 (strain ATCC BAA-334/ TIGR4) GN = trmFO PE = 3 SV = 2 − [TRMFO_STRPN] | Intracellular |
| Q97PK2 | 19.17 | 5 | 339 | 35.39 | UDP-glucose 4-epimerase OS = *Streptococcus pneumoniae* serotype 4 (strain ATCC BAA-334/ TIGR4) GN = galE-1 PE = 3 SV = 1 − [Q97PK2_STRPN] | Intracellular |
| Q97RP6 | 41.53 | 6 | 236 | 35.16 | Branched-chain amino acid ABC transporter, ATP-binding protein OS = *Streptococcus pneumoniae* serotype 4 (strain ATCC BAA-334/ TIGR4) GN = livF PE = 3 SV = 1 − [Q97RP6_STRPN] | Intracellular |
| Q97NM3 | 30.74 | 10 | 462 | 35.12 | Cof family protein OS = *Streptococcus pneumoniae* serotype 4 (strain ATCC BAA-334/TIGR4) GN = SP_1997 PE = 4 SV = 1 − [Q97NM3_STRPN] | Intracellular |
| Q97S34 | 10.86 | 7 | 801 | 34.77 | Phenylalanine-tRNA ligase beta subunit OS = *Streptococcus pneumoniae* serotype 4 (strain ATCC BAA-334/TIGR4) GN = pheT PE = 3 SV = 1 − [SYFB_STRPN] | Intracellular |
| Q97NQ4 | 31.38 | 9 | 427 | 34.05 | UDP-N-acetylglucosamine 1-carboxyvinyltransferase 1 OS = *Streptococcus pneumoniae* serotype 4 (strain ATCC BAA-334/ TIGR4) GN = murA1 PE = 3 SV = 1 − [MURA1_STRPN] | Intracellular |
| Q97PY0 | 33.2 | 6 | 247 | 34.04 | Amino acid ABC transporter, ATP-binding protein OS = *Streptococcus pneumoniae* serotype 4 (strain ATCC BAA-334/TIGR4) GN = SP_1460 PE = 3 SV = 1 − [Q97PY0_STRPN] | Intracellular |
| Q97RQ3 | 44.5 | 6 | 209 | 33.91 | Uracil phosphoribosyltransferase OS = *Streptococcus pneumoniae* serotype 4 (strain ATCC BAA-334/ TIGR4) GN = upp PE = 3 SV = 1 − [UPP_STRPN] | Intracellular |
| Q97QP0 | 15.87 | 7 | 567 | 33.86 | Dihydrolipoyl dehydrogenase OS = *Streptococcus pneumoniae* serotype 4 (strain ATCC BAA-334/ TIGR4) GN = SP_1161 PE = 4 SV = 1 − [Q97QP0_STRPN] | Intracellular |
| P64062 | 24.77 | 8 | 436 | 33.49 | GTPase Der OS = *Streptococcus pneumoniae* serotype 4 (strain ATCC BAA-334/TIGR4) GN = der PE = 3 SV = 1 − [DER_STRPN] | Intracellular |
| Q97N48 | 22.83 | 6 | 276 | 33.26 | Uncharacterized protein OS = *Streptococcus pneumoniae* serotype 4 (strain ATCC BAA-334/ TIGR4) GN = SP_2223 PE = 4 SV = 1 − [Q97N48_STRPN] | Intracellular/ TMH start AFTER 60 |
| Q97SJ5 | 22.98 | 7 | 409 | 32.72 | Capsular polysaccharide biosynthesis protein Cps4F OS = *Streptococcus pneumoniae* serotype 4 (strain ATCC BAA-334/TIGR4) GN = cps4F PE = 4 SV = 1 − [Q97SJ5_STRPN] | Multi-trans-membrane |
| P65832 | 36.73 | 6 | 275 | 32.69 | Pur operon repressor OS = *Streptococcus pneumoniae* serotype 4 (strain ATCC BAA-334/ TIGR4) GN = purR PE = 3 SV = 1 − [PURR_STRPN] | Intracellular |

TABLE 3-continued

Proteins identified in MV$_L$ from TIGR4. The accession numbers refer to SwissProt on the date of filing.

| Accession | Coverage | # Peptides | #AAs | Score | Desription | Localization |
|---|---|---|---|---|---|---|
| P63384 | 12.09 | 9 | 943 | 31.63 | UvrABC system protein A OS = *Streptococcus pneumoniae* serotype 4 (strain ATCC BAA-334/ TIGR4) GN = uvrA PE = 3 SV = 1 – [UVRA_STRPN] | Intracellular |
| I6L8W3 | 33.88 | 8 | 242 | 31.53 | Choline transporter OS = *Streptococcus pneumoniae* serotype 4 (strain ATCC BAA-334/TIGR4) GN = proV PE = 3 SV = 1 – [I6L8W3_STRPN] | Intracellular |
| Q9AHD2 | 40.97 | 8 | 227 | 31.44 | Tyrosine-protein kinase CpsD OS = *Streptococcus pneumoniae* serotype 4 (strain ATCC BAA-334/ TIGR4) GN = cpsD PE = 3 SV = 1 – [CPSD_STRPN] | Intracellular |
| O08397 | 23.84 | 8 | 453 | 31.17 | Chromosomal replication initiator protein DnaA OS = *Streptococcus pneumoniae* serotype 4 (strain ATCC BAA-334/TIGR4) GN = dnaA PE = 3 SV = 2 – [DNAA_STRPN] | Intracellular |
| Q97PT5 | 23.63 | 7 | 292 | 30.59 | ATP synthase gamma chain OS = *Streptococcus pneumoniae* serotype 4 (strain ATCC BAA-334/ TIGR4) GN = atpG PE = 3 SV = 1 – [ATPG_STRPN] | Intracellular |
| Q97PJ1 | 22.09 | 5 | 249 | 30.29 | Acyltransferase family protein OS = *Streptococcus pneumoniae* serotype 4 (strain ATCC BAA-334/ TIGR4) GN = SP_1624 PE = 4 SV = 1 – [Q97PJ1_STRPN] | Multi- trans- membrane |
| Q97NF6 | 14.36 | 6 | 564 | 30.07 | ABC transporter, ATP- binding/permease protein OS = *Streptococcus pneumoniae* serotype 4 (strain ATCC BAA-334/ TIGR4) GN = SP_2075 PE = 3 SV = 1 – [Q97NF6_STRPN] | Multi- trans- membrane |
| Q97PW8 | 18.36 | 6 | 414 | 30.06 | Putative oxidoreductase OS = *Streptococcus pneumoniae* serotype 4 (strain ATCC BAA-334/ TIGR4) GN = SP_1472 PE = 4 SV = 1 – [Q97PW8_STRPN] | Intracellular |
| Q97QT0 | 15.61 | 5 | 474 | 29.86 | Glyceraldehyde-3-phosphate dehydrogenase, NADP-dependent OS = *Streptococcus pneumoniae* serotype 4 (strain ATCC BAA-334/ TIGR4) GN = gapN PE = 3 SV = 1 – [Q97QT0_STRPN] | Intracellular |
| Q97PW6 | 12.24 | 6 | 678 | 29.5 | Glycine-tRNA ligase beta subunit OS = *Streptococcus pneumoniae* serotype 4 (strain ATCC BAA-334/ TIGR4) GN = glyS PE = 3 SV = 1 – [SYGB_STRPN] | Intracellular |
| Q97T93 | 25.93 | 8 | 432 | 29.32 | Adenylosuccinate lyase OS = *Streptococcus pneumoniae* serotype 4 (strain ATCC BAA-334/ TIGR4) GN = purB PE = 3 SV = 1 – [Q97T93_STRPN] | Intracellular |
| Q97RG3 | 5.68 | 2 | 229 | 29.15 | Putative membrane protein OS = *Streptococcus pneumoniae* serotype 4 (strain ATCC BAA-334/ TIGR4) GN = SP_0858 PE = 4 SV = 1 – [Q97RG3_STRPN] | Multi- trans- membrane |
| Q97TA6 | 12.42 | 3 | 330 | 28.21 | Phosphate acyltransferase OS = *Streptococcus pneumoniae* serotype 4 (strain ATCC BAA-334/ TIGR4) GN = plsX PE = 3 SV = 1 – [PLSX_STRPN] | Intracellular |
| Q97TA8 | 19.02 | 6 | 389 | 27.91 | Aromatic amino acid aminotransferase OS = *Streptococcus pneumoniae* serotype 4 (strain ATCC BAA-334/ TIGR4) GN = araT PE = 3 SV = 1 – [Q97TA8_STRPN] | Intracellular |
| P0A3B7 | 23.99 | 5 | 346 | 27.48 | Elongation factor Ts OS = *Streptococcus pneumoniae* serotype 4 (strain ATCC BAA-334/TIGR4) GN = tsf PE = 1 SV = 2 – [EFTS_STRPN] | Intracellular |

TABLE 3-continued

Proteins identified in MV$_L$ from TIGR4. The accession numbers refer to SwissProt on the date of filing.

| Accession | Coverage | # Peptides | #AAs | Score | Desription | Localization |
|---|---|---|---|---|---|---|
| I6L8Q7 | 20.99 | 4 | 324 | 27.27 | Enoyl-(Acyl-carrier-protein) reductase OS = *Streptococcus pneumoniae* serotype 4 (strain ATCC BAA-334/TIGR4) GN = fabK PE = 4 SV = 1 – [I6L8Q7_STRPN] | Intracellular |
| Q97SG5 | 9.38 | 5 | 778 | 26.77 | Endonuclease MutS2 OS = *Streptococcus pneumoniae* serotype 4 (strain ATCC BAA-334/TIGR4) GN = mutS2 PE = 3 SV = 1 – [MUTS2_STRPN] | Intracellular |
| Q97S79 | 15.4 | 5 | 487 | 26.69 | Type I restriction-modification system, M subunit OS = *Streptococcus pneumoniae* serotype 4 (strain ATCC BAA-334/TIGR4) GN = hsdM PE = 4 SV = 1 – [Q97S79_STRPN] | Intracellular |
| Q97SF8 | 12.78 | 4 | 454 | 26.54 | Aspartokinase OS = *Streptococcus pneumoniae* serotype 4 (strain ATCC BAA-334/TIGR4) GN = SP_0413 PE = 3 SV = 1 – [Q97SF8_STRPN] | Intracellular |
| Q97S89 | 19.1 | 5 | 398 | 26.46 | Phosphoglycerate kinase OS = *Streptococcus pneumoniae* serotype 4 (strain ATCC BAA-334/TIGR4) GN = pgk PE = 3 SV = 1 – [PGK_STRPN] | Intracellular |
| Q97QH0 | 22.14 | 6 | 429 | 26.44 | Signal recognition particle receptor FtsY OS = *Streptococcus pneumoniae* serotype 4 (strain ATCC BAA-334/TIGR4) GN = ftsY PE = 1 SV = 1 – [Q97QH0_STRPN] | Intracellular |
| P0CB59 | 5.83 | 3 | 326 | 26.31 | Phospho-N-acetylmuramoyl-pentapeptide-transferase OS = *Streptococcus pneumoniae* serotype 4 (strain ATCC BAA-334/TIGR4) GN = mraY PE = 3 SV = 1 – [MRAY_STRPN] | Multi-trans-membrane |
| Q97P92 | 23.64 | 5 | 368 | 26.11 | GTP-binding protein OS = *Streptococcus pneumoniae* serotype 4 (strain ATCC BAA-334/TIGR4) GN = SP_1749 PE = 4 SV = 1 – [Q97P92_STRPN] | Intracellular |
| P63733 | 20.06 | 6 | 359 | 25.98 | Carbamoyl-phosphate synthase small chain OS = *Streptococcus pneumoniae* serotype 4 (strain ATCC BAA-334/TIGR4) GN = carA PE = 3 SV = 1 – [CARA_STRPN] | Intracellular |
| Q97SP1 | 28.61 | 6 | 339 | 25.89 | Alcohol dehydrogenase, zinc-containing OS = *Streptococcus pneumoniae* serotype 4 (strain ATCC BAA-334/TIGR4) GN = SP_0285 PE = 3 SV = 1 – [Q97SP1_STRPN] | Intracellular |
| Q97PP2 | 19.92 | 4 | 256 | 25.75 | Uncharacterized protein OS = *Streptococcus pneumoniae* serotype 4 (strain ATCC BAA-334/TIGR4) GN = SP_1561 PE = 1 SV = 1 – [Q97PP2_STRPN] | Multi-trans-membrane |
| P66339 | 48.04 | 4 | 102 | 25.74 | 30S ribosomal protein S10 OS = *Streptococcus pneumoniae* serotype 4 (strain ATCC BAA-334/TIGR4) GN = rpsJ PE = 3 SV = 1 – [RS10_STRPN] | Intracellular |
| P0A335 | 13.52 | 6 | 540 | 25.62 | 60 kDa chaperonin OS = *Streptococcus pneumoniae* serotype 4 (strain ATCC BAA-334/TIGR4) GN = groL PE = 1 SV = 1 – [CH60_STRPN] | Intracellular |
| O07344 | 15.69 | 3 | 204 | 25.56 | Signal peptidase I OS = *Streptococcus pneumoniae* serotype 4 (strain ATCC BAA-334/TIGR4) GN = lepB PE = 3 SV = 2 – [LEP_STRPN] | N-terminally anchored (No CS) |
| Q97PP5 | 41.41 | 3 | 128 | 25.55 | Uncharacterized protein OS = *Streptococcus pneumoniae* serotype 4 (strain ATCC BAA-334/TIGR4) GN = SP_1558 PE = 1 SV = 1 – [Q97PP5_STRPN] | Intracellular |

TABLE 3-continued

Proteins identified in MV$_L$ from TIGR4. The accession numbers refer to SwissProt on the date of filing.

| Accession | Coverage | # Peptides | #AAs | Score | Desription | Localization |
|---|---|---|---|---|---|---|
| Q97RP7 | 15.75 | 2 | 254 | 25.33 | Branched-chain amino acid ABC transporter, ATP-binding protein OS = Streptococcus pneumoniae serotype 4 (strain ATCC BAA-334/ TIGR4) GN = livG PE = 3 SV = 1 − [Q97RP7_STRPN] | Intracellular |
| Q97Q12 | 13.37 | 5 | 486 | 24.99 | Nicotinate phosphoribosyltransferase OS = Streptococcus pneumoniae serotype 4 (strain ATCC BAA-334/ TIGR4) GN = SP_1421 PE = 3 SV = 1 − [Q97Q12_STRPN] | Intracellular |
| P67506 | 26.07 | 5 | 211 | 24.79 | tRNA (guanine-N(7)-)- methyltransferase OS = Streptococcus pneumoniae serotype 4 (strain ATCC BAA-334/TIGR4) GN = trmB PE = 1 SV = 1 − [TRMB_STRPN] | Intracellular |
| P66155 | 17.74 | 2 | 62 | 24.21 | 50S ribosomal protein L28 OS = Streptococcus pneumoniae serotype 4 (strain ATCC BAA-334/ TIGR4) GN = rpmB PE = 3 SV = 1 − [RL28_STRPN] | Intracellular |
| P66200 | 71.25 | 3 | 80 | 23.95 | 50S ribosomal protein L31 type B OS = Streptococcus pneumoniae serotype 4 (strain ATCC BAA-334/ TIGR4) GN = rpmE2 PE = 3 SV = 1 − [RL31B_STRPN] | Intracellular |
| Q97NH2 | 17.69 | 5 | 605 | 23.83 | Uncharacterized protein OS = Streptococcus pneumoniae serotype 4 (strain ATCC BAA-334/ TIGR4) GN = SP_2057 PE = 4 SV = 1 − [Q97NH2_STRPN] | Multi- trans- membrane |
| Q97PP4 | 12.89 | 4 | 450 | 23.67 | Phosphoglucosamine mutase OS = Streptococcus pneumoniae serotype 4 (strain ATCC BAA-334/ TIGR4) GN = glmM PE = 3 SV = 1 − [GLMM_STRPN] | Intracellular |
| Q97R44 | 50.43 | 4 | 115 | 23.65 | Uncharacterized protein OS = Streptococcus pneumoniae serotype 4 (strain ATCC BAA-334/ TIGR4) GN = SP_0990 PE = 4 SV = 1 − [Q97R44_STRPN] | Intracellular/ TMH start AFTER 60 |
| Q97QB4 | 15.18 | 4 | 448 | 23.57 | Glutamate dehydrogenase OS = Streptococcus pneumoniae serotype 4 (strain ATCC BAA-334/ TIGR4) GN = gdhA PE = 3 SV = 1 − [Q97QB4_STRPN] | Intracellular |
| Q97SW6 | 23.68 | 2 | 152 | 23.55 | Uncharacterized protein OS = Streptococcus pneumoniae serotype 4 (strain ATCC BAA-334/ TIGR4) GN = SP_0198 PE = 1 SV = 1 − [Q97SW6_STRPN] | Lipid anchored |
| Q97PW5 | 16.07 | 4 | 305 | 23.51 | Glycine-tRNA ligase alpha subunit OS = Streptococcus pneumoniae serotype 4 (strain ATCC BAA-334/ TIGR4) GN = glyQ PE = 3 SV = 1 − [SYGA_STRPN] | Intracellular |
| Q97Q69 | 19.63 | 5 | 428 | 23.47 | Homoserine dehydrogenase OS = Streptococcus pneumoniae serotype 4 (strain ATCC BAA-334/ TIGR4) GN = hom PE = 3 SV = 1 − [Q97Q69_STRPN] | Intracellular |
| Q97QT2 | 12.27 | 6 | 652 | 23.37 | DNA ligase OS = Streptococcus pneumoniae serotype 4 (strain ATCC BAA-334/TIGR4) GN = ligA PE = 3 SV = 1 − [DNLI_STRPN] | Intracellular |
| P0A4B3 | 33.72 | 3 | 86 | 23.26 | 30S ribosomal protein S17 OS = Streptococcus pneumoniae serotype 4 (strain ATCC BAA-334/ TIGR4) GN = rpsQ PE = 3 SV = 1 − [RS17_STRPN] | Intracellular |
| Q97NG0 | 14.92 | 4 | 449 | 23.07 | Glucose-6-phosphate isomerase OS = Streptococcus pneumoniae serotype 4 (strain ATCC BAA-334/ TIGR4) GN = pgi PE = 3 SV = 1 − [G6PI_STRPN] | Intracellular |

TABLE 3-continued

Proteins identified in MV$_L$ from TIGR4. The accession numbers refer to SwissProt on the date of filing.

| Accession | Coverage | # Peptides | #AAs | Score | Desription | Localization |
|---|---|---|---|---|---|---|
| Q97T58 | 14.41 | 3 | 354 | 22.73 | Conserved domain protein OS = Streptococcus pneumoniae serotype 4 (strain ATCC BAA-334/ TIGR4) GN = SP_0097 PE = 4 SV = 1 – [Q97T58_STRPN] | Multi-trans-membrane |
| Q97P32 | 16.46 | 4 | 407 | 22.04 | Tryptophan synthase beta chain OS = Streptococcus pneumoniae serotype 4 (strain ATCC BAA-334/ TIGR4) GN = trpB PE = 3 SV = 1 – [TRPB_STRPN] | Intracellular |
| Q97QX3 | 28.57 | 5 | 252 | 21.94 | ABC transporter, ATP-binding protein OS = Streptococcus pneumoniae serotype 4 (strain ATCC BAA-334/ TIGR4) GN = SP_1071 PE = 3 SV = 1 – [Q97QX3_STRPN] | Intracellular |
| Q97ST6 | 32.03 | 2 | 128 | 21.84 | 50S ribosomal protein L17 OS = Streptococcus pneumoniae serotype 4 (strain ATCC BAA-334/ TIGR4) GN = rplQ PE = 3 SV = 1 – [RL17_STRPN] | Intracellular |
| Q97RB6 | 8.74 | 5 | 709 | 21.38 | Putative transcriptional regulator OS = Streptococcus pneumoniae serotype 4 (strain ATCC BAA-334/ TIGR4) GN = SP_0908 PE = 4 SV = 1 – [Q97RB6_STRPN] | Intracellular |
| Q97NB9 | 17.91 | 4 | 335 | 21.02 | Uncharacterized protein OS = Streptococcus pneumoniae serotype 4 (strain ATCC BAA-334/ TIGR4) GN = SP_2132 PE = 4 SV = 1 – [Q97NB9_STRPN] | Multi-trans-membrane |
| P66524 | 37.93 | 3 | 58 | 20.52 | 30S ribosomal protein S21 OS = Streptococcus pneumoniae serotype 4 (strain ATCC BAA-334/ TIGR4) GN = rpsU PE = 3 SV = 1 – [RS21_STRPN] | Intracellular |
| Q97SI6 | 14.98 | 5 | 474 | 20.22 | 6-phosphogluconate dehydrogenase, decarboxylating OS = Streptococcus pneumoniae serotype 4 (strain ATCC BAA-334/TIGR4) GN = gnd PE = 3 SV = 1 – [Q97SI6_STRPN] | Intracellular |
| Q97R47 | 30.45 | 4 | 266 | 20.09 | Uncharacterized protein OS = Streptococcus pneumoniae serotype 4 (strain ATCC BAA-334/ TIGR4) GN = SP_0987 PE = 1 SV = 1 – [Q97R47_STRPN] | N-terminally anchored (No CS) |

TABLE 4

Proteins identified in MP from TIGR4. The accession numbers refer to SwissProt on the date of filing.

| Accession # | Coverage | # Peptides | #AAs | Score | Description | Localization |
|---|---|---|---|---|---|---|
| Q97RH0 | 76.86 | 46 | 350 | 2085.84 | Lipoprotein OS = Streptococcus pneumoniae serotype 4 (strain ATCC BAA-334/TIGR4) GN = SP_0845 PE = 4 SV = 1 - [Q97RH0_STRPN] | Lipid anchored |
| Q97PE6 | 90.27 | 56 | 442 | 1745.9 | Sugar ABC transporter, sugar-binding protein OS = Streptococcus pneumoniae serotype 4 (strain ATCC BAA-334/ TIGR4) GN = SP_1683 PE = 4 SV = 1 - [Q97PE6_STRPN] | Lipid anchored |
| Q97T39 | 61.29 | 50 | 744 | 1569.47 | Pneumococcal surface protein A OS = Streptococcus pneumoniae serotype 4 (strain ATCC BAA-334/ TIGR4) GN = pspA PE = 4 SV = 1 - [Q97T39_STRPN] | N-terminally anchored (with CS) |
| P59213 | 82.74 | 62 | 423 | 1500.08 | Maltose/maltodextrin-binding protein OS = Streptococcus pneumoniae serotype 4 (strain ATCC BAA-334/ TIGR4) GN = malX PE = 1 SV = 1 - [MALX_STRPN] | Lipid anchored |

TABLE 4-continued

Proteins identified in MP from TIGR4. The accession numbers refer to SwissProt on the date of filing.

| Accession # | Coverage | # Peptides | #AAs | Score | Description | Localization |
|---|---|---|---|---|---|---|
| Q97N74 | 53.25 | 47 | 693 | 1294.91 | Choline binding protein A OS = Streptococcus pneumoniae serotype 4 (strain ATCC BAA-334/ TIGR4) GN = cbpA PE = 1 SV = 1 - [Q97N74_STRPN] | N-terminally anchored (with CS) |
| Q97R51 | 87.86 | 45 | 313 | 1201.93 | Foldase protein PrsA OS = Streptococcus pneumoniae serotype 4 (strain ATCC BAA-334/ TIGR4) GN = prsA PE = 3 SV = 1 - [PRSA_STRPN] | Lipid anchored |
| Q54970 | 70.05 | 54 | 591 | 1000.77 | Pyruvate oxidase OS = Streptococcus pneumoniae serotype 4 (strain ATCC BAA-334/TIGR4) GN = spxB PE = 3 SV = 2 - [POXB_STRPN] | Intracellular |
| Q2MGF6 | 75.51 | 50 | 490 | 957.09 | Lysozyme OS = Streptococcus pneumoniae serotype 4 (strain ATCC BAA-334/TIGR4) GN = lytC PE = 4 SV = 1 - [Q2MGF6_STRPN] | Secretory (released) (with CS) |
| Q97PT1 | 77.13 | 52 | 551 | 947.11 | Uncharacterized protein OS = Streptococcus pneumoniae serotype 4 (strain ATCC BAA-334/ TIGR4) GN = SP_1518 PE = 4 SV = 1 - [Q97PT1_STRPN] | Intracellular/ TMH start AFTER 60 |
| Q97QS2 | 75.35 | 31 | 434 | 783.92 | Enolase OS = Streptococcus pneumoniae serotype 4 (strain ATCC BAA-334/TIGR4) GN = eno PE = 1 SV = 1 - [ENO_STRPN] | Intracellular |
| P64022 | 76.77 | 48 | 693 | 749.91 | Elongation factor G OS = Streptococcus pneumoniae serotype 4 (strain ATCC BAA-334/TIGR4) GN = fusA PE = 3 SV = 1 - [EFG_STRPN] | Intracellular |
| Q04707 | 72.6 | 47 | 719 | 715.79 | Penicillin-binding protein 1A OS = Streptococcus pneumoniae serotype 4 (strain ATCC BAA-334/ TIGR4) GN = ponA PE = 1 SV = 2 - [PBPA_STRPN] | N-terminally anchored (No CS) |
| P0C2J9 | 87.47 | 49 | 471 | 703.79 | Pneumolysin OS = Streptococcus pneumoniae serotype 4 (strain ATCC BAA-334/TIGR4) GN = ply PE = 3 SV = 1 - [TACY_STRPN] | Intracellular |
| Q97PE1 | 73.93 | 35 | 445 | 655.97 | ABC transporter, substrate-binding protein OS = Streptococcus pneumoniae serotype 4 (strain ATCC BAA-334/ TIGR4) GN = SP_1690 PE = 4 SV = 1 - [Q97PE1_STRPN] | Lipid anchored |
| Q97NQ8 | 61.8 | 68 | 1225 | 650.84 | DNA-directed RNA polymerase subunit beta' OS = Streptococcus pneumoniae serotype 4 (strain ATCC BAA-334/ TIGR4) GN = rpoC PE = 3 SV = 1 - [RPOC_STRPN] | Intracellular |
| Q97NL1 | 79.1 | 29 | 335 | 611.32 | Glyceraldehyde-3-phosphate dehydrogenase OS = Streptococcus pneumoniae serotype 4 (strain ATCC BAA-334/TIGR4) GN = gap PE = 3 SV = 1 - [Q97NL1_STRPN] | Intracellular |
| Q97T12 | 82.97 | 33 | 276 | 589.52 | ABC transporter, substrate-binding protein OS = Streptococcus pneumoniae serotype 4 (strain ATCC BAA-334/ TIGR4) GN = SP_0148 PE = 4 SV = 1 - [Q97T12_STRPN] | Lipid anchored |
| Q97T63 | 83.3 | 36 | 491 | 576.45 | ABC transporter, substrate-binding protein OS = Streptococcus pneumoniae serotype 4 (strain ATCC BAA-334/ TIGR4) GN = SP_0092 PE = 4 SV = 1 - [Q97T63_STRPN] | Lipid anchored |
| I6L8V7 | 44.02 | 33 | 627 | 457.19 | Choline binding protein E OS = Streptococcus pneumoniae serotype 4 (strain ATCC BAA-334/ TIGR4) GN = cbpE PE = 4 SV = 1 - [I6L8V7_STRPN] | Secretory (released) (with CS) |
| Q97NQ7 | 55.61 | 50 | 1203 | 449.03 | DNA-directed RNA polymerase subunit beta OS = Streptococcus pneumoniae serotype 4 (strain ATCC BAA-334/ TIGR4) GN = rpoB PE = 3 SV = 1 - [RPOB_STRPN] | Intracellular |

TABLE 4-continued

Proteins identified in MP from TIGR4. The accession numbers refer to SwissProt on the date of filing.

| Accession # | Coverage | # Peptides | #AAs | Score | Description | Localization |
|---|---|---|---|---|---|---|
| Q97SV2 | 64.62 | 18 | 277 | 395.51 | 50S ribosomal protein L2 OS = *Streptococcus pneumoniae* serotype 4 (strain ATCC BAA-334/TIGR4) GN = rplB PE = 3 SV = 1 - [RL2_STRPN] | Intracellular |
| P59205 | 60.33 | 29 | 658 | 388.39 | Putative endo-beta-N-acetylglucosaminidase OS = *Streptococcus pneumoniae* serotype 4 (strain ATCC BAA-334/TIGR4) GN = lytB PE = 1 SV = 1 - [LYTB_STRPN] | Secretory (released) (with CS) |
| O69076 | 55.98 | 31 | 652 | 385.64 | ATP-dependent zinc metalloprotease FtsH OS = *Streptococcus pneumoniae* serotype 4 (strain ATCC BAA-334/TIGR4) GN = ftsH PE = 3 SV = 3 - [FTSH_STRPN] | Multi-transmembrane |
| Q97SP2 | 67.47 | 25 | 332 | 369.57 | PTS system, mannose-specific IIAB components OS = *Streptococcus pneumoniae* serotype 4 (strain ATCC BAA-334/TIGR4) GN = manL PE = 4 SV = 1 - [Q97SP2_STRPN] | Intracellular |
| Q97T11 | 66.55 | 23 | 284 | 361.41 | Lipoprotein OS = *Streptococcus pneumoniae* serotype 4 (strain ATCC BAA-334/TIGR4) GN = SP_0149 PE = 3 SV = 1 - [Q97T11_STRPN] | Lipid anchored |
| I6L8Q3 | 52.65 | 17 | 340 | 354.19 | Choline binding protein F OS = *Streptococcus pneumoniae* serotype 4 (strain ATCC BAA-334/TIGR4) GN = cbpF PE = 4 SV = 1 - [I6L8Q3_STRPN] | N-terminally anchored (with CS) |
| Q97NX9 | 80.69 | 25 | 321 | 336.18 | Iron-compound ABC transporter, iron-compound-binding protein OS = *Streptococcus pneumoniae* serotype 4 (strain ATCC BAA-334/TIGR4) GN = SP_1872 PE = 4 SV = 1 - [Q97NX9_STRPN] | Lipid anchored |
| P64030 | 57.29 | 25 | 398 | 336.06 | Elongation factor Tu OS = *Streptococcus pneumoniae* serotype 4 (strain ATCC BAA-334/TIGR4) GN = tuf PE = 3 SV = 1 - [EFTU_STRPN] | Intracellular |
| Q97NW2 | 64.44 | 25 | 419 | 331.55 | Sugar ABC transporter, sugar-binding protein OS = *Streptococcus pneumoniae* serotype 4 (strain ATCC BAA-334/TIGR4) GN = rafE PE = 1 SV = 1 - [Q97NW2_STRPN] | Lipid anchored |
| Q97QH2 | 42.86 | 29 | 721 | 330.61 | Amino acid ABC transporter, amino acid-binding protein/permease protein OS = *Streptococcus pneumoniae* serotype 4 (strain ATCC BAA-334/TIGR4) GN = SP_1241 PE = 1 SV = 1 - [Q97QH2_STRPN] | Multi-transmembrane |
| Q97RS8 | 78.31 | 29 | 378 | 328.02 | Lactate oxidase OS = *Streptococcus pneumoniae* serotype 4 (strain ATCC BAA-334/TIGR4) GN = lctO-2 PE = 4 SV = 1 - [Q97RS8_STRPN] | Intracellular |
| Q97PW1 | 63.71 | 25 | 463 | 316.66 | Peptidoglycan N-acetylglucosamine deacetylase A OS = *Streptococcus pneumoniae* serotype 4 (strain ATCC BAA-334/TIGR4) GN = pgdA PE = 4 SV = 1 - [Q97PW1_STRPN] | N-terminally anchored (No CS) |
| Q97PT6 | 75.85 | 26 | 468 | 315.76 | ATP synthase subunit beta OS = *Streptococcus pneumoniae* serotype 4 (strain ATCC BAA-334/TIGR4) GN = atpD PE = 3 SV = 1 - [ATPB_STRPN] | Intracellular |
| Q97NQ3 | 58.55 | 22 | 345 | 310 | Uncharacterized protein OS = *Streptococcus pneumoniae* serotype 4 (strain ATCC BAA-334/TIGR4) GN = SP_1967 PE = 4 SV = 1 - [Q97NQ3_STRPN] | N-terminally anchored (No CS) |

TABLE 4-continued

Proteins identified in MP from TIGR4. The accession numbers refer to SwissProt on the date of filing.

| Accession # | Coverage | # Peptides | #AAs | Score | Description | Localization |
|---|---|---|---|---|---|---|
| Q97R09 | 58.94 | 17 | 341 | 309.62 | Iron-compound ABC transporter, iron compound-binding protein OS = Streptococcus pneumoniae serotype 4 (strain ATCC BAA-334/TIGR4) GN = SP_1032 PE = 1 SV = 1 - [Q97R09_STRPN] | Lipid anchored |
| P18791 | 69.8 | 28 | 659 | 298.67 | Oligopeptide-binding protein AmiA OS = Streptococcus pneumoniae serotype 4 (strain ATCC BAA-334/TIGR4) GN = amiA PE = 1 SV = 3 - [AMIA_STRPN] | Lipid anchored |
| Q97RZ7 | 63.03 | 15 | 238 | 283.45 | Uncharacterized protein OS = Streptococcus pneumoniae serotype 4 (strain ATCC BAA-334/TIGR4) GN = SP_0629 PE = 1 SV = 1 - [Q97RZ7_STRPN] | Lipid anchored |
| P0A4G2 | 65.05 | 18 | 309 | 281.58 | Manganese ABC transporter substrate-binding lipoprotein OS = Streptococcus pneumoniae serotype 4 (strain ATCC BAA-334/TIGR4) GN = psaA PE = 1 SV = 1 - [MTSA_STRPN] | Lipid anchored |
| P66112 | 60.5 | 10 | 119 | 280.56 | 50S ribosomal protein L20 OS = Streptococcus pneumoniae serotype 4 (strain ATCC BAA-334/TIGR4) GN = rplT PE = 3 SV = 1 - [RL20_STRPN] | Intracellular |
| Q97PM5 | 63.3 | 23 | 376 | 278.8 | Sugar ABC transporter, ATP-binding protein OS = Streptococcus pneumoniae serotype 4 (strain ATCC BAA-334/TIGR4) GN = msmK PE = 4 SV = 1 - [Q97PM5_STRPN] | Intracellular |
| P0A4M7 | 41.57 | 23 | 498 | 271.04 | Oligopeptide transport system permease protein AmiC OS = Streptococcus pneumoniae serotype 4 (strain ATCC BAA-334/TIGR4) GN = amiC PE = 3 SV = 1 - [AMIC_STRPN] | Multi-transmembrane |
| Q97SP4 | 48.18 | 12 | 303 | 262.56 | PTS system, mannose-specific IID component OS = Streptococcus pneumoniae serotype 4 (strain ATCC BAA-334/TIGR4) GN = SP_0282 PE = 4 SV = 1 - [Q97SP4_STRPN] | Multi-transmembrane |
| Q97NL3 | 60.74 | 34 | 731 | 258.29 | Penicillin-binding protein 2A OS = Streptococcus pneumoniae serotype 4 (strain ATCC BAA-334/TIGR4) GN = pbp2A PE = 4 SV = 1 - [Q97NL3_STRPN] | N-terminally anchored (No CS) |
| P14677 | 61.33 | 32 | 750 | 257.72 | Penicillin-binding protein 2x OS = Streptococcus pneumoniae serotype 4 (strain ATCC BAA-334/TIGR4) GN = pbpX PE = 1 SV = 2 - [PBPX_STRPN] | N-terminally anchored (No CS) |
| Q97PT4 | 38.92 | 21 | 501 | 249.37 | ATP synthase subunit alpha OS = Streptococcus pneumoniae serotype 4 (strain ATCC BAA-334/TIGR4) GN = atpA PE = 3 SV = 1 - [ATPA_STRPN] | Multi-transmembrane |
| Q97NB5 | 52.66 | 30 | 621 | 236.54 | Choline binding protein PcpA OS = Streptococcus pneumoniae serotype 4 (strain ATCC BAA-334/TIGR4) GN = pcpA PE = 1 SV = 1 - [Q97NB5_STRPN] | Secretory (released) (with CS) |
| Q97PQ2 | 33.26 | 21 | 914 | 236.23 | Cation-transporting ATPase, E1-E2 family OS = Streptococcus pneumoniae serotype 4 (strain ATCC BAA-334/TIGR4) GN = SP_1551 PE = 3 SV = 1 - [Q97PQ2_STRPN] | Multi-transmembrane |
| P0A475 | 50.36 | 8 | 137 | 229.6 | 50S ribosomal protein L16 OS = Streptococcus pneumoniae serotype 4 (strain ATCC BAA-334/TIGR4) GN = rplP PE = 1 SV = 1 - [RL16_STRPN] | Intracellular |

TABLE 4-continued

Proteins identified in MP from TIGR4. The accession numbers refer to SwissProt on the date of filing.

| Accession # | Coverage | # Peptides | #AAs | Score | Description | Localization |
|---|---|---|---|---|---|---|
| Q97PU3 | 64.03 | 23 | 278 | 227.7 | Amino acid ABC transporter, amino acid-binding protein OS = Streptococcus pneumoniae serotype 4 (strain ATCC BAA-334/TIGR4) GN = aatB PE = 4 SV = 1 - [Q97PU3_STRPN] | Lipid anchored |
| Q97RC5 | 50.3 | 20 | 501 | 223.13 | Pyruvate kinase OS = Streptococcus pneumoniae serotype 4 (strain ATCC BAA-334/TIGR4) GN = pyk PE = 3 SV = 1 - [Q97RC5_STRPN] | Intracellular |
| Q97NS5 | 65.68 | 19 | 338 | 221.3 | Putative transcriptional regulator OS = Streptococcus pneumoniae serotype 4 (strain ATCC BAA-334/TIGR4) GN = SP_1942 PE = 4 SV = 1 - [Q97NS5_STRPN] | Secretory (released) (with CS) |
| Q97RP4 | 75.22 | 14 | 230 | 213.93 | Cell division ABC transporter, ATP-binding protein FtsE OS = Streptococcus pneumoniae serotype 4 (strain ATCC BAA-334/TIGR4) GN = ftsE PE = 3 SV = 1 - [Q97RP4_STRPN] | Intracellular |
| Q97RN2 | 66.67 | 13 | 267 | 207.19 | Peptidyl-prolyl cis-trans isomerase, cyclophilin-type OS = Streptococcus pneumoniae serotype 4 (strain ATCC BAA-334/TIGR4) GN = SP_0771 PE = 3 SV = 1 - [Q97RN2_STRPN] | Lipid anchored |
| P66565 | 61.58 | 21 | 203 | 205.82 | 30S ribosomal protein S4 OS = Streptococcus pneumoniae serotype 4 (strain ATCC BAA-334/TIGR4) GN = rpsD PE = 3 SV = 1 - [RS4_STRPN] | Intracellular |
| Q97QH1 | 61.79 | 10 | 246 | 202.96 | Amino acid ABC transporter, ATP-binding protein OS = Streptococcus pneumoniae serotype 4 (strain ATCC BAA-334/TIGR4) GN = SP_1242 PE = 3 SV = 1 - [Q97QH1_STRPN] | Intracellular |
| I6L8N9 | 40.91 | 18 | 506 | 201.9 | Choline transporter OS = Streptococcus pneumoniae serotype 4 (strain ATCC BAA-334/TIGR4) GN = proWX PE = 3 SV = 1 - [I6L8N9_STRPN] | Multi-transmembrane |
| Q97N69 | 55.22 | 15 | 335 | 201.71 | Putative ABC transporter, substrate-binding protein OS = Streptococcus pneumoniae serotype 4 (strain ATCC BAA-334/TIGR4) GN = SP_2197 PE = 4 SV = 1 - [Q97N69_STRPN] | Lipid anchored |
| P65887 | 53.97 | 23 | 428 | 199.01 | Adenylosuccinate synthetase OS = Streptococcus pneumoniae serotype 4 (strain ATCC BAA-334/TIGR4) GN = purA PE = 1 SV = 1 - [PURA_STRPN] | Intracellular |
| P18766 | 60.71 | 13 | 308 | 198.48 | Oligopeptide transport ATP-binding protein AmiF OS = Streptococcus pneumoniae serotype 4 (strain ATCC BAA-334/TIGR4) GN = amiF PE = 3 SV = 2 - [AMIF_STRPN] | Intracellular |
| Q97QB4 | 61.83 | 23 | 448 | 197.42 | Glutamate dehydrogenase OS = Streptococcus pneumoniae serotype 4 (strain ATCC BAA-334/TIGR4) GN = gdhA PE = 3 SV = 1 - [Q97QB4_STRPN] | Intracellular |
| Q97SP5 | 55.18 | 19 | 444 | 196.27 | Aminopeptidase C OS = Streptococcus pneumoniae serotype 4 (strain ATCC BAA-334/TIGR4) GN = pepC PE = 4 SV = 1 - [Q97SP5_STRPN] | Intracellular |
| Q97RP3 | 40.58 | 17 | 308 | 193.01 | Cell division protein FtsX OS = Streptococcus pneumoniae serotype 4 (strain ATCC BAA-334/TIGR4) GN = ftsX PE = 3 SV = 1 - [Q97RP3_STRPN] | Multi-transmembrane |
| Q97T46 | 36.84 | 5 | 95 | 189.78 | Putative bacteriocin OS = Streptococcus pneumoniae serotype 4 (strain ATCC BAA-334/TIGR4) GN = SP_0109 PE = 4 SV = 1 - [Q97T46_STRPN] | Secretory (released) (no CS) |

TABLE 4-continued

Proteins identified in MP from TIGR4. The accession numbers refer to SwissProt on the date of filing.

| Accession # | Coverage | # Peptides | #AAs | Score | Description | Localization |
|---|---|---|---|---|---|---|
| Q97PD6 | 51.85 | 31 | 837 | 188.69 | Protein translocase subunit SecA 1 OS = *Streptococcus pneumoniae* serotype 4 (strain ATCC BAA-334/TIGR4) GN = secA1 PE = 3 SV = 1 - [SECA1_STRPN] | Intracellular |
| P0A4A7 | 60.58 | 13 | 137 | 187.87 | 30S ribosomal protein S12 OS = *Streptococcus pneumoniae* serotype 4 (strain ATCC BAA-334/TIGR4) GN = rpsL PE = 3 SV = 1 - [RS12_STRPN] | Intracellular |
| P0A2U8 | 52.96 | 20 | 355 | 185.88 | Oligopeptide transport ATP-binding protein AmiE OS = *Streptococcus pneumoniae* serotype 4 (strain ATCC BAA-334/TIGR4) GN = amiE PE = 3 SV = 1 - [AMIE_STRPN] | Intracellular |
| Q97RQ0 | 70.21 | 18 | 386 | 182.7 | Branched-chain amino acid ABC transporter, amino acid-binding protein OS = *Streptococcus pneumoniae* serotype 4 (strain ATCC BAA-334/TIGR4) GN = livJ PE = 4 SV = 1 - [Q97RQ0_STRPN] | Lipid anchored |
| P0A3M9 | 67.68 | 16 | 328 | 176.61 | L-lactate dehydrogenase OS = *Streptococcus pneumoniae* serotype 4 (strain ATCC BAA-334/TIGR4) GN = ldh PE = 3 SV = 2 - [LDH_STRPN] | Intracellular |
| Q97RG9 | 49.51 | 20 | 511 | 174.4 | Sugar ABC transporter, ATP-binding protein OS = *Streptococcus pneumoniae* serotype 4 (strain ATCC BAA-334/TIGR4) GN = SP_0846 PE = 3 SV = 1 - [Q97RG9_STRPN] | Intracellular |
| P0A3M5 | 43.38 | 22 | 680 | 166.84 | Penicillin-binding protein 2B OS = *Streptococcus pneumoniae* serotype 4 (strain ATCC BAA-334/TIGR4) GN = penA PE = 3 SV = 1 - [PBP2_STRPN] | N-terminally anchored (No CS) |
| Q97N53 | 63.24 | 12 | 272 | 163.14 | Cell shape-determining protein MreC OS = *Streptococcus pneumoniae* serotype 4 (strain ATCC BAA-334/TIGR4) GN = mreC PE = 3 SV = 1 - [Q97N53_STRPN] | N-terminally anchored (No CS) |
| P95829 | 49.26 | 20 | 607 | 161.66 | Chaperone protein DnaK OS = *Streptococcus pneumoniae* serotype 4 (strain ATCC BAA-334/TIGR4) GN = dnaK PE = 3 SV = 2 - [DNAK_STRPN] | Intracellular |
| Q97SI9 | 67.89 | 7 | 109 | 156.35 | Cell cycle protein GpsB OS = *Streptococcus pneumoniae* serotype 4 (strain ATCC BAA-334/TIGR4) GN = gpsB PE = 3 SV = 1 - [GPSB_STRPN] | Intracellular |
| Q97NE4 | 36.3 | 26 | 821 | 153.09 | Penicillin-binding protein 1B OS = *Streptococcus pneumoniae* serotype 4 (strain ATCC BAA-334/TIGR4) GN = pbp1B PE = 4 SV = 1 - [Q97NE4_STRPN] | N-terminally anchored (No CS) |
| I6L8W3 | 71.49 | 15 | 242 | 152.01 | Choline transporter OS = *Streptococcus pneumoniae* serotype 4 (strain ATCC BAA-334/TIGR4) GN = proV PE = 3 SV = 1 - [I6L8W3_STRPN] | Intracellular |
| P0A335 | 52.04 | 21 | 540 | 151.44 | 60 kDa chaperonin OS = *Streptococcus pneumoniae* serotype 4 (strain ATCC BAA-334/TIGR4) GN = groL PE = 1 SV = 1 - [CH60_STRPN] | Intracellular |
| Q97NG0 | 44.77 | 17 | 449 | 145.04 | Glucose-6-phosphate isomerase OS = *Streptococcus pneumoniae* serotype 4 (strain ATCC BAA-334/TIGR4) GN = pgi PE = 3 SV = 1 - [G6PI_STRPN] | Intracellular |
| Q97Q31 | 57.53 | 12 | 292 | 143.85 | Phosphate-binding protein PstS 1 OS = *Streptococcus pneumoniae* serotype 4 (strain ATCC BAA-334/TIGR4) GN = pstS1 PE = 1 SV = 1 - [PSTS1_STRPN] | Lipid anchored |

TABLE 4-continued

Proteins identified in MP from TIGR4. The accession numbers refer to SwissProt on the date of filing.

| Accession # | Coverage | # Peptides | #AAs | Score | Description | Localization |
|---|---|---|---|---|---|---|
| Q97RW9 | 51.81 | 16 | 332 | 139.95 | Putative pneumococcal surface protein OS = Streptococcus pneumoniae serotype 4 (strain ATCC BAA-334/ TIGR4) GN = SP_0667 PE = 1 SV = 1 - [Q97RW9_STRPN] | Lipid anchored |
| P22976 | 44.98 | 18 | 658 | 139.63 | Probable transketolase OS = Streptococcus pneumoniae serotype 4 (strain ATCC BAA-334/ TIGR4) GN = tkt PE = 3 SV = 2 - [TKT_STRPN] | Intracellular |
| Q97SQ9 | 42.52 | 17 | 602 | 138.65 | Glutamine--fructose-6-phosphate aminotransferase [isomerizing] OS = Streptococcus pneumoniae serotype 4 (strain ATCC BAA-334/ TIGR4) GN = glmS PE = 3 SV = 3 - [GLMS_STRPN] | Intracellular |
| Q97PA9 | 33.84 | 18 | 659 | 132.79 | Serine/threonine-protein kinase StkP OS = Streptococcus pneumoniae serotype 4 (strain ATCC BAA-334/ TIGR4) GN = stkP PE = 1 SV = 1 - [STKP2_STRPN] | Intracellular/ TMH start AFTER 60 |
| Q97Q34 | 70.41 | 18 | 267 | 131.91 | Phosphate import ATP-binding protein PstB 2 OS = Streptococcus pneumoniae serotype 4 (strain ATCC BAA-334/ TIGR4) GN = pstB2 PE = 3 SV = 1 - [PSTB_STRPN] | Intracellular |
| Q97QX5 | 55.81 | 14 | 344 | 130.66 | Uncharacterized protein OS = Streptococcus pneumoniae serotype 4 (strain ATCC BAA-334/ TIGR4) GN = SP_1069 PE = 1 SV = 1 - [Q97QX5_STRPN] | Secretory (released) (with CS) |
| I6L8V0 | 55.84 | 18 | 351 | 130.62 | Capsular polysaccharide biosynthesis protein Cps4J OS = Streptococcus pneumoniae serotype 4 (strain ATCC BAA-334/TIGR4) GN = cap4J PE = 4 SV = 1 - [I6L8V0_STRPN] | Intracellular |
| Q97SD1 | 43.38 | 17 | 521 | 119.96 | Amino acid ABC transporter, amino acid-binding protein/permease protein OS = Streptococcus pneumoniae serotype 4 (strain ATCC BAA-334/ TIGR4) GN = SP_0453 PE = 4 SV = 1 - [Q97SD1_STRPN] | Multi-transmembrane |
| Q97SR1 | 50.73 | 21 | 617 | 119.02 | Proline--tRNA ligase OS = Streptococcus pneumoniae serotype 4 (strain ATCC BAA-334/TIGR4) GN = proS PE = 3 SV = 1 - [SYP_STRPN] | Intracellular |
| P0A4D7 | 36.07 | 14 | 524 | 117.93 | DEAD-box ATP-dependent RNA helicase CshA OS = Streptococcus pneumoniae serotype 4 (strain ATCC BAA-334/TIGR4) GN = cshA PE = 3 SV = 1 - [CSHA_STRPN] | Intracellular |
| Q97P40 | 68.81 | 12 | 202 | 117.92 | Putative general stress protein 24 OS = Streptococcus pneumoniae serotype 4 (strain ATCC BAA-334/ TIGR4) GN = SP_1804 PE = 4 SV = 1 - [Q97P40_STRPN] | Intracellular |
| Q97NK0 | 41 | 21 | 883 | 117.4 | Aldehyde-alcohol dehydrogenase OS = Streptococcus pneumoniae serotype 4 (strain ATCC BAA-334/ TIGR4) GN = SP_2026 PE = 3 SV = 1 - [Q97NK0_STRPN] | Intracellular |
| Q97N99 | 51.82 | 14 | 274 | 115.56 | SPFH domain/Band 7 family OS = Streptococcus pneumoniae serotype 4 (strain ATCC BAA-334/ TIGR4) GN = SP_2156 PE = 4 SV = 1 - [Q97N99_STRPN] | Intracellular |
| Q9L7Q2 | 17.63 | 23 | 1906 | 114.8 | Zinc metalloprotease ZmpB OS = Streptococcus pneumoniae serotype 4 (strain ATCC BAA-334/ TIGR4) GN = zmpB PE = 3 SV = 2 - [ZMPB_STRPN] | Multi-transmembrane |

TABLE 4-continued

Proteins identified in MP from TIGR4. The accession numbers refer to SwissProt on the date of filing.

| Accession # | Coverage | # Peptides | #AAs | Score | Description | Localization |
|---|---|---|---|---|---|---|
| P67293 | 43.9 | 4 | 82 | 114.56 | UPF0154 protein SP_1882 OS = Streptococcus pneumoniae serotype 4 (strain ATCC BAA-334/ TIGR4) GN = SP_1882 PE = 3 SV = 1 - [Y1882_STRPN] | N-terminally anchored (No CS) |
| Q97N37 | 61.83 | 14 | 393 | 114.16 | Serine protease OS = Streptococcus pneumoniae serotype 4 (strain ATCC BAA-334/TIGR4) GN = SP_2239 PE = 1 SV = 1 - [Q97N37_STRPN] | N-terminally anchored (No CS) |
| P66359 | 55.12 | 8 | 127 | 112.68 | 30S ribosomal protein S11 OS = Streptococcus pneumoniae serotype 4 (strain ATCC BAA-334/ TIGR4) GN = rpsK PE = 3 SV = 1 - [RS11_STRPN] | Intracellular |
| Q97PX1 | 30.72 | 12 | 459 | 110.91 | NADH oxidase OS = Streptococcus pneumoniae serotype 4 (strain ATCC BAA-334/TIGR4) GN = nox PE = 4 SV = 1 - [Q97PX1_STRPN] | Intracellular |
| P35592 | 43.64 | 21 | 660 | 109.44 | Oligopeptide-binding protein AliA OS = Streptococcus pneumoniae serotype 4 (strain ATCC BAA-334/ TIGR4) GN = aliA PE = 3 SV = 4 - [ALIA_STRPN] | Lipid anchored |
| Q97PC4 | 28.66 | 11 | 492 | 108.41 | ABC transporter, ATP-binding protein OS = Streptococcus pneumoniae serotype 4 (strain ATCC BAA-334/ TIGR4) GN = SP_1715 PE = 4 SV = 1 - [Q97PC4_STRPN] | Multi-transmembrane |
| Q97P68 | 69.23 | 8 | 104 | 104.87 | Thioredoxin OS = Streptococcus pneumoniae serotype 4 (strain ATCC BAA-334/TIGR4) GN = trx PE = 3 SV = 1 - [Q97P68_STRPN] | Intracellular |
| Q97PL8 | 41.55 | 12 | 438 | 101 | Oxidoreductase, pyridine nucleotide-disulfide, class I OS = Streptococcus pneumoniae serotype 4 (strain ATCC BAA-334/TIGR4) GN = SP_1588 PE = 3 SV = 1 - [Q97PL8_STRPN] | Intracellular |
| Q97SX2 | 68.78 | 17 | 189 | 97.17 | Uncharacterized protein OS = Streptococcus pneumoniae serotype 4 (strain ATCC BAA-334/ TIGR4) GN = SP_0191 PE = 1 SV = 1 - [Q97SX2_STRPN] | Lipid anchored |
| P63413 | 43.94 | 14 | 396 | 96.43 | Acetate kinase OS = Streptococcus pneumoniae serotype 4 (strain ATCC BAA-334/TIGR4) GN = ackA PE = 3 SV = 1 - [ACKA_STRPN] | Intracellular |
| Q97SJ6 | 52.61 | 11 | 230 | 96.34 | Capsular polysaccharide biosynthesis protein CpsC OS = Streptococcus pneumoniae serotype 4 (strain ATCC BAA-334/TIGR4) GN = cpsC PE = 3 SV = 1 - [CPSC_STRPN] | Multi-transmembrane |
| Q97Q67 | 38.08 | 11 | 344 | 95.87 | Conserved domain protein OS = Streptococcus pneumoniae serotype 4 (strain ATCC BAA-334/ TIGR4) GN = SP_1363 PE = 4 SV = 1 - [Q97Q67_STRPN] | Multi-transmembrane |
| P0A4S1 | 49.15 | 10 | 293 | 93.48 | Fructose-bisphosphate aldolase OS = Streptococcus pneumoniae serotype 4 (strain ATCC BAA-334/ TIGR4) GN = fba PE = 3 SV = 1 - [ALF_STRPN] | Intracellular |
| Q97SR2 | 37.71 | 11 | 419 | 93.31 | Putative zinc metalloprotease SP_0263 OS = Streptococcus pneumoniae serotype 4 (strain ATCC BAA-334/TIGR4) GN = SP_0263 PE = 3 SV = 1 - [Y263_STRPN] | Multi-transmembrane |
| Q97NP5 | 25.65 | 9 | 308 | 92.53 | Membrane protein insertase YidC 1 OS = Streptococcus pneumoniae serotype 4 (strain ATCC BAA-334/ TIGR4) GN = yidC1 PE = 3 SV = 1 - [YIDC1_STRPN] | Multi-transmembrane |

TABLE 4-continued

Proteins identified in MP from TIGR4. The accession numbers refer to SwissProt on the date of filing.

| Accession # | Coverage | # Peptides | #AAs | Score | Description | Localization |
|---|---|---|---|---|---|---|
| Q97SJ4 | 44.44 | 15 | 360 | 91.77 | Uncharacterized protein OS = *Streptococcus pneumoniae* serotype 4 (strain ATCC BAA-334/TIGR4) GN = SP_0355 PE = 4 SV = 1 - [Q97SJ4_STRPN] | Intracellular |
| Q97RK0 | 19.83 | 10 | 575 | 91.07 | Septation ring formation regulator EzrA OS = *Streptococcus pneumoniae* serotype 4 (strain ATCC BAA-334/TIGR4) GN = ezrA PE = 3 SV = 1 - [EZRA_STRPN] | N-terminally anchored (No CS) |
| P63373 | 71.43 | 11 | 252 | 91.01 | Phosphate import ATP-binding protein PstB 1 OS = *Streptococcus pneumoniae* serotype 4 (strain ATCC BAA-334/TIGR4) GN = pstB1 PE = 3 SV = 1 - [PSTB1_STRPN] | Intracellular |
| Q97S89 | 51.01 | 13 | 398 | 89.47 | Phosphoglycerate kinase OS = *Streptococcus pneumoniae* serotype 4 (strain ATCC BAA-334/TIGR4) GN = pgk PE = 3 SV = 1 - [PGK_STRPN] | Intracellular |
| Q97PT5 | 47.26 | 12 | 292 | 85.91 | ATP synthase gamma chain OS = *Streptococcus pneumoniae* serotype 4 (strain ATCC BAA-334/TIGR4) GN = atpG PE = 3 SV = 1 - [ATPG_STRPN] | Intracellular |
| Q97SI4 | 32.65 | 9 | 340 | 85.66 | Choline binding protein C OS = *Streptococcus pneumoniae* serotype 4 (strain ATCC BAA-334/TIGR4) GN = cbpC PE = 4 SV = 1 - [Q97SI4_STRPN] | N-terminally anchored (with CS) |
| I6L8S8 | 39.71 | 14 | 481 | 85.62 | Capsular polysaccharide biosynthesis protein Cps4A OS = *Streptococcus pneumoniae* serotype 4 (strain ATCC BAA-334/TIGR4) GN = cps4A PE = 4 SV = 1 - [I6L8S8_STRPN] | Multi-transmembrane |
| Q97PY0 | 65.59 | 13 | 247 | 85.07 | Amino acid ABC transporter, ATP-binding protein OS = *Streptococcus pneumoniae* serotype 4 (strain ATCC BAA-334/TIGR4) GN = SP_1460 PE = 3 SV = 1 - [Q97PY0_STRPN] | Intracellular |
| Q97SQ4 | 46.79 | 9 | 156 | 83.39 | 30S ribosomal protein S7 OS = *Streptococcus pneumoniae* serotype 4 (strain ATCC BAA-334/TIGR4) GN = rpsG PE = 3 SV = 1 - [RS7_STRPN] | Intracellular |
| P0A3Y3 | 60 | 10 | 230 | 82.54 | 2,3-bisphosphoglycerate-dependent phosphoglycerate mutase OS = *Streptococcus pneumoniae* serotype 4 (strain ATCC BAA-334/TIGR4) GN = gpmA PE = 3 SV = 1 - [GPMA_STRPN] | Intracellular |
| P0A4C3 | 59.91 | 11 | 217 | 82.05 | 30S ribosomal protein S3 OS = *Streptococcus pneumoniae* serotype 4 (strain ATCC BAA-334/TIGR4) GN = rpsC PE = 3 SV = 1 - [RS3_STRPN] | Intracellular |
| P65607 | 38.46 | 11 | 338 | 79.74 | Ornithine carbamoyltransferase, catabolic OS = *Streptococcus pneumoniae* serotype 4 (strain ATCC BAA-334/TIGR4) GN = arcB PE = 3 SV = 1 - [OTCC_STRPN] | Intracellular |
| O05703 | 39.92 | 12 | 501 | 79.68 | Zinc-binding lipoprotein AdcA OS = *Streptococcus pneumoniae* serotype 4 (strain ATCC BAA-334/TIGR4) GN = adcA PE = 3 SV = 4 - [ADCA_STRPN] | Lipid anchored |
| I6L8U0 | 27.16 | 11 | 394 | 79.39 | UDP-N-acetylglucosamine 2-epimerase OS = *Streptococcus pneumoniae* serotype 4 (strain ATCC BAA-334/TIGR4) GN = cps4L PE = 3 SV = 1 - [I6L8U0_STRPN] | Intracellular |

TABLE 4-continued

Proteins identified in MP from TIGR4. The accession numbers refer to SwissProt on the date of filing.

| Accession # | Coverage | # Peptides | #AAs | Score | Description | Localization |
|---|---|---|---|---|---|---|
| Q97SI7 | 28.23 | 8 | 464 | 78.19 | Mid-cell-anchored protein Z OS = *Streptococcus pneumoniae* serotype 4 (strain ATCC BAA-334/TIGR4) GN = mapZ PE = 1 SV = 1 - [Q97SI7_STRPN] | Intracellular |
| Q97N56 | 58.3 | 15 | 259 | 78.07 | 30S ribosomal protein S2 OS = *Streptococcus pneumoniae* serotype 4 (strain ATCC BAA-334/TIGR4) GN = rpsB PE = 3 SV = 1 - [RS2_STRPN] | Intracellular |
| Q97SI6 | 35.44 | 13 | 474 | 77.15 | 6-phosphogluconate dehydrogenase, decarboxylating OS = *Streptococcus pneumoniae* serotype 4 (strain ATCC BAA-334/TIGR4) GN = gnd PE = 3 SV = 1 - [Q97SI6_STRPN] | Intracellular |
| Q97PG0 | 27.1 | 7 | 262 | 77.07 | Cell division protein DivIVA OS = *Streptococcus pneumoniae* serotype 4 (strain ATCC BAA-334/TIGR4) GN = divIVA PE = 4 SV = 1 - [Q97PG0_STRPN] | Intracellular |
| Q97RF9 | 32 | 11 | 400 | 76.46 | Ribosomal protein S1 OS = *Streptococcus pneumoniae* serotype 4 (strain ATCC BAA-334/TIGR4) GN = rpsA PE = 4 SV = 1 - [Q97RF9_STRPN] | Intracellular |
| Q97T80 | 15.68 | 17 | 1856 | 76.28 | Zinc metalloprotease ZmpC OS = *Streptococcus pneumoniae* serotype 4 (strain ATCC BAA-334/TIGR4) GN = zmpC PE = 3 SV = 1 - [ZMPC_STRPN] | LPxTG Cell-wall anchored |
| P0A2Z2 | 62.8 | 9 | 164 | 75.56 | ATP synthase subunit b OS = *Streptococcus pneumoniae* serotype 4 (strain ATCC BAA-334/TIGR4) GN = atpF PE = 3 SV = 1 - [ATPF_STRPN] | Intracellular |
| I6L8S9 | 47.7 | 10 | 413 | 73.22 | D-alanyl-D-alanine carboxypeptidase OS = *Streptococcus pneumoniae* serotype 4 (strain ATCC BAA-334/TIGR4) GN = dacA PE = 3 SV = 1 - [I6L8S9_STRPN] | N-terminally anchored (with CS) |
| Q97PU4 | 80 | 7 | 115 | 71.8 | Bacterocin transport accessory protein OS = *Streptococcus pneumoniae* serotype 4 (strain ATCC BAA-334/TIGR4) GN = bta PE = 4 SV = 1 - [Q97PU4_STRPN] | Intracellular |
| Q97SU6 | 70.34 | 7 | 118 | 71.64 | 50S ribosomal protein L18 OS = *Streptococcus pneumoniae* serotype 4 (strain ATCC BAA-334/TIGR4) GN = rplR PE = 3 SV = 1 - [RL18_STRPN] | Intracellular |
| P63742 | 35.46 | 11 | 502 | 71.21 | Glycerol kinase OS = *Streptococcus pneumoniae* serotype 4 (strain ATCC BAA-334/TIGR4) GN = glpK PE = 3 SV = 1 - [GLPK_STRPN] | Intracellular |
| Q97SN4 | 32.31 | 6 | 130 | 68.89 | 30S ribosomal protein S9 OS = *Streptococcus pneumoniae* serotype 4 (strain ATCC BAA-334/TIGR4) GN = rpsI PE = 3 SV = 1 - [RS9_STRPN] | Intracellular |
| P66907 | 31.84 | 6 | 380 | 68.13 | Queuine tRNA-ribosyltransferase OS = *Streptococcus pneumoniae* serotype 4 (strain ATCC BAA-334/TIGR4) GN = tgt PE = 3 SV = 1 - [TGT_STRPN] | Intracellular |
| Q97SF8 | 32.16 | 12 | 454 | 65.06 | Aspartokinase OS = *Streptococcus pneumoniae* serotype 4 (strain ATCC BAA-334/TIGR4) GN = SP_0413 PE = 3 SV = 1 - [Q97SF8_STRPN] | Intracellular |
| P0A471 | 82.79 | 9 | 122 | 62.07 | 50S ribosomal protein L7/L12 OS = *Streptococcus pneumoniae* serotype 4 (strain ATCC BAA-334/TIGR4) GN = rplL PE = 1 SV = 2 - [RL7_STRPN] | Intracellular |

TABLE 4-continued

Proteins identified in MP from TIGR4. The accession numbers refer to SwissProt on the date of filing.

| Accession # | Coverage | # Peptides | #AAs | Score | Description | Localization |
|---|---|---|---|---|---|---|
| I6L8W8 | 21.08 | 8 | 332 | 61.96 | Choline binding protein J OS = *Streptococcus pneumoniae* serotype 4 (strain ATCC BAA-334/TIGR4) GN = cbpJ PE = 4 SV = 1 - [I6L8W8_STRPN] | N-terminally anchored (with CS) |
| P0A4J6 | 40.8 | 5 | 201 | 61.71 | Superoxide dismutase [Mn] OS = *Streptococcus pneumoniae* serotype 4 (strain ATCC BAA-334/TIGR4) GN = sodA PE = 1 SV = 2 - [SODM_STRPN] | Intracellular |
| Q97T52 | 30.03 | 14 | 616 | 60.5 | Putative capsular polysaccharide biosynthesis protein OS = *Streptococcus pneumoniae* serotype 4 (strain ATCC BAA-334/TIGR4) GN = SP_0103 PE = 4 SV = 1 - [Q97T52_STRPN] | Multi-transmembrane |
| Q97RE5 | 17.08 | 6 | 650 | 60.23 | PTS system, fructose specific IIABC components OS = *Streptococcus pneumoniae* serotype 4 (strain ATCC BAA-334/TIGR4) GN = SP_0877 PE = 4 SV = 1 - [Q97RE5_STRPN] | Multi-transmembrane |
| Q97SV4 | 54.11 | 9 | 207 | 60.13 | 50S ribosomal protein L4 OS = *Streptococcus pneumoniae* serotype 4 (strain ATCC BAA-334/TIGR4) GN = rplD PE = 3 SV = 1 - [RL4_STRPN] | Intracellular |
| Q97RK7 | 19.46 | 12 | 848 | 59.83 | Aminopeptidase N OS = *Streptococcus pneumoniae* serotype 4 (strain ATCC BAA-334/TIGR4) GN = pepN PE = 4 SV = 1 - [Q97RK7_STRPN] | Intracellular |
| Q97Q62 | 34.67 | 11 | 424 | 59.21 | Psr protein OS = *Streptococcus pneumoniae* serotype 4 (strain ATCC BAA-334/TIGR4) GN = SP_1368 PE = 4 SV = 1 - [Q97Q62_STRPN] | Intracellular/TMH start AFTER 60 |
| O07344 | 26.96 | 5 | 204 | 58.64 | Signal peptidase I OS = *Streptococcus pneumoniae* serotype 4 (strain ATCC BAA-334/TIGR4) GN = lepB PE = 3 SV = 2 - [LEP_STRPN] | N-terminally anchored (No CS) |
| P0A3S3 | 34.67 | 6 | 274 | 57.63 | DNA-entry nuclease OS = *Streptococcus pneumoniae* serotype 4 (strain ATCC BAA-334/TIGR4) GN = endA PE = 1 SV = 1 - [NUCE_STRPN] | N-terminally anchored (No CS) |
| Q97PU5 | 29.55 | 10 | 572 | 57.38 | Phosphoglucomutase OS = *Streptococcus pneumoniae* serotype 4 (strain ATCC BAA-334/TIGR4) GN = pgm PE = 3 SV = 1 - [Q97PU5_STRPN] | Intracellular |
| Q97RC6 | 31.34 | 8 | 335 | 57.3 | ATP-dependent 6-phosphofructokinase OS = *Streptococcus pneumoniae* serotype 4 (strain ATCC BAA-334/TIGR4) GN = pfkA PE = 3 SV = 1 - [PFKA_STRPN] | Intracellular |
| Q97SV5 | 37.5 | 6 | 208 | 56.96 | 50S ribosomal protein L3 OS = *Streptococcus pneumoniae* serotype 4 (strain ATCC BAA-334/TIGR4) GN = rplC PE = 3 SV = 1 - [RL3_STRPN] | Intracellular |
| Q97RL9 | 25.56 | 6 | 399 | 56.21 | Uncharacterized protein OS = *Streptococcus pneumoniae* serotype 4 (strain ATCC BAA-334/TIGR4) GN = SP_0785 PE = 4 SV = 1 - [Q97RL9_STRPN] | N-terminally anchored (No CS) |
| P66278 | 18.18 | 2 | 66 | 55.84 | 50S ribosomal protein L35 OS = *Streptococcus pneumoniae* serotype 4 (strain ATCC BAA-334/TIGR4) GN = rpmI PE = 3 SV = 1 - [RL35_STRPN] | Intracellular |
| I6L8N0 | 40.82 | 12 | 365 | 55.32 | UDP-N-acetylglucosamine-2-epimerase OS = *Streptococcus pneumoniae* serotype 4 (strain ATCC BAA-334/TIGR4) GN = cps4I PE = 3 SV = 1 - [I6L8N0_STRPN] | Intracellular |

TABLE 4-continued

Proteins identified in MP from TIGR4. The accession numbers refer to SwissProt on the date of filing.

| Accession # | Coverage | # Peptides | #AAs | Score | Description | Localization |
|---|---|---|---|---|---|---|
| Q97PQ8 | 57.34 | 6 | 143 | 54.74 | Uncharacterized protein OS = Streptococcus pneumoniae serotype 4 (strain ATCC BAA-334/TIGR4) GN = SP_1545 PE = 4 SV = 1 - [Q97PQ8_STRPN] | Intracellular |
| Q97TA6 | 33.64 | 10 | 330 | 52.71 | Phosphate acyltransferase OS = Streptococcus pneumoniae serotype 4 (strain ATCC BAA-334/TIGR4) GN = plsX PE = 3 SV = 1 - [PLSX_STRPN] | Intracellular |
| Q97PK5 | 27.22 | 2 | 158 | 52.32 | Uncharacterized protein OS = Streptococcus pneumoniae serotype 4 (strain ATCC BAA-334/TIGR4) GN = SP_1604 PE = 4 SV = 1 - [Q97PK5_STRPN] | N-terminally anchored (No CS) |
| Q97SN5 | 67.57 | 8 | 148 | 51.12 | 50S ribosomal protein L13 OS = Streptococcus pneumoniae serotype 4 (strain ATCC BAA-334/TIGR4) GN = rplM PE = 3 SV = 1 - [Q97SN5_STRPN] | Intracellular |
| Q97RV8 | 60.32 | 8 | 126 | 49.28 | Uncharacterized protein OS = Streptococcus pneumoniae serotype 4 (strain ATCC BAA-334/TIGR4) GN = SP_0678 PE = 4 SV = 1 - [Q97RV8_STRPN] | N-terminally anchored (No CS) |
| Q97R14 | 30.25 | 7 | 324 | 48.6 | Uncharacterized protein OS = Streptococcus pneumoniae serotype 4 (strain ATCC BAA-334/TIGR4) GN = SP_1027 PE = 4 SV = 1 - [Q97R14_STRPN] | Secretory (released) (with CS) |
| P35597 | 15.04 | 7 | 778 | 48.34 | Probable cation-transporting ATPase exp7 OS = Streptococcus pneumoniae serotype 4 (strain ATCC BAA-334/TIGR4) GN = exp7 PE = 3 SV = 2 - [EXP7_STRPN] | Multi-transmembrane |
| P65239 | 41.61 | 9 | 322 | 48.08 | Ribose-phosphate pyrophosphokinase 1 OS = Streptococcus pneumoniae serotype 4 (strain ATCC BAA-334/TIGR4) GN = prs1 PE = 3 SV = 1 - [KPRS1_STRPN] | Intracellular |
| Q97Q37 | 46.13 | 7 | 271 | 47.67 | Amino acid ABC transporter, amino acid-binding protein OS = Streptococcus pneumoniae serotype 4 (strain ATCC BAA-334/TIGR4) GN = SP_1394 PE = 4 SV = 1 - [Q97Q37_STRPN] | Lipid anchored |
| Q97R36 | 52.43 | 8 | 185 | 47.65 | Thioredoxin family protein OS = Streptococcus pneumoniae serotype 4 (strain ATCC BAA-334/TIGR4) GN = SP_1000 PE = 1 SV = 1 - [Q97R36_STRPN] | Lipid anchored |
| Q97N48 | 26.81 | 5 | 276 | 45.87 | Uncharacterized protein OS = Streptococcus pneumoniae serotype 4 (strain ATCC BAA-334/TIGR4) GN = SP_2223 PE = 4 SV = 1 - [Q97N48_STRPN] | Intracellular/TMH start AFTER 60 |
| I6L8R1 | 22.79 | 4 | 215 | 45.06 | ABC transporter, ATP-binding protein Vexp2 OS = Streptococcus pneumoniae serotype 4 (strain ATCC BAA-334/TIGR4) GN = vex2 PE = 3 SV = 1 - [I6L8R1_STRPN] | Intracellular |
| Q97SC6 | 20.93 | 10 | 774 | 44.93 | Formate acetyltransferase OS = Streptococcus pneumoniae serotype 4 (strain ATCC BAA-334/TIGR4) GN = pfl PE = 4 SV = 1 - [Q97SC6_STRPN] | Intracellular |
| Q97QD5 | 51.08 | 8 | 186 | 44.75 | LemA protein OS = Streptococcus pneumoniae serotype 4 (strain ATCC BAA-334/TIGR4) GN = lemA PE = 1 SV = 1 - [Q97QD5_STRPN] | N-terminally anchored (No CS) |
| Q97PF9 | 37.71 | 9 | 419 | 44.71 | Cell division protein FtsZ OS = Streptococcus pneumoniae serotype 4 (strain ATCC BAA-334/TIGR4) GN = ftsZ PE = 3 SV = 1 - [Q97PF9_STRPN] | Intracellular |

TABLE 4-continued

Proteins identified in MP from TIGR4. The accession numbers refer to SwissProt on the date of filing.

| Accession # | Coverage | # Peptides | #AAs | Score | Description | Localization |
|---|---|---|---|---|---|---|
| P0A3B7 | 36.71 | 7 | 346 | 44.56 | Elongation factor Ts OS = *Streptococcus pneumoniae* serotype 4 (strain ATCC BAA-334/TIGR4) GN = tsf PE = 1 SV = 2 - [EFTS_STRPN] | Intracellular |
| P72524 | 20.56 | 10 | 822 | 44.46 | DNA gyrase subunit A OS = *Streptococcus pneumoniae* serotype 4 (strain ATCC BAA-334/TIGR4) GN = gyrA PE = 3 SV = 3 - [GYRA_STRPN] | Intracellular |
| P67282 | 26.22 | 11 | 534 | 43.28 | Ribonuclease Y OS = *Streptococcus pneumoniae* serotype 4 (strain ATCC BAA-334/TIGR4) GN = rny PE = 3 SV = 1 - [RNY_STRPN] | N-terminally anchored (No CS) |
| P66419 | 38.2 | 6 | 89 | 42.98 | 30S ribosomal protein S14 OS = *Streptococcus pneumoniae* serotype 4 (strain ATCC BAA-334/TIGR4) GN = rpsN PE = 3 SV = 1 - [RS14_STRPN] | Intracellular |
| Q97SV1 | 48.89 | 6 | 180 | 42.64 | 50S ribosomal protein L5 OS = *Streptococcus pneumoniae* serotype 4 (strain ATCC BAA-334/TIGR4) GN = rplE PE = 3 SV = 1 - [RL5_STRPN] | Intracellular |
| Q97NW9 | 7.48 | 5 | 655 | 42.08 | Trehalose PTS system, IIABC components OS = *Streptococcus pneumoniae* serotype 4 (strain ATCC BAA-334/TIGR4) GN = SP_1884 PE = 4 SV = 1 - [Q97NW9_STRPN] | Multi-transmembrane |
| Q97QI8 | 91.06 | 6 | 123 | 40.86 | Uncharacterized protein OS = *Streptococcus pneumoniae* serotype 4 (strain ATCC BAA-334/TIGR4) GN = SP_1218 PE = 4 SV = 1 - [Q97QI8_STRPN] | Intracellular |
| Q97T04 | 11.92 | 2 | 193 | 39.59 | Uncharacterized protein OS = *Streptococcus pneumoniae* serotype 4 (strain ATCC BAA-334/TIGR4) GN = SP_0157 PE = 4 SV = 1 - [Q97T04_STRPN] | Multi-transmembrane |
| Q97PB8 | 9.09 | 4 | 627 | 39.49 | PTS system IIABC components OS = *Streptococcus pneumoniae* serotype 4 (strain ATCC BAA-334/TIGR4) GN = SP_1722 PE = 4 SV = 1 - [Q97PB8_STRPN] | Multi-transmembrane |
| Q97PI9 | 57.3 | 5 | 89 | 39.48 | 30S ribosomal protein S15 OS = *Streptococcus pneumoniae* serotype 4 (strain ATCC BAA-334/TIGR4) GN = rpsO PE = 3 SV = 1 - [RS15_STRPN] | Intracellular |
| P61182 | 40.35 | 4 | 114 | 39.35 | 50S ribosomal protein L22 OS = *Streptococcus pneumoniae* serotype 4 (strain ATCC BAA-334/TIGR4) GN = rplV PE = 1 SV = 1 - [RL22_STRPN] | Intracellular |
| Q97SU7 | 51.69 | 6 | 178 | 38.14 | 50S ribosomal protein L6 OS = *Streptococcus pneumoniae* serotype 4 (strain ATCC BAA-334/TIGR4) GN = rplF PE = 3 SV = 1 - [RL6_STRPN] | Intracellular |
| Q97NB9 | 39.1 | 8 | 335 | 38.04 | Uncharacterized protein OS = *Streptococcus pneumoniae* serotype 4 (strain ATCC BAA-334/TIGR4) GN = SP_2132 PE = 4 SV = 1 - [Q97NB9_STRPN] | Multi-transmembrane |
| Q97QP7 | 5.34 | 8 | 2004 | 37.84 | Immunoglobulin A1 protease OS = *Streptococcus pneumoniae* serotype 4 (strain ATCC BAA-334/TIGR4) GN = iga PE = 3 SV = 1 - [IGA1A_STRPN] | Multi-transmembrane |
| Q97N55 | 23.72 | 6 | 392 | 37.16 | Secreted 45 kd protein OS = *Streptococcus pneumoniae* serotype 4 (strain ATCC BAA-334/TIGR4) GN = usp45 PE = 4 SV = 1 - [Q97N55_STRPN] | Secretory (released) (with CS) |

TABLE 4-continued

Proteins identified in MP from TIGR4. The accession numbers refer to SwissProt on the date of filing.

| Accession # | Coverage | # Peptides | #AAs | Score | Description | Localization |
|---|---|---|---|---|---|---|
| P66942 | 18.25 | 4 | 252 | 36.63 | Triosephosphate isomerase OS = Streptococcus pneumoniae serotype 4 (strain ATCC BAA-334/TIGR4) GN = tpiA PE = 3 SV = 1 - [TPIS_STRPN] | Intracellular |
| Q97QC6 | 66.09 | 7 | 115 | 35.81 | 50S ribosomal protein L19 OS = Streptococcus pneumoniae serotype 4 (strain ATCC BAA-334/TIGR4) GN = rplS PE = 3 SV = 1 - [RL19_STRPN] | Intracellular |
| I6L8S7 | 14.6 | 5 | 459 | 35.54 | Transmembrane protein Vexp3 OS = Streptococcus pneumoniae serotype 4 (strain ATCC BAA-334/TIGR4) GN = vex3 PE = 4 SV = 1 - [I6L8S7_STRPN] | Multi-transmembrane |
| P35595 | 12.4 | 6 | 726 | 35.44 | PTS system glucose-specific EIICBA component OS = Streptococcus pneumoniae serotype 4 (strain ATCC BAA-334/TIGR4) GN = exp5 PE = 3 SV = 2 - [PTG3C_STRPN] | Multi-transmembrane |
| Q97PV1 | 14.88 | 3 | 289 | 34.89 | Putative glycerol uptake facilitator protein OS = Streptococcus pneumoniae serotype 4 (strain ATCC BAA-334/TIGR4) GN = SP_1491 PE = 3 SV = 1 - [Q97PV1_STRPN] | Multi-transmembrane |
| Q97NM6 | 21.04 | 6 | 404 | 33.79 | Aminotransferase, class I OS = Streptococcus pneumoniae serotype 4 (strain ATCC BAA-334/TIGR4) GN = SP_1994 PE = 4 SV = 1 - [Q97NM6_STRPN] | Intracellular |
| Q97SD2 | 45.93 | 5 | 246 | 33.44 | Amino acid ABC transporter, ATP-binding protein OS = Streptococcus pneumoniae serotype 4 (strain ATCC BAA-334/TIGR4) GN = SP_0452 PE = 3 SV = 1 - [Q97SD2_STRPN] | Intracellular |
| Q97NN3 | 36.15 | 6 | 213 | 33.1 | ABC transporter, ATP-binding protein OS = Streptococcus pneumoniae serotype 4 (strain ATCC BAA-334/TIGR4) GN = SP_1987 PE = 1 SV = 1 - [Q97NN3_STRPN] | Intracellular |
| Q97RJ0 | 23.77 | 5 | 244 | 33.09 | Amino acid ABC transporter, ATP-binding protein OS = Streptococcus pneumoniae serotype 4 (strain ATCC BAA-334/TIGR4) GN = SP_0824 PE = 3 SV = 1 - [Q97RJ0_STRPN] | Intracellular |
| Q97NJ7 | 27.27 | 3 | 99 | 32.76 | Preprotein translocase, YajC subunit OS = Streptococcus pneumoniae serotype 4 (strain ATCC BAA-334/TIGR4) GN = yajC-2 PE = 4 SV = 1 - [Q97NJ7_STRPN] | N-terminally anchored (No CS) |
| P66095 | 34.5 | 8 | 229 | 32.4 | 50S ribosomal protein L1 OS = Streptococcus pneumoniae serotype 4 (strain ATCC BAA-334/TIGR4) GN = rplA PE = 3 SV = 1 - [RL1_STRPN] | Intracellular |
| Q97NT7 | 38.61 | 6 | 158 | 32.3 | Uncharacterized protein OS = Streptococcus pneumoniae serotype 4 (strain ATCC BAA-334/TIGR4) GN = SP_1926 PE = 4 SV = 1 - [Q97NT7_STRPN] | Multi-transmembrane |
| P63667 | 29.5 | 4 | 139 | 31.7 | ATP synthase epsilon chain OS = Streptococcus pneumoniae serotype 4 (strain ATCC BAA-334/TIGR4) GN = atpC PE = 3 SV = 1 - [ATPE_STRPN] | Intracellular |
| Q97T58 | 18.08 | 4 | 354 | 31.6 | Conserved domain protein OS = Streptococcus pneumoniae serotype 4 (strain ATCC BAA-334/TIGR4) GN = SP_0097 PE = 4 SV = 1 - [Q97T58_STRPN] | Multi-transmembrane |
| Q97R06 | 36.74 | 6 | 264 | 31.17 | Iron-compound ABC transporter, ATP-binding protein OS = Streptococcus pneumoniae serotype 4 (strain ATCC BAA-334/TIGR4) GN = SP_1035 PE = 3 SV = 1 - [Q97R06_STRPN] | Intracellular |

TABLE 4-continued

Proteins identified in MP from TIGR4. The accession numbers refer to SwissProt on the date of filing.

| Accession # | Coverage | # Peptides | #AAs | Score | Description | Localization |
|---|---|---|---|---|---|---|
| Q97PQ5 | 20.34 | 6 | 531 | 30.81 | Uncharacterized protein OS = Streptococcus pneumoniae serotype 4 (strain ATCC BAA-334/ TIGR4) GN = SP_1548 PE = 4 SV = 1 - [Q97PQ5_STRPN] | Multi-transmembrane |
| Q97R44 | 33.91 | 2 | 115 | 30.62 | Uncharacterized protein OS = Streptococcus pneumoniae serotype 4 (strain ATCC BAA-334/ TIGR4) GN = SP_0990 PE = 4 SV = 1 - [Q97R44_STRPN] | Intracellular/ TMH start AFTER 60 |
| Q97SW3 | 47.73 | 3 | 88 | 29.98 | Uncharacterized protein OS = Streptococcus pneumoniae serotype 4 (strain ATCC BAA-334/ TIGR4) GN = SP_0201 PE = 4 SV = 1 - [Q97SW3_STRPN] | Intracellular |
| I6L8N6 | 27.01 | 4 | 211 | 29.5 | Capsular polysaccharide biosynthesis protein Cps4E OS = Streptococcus pneumoniae serotype 4 (strain ATCC BAA-334/TIGR4) GN = cps4E PE = 4 SV = 1 - [I6L8N6_STRPN] | N-terminally anchored (No CS) |
| Q97SU3 | 34.25 | 5 | 146 | 28.53 | 50S ribosomal protein L15 OS = Streptococcus pneumoniae serotype 4 (strain ATCC BAA-334/ TIGR4) GN = rplO PE = 3 SV = 1 - [RL15_STRPN] | Intracellular |
| Q97QS6 | 25.86 | 6 | 379 | 28.15 | Glycogen biosynthesis protein GlgD OS = Streptococcus pneumoniae serotype 4 (strain ATCC BAA-334/ TIGR4) GN = glgD PE = 4 SV = 1 - [Q97QS6_STRPN] | Intracellular |
| Q97P39 | 52.24 | 2 | 67 | 27.23 | UPF0337 protein SP_1805 OS = Streptococcus pneumoniae serotype 4 (strain ATCC BAA-334/ TIGR4) GN = SP_1805 PE = 3 SV = 1 - [Y1805_STRPN] | Intracellular |
| P06653 | 20.44 | 6 | 318 | 25.81 | Autolysin OS = Streptococcus pneumoniae serotype 4 (strain ATCC BAA-334/TIGR4) GN = lytA PE = 1 SV = 2 - [ALYS_STRPN] | Intracellular |
| Q97PX9 | 12.78 | 5 | 266 | 25.41 | Amino acid ABC transporter, permease protein OS = Streptococcus pneumoniae serotype 4 (strain ATCC BAA-334/ TIGR4) GN = SP_1461 PE = 3 SV = 1 - [Q97PX9_STRPN] | Multi-transmembrane |
| Q97QW4 | 17.65 | 5 | 425 | 24.84 | Uncharacterized protein OS = Streptococcus pneumoniae serotype 4 (strain ATCC BAA-334/ TIGR4) GN = SP_1083 PE = 4 SV = 1 - [Q97QW4_STRPN] | Intracellular |
| Q97S93 | 13.27 | 7 | 535 | 23.79 | CTP synthase OS = Streptococcus pneumoniae serotype 4 (strain ATCC BAA-334/TIGR4) GN = pyrG PE = 3 SV = 1 - [PYRG_STRPN] | Intracellular |
| Q97SX1 | 26.14 | 2 | 88 | 22 | UPF0297 protein SP_0192 OS = Streptococcus pneumoniae serotype 4 (strain ATCC BAA-334/ TIGR4) GN = SP_0192 PE = 1 SV = 1 - [Y192_STRPN] | Intracellular |
| Q97RH7 | 50 | 4 | 78 | 21.34 | 30S ribosomal protein S20 OS = Streptococcus pneumoniae serotype 4 (strain ATCC BAA-334/ TIGR4) GN = rpsT PE = 3 SV = 1 - [RS20_STRPN] | Intracellular |
| P66050 | 45.78 | 5 | 166 | 20.98 | 50S ribosomal protein L10 OS = Streptococcus pneumoniae serotype 4 (strain ATCC BAA-334/ TIGR4) GN = rplJ PE = 3 SV = 2 - [RL10_STRPN] | Intracellular |
| Q97RW6 | 32.14 | 3 | 56 | 20.85 | Uncharacterized protein OS = Streptococcus pneumoniae serotype 4 (strain ATCC BAA-334/ TIGR4) GN = SP_0670 PE = 4 SV = 1 - [Q97RW6_STRPN] | Secretory (released) (with CS) |

TABLE 4-continued

Proteins identified in MP from TIGR4. The accession numbers refer to SwissProt on the date of filing.

| Accession # | Coverage | # Peptides | #AAs | Score | Description | Localization |
|---|---|---|---|---|---|---|
| Q9FBB7 | 29.41 | 4 | 255 | 20.65 | Acetyl-coenzyme A carboxylase carboxyl transferase subunit alpha OS = *Streptococcus pneumoniae* serotype 4 (strain ATCC BAA-334/ TIGR4) GN = accA PE = 1 SV = 1 - [ACCA_STRPN] | Intracellular |
| I6L8V8 | 30.45 | 4 | 243 | 20.58 | 3-oxoacyl-[acyl-carrier protein] reductase OS = *Streptococcus pneumoniae* serotype 4 (strain ATCC BAA-334/TIGR4) GN = fabG PE = 3 SV = 1 - [I6L8V8_STRPN] | Intracellular |
| P66581 | 41.46 | 4 | 164 | 20.46 | 30S ribosomal protein S5 OS = *Streptococcus pneumoniae* serotype 4 (strain ATCC BAA-334/ TIGR4) GN = rpsE PE = 3 SV = 1 - [RS5_STRPN] | Intracellular |
| Q97T45 | 11.82 | 5 | 694 | 20.39 | Uncharacterized protein OS = *Streptococcus pneumoniae* serotype 4 (strain ATCC BAA-334/ TIGR4) GN = SP_0110 PE = 4 SV = 1 - [Q97T45_STRPN] | Multi-transmembrane |
| Q97P18 | 18.31 | 4 | 355 | 20.06 | ABC transporter, substrate-binding protein OS = *Streptococcus pneumoniae* serotype 4 (strain ATCC BAA-334/ TIGR4) GN = SP_1826 PE = 4 SV = 1 - [Q97P18_STRPN] | Lipid anchored |

TABLE 5

Proteins identified in $MV_L$ from serotype 3. The accession numbers refer to SwissProt on the date of filing.

| Accession # | Coverage | # Peptides | #AAs | Score | Description | Localization |
|---|---|---|---|---|---|---|
| B2IQV2 | 91.09 | 50 | 404 | 5251.94 | Elongation factor Tu OS = *Streptococcus pneumoniae* (strain CGSP14) GN = tuf PE = 3 SV = 1 - [B2IQV2_STRPS] | Intracellular |
| B2IPX8 | 95.62 | 40 | 434 | 2291.84 | Enolase OS = *Streptococcus pneumoniae* (strain CGSP14) GN = eno PE = 3 SV = 1 - [ENO_STRPS] | Intracellular |
| B2INW2 | 70.86 | 42 | 374 | 2221.7 | Lipoprotein OS = *Streptococcus pneumoniae* (strain CGSP14) GN = SPCG_0787 PE = 4 SV = 1 - [B2INW2_STRPS] | Lipid anchored |
| B2ISJ9 | 85.28 | 67 | 693 | 1851.66 | Elongation factor G OS = *Streptococcus pneumoniae* (strain CGSP14) GN = fusA PE = 3 SV = 1 - [EFG_STRPS] | Intracellular |
| B2IMI7 | 73.82 | 33 | 359 | 1675.28 | Glyceraldehyde-3-phosphate dehydrogenase OS = *Streptococcus pneumoniae* (strain CGSP14) GN = gapA PE = 3 SV = 1 - [B2IMI7_STRPS] | Intracellular |
| B2IM39 | 82.94 | 101 | 1225 | 1348.46 | DNA-directed RNA polymerase subunit beta' OS = *Streptococcus pneumoniae* (strain CGSP14) GN = rpoC PE = 3 SV = 1 - [RPOC_STRPS] | Intracellular |
| B2IMJ9 | 86.85 | 68 | 890 | 1321.16 | Aldehyde-alcohol dehydrogenase OS = *Streptococcus pneumoniae* (strain CGSP14) GN = adhE PE = 3 SV = 1 - [B2IMJ9_STRPS] | Intracellular |
| B2IPD4 | 73.16 | 38 | 313 | 1171.98 | Foldase protein PrsA OS = *Streptococcus pneumoniae* (strain CGSP14) GN = prsA PE = 3 SV = 1 - [PRSA_STRPS] | Lipid anchored |
| B2INY1 | 91 | 53 | 400 | 1141.84 | 30S ribosomal protein S1 OS = *Streptococcus pneumoniae* (strain CGSP14) GN = rpsA PE = 4 SV = 1 - [B2INY1_STRPS] | Intracellular |

TABLE 5-continued

Proteins identified in MV$_L$ from serotype 3. The accession numbers refer to SwissProt on the date of filing.

| Accession # | Coverage | # Peptides | #AAs | Score | Description | Localization |
|---|---|---|---|---|---|---|
| B2IP53 | 87.46 | 27 | 335 | 830.14 | ATP-dependent 6-phosphofructokinase OS = Streptococcus pneumoniae (strain CGSP14) GN = pfkA PE = 3 SV = 1 - [PFKA_STRPS] | Intracellular |
| B2IQX0 | 90.6 | 38 | 468 | 772.66 | ATP synthase subunit beta OS = Streptococcus pneumoniae (strain CGSP14) GN = atpD PE = 3 SV = 1 - [ATPB_STRPS] | Intracellular |
| B2IRV7 | 72.76 | 62 | 837 | 760.12 | Protein translocase subunit SecA OS = Streptococcus pneumoniae (strain CGSP14) GN = secA PE = 3 SV = 1 - [B2IRV7_STRPS] | Intracellular |
| B2IN25 | 78.22 | 51 | 450 | 751.01 | Maltose/maltodextrin ABC transporter, maltose/maltodextrin-binding protein OS = Streptococcus pneumoniae (strain CGSP14) GN = SPCG_2072 PE = 4 SV = 1 - [B2IN25_STRPS] | Lipid anchored |
| B2INB2 | 72.76 | 41 | 591 | 749.62 | Pyruvate oxidase OS = Streptococcus pneumoniae (strain CGSP14) GN = spxB PE = 3 SV = 1 - [B2INB2_STRPS] | Intracellular |
| B2ISZ0 | 69.04 | 47 | 659 | 746.61 | Oligopeptide ABC transporter, oligopeptide-binding protein AmiA OS = Streptococcus pneumoniae (strain CGSP14) GN = amiA PE = 4 SV = 1 - [B2ISZ0_STRPS] | Lipid anchored |
| B2ISK8 | 56.44 | 22 | 303 | 734.11 | PTS system, mannose-specific IID component OS = Streptococcus pneumoniae (strain CGSP14) GN = manN PE = 4 SV = 1 - [B2ISK8_STRPS] | Multi-transmembrane |
| B2INN2 | 85.33 | 30 | 259 | 682.23 | 30S ribosomal protein S2 OS = Streptococcus pneumoniae (strain CGSP14) GN = rpsB PE = 3 SV = 2 - [RS2_STRPS] | Intracellular |
| B2IP54 | 76.05 | 39 | 501 | 676.55 | Pyruvate kinase OS = Streptococcus pneumoniae (strain CGSP14) GN = SPCG_0873 PE = 3 SV = 1 - [B2IP54_STRPS] | Intracellular |
| B2IR47 | 69.48 | 50 | 652 | 673.91 | Oligopeptide ABC transporter, oligopeptide-binding protein AliB OS = Streptococcus pneumoniae (strain CGSP14) GN = aliB PE = 4 SV = 1 - [B2IR47_STRPS] | Lipid anchored |
| B2IR00 | 66.26 | 44 | 652 | 636.95 | ATP-dependent zinc metalloprotease FtsH OS = Streptococcus pneumoniae (strain CGSP14) GN = ftsH PE = 3 SV = 1 - [B2IR00_STRPS] | Multi-transmembrane |
| B2IM40 | 77.67 | 50 | 824 | 633.52 | DNA-directed RNA polymerase subunit beta OS = Streptococcus pneumoniae (strain CGSP14) GN = rpoB PE = 3 SV = 1 - [B2IM40_STRPS] | Intracellular |
| B2IS43 | 70.76 | 23 | 277 | 575.93 | 50S ribosomal protein L2 OS = Streptococcus pneumoniae (strain CGSP14) GN = rplB PE = 3 SV = 1 - [RL2_STRPS] | Intracellular |
| B2IS46 | 79.26 | 27 | 217 | 569.56 | 30S ribosomal protein S3 OS = Streptococcus pneumoniae (strain CGSP14) GN = rpsC PE = 3 SV = 1 - [RS3_STRPS] | Intracellular |
| B2IME4 | 64.95 | 51 | 930 | 553.42 | Translation initiation factor IF-2 OS = Streptococcus pneumoniae (strain CGSP14) GN = infB PE = 3 SV = 1 - [IF2_STRPS] | Intracellular |
| B2IQY1 | 73.14 | 43 | 551 | 550.86 | Uncharacterized protein OS = Streptococcus pneumoniae (strain CGSP14) GN = SPCG_1503 PE = 4 SV = 1 - [B2IQY1_STRPS] | Intracellular/ TMH start AFTER 60 |

TABLE 5-continued

Proteins identified in MV$_L$ from serotype 3. The accession numbers refer to SwissProt on the date of filing.

| Accession # | Coverage | # Peptides | #AAs | Score | Description | Localization |
|---|---|---|---|---|---|---|
| B2INT1 | 58.9 | 34 | 584 | 531.45 | Septation ring formation regulator EzrA OS = Streptococcus pneumoniae (strain CGSP14) GN = ezrA PE = 3 SV = 1 - [B2INT1_STRPS] | N-terminally anchored (No CS) |
| B2IPY8 | 67.93 | 32 | 474 | 511.28 | Glyceraldehyde-3-phosphate dehydrogenase, NADP-dependent OS = Streptococcus pneumoniae (strain CGSP14) GN = gapN PE = 3 SV = 1 - [B2IPY8_STRPS] | Intracellular |
| B2IRQ6 | 79.23 | 20 | 313 | 461.56 | Manganese ABC transporter, manganese-binding adhesion liprotein OS = Streptococcus pneumoniae (strain CGSP14) GN = SPCG_1623 PE = 3 SV = 1 - [B2IRQ6_STRPS] | Lipid anchored |
| B2IPU8 | 63.14 | 36 | 719 | 457.32 | Ribonucleoside-diphosphate reductase OS = Streptococcus pneumoniae (strain CGSP14) GN = nrdE PE = 3 SV = 1 - [B2IPU8_STRPS] | Intracellular |
| B2IM49 | 72.42 | 27 | 330 | 449.87 | Aspartate--ammonia ligase OS = Streptococcus pneumoniae (strain CGSP14) GN = asnA PE = 3 SV = 1 - [ASNA_STRPS] | Intracellular |
| B2IQX2 | 68.86 | 31 | 501 | 447.54 | ATP synthase subunit alpha OS = Streptococcus pneumoniae (strain CGSP14) GN = atpA PE = 3 SV = 1 - [ATPA_STRPS] | Intracellular |
| B2IMK3 | 70.36 | 32 | 658 | 435.4 | Transketolase OS = Streptococcus pneumoniae (strain CGSP14) GN = tktA PE = 3 SV = 1 - [B2IMK3_STRPS] | Intracellular |
| B2IRH9 | 64.45 | 36 | 616 | 434.01 | Capsular polysaccharide biosynthesis protein, putative OS = Streptococcus pneumoniae (strain CGSP14) GN = SPCG_0098 PE = 4 SV = 1 - [B2IRH9_STRPS] | Multi-transmembrane |
| B2IN95 | 82.06 | 37 | 496 | 432.16 | Lysine--tRNA ligase OS = Streptococcus pneumoniae (strain CGSP14) GN = lysS PE = 3 SV = 1 - [SYK_STRPS] | Intracellular |
| B2IS90 | 71.32 | 40 | 537 | 413.57 | Ribonuclease Y OS = Streptococcus pneumoniae (strain CGSP14) GN = rny PE = 3 SV = 1 - [B2IS90_STRPS] | Intracellular |
| B2IRT9 | 66.06 | 32 | 442 | 412.96 | Sugar ABC transporter, sugar-binding protein OS = Streptococcus pneumoniae (strain CGSP14) GN = SPCG_1656 PE = 4 SV = 1 - [B2IRT9_STRPS] | Lipid anchored |
| B2IN10 | 73.37 | 15 | 338 | 401 | Glycerol-3-phosphate dehydrogenase [NAD(P)+] OS = Streptococcus pneumoniae (strain CGSP14) GN = gpsA PE = 3 SV = 1 - [GPDA_STRPS] | Intracellular |
| B2IP07 | 38.46 | 23 | 650 | 398.03 | PTS system, fructose specific IIABC components OS = Streptococcus pneumoniae (strain CGSP14) GN = fruA PE = 4 SV = 1 - [B2IP07_STRPS] | Multi-transmembrane |
| B2IPB5 | 52.94 | 10 | 119 | 388.03 | 50S ribosomal protein L20 OS = Streptococcus pneumoniae (strain CGSP14) GN = rplT PE = 3 SV = 1 - [RL20_STRPS] | Intracellular |
| B2ISI9 | 66.29 | 35 | 617 | 385.71 | Proline--tRNA ligase OS = Streptococcus pneumoniae (strain CGSP14) GN = proS PE = 3 SV = 1 - [SYP_STRPS] | Intracellular |
| B2INH5 | 83.95 | 31 | 299 | 370.13 | SPFH domain/Band 7 family OS = Streptococcus pneumoniae (strain CGSP14) GN = SPCG_2124 PE = 4 SV = 1 - [B2INH5_STRPS] | N-terminally anchored (No CS) |

TABLE 5-continued

Proteins identified in MV$_L$ from serotype 3. The accession numbers refer to SwissProt on the date of filing.

| Accession # | Coverage | # Peptides | #AAs | Score | Description | Localization |
|---|---|---|---|---|---|---|
| B2IQ40 | 64.14 | 46 | 898 | 367.23 | Phosphoenolpyruvate carboxylase OS = *Streptococcus pneumoniae* (strain CGSP14) GN = ppc PE = 3 SV = 1 - [B2IQ40_STRPS] | Intracellular |
| B2IML8 | 76.35 | 25 | 406 | 358.33 | Acetate kinase OS = *Streptococcus pneumoniae* (strain CGSP14) GN = ackA PE = 3 SV = 1 - [B2IML8_STRPS] | Intracellular |
| B2IRS1 | 53.94 | 28 | 419 | 341.4 | Cell division protein FtsZ OS = *Streptococcus pneumoniae* (strain CGSP14) GN = ftsZ PE = 3 SV = 1 - [B2IRS1_STRPS] | Intracellular |
| B2IMN0 | 96.59 | 22 | 352 | 339.61 | Alcohol dehydrogenase, zinc-containing OS = *Streptococcus pneumoniae* (strain CGSP14) GN = adh PE = 3 SV = 1 - [B2IMN0_STRPS] | Intracellular |
| B2ISJ7 | 51.09 | 13 | 137 | 337.74 | 30S ribosomal protein S12 OS = *Streptococcus pneumoniae* (strain CGSP14) GN = rpsL PE = 3 SV = 1 - [RS12_STRPS] | Intracellular |
| B2IS41 | 63.29 | 16 | 207 | 337.71 | 50S ribosomal protein L4 OS = *Streptococcus pneumoniae* (strain CGSP14) GN = rplD PE = 3 SV = 1 - [RL4_STRPS] | Intracellular |
| B2ILW7 | 80.68 | 18 | 414 | 332.02 | 3-oxoacyl-[acyl-carrier-protein] synthase 2 OS = *Streptococcus pneumoniae* (strain CGSP14) GN = fabF PE = 3 SV = 1 - [B2ILW7_STRPS] | Intracellular |
| B2IRM9 | 70.29 | 22 | 276 | 330.56 | ABC transporter, substrate-binding protein OS = *Streptococcus pneumoniae* (strain CGSP14) GN = SPCG_0152 PE = 4 SV = 1 - [B2IRM9_STRPS] | Lipid anchored |
| B2ISY9 | 47.99 | 21 | 498 | 319.21 | Oligopeptide ABC transporter, permease protein AmiC OS = *Streptococcus pneumoniae* (strain CGSP14) GN = amiC PE = 3 SV = 1 - [B2ISY9_STRPS] | Multi-transmembrane |
| B2IQT6 | 62.75 | 22 | 459 | 313.52 | NADH oxidase OS = *Streptococcus pneumoniae* (strain CGSP14) GN = nox PE = 4 SV = 1 - [B2IQT6_STRPS] | Intracellular |
| B2IPP2 | 47.02 | 32 | 721 | 312 | Amino acid ABC transporter, amino acid-binding protein/permease protein OS = *Streptococcus pneumoniae* (strain CGSP14) GN = SPCG_1062 PE = 3 SV = 1 - [B2IPP2_STRPS] | Multi-transmembrane |
| B2IS47 | 63.5 | 13 | 137 | 300.82 | 50S ribosomal protein L16 OS = *Streptococcus pneumoniae* (strain CGSP14) GN = rplP PE = 3 SV = 1 - [RL16_STRPS] | Intracellular |
| B2IRC1 | 66.67 | 19 | 339 | 299.62 | UDP-glucose 4-epimerase OS = *Streptococcus pneumoniae* (strain CGSP14) GN = galE PE = 4 SV = 1 - [B2IRC1_STRPS] | Intracellular |
| B2IQW3 | 71.22 | 25 | 278 | 296.15 | Amino acid ABC transporter, amino acid-binding protein OS = *Streptococcus pneumoniae* (strain CGSP14) GN = SPCG_1485 PE = 4 SV = 1 - [B2IQW3_STRPS] | Lipid anchored |
| B2IRR1 | 67.83 | 19 | 230 | 295.06 | 2,3-bisphosphoglycerate-dependent phosphoglycerate mutase OS = *Streptococcus pneumoniae* (strain CGSP14) GN = gpmA PE = 3 SV = 1 - [GPMA_STRPS] | Intracellular |
| B2IS34 | 61.87 | 39 | 737 | 290.83 | Anaerobic ribonucleoside triphosphate reductase OS = *Streptococcus pneumoniae* (strain CGSP14) GN = SPCG_0212 PE = 4 SV = 1 - [B2IS34_STRPS] | Intracellular |

TABLE 5-continued

Proteins identified in MV$_L$ from serotype 3. The accession numbers refer to SwissProt on the date of filing.

| Accession # | Coverage | # Peptides | #AAs | Score | Description | Localization |
|---|---|---|---|---|---|---|
| B2IS52 | 87.78 | 18 | 180 | 288.42 | 50S ribosomal protein L5 OS = *Streptococcus pneumoniae* (strain CGSP14) GN = rplE PE = 3 SV = 1 - [RL5_STRPS] | Intracellular |
| B2IQU1 | 65.63 | 33 | 678 | 288.36 | Glycine--tRNA ligase beta subunit OS = *Streptococcus pneumoniae* (strain CGSP14) GN = glyS PE = 3 SV = 1 - [SYGB_STRPS] | Intracellular |
| B2ILY5 | 60.36 | 21 | 555 | 284.08 | Uncharacterized protein OS = *Streptococcus pneumoniae* (strain CGSP14) GN = SPCG_0438 PE = 4 SV = 1 - [B2ILY5_STRPS] | Intracellular |
| B2IS40 | 59.62 | 14 | 208 | 283.69 | 50S ribosomal protein L3 OS = *Streptococcus pneumoniae* (strain CGSP14) GN = rplC PE = 3 SV = 1 - [RL3_STRPS] | Intracellular |
| B2IM73 | 32.44 | 18 | 521 | 281.46 | Amino acid ABC transporter, amino acid-binding protein/permease protein OS = *Streptococcus pneumoniae* (strain CGSP14) GN = glnH PE = 3 SV = 1 - [B2IM73_STRPS] | Multi-transmembrane |
| B2IRI9 | 52.65 | 17 | 302 | 275.76 | Amino acid ABC transporter, periplasmic amino acid-binding protein, putative OS = *Streptococcus pneumoniae* (strain CGSP14) GN = SPCG_0108 PE = 4 SV = 1 - [B2IRI9_STRPS] | Lipid anchored |
| B2IRN0 | 57.75 | 22 | 284 | 275.2 | Lipoprotein OS = *Streptococcus pneumoniae* (strain CGSP14) GN = SPCG_0153 PE = 3 SV = 1 - [B2IRN0_STRPS] | Lipid anchored |
| B2IM81 | 70.93 | 36 | 774 | 270.81 | Formate acetyltransferase OS = *Streptococcus pneumoniae* (strain CGSP14) GN = pfl PE = 4 SV = 1 - [B2IM81_STRPS] | Intracellular |
| B2IRN7 | 65.61 | 30 | 660 | 269.02 | Threonine--tRNA ligase OS = *Streptococcus pneumoniae* (strain CGSP14) GN = thrS PE = 3 SV = 1 - [B2IRN7_STRPS] | Intracellular |
| B2IMN6 | 63.36 | 22 | 494 | 268.42 | Threonine synthase OS = *Streptococcus pneumoniae* (strain CGSP14) GN = thrC PE = 4 SV = 1 - [B2IMN6_STRPS] | Intracellular |
| B2IR98 | 69.68 | 20 | 376 | 261.66 | Sugar ABC transporter, ATP-binding protein OS = *Streptococcus pneumoniae* (strain CGSP14) GN = SPCG_1565 PE = 3 SV = 1 - [B2IR98_STRPS] | Intracellular |
| B2IMG8 | 58.42 | 23 | 404 | 253.09 | Aspartate aminotransferase OS = *Streptococcus pneumoniae* (strain CGSP14) GN = aspC PE = 4 SV = 1 - [B2IMG8_STRPS] | Intracellular |
| B2ILW6 | 65.43 | 13 | 243 | 252.82 | 3-ketoacyl-(Acyl-carrier-protein) reductase OS = *Streptococcus pneumoniae* (strain CGSP14) GN = fabG PE = 4 SV = 1 - [B2ILW6_STRPS] | Intracellular |
| B2INF2 | 70.18 | 25 | 513 | 248.48 | ABC transporter, ATP-binding protein OS = *Streptococcus pneumoniae* (strain CGSP14) GN = SPCG_0719 PE = 4 SV = 1 - [B2INF2_STRPS] | Intracellular |
| B2IRS2 | 78.12 | 20 | 457 | 247.37 | Cell division protein FtsA OS = *Streptococcus pneumoniae* (strain CGSP14) GN = ftsZ PE = 3 SV = 1 - [B2IRS2_STRPS] | Multi-transmembrane |
| B2IM41 | 70.82 | 22 | 377 | 246.54 | Uncharacterized protein OS = *Streptococcus pneumoniae* (strain CGSP14) GN = SPCG_1926 PE = 3 SV = 1 - [B2IM41_STRPS] | Intracellular |
| B2IQ88 | 66.09 | 13 | 115 | 240.71 | 50S ribosomal protein L19 OS = *Streptococcus pneumoniae* (strain CGSP14) GN = rplS PE = 3 SV = 1 - [RL19_STRPS] | Intracellular |

TABLE 5-continued

Proteins identified in MV$_L$ from serotype 3. The accession numbers refer to SwissProt on the date of filing.

| Accession # | Coverage | # Peptides | #AAs | Score | Description | Localization |
|---|---|---|---|---|---|---|
| B2IQI0 | 56.1 | 22 | 344 | 240.32 | Uncharacterized protein OS = Streptococcus pneumoniae (strain CGSP14) GN = SPCG_1352 PE = 4 SV = 1 - [B2IQI0_STRPS] | Multi-transmembrane |
| B2IND2 | 63.73 | 18 | 386 | 236.96 | Branched-chain amino acid ABC transporter, amino acid-binding protein OS = Streptococcus pneumoniae (strain CGSP14) GN = SPCG_0699 PE = 4 SV = 1 - [B2IND2_STRPS] | Lipid anchored |
| B2INP5 | 71.34 | 24 | 492 | 236.94 | Inosine-5'-monophosphate dehydrogenase OS = Streptococcus pneumoniae (strain CGSP14) GN = imdH PE = 3 SV = 1 - [B2INP5_STRPS] | Intracellular |
| B2ISL2 | 67.26 | 18 | 339 | 235.53 | Alcohol dehydrogenase OS = Streptococcus pneumoniae (strain CGSP14) GN = adhP PE = 3 SV = 1 - [B2ISL2_STRPS] | Intracellular |
| B2ISM4 | 59.23 | 9 | 130 | 228.51 | 30S ribosomal protein S9 OS = Streptococcus pneumoniae (strain CGSP14) GN = rpsI PE = 3 SV = 1 - [RS9_STRPS] | Intracellular |
| B2IR71 | 40.26 | 23 | 914 | 227.01 | Cation-transporting ATPase, E1-E2 family OS = Streptococcus pneumoniae (strain CGSP14) GN = pacL PE = 3 SV = 1 - [B2IR71_STRPS] | Multi-transmembrane |
| B2IPP1 | 85.77 | 17 | 246 | 225.41 | Amino acid ABC transporter, ATP-binding protein OS = Streptococcus pneumoniae (strain CGSP14) GN = SPCG_1061 PE = 4 SV = 1 - [B2IPP1_STRPS] | Intracellular |
| B2ISY7 | 58.31 | 18 | 355 | 221.22 | Oligopeptide ABC transporter, ATP-binding protein AmiE OS = Streptococcus pneumoniae (strain CGSP14) GN = amiE PE = 3 SV = 1 - [B2ISY7_STRPS] | Intracellular |
| B2IQL1 | 56.83 | 16 | 271 | 219.73 | Amino acid ABC transporter, amino acid-binding protein OS = Streptococcus pneumoniae (strain CGSP14) GN = SPCG_1383 PE = 4 SV = 1 - [B2IQL1_STRPS] | Lipid anchored |
| B2ISG3 | 77.23 | 19 | 202 | 219.45 | General stress protein 24, putative OS = Streptococcus pneumoniae (strain CGSP14) GN = SPCG_1781 PE = 4 SV = 1 - [B2ISG3_STRPS] | Intracellular |
| B2IMA2 | 70.1 | 20 | 398 | 216.35 | Phosphoglycerate kinase OS = Streptococcus pneumoniae (strain CGSP14) GN = pgk PE = 3 SV = 1 - [PGK_STRPS] | Intracellular |
| B2IN71 | 49.03 | 25 | 620 | 212.01 | Elongation factor Tu family protein OS = Streptococcus pneumoniae (strain CGSP14) GN = SPCG_0638 PE = 4 SV = 1 - [B2IN71_STRPS] | Intracellular |
| B2IPR1 | 75.6 | 16 | 332 | 210.14 | L-lactate dehydrogenase OS = Streptococcus pneumoniae (strain CGSP14) GN = ldh PE = 3 SV = 1 - [B2IPR1_STRPS] | Intracellular |
| B2IQK0 | 51.83 | 30 | 872 | 209.16 | Alanine--tRNA ligase OS = Streptococcus pneumoniae (strain CGSP14) GN = alaS PE = 3 SV = 1 - [SYA_STRPS] | Intracellular |
| B2IS44 | 61.29 | 12 | 93 | 208.67 | 30S ribosomal protein S19 OS = Streptococcus pneumoniae (strain CGSP14) GN = rpsS PE = 3 SV = 1 - [RS19_STRPS] | Intracellular |
| B2IMN9 | 48.47 | 17 | 425 | 208.24 | Uncharacterized protein OS = Streptococcus pneumoniae (strain CGSP14) GN = SPCG_2034 PE = 4 SV = 1 - [B2IMN9_STRPS] | Intracellular |

TABLE 5-continued

Proteins identified in MV$_L$ from serotype 3. The accession numbers refer to SwissProt on the date of filing.

| Accession # | Coverage | # Peptides | #AAs | Score | Description | Localization |
|---|---|---|---|---|---|---|
| B2IR17 | 72.27 | 16 | 339 | 208.13 | Ribose-phosphate pyrophosphokinase OS = Streptococcus pneumoniae (strain CGSP14) GN = prsA PE = 3 SV = 1 - [B2IR17_STRPS] | Intracellular |
| B2IQR1 | 62.69 | 25 | 520 | 208 | GMP synthase [glutamine-hydrolyzing] OS = Streptococcus pneumoniae (strain CGSP14) GN = guaA PE = 3 SV = 1 - [GUAA_STRPS] | Intracellular |
| B2INL3 | 50.25 | 23 | 810 | 202.66 | ATP-dependent Clp protease, ATP-binding subunit OS = Streptococcus pneumoniae (strain CGSP14) GN = SPCG_2162 PE = 3 SV = 1 - [B2INL3_STRPS] | Intracellular |
| B2IN11 | 58.53 | 17 | 299 | 197.31 | UTP--glucose-1-phosphate uridylyltransferase OS = Streptococcus pneumoniae (strain CGSP14) GN = galU PE = 3 SV = 1 - [B2IN11_STRPS] | Secretory (released) (with CS) |
| B2IQU5 | 44.38 | 17 | 480 | 197.17 | Peptidoglycan N-acetylglucosamine deacetylase A OS = Streptococcus pneumoniae (strain CGSP14) GN = pgdA PE = 4 SV = 1 - [B2IQU5_STRPS] | N-terminally anchored (No CS) |
| B2INE4 | 57.49 | 19 | 447 | 196.45 | DEAD-box ATP-dependent RNA helicase CshB OS = Streptococcus pneumoniae (strain CGSP14) GN = rheB PE = 3 SV = 1 - [B2INE4_STRPS] | Intracellular |
| B2IMU6 | 65.97 | 15 | 238 | 196.17 | Uncharacterized protein OS = Streptococcus pneumoniae (strain CGSP14) GN = SPCG_0590 PE = 4 SV = 1 - [B2IMU6_STRPS] | Lipid anchored |
| B2INT7 | 54.92 | 27 | 752 | 195.47 | ATP-dependent Clp protease, ATP-binding subunit ClpE OS = Streptococcus pneumoniae (strain CGSP14) GN = clpE PE = 3 SV = 1 - [B2INT7_STRPS] | Intracellular |
| B2IM28 | 44.59 | 17 | 388 | 194.98 | Protein RecA OS = Streptococcus pneumoniae (strain CGSP14) GN = recA PE = 3 SV = 1 - [RECA_STRPS] | Intracellular |
| B2IQL4 | 79.78 | 18 | 267 | 192.86 | Phosphate import ATP-binding protein PstB OS = Streptococcus pneumoniae (strain CGSP14) GN = pstB PE = 3 SV = 1 - [B2IQL4_STRPS] | Intracellular |
| B2ISL0 | 43.67 | 13 | 332 | 190.43 | PTS system, mannose-specific IIAB components OS = Streptococcus pneumoniae (strain CGSP14) GN = manL PE = 4 SV = 1 - [B2ISL0_STRPS] | Intracellular |
| B2INW3 | 54.6 | 19 | 511 | 188.38 | Sugar ABC transporter, ATP-binding protein OS = Streptococcus pneumoniae (strain CGSP14) GN = SPCG_0788 PE = 4 SV = 1 - [B2INW3_STRPS] | Intracellular |
| B2INT0 | 40.9 | 22 | 648 | 185.21 | DNA gyrase subunit B OS = Streptococcus pneumoniae (strain CGSP14) GN = gyrB PE = 3 SV = 1 - [B2INT0_STRPS] | Intracellular |
| B2IPI7 | 57.18 | 13 | 341 | 184.52 | Iron-compound ABC transporter, iron compound-binding protein OS = Streptococcus pneumoniae (strain CGSP14) GN = SPCG_1009 PE = 4 SV = 1 - [B2IPI7_STRPS] | Lipid anchored |
| B2IPT0 | 48.09 | 22 | 628 | 183.98 | Elongation factor 4 OS = Streptococcus pneumoniae (strain CGSP14) GN = lepA PE = 3 SV = 1 - [B2IPT0_STRPS] | Intracellular |
| B2IN23 | 39.89 | 17 | 752 | 181.97 | Alpha-1,4 glucan phosphorylase OS = Streptococcus pneumoniae (strain CGSP14) GN = malP PE = 3 SV = 1 - [B2IN23_STRPS] | Intracellular |

TABLE 5-continued

Proteins identified in MV$_L$ from serotype 3. The accession numbers refer to SwissProt on the date of filing.

| Accession # | Coverage | # Peptides | #AAs | Score | Description | Localization |
|---|---|---|---|---|---|---|
| B2IQZ2 | 64.71 | 20 | 374 | 180.03 | Ribosome-binding ATPase YchF OS = *Streptococcus pneumoniae* (strain CGSP14) GN = ychF PE = 3 SV = 1 - [B2IQZ2_STRPS] | Intracellular |
| B2IMU8 | 66.81 | 17 | 229 | 179.85 | 50S ribosomal protein L1 OS = *Streptococcus pneumoniae* (strain CGSP14) GN = rplA PE = 3 SV = 1 - [RL1_STRPS] | Intracellular |
| B2ISY6 | 51.06 | 14 | 331 | 178.98 | Oligopeptide ABC transporter, ATP-binding protein AmiF OS = *Streptococcus pneumoniae* (strain CGSP14) GN = amiF PE = 3 SV = 1 - [B2ISY6_STRPS] | Intracellular |
| B2IR87 | 54.15 | 18 | 410 | 170.5 | ATP-dependent Clp protease ATP-binding subunit ClpX OS = *Streptococcus pneumoniae* (strain CGSP14) GN = clpX PE = 3 SV = 1 - [CLPX_STRPS] | Intracellular |
| B2IR07 | 58.6 | 24 | 442 | 169.98 | Adenylosuccinate synthetase OS = *Streptococcus pneumoniae* (strain CGSP14) GN = purA PE = 3 SV = 1 - [B2IR07_STRPS] | Intracellular |
| B2ILV9 | 61.23 | 20 | 454 | 169.93 | Aspartokinase OS = *Streptococcus pneumoniae* (strain CGSP14) GN = lysC PE = 3 SV = 1 - [B2ILV9_STRPS] | Intracellular |
| B2IMZ6 | 42.12 | 25 | 857 | 169.84 | DNA mismatch repair protein MutS OS = *Streptococcus pneumoniae* (strain CGSP14) GN = hexA PE = 3 SV = 1 - [B2IMZ6_STRPS] | Intracellular |
| B2IS57 | 84.76 | 17 | 164 | 169.34 | 30S ribosomal protein S5 OS = *Streptococcus pneumoniae* (strain CGSP14) GN = rpsE PE = 3 SV = 1 - [B2IS57_STRPS] | Intracellular |
| B2ILR1 | 29.62 | 20 | 719 | 166.63 | Penicillin-binding protein 1A OS = *Streptococcus pneumoniae* (strain CGSP14) GN = pbp1A PE = 4 SV = 1 - [B2ILR1_STRPS] | N-terminally anchored (No CS) |
| B2IQ78 | 53.73 | 22 | 523 | 165.23 | Signal recognition particle protein OS = *Streptococcus pneumoniae* (strain CGSP14) GN = ffh PE = 3 SV = 1 - [B2IQ78_STRPS] | Intracellular |
| B2ISM3 | 78.38 | 17 | 148 | 163.82 | 50S ribosomal protein L13 OS = *Streptococcus pneumoniae* (strain CGSP14) GN = rplM PE = 3 SV = 1 - [B2ISM3_STRPS] | Intracellular |
| B2INJ2 | 70.02 | 21 | 427 | 163.61 | DltD protein OS = *Streptococcus pneumoniae* (strain CGSP14) GN = dltD PE = 4 SV = 1 - [B2INJ2_STRPS] | N-terminally anchored (No CS) |
| B2ISJ1 | 48.84 | 19 | 602 | 159.21 | Glutamine--fructose-6-phosphate aminotransferase [isomerizing] OS = *Streptococcus pneumoniae* (strain CGSP14) GN = glmS PE = 3 SV = 1 - [B2ISJ1_STRPS] | Intracellular |
| B2IPM7 | 52.69 | 18 | 577 | 159.04 | Phosphoenolpyruvate-protein phosphotransferase OS = *Streptococcus pneumoniae* (strain CGSP14) GN = SPCG_1121 PE = 3 SV = 1 - [B2IPM7_STRPS] | Intracellular |
| B2IQ29 | 61.01 | 17 | 436 | 157.98 | GTPase Obg OS = *Streptococcus pneumoniae* (strain CGSP14) GN = obg PE = 3 SV = 1 - [OBG_STRPS] | Intracellular |
| B2IS66 | 74.8 | 9 | 127 | 157.55 | 30S ribosomal protein S11 OS = *Streptococcus pneumoniae* (strain CGSP14) GN = rpsK PE = 3 SV = 1 - [RS11_STRPS] | Intracellular |
| B2IQ67 | 33.36 | 24 | 1058 | 157.35 | Carbamoyl-phosphate synthase large chain OS = *Streptococcus pneumoniae* (strain CGSP14) GN = carB PE = 3 SV = 1 - [CARB_STRPS] | Intracellular |

TABLE 5-continued

Proteins identified in MV$_L$ from serotype 3. The accession numbers refer to SwissProt on the date of filing.

| Accession # | Coverage | # Peptides | #AAs | Score | Description | Localization |
|---|---|---|---|---|---|---|
| B2IQ25 | 62.29 | 16 | 419 | 154.75 | UDP-N-acetylglucosamine 1-carboxyvinyltransferase OS = *Streptococcus pneumoniae* (strain CGSP14) GN = murZ PE = 3 SV = 1 - [B2IQ25_STRPS] | Intracellular |
| B2IQX4 | 82.93 | 14 | 164 | 154.18 | ATP synthase subunit b OS = *Streptococcus pneumoniae* (strain CGSP14) GN = atpF PE = 3 SV = 1 - [ATPF_STRPS] | N-terminally anchored (No CS) |
| B2IM72 | 69.51 | 10 | 246 | 154.11 | Amino acid ABC transporter, ATP-binding protein OS = *Streptococcus pneumoniae* (strain CGSP14) GN = glnQ PE = 4 SV = 1 - [B2IM72_STRPS] | Intracellular |
| B2INR2 | 35.79 | 19 | 679 | 153.3 | Methionine--tRNA ligase OS = *Streptococcus pneumoniae* (strain CGSP14) GN = metG PE = 3 SV = 1 - [B2INR2_STRPS] | Intracellular |
| B2IS42 | 81.63 | 6 | 98 | 152.99 | 50S ribosomal protein L23 OS = *Streptococcus pneumoniae* (strain CGSP14) GN = rplW PE = 3 SV = 1 - [RL23_STRPS] | Intracellular |
| B2IPI0 | 44.02 | 18 | 418 | 152.53 | Serine hydroxymethyltransferase OS = *Streptococcus pneumoniae* (strain CGSP14) GN = glyA PE = 3 SV = 1 - [GLYA_STRPS] | Intracellular |
| B2IRG4 | 73.89 | 21 | 203 | 151.28 | 30S ribosomal protein S4 OS = *Streptococcus pneumoniae* (strain CGSP14) GN = rpsD PE = 3 SV = 1 - [RS4_STRPS] | Intracellular |
| B2ILV7 | 59.29 | 21 | 452 | 150.33 | Serine--tRNA ligase OS = *Streptococcus pneumoniae* (strain CGSP14) GN = serS PE = 3 SV = 1 - [B2ILV7_STRPS] | Intracellular |
| B2INC8 | 60.65 | 13 | 216 | 146.88 | Uracil phosphoribosyltransferase OS = *Streptococcus pneumoniae* (strain CGSP14) GN = upp PE = 3 SV = 1 - [B2INC8_STRPS] | Intracellular |
| B2IQL3 | 70.63 | 16 | 252 | 145.61 | Phosphate import ATP-binding protein PstB OS = *Streptococcus pneumoniae* (strain CGSP14) GN = pstB PE = 3 SV = 1 - [B2IQL3_STRPS] | Intracellular |
| B2IMZ5 | 31.91 | 19 | 564 | 144.21 | ABC transporter, ATP-binding/permease protein OS = *Streptococcus pneumoniae* (strain CGSP14) GN = SPCG_2042 PE = 4 SV = 1 - [B2IMZ5_STRPS] | Multi-transmembrane |
| B2IS39 | 59.8 | 8 | 102 | 143.18 | 30S ribosomal protein S10 OS = *Streptococcus pneumoniae* (strain CGSP14) GN = rpsJ PE = 3 SV = 1 - [RS10_STRPS] | Intracellular |
| B2IP78 | 53.87 | 13 | 375 | 141.59 | Carboxynorspermidine decarboxylase OS = *Streptococcus pneumoniae* (strain CGSP14) GN = nspC PE = 4 SV = 1 - [B2IP78_STRPS] | Intracellular |
| B2IM60 | 54.81 | 13 | 416 | 139.41 | Diaminopimelate decarboxylase OS = *Streptococcus pneumoniae* (strain CGSP14) GN = lysA PE = 3 SV = 1 - [B2IM60_STRPS] | Intracellular |
| B2IMH3 | 65.03 | 14 | 346 | 139.16 | Catabolite control protein A OS = *Streptococcus pneumoniae* (strain CGSP14) GN = ccpA PE = 4 SV = 1 - [B2IMH3_STRPS] | Intracellular |
| B2IS68 | 57.03 | 8 | 128 | 139.07 | 50S ribosomal protein L17 OS = *Streptococcus pneumoniae* (strain CGSP14) GN = rplQ PE = 3 SV = 1 - [RL17_STRPS] | Intracellular |
| B2INE0 | 34.95 | 13 | 329 | 136.77 | Cell division protein FtsX OS = *Streptococcus pneumoniae* (strain CGSP14) GN = ftsX PE = 3 SV = 1 - [B2INE0_STRPS] | Multi-transmembrane |

TABLE 5-continued

Proteins identified in MV$_L$ from serotype 3. The accession numbers refer to SwissProt on the date of filing.

| Accession # | Coverage | # Peptides | #AAs | Score | Description | Localization |
|---|---|---|---|---|---|---|
| B2ILV2 | 41.65 | 20 | 778 | 134.89 | Endonuclease MutS2 OS = *Streptococcus pneumoniae* (strain CGSP14) GN = mutS2 PE = 3 SV = 1 - [MUTS2_STRPS] | Intracellular |
| B2IQU4 | 63.93 | 15 | 280 | 133.96 | Oxidoreductase, aldo/keto reductase family OS = *Streptococcus pneumoniae* (strain CGSP14) GN = SPCG_1466 PE = 4 SV = 1 - [B2IQU4_STRPS] | Intracellular |
| B2IS55 | 71.35 | 14 | 178 | 129.78 | 50S ribosomal protein L6 OS = *Streptococcus pneumoniae* (strain CGSP14) GN = rplF PE = 3 SV = 1 - [RL6_STRPS] | Intracellular |
| B2ISJ8 | 67.95 | 15 | 156 | 129.16 | 30S ribosomal protein S7 OS = *Streptococcus pneumoniae* (strain CGSP14) GN = rpsG PE = 3 SV = 1 - [RS7_STRPS] | Intracellular |
| B2IRR6 | 24.81 | 8 | 266 | 128.96 | Cell division protein DivIVA OS = *Streptococcus pneumoniae* (strain CGSP14) GN = SPCG_1633 PE = 4 SV = 1 - [B2IRR6_STRPS] | Intracellular |
| B2ISI8 | 43.68 | 14 | 419 | 128.49 | Zinc metalloprotease OS = *Streptococcus pneumoniae* (strain CGSP14) GN = eep PE = 3 SV = 1 - [B2ISI8_STRPS] | Multi-transmembrane |
| B2INF3 | 47.94 | 9 | 267 | 128.19 | Peptidyl-prolyl cis-trans isomerase OS = *Streptococcus pneumoniae* (strain CGSP14) GN = ppiA PE = 3 SV = 1 - [B2INF3_STRPS] | Lipid anchored |
| B2IR96 | 96.59 | 13 | 176 | 127.15 | Adenine phosphoribosyltransferase OS = *Streptococcus pneumoniae* (strain CGSP14) GN = apt PE = 3 SV = 1 - [B2IR96_STRPS] | Intracellular |
| B2IQX1 | 63.36 | 12 | 292 | 124.75 | ATP synthase gamma chain OS = *Streptococcus pneumoniae* (strain CGSP14) GN = atpG PE = 3 SV = 1 - [ATPG_STRPS] | Intracellular |
| B2IQL7 | 40.41 | 12 | 292 | 124.49 | Phosphate ABC transporter, phosphate-binding protein, putative OS = *Streptococcus pneumoniae* (strain CGSP14) GN = SPCG_1389 PE = 4 SV = 1 - [B2IQL7_STRPS] | Lipid anchored |
| B2IS49 | 69.77 | 10 | 86 | 124.47 | 30S ribosomal protein S17 OS = *Streptococcus pneumoniae* (strain CGSP14) GN = rpsQ PE = 3 SV = 1 - [RS17_STRPS] | Intracellular |
| B2IQV3 | 35.99 | 8 | 289 | 123.64 | Glycerol uptake facilitator protein, putative OS = *Streptococcus pneumoniae* (strain CGSP14) GN = glpF PE = 3 SV = 1 - [B2IQV3_STRPS] | Multi-transmembrane |
| B2IM98 | 46.54 | 14 | 535 | 123.63 | CTP synthase OS = *Streptococcus pneumoniae* (strain CGSP14) GN = pyrG PE = 3 SV = 1 - [B2IM98_STRPS] | Intracellular |
| B2IQ39 | 47.38 | 9 | 344 | 123.25 | Uncharacterized protein OS = *Streptococcus pneumoniae* (strain CGSP14) GN = SPCG_1211 PE = 4 SV = 1 - [B2IQ39_STRPS] | Secretory (released) (with CS) |
| B2IP00 | 65.99 | 14 | 397 | 123.01 | Serine protease OS = *Streptococcus pneumoniae* (strain CGSP14) GN = sphtra PE = 4 SV = 1 - [B2IP00_STRPS] | N-terminally anchored (No CS) |
| B2IN41 | 35.2 | 16 | 429 | 122.13 | Histidine--tRNA ligase OS = *Streptococcus pneumoniae* (strain CGSP14) GN = hisS PE = 3 SV = 1 - [SYH_STRPS] | Intracellular |
| B2IRW4 | 40.6 | 15 | 436 | 120.41 | GTPase Der OS = *Streptococcus pneumoniae* (strain CGSP14) GN = der PE = 3 SV = 1 - [DER_STRPS] | Intracellular |
| B2IR68 | 35.97 | 13 | 531 | 119.86 | Uncharacterized protein OS = *Streptococcus pneumoniae* (strain CGSP14) GN = SPCG_1535 PE = 4 SV = 1 - [B2IR68_STRPS] | Multi-transmembrane |

TABLE 5-continued

Proteins identified in MV$_L$ from serotype 3. The accession numbers refer to SwissProt on the date of filing.

| Accession # | Coverage | # Peptides | #AAs | Score | Description | Localization |
|---|---|---|---|---|---|---|
| B2IPR2 | 27.94 | 18 | 841 | 118.97 | DNA gyrase subunit A OS = *Streptococcus pneumoniae* (strain CGSP14) GN = gyrA PE = 3 SV = 1 - [B2IPR2_STRPS] | Intracellular |
| B2IRA1 | 44.08 | 17 | 524 | 118.46 | DEAD-box ATP-dependent RNA helicase CshA OS = *Streptococcus pneumoniae* (strain CGSP14) GN = cshA PE = 3 SV = 1 - [B2IRA1_STRPS] | Intracellular |
| B2IM46 | 55.94 | 11 | 345 | 117.68 | Uncharacterized protein OS = *Streptococcus pneumoniae* (strain CGSP14) GN = SPCG_1931 PE = 4 SV = 1 - [B2IM46_STRPS] | N-terminally anchored (No CS) |
| B2ILR7 | 48.44 | 16 | 481 | 117.48 | 6-phosphogluconate dehydrogenase, decarboxylating OS = *Streptococcus pneumoniae* (strain CGSP14) GN = gnd PE = 3 SV = 1 - [B2ILR7_STRPS] | Intracellular |
| B2IR57 | 62.02 | 19 | 466 | 116.97 | Cof family protein/peptidyl-prolyl cis-trans isomerase, cyclophilin type OS = *Streptococcus pneumoniae* (strain CGSP14) GN = SPCG_1524 PE = 4 SV = 1 - [B2IR57_STRPS] | Intracellular |
| B2IND9 | 76.09 | 12 | 230 | 114.4 | Cell division ABC transporter, ATP-binding protein FtsE OS = *Streptococcus pneumoniae* (strain CGSP14) GN = ftsE PE = 4 SV = 1 - [B2IND9_STRPS] | Intracellular |
| B2IPU7 | 45 | 13 | 320 | 113.45 | Ribonucleoside-diphosphate reductase subunit beta OS = *Streptococcus pneumoniae* (strain CGSP14) GN = nrdF PE = 3 SV = 1 - [B2IPU7_STRPS] | Intracellular |
| B2IMS9 | 43.58 | 20 | 553 | 112.79 | Ribonuclease J OS = *Streptococcus pneumoniae* (strain CGSP14) GN = rnj PE = 3 SV = 1 - [B2IMS9_STRPS] | Intracellular |
| B2ISQ9 | 52.02 | 15 | 494 | 111.9 | UPF0371 protein SPCG_0344 OS = *Streptococcus pneumoniae* (strain CGSP14) GN = SPCG_0344 PE = 3 SV = 1 - [Y344_STRPS] | Intracellular |
| B2IPF4 | 53.38 | 14 | 311 | 110.86 | Adhesion lipoprotein OS = *Streptococcus pneumoniae* (strain CGSP14) GN = lmb PE = 3 SV = 1 - [B2IPF4_STRPS] | Lipid anchored |
| B2IM45 | 50.82 | 12 | 427 | 110.79 | UDP-N-acetylglucosamine 1-carboxyvinyltransferase OS = *Streptococcus pneumoniae* (strain CGSP14) GN = murA PE = 3 SV = 1 - [B2IM45_STRPS] | Intracellular |
| B2INN5 | 58.46 | 10 | 272 | 109.88 | Cell shape-determining protein MreC OS = *Streptococcus pneumoniae* (strain CGSP14) GN = mreC PE = 3 SV = 1 - [B2INN5_STRPS] | N-terminally anchored (No CS) |
| B2IM15 | 46.84 | 10 | 158 | 109.73 | Uncharacterized protein OS = *Streptococcus pneumoniae* (strain CGSP14) GN = SPCG_1901 PE = 4 SV = 1 - [B2IM15_STRPS] | Multi-transmembrane |
| B2IRP9 | 25.68 | 14 | 740 | 109.17 | GTP pyrophosphokinase OS = *Streptococcus pneumoniae* (strain CGSP14) GN = relA PE = 3 SV = 1 - [B2IRP9_STRPS] | Intracellular |
| B2INE1 | 34.71 | 11 | 726 | 108.73 | PTS system, IIABC components OS = *Streptococcus pneumoniae* (strain CGSP14) GN = ptsG PE = 4 SV = 1 - [B2INE1_STRPS] | Multi-transmembrane |
| B2IST7 | 48.44 | 12 | 417 | 108.26 | Capsular polysaccharide biosynthesis protein, putative OS = *Streptococcus pneumoniae* (strain CGSP14) GN = SPCG_1812 PE = 3 SV = 1 - [B2IST7_STRPS] | Intracellular |

TABLE 5-continued

Proteins identified in $MV_L$ from serotype 3. The accession numbers refer to SwissProt on the date of filing.

| Accession # | Coverage | # Peptides | #AAs | Score | Description | Localization |
|---|---|---|---|---|---|---|
| B2IP76 | 71.33 | 14 | 286 | 106.74 | Polyamine aminopropyltransferase OS = Streptococcus pneumoniae (strain CGSP14) GN = speE PE = 3 SV = 1 - [B2IP76_STRPS] | Intracellular |
| B2IS23 | 34.49 | 22 | 954 | 105.34 | UvrABC system protein A OS = Streptococcus pneumoniae (strain CGSP14) GN = uvrA PE = 3 SV = 1 - [B2IS23_STRPS] | Intracellular |
| B2IS53 | 52.81 | 7 | 89 | 105.15 | 30S ribosomal protein S14 OS = Streptococcus pneumoniae (strain CGSP14) GN = rpsN PE = 3 SV = 1 - [RS14_STRPS] | Intracellular |
| B2IQN9 | 49.79 | 20 | 486 | 105.03 | Nicotinate phosphoribosyltransferase OS = Streptococcus pneumoniae (strain CGSP14) GN = SPCG_1408 PE = 3 SV = 1 - [B2IQN9_STRPS] | Intracellular |
| B2ISZ6 | 49.88 | 13 | 419 | 104.34 | Sugar ABC transporter, sugar-binding protein OS = Streptococcus pneumoniae (strain CGSP14) GN = SPCG_1871 PE = 4 SV = 1 - [B2ISZ6_STRPS] | Lipid anchored |
| B2IMA9 | 47.02 | 17 | 487 | 101.63 | Type I restriction-modification system, M subunit OS = Streptococcus pneumoniae (strain CGSP14) GN = hsdM PE = 4 SV = 1 - [B2IMA9_STRPS] | Intracellular |
| B2IQH2 | 72.19 | 13 | 187 | 100.73 | 50S ribosomal protein L10 OS = Streptococcus pneumoniae (strain CGSP14) GN = rplJ PE = 3 SV = 1 - [B2IQH2_STRPS] | Intracellular |
| B2IR61 | 39.82 | 14 | 447 | 100.57 | Asparagine--tRNA ligase OS = Streptococcus pneumoniae (strain CGSP14) GN = asnS PE = 3 SV = 1 - [B2IR61_STRPS] | Intracellular |
| B2IM30 | 50 | 15 | 338 | 100.22 | Transcriptional regulator, putative OS = Streptococcus pneumoniae (strain CGSP14) GN = lytR PE = 4 SV = 1 - [B2IM30_STRPS] | Secretory (released) (with CS) |
| B2ISV9 | 32.29 | 10 | 511 | 99.16 | Choline transporter OS = Streptococcus pneumoniae (strain CGSP14) GN = SPCG_1834 PE = 3 SV = 1 - [B2ISV9_STRPS] | Multi-transmembrane |
| B2IS51 | 78.22 | 12 | 101 | 98.15 | 50S ribosomal protein L24 OS = Streptococcus pneumoniae (strain CGSP14) GN = rplX PE = 3 SV = 1 - [RL24_STRPS] | Intracellular |
| B2IRX0 | 76.67 | 11 | 240 | 97.84 | ABC transporter, ATP-binding protein OS = Streptococcus pneumoniae (strain CGSP14) GN = SPCG_1687 PE = 4 SV = 1 - [B2IRX0_STRPS] | Intracellular |
| B2ISX8 | 46.73 | 11 | 336 | 97.53 | Non-canonical purine NTP pyrophosphatase OS = Streptococcus pneumoniae (strain CGSP14) GN = SPCG_1853 PE = 3 SV = 1 - [B2ISX8_STRPS] | Intracellular |
| B2IN24 | 45.35 | 14 | 505 | 97.46 | 4-alpha-glucanotransferase OS = Streptococcus pneumoniae (strain CGSP14) GN = malM PE = 3 SV = 1 - [B2IN24_STRPS] | Intracellular |
| B2IM61 | 54.55 | 12 | 275 | 97.4 | Purine operon repressor OS = Streptococcus pneumoniae (strain CGSP14) GN = purR PE = 4 SV = 1 - [B2IM61_STRPS] | Intracellular |
| B2ILX0 | 55.38 | 16 | 455 | 97.1 | Acetyl-CoA carboxylase OS = Streptococcus pneumoniae (strain CGSP14) GN = accC PE = 4 SV = 1 - [B2ILX0_STRPS] | Intracellular |
| B2IQ19 | 35.91 | 15 | 763 | 96.38 | DNA helicase OS = Streptococcus pneumoniae (strain CGSP14) GN = pcrA PE = 3 SV = 1 - [B2IQ19_STRPS] | Intracellular |

TABLE 5-continued

Proteins identified in MV$_L$ from serotype 3. The accession numbers refer to SwissProt on the date of filing.

| Accession # | Coverage | # Peptides | #AAs | Score | Description | Localization |
|---|---|---|---|---|---|---|
| B2IPZ6 | 69.23 | 10 | 91 | 95.95 | DNA-binding protein HU OS = *Streptococcus pneumoniae* (strain CGSP14) GN = hlpA PE = 3 SV = 1 - [B2IPZ6_STRPS] | Intracellular |
| B2INE5 | 31.57 | 12 | 396 | 95.45 | S-adenosylmethionine synthase OS = *Streptococcus pneumoniae* (strain CGSP14) GN = metK PE = 3 SV = 1 - [METK_STRPS] | Intracellular |
| B2IS82 | 28.53 | 15 | 659 | 94.22 | Serine/threonine protein kinase OS = *Streptococcus pneumoniae* (strain CGSP14) GN = pkn2 PE = 3 SV = 1 - [B2IS82_STRPS] | Intracellular/ TMH start AFTER 60 |
| B2IS65 | 58.68 | 10 | 121 | 93.19 | 30S ribosomal protein S13 OS = *Streptococcus pneumoniae* (strain CGSP14) GN = rpsM PE = 3 SV = 1 - [RS13_STRPS] | Intracellular |
| B2IMI4 | 35.02 | 18 | 731 | 92.99 | Penicillin-binding protein 2A OS = *Streptococcus pneumoniae* (strain CGSP14) GN = pbp2A PE = 4 SV = 1 - [B2IMI4_STRPS] | N-terminally anchored (No CS) |
| B2IRK4 | 37.05 | 17 | 637 | 92.87 | tRNA uridine 5-carboxymethylaminomethyl modification enzyme MnmG OS = *Streptococcus pneumoniae* (strain CGSP14) GN = mnmG PE = 3 SV = 1 - [B2IRK4_STRPS] | Intracellular |
| B2ISW0 | 69.01 | 11 | 242 | 92.71 | Choline transporter OS = *Streptococcus pneumoniae* (strain CGSP14) GN = SPCG_1835 PE = 4 SV = 1 - [B2ISW0_STRPS] | Intracellular |
| B2INP6 | 39.59 | 10 | 341 | 92.59 | Tryptophan--tRNA ligase OS = *Streptococcus pneumoniae* (strain CGSP14) GN = trpS PE = 3 SV = 1 - [B2INP6_STRPS] | Intracellular |
| B2INC5 | 39.5 | 11 | 281 | 92.15 | Uncharacterized protein OS = *Streptococcus pneumoniae* (strain CGSP14) GN = SPCG_0692 PE = 4 SV = 1 - [B2INC5_STRPS] | Intracellular |
| B2IP66 | 36.64 | 17 | 715 | 91.51 | Transcriptional regulator, putative OS = *Streptococcus pneumoniae* (strain CGSP14) GN = SPCG_0885 PE = 4 SV = 1 - [B2IP66_STRPS] | Intracellular |
| B2ISY1 | 46.58 | 14 | 541 | 91.27 | Dextran glucosidase DexS, putative OS = *Streptococcus pneumoniae* (strain CGSP14) GN = dexS PE = 4 SV = 1 - [B2ISY1_STRPS] | Intracellular |
| B2ISK7 | 38.51 | 11 | 444 | 91.26 | Aminopeptidase C OS = *Streptococcus pneumoniae* (strain CGSP14) GN = pepC PE = 4 SV = 1 - [B2ISK7_STRPS] | Intracellular |
| B2INL6 | 30.75 | 8 | 335 | 91.2 | ABC transporter, substrate-binding protein, putative OS = *Streptococcus pneumoniae* (strain CGSP14) GN = SPCG_2165 PE = 4 SV = 1 - [B2INL6_STRPS] | Lipid anchored |
| B2IQY9 | 25.83 | 11 | 453 | 90.37 | Chromosomal replication initiator protein DnaA OS = *Streptococcus pneumoniae* (strain CGSP14) GN = dnaA PE = 3 SV = 1 - [DNAA_STRPS] | Intracellular |
| B2IRS8 | 22.34 | 13 | 685 | 90.12 | Penicillin-binding protein 2B OS = *Streptococcus pneumoniae* (strain CGSP14) GN = pbp2B PE = 4 SV = 1 - [B2IRS8_STRPS] | N-terminally anchored (No CS) |
| B2IS56 | 53.44 | 8 | 131 | 88.46 | 50S ribosomal protein L18 OS = *Streptococcus pneumoniae* (strain CGSP14) GN = rplR PE = 3 SV = 1 - [B2IS56_STRPS] | Intracellular |
| B2IQ12 | 40.13 | 9 | 319 | 88.41 | Ribose-phosphate pyrophosphokinase OS = *Streptococcus pneumoniae* (strain CGSP14) GN = prs PE = 3 SV = 1 - [B2IQ12_STRPS] | Intracellular |

TABLE 5-continued

Proteins identified in MV$_L$ from serotype 3. The accession numbers refer to SwissProt on the date of filing.

| Accession # | Coverage | # Peptides | #AAs | Score | Description | Localization |
|---|---|---|---|---|---|---|
| B2IS67 | 52.73 | 9 | 311 | 88.17 | DNA-directed RNA polymerase subunit alpha OS = *Streptococcus pneumoniae* (strain CGSP14) GN = rpoA PE = 3 SV = 1 - [B2IS67_STRPS] | Intracellular |
| B2IS59 | 64.38 | 9 | 146 | 88.05 | 50S ribosomal protein L15 OS = *Streptococcus pneumoniae* (strain CGSP14) GN = rplO PE = 3 SV = 1 - [RL15_STRPS] | Intracellular |
| B2IQ61 | 41.52 | 9 | 289 | 87.7 | Choline kinase OS = *Streptococcus pneumoniae* (strain CGSP14) GN = pck PE = 4 SV = 1 - [B2IQ61_STRPS] | Intracellular |
| B2ISY2 | 24.4 | 10 | 705 | 87.27 | Trehalose PTS system, IIABC components OS = *Streptococcus pneumoniae* (strain CGSP14) GN = treP PE = 4 SV = 1 - [B2ISY2_STRPS] | Multi-transmembrane |
| B2IMQ3 | 25.97 | 12 | 801 | 86.8 | Phenylalanine--tRNA ligase beta subunit OS = *Streptococcus pneumoniae* (strain CGSP14) GN = pheT PE = 3 SV = 1 - [B2IMQ3_STRPS] | Intracellular |
| B2IQ02 | 60.82 | 9 | 97 | 86.49 | 50S ribosomal protein L27 OS = *Streptococcus pneumoniae* (strain CGSP14) GN = rpmA PE = 3 SV = 1 - [RL27_STRPS] | Intracellular |
| B2IN58 | 40.3 | 11 | 335 | 86.4 | Uncharacterized protein OS = *Streptococcus pneumoniae* (strain CGSP14) GN = SPCG_2101 PE = 4 SV = 1 - [B2IN58_STRPS] | Multi-transmembrane |
| B2IQW4 | 62.2 | 10 | 209 | 84.4 | Amino acid ABC transporter, ATP-binding protein OS = *Streptococcus pneumoniae* (strain CGSP14) GN = SPCG_1486 PE = 4 SV = 1 - [B2IQW4_STRPS] | Intracellular |
| B2IP74 | 35.23 | 13 | 491 | 84.24 | Lysine decarboxylase OS = *Streptococcus pneumoniae* (strain CGSP14) GN = cad PE = 4 SV = 1 - [B2IP74_STRPS] | Intracellular |
| B2IS70 | 42.49 | 11 | 433 | 83.11 | UPF0210 protein SPCG_0246 OS = *Streptococcus pneumoniae* (strain CGSP14) GN = SPCG_0246 PE = 3 SV = 1 - [B2IS70_STRPS] | Intracellular |
| B2IQ66 | 64.29 | 13 | 280 | 83.05 | LicD2 protein OS = *Streptococcus pneumoniae* (strain CGSP14) GN = licD2 PE = 4 SV = 1 - [B2IQ66_STRPS] | Intracellular |
| B2IRK5 | 34.17 | 12 | 559 | 81.76 | Ribonuclease J OS = *Streptococcus pneumoniae* (strain CGSP14) GN = rnj PE = 3 SV = 1 - [B2IRK5_STRPS] | Intracellular |
| B2IR84 | 68.24 | 12 | 296 | 81.42 | Nucleotide-binding protein SPCG_1551 OS = *Streptococcus pneumoniae* (strain CGSP14) GN = SPCG_1551 PE = 3 SV = 1 - [Y1551_STRPS] | Intracellular |
| B2IMB5 | 34.93 | 15 | 607 | 81.24 | Chaperone protein DnaK OS = *Streptococcus pneumoniae* (strain CGSP14) GN = dnaK PE = 3 SV = 1 - [DNAK_STRPS] | Intracellular |
| B2IQ62 | 58.09 | 12 | 346 | 80.31 | Alcohol dehydrogenase, zinc-containing OS = *Streptococcus pneumoniae* (strain CGSP14) GN = SPCG_1234 PE = 4 SV = 1 - [B2IQ62_STRPS] | Intracellular |
| B2IMB9 | 37.86 | 11 | 243 | 79.94 | ABC transporter, ATP-binding protein OS = *Streptococcus pneumoniae* (strain CGSP14) GN = SPCG_0494 PE = 4 SV = 1 - [B2IMB9_STRPS] | Intracellular |
| B2IRD4 | 56.18 | 5 | 89 | 79.7 | 30S ribosomal protein S15 OS = *Streptococcus pneumoniae* (strain CGSP14) GN = rpsO PE = 3 SV = 1 - [RS15_STRPS] | Intracellular |

TABLE 5-continued

Proteins identified in MV$_L$ from serotype 3. The accession numbers refer to SwissProt on the date of filing.

| Accession # | Coverage | # Peptides | #AAs | Score | Description | Localization |
|---|---|---|---|---|---|---|
| B2IN68 | 50.79 | 8 | 126 | 79.14 | Uncharacterized protein OS = Streptococcus pneumoniae (strain CGSP14) GN = SPCG_0635 PE = 4 SV = 1 - [B2IN68_STRPS] | N-terminally anchored (No CS) |
| B2IQN0 | 44.09 | 3 | 127 | 78.99 | Uncharacterized protein OS = Streptococcus pneumoniae (strain CGSP14) GN = SPCG_1399 PE = 4 SV = 1 - [B2IQN0_STRPS] | N-terminally anchored (No CS) |
| B2ILY0 | 36.58 | 14 | 514 | 78.96 | Peptide chain release factor 3 OS = Streptococcus pneumoniae (strain CGSP14) GN = prfC PE = 3 SV = 1 - [RF3_STRPS] | Intracellular |
| B2IS54 | 57.58 | 8 | 132 | 78.42 | 30S ribosomal protein S8 OS = Streptococcus pneumoniae (strain CGSP14) GN = rpsH PE = 3 SV = 1 - [RS8_STRPS] | Intracellular |
| B2IMB6 | 35.19 | 13 | 378 | 78.27 | Chaperone protein DnaJ OS = Streptococcus pneumoniae (strain CGSP14) GN = dnaJ PE = 3 SV = 1 - [B2IMB6_STRPS] | Intracellular |
| B2IQS5 | 42.11 | 12 | 247 | 78.16 | Amino acid ABC transporter, ATP-binding protein OS = Streptococcus pneumoniae (strain CGSP14) GN = SPCG_1447 PE = 4 SV = 1 - [B2IQS5_STRPS] | Intracellular |
| B2IRH0 | 33.01 | 12 | 512 | 76.84 | ABC transporter, substrate-binding protein OS = Streptococcus pneumoniae (strain CGSP14) GN = SPCG_0089 PE = 4 SV = 1 - [B2IRH0_STRPS] | Lipid anchored |
| B2IPW9 | 50.88 | 11 | 283 | 76.72 | Ribosome biogenesis GTPase A OS = Streptococcus pneumoniae (strain CGSP14) GN = SPCG_1141 PE = 3 SV = 1 - [B2IPW9_STRPS] | Intracellular |
| B2IN18 | 48.09 | 11 | 418 | 76.44 | Tyrosine--tRNA ligase OS = Streptococcus pneumoniae (strain CGSP14) GN = tyrS PE = 3 SV = 1 - [SYY_STRPS] | Intracellular |
| B2IQV9 | 33.39 | 13 | 572 | 75.14 | Phosphoglucomutase OS = Streptococcus pneumoniae (strain CGSP14) GN = pgm PE = 3 SV = 1 - [B2IQV9_STRPS] | Intracellular |
| B2IP77 | 38.9 | 9 | 419 | 74.94 | Uncharacterized protein OS = Streptococcus pneumoniae (strain CGSP14) GN = SPCG_0896 PE = 4 SV = 1 - [B2IP77_STRPS] | Intracellular |
| B2IQ63 | 53.19 | 8 | 235 | 74.22 | 2-C-methyl-D-erythritol 4-phosphate cytidylyltransferase OS = Streptococcus pneumoniae (strain CGSP14) GN = ispD PE = 3 SV = 1 - [ISPD_STRPS] | Intracellular |
| B2IRQ4 | 65.34 | 11 | 251 | 74.2 | Manganese ABC transporter, ATP-binding protein OS = Streptococcus pneumoniae (strain CGSP14) GN = SPCG_1621 PE = 4 SV = 1 - [B2IRQ4_STRPS] | Intracellular |
| B2IQX3 | 62.36 | 8 | 178 | 73.32 | ATP synthase subunit delta OS = Streptococcus pneumoniae (strain CGSP14) GN = atpH PE = 3 SV = 1 - [ATPD_STRPS] | Intracellular |
| B2INX4 | 27.48 | 12 | 826 | 73.21 | DNA topoisomerase 4 subunit A OS = Streptococcus pneumoniae (strain CGSP14) GN = parC PE = 3 SV = 1 - [B2INX4_STRPS] | Intracellular |
| B2IN76 | 40.67 | 12 | 450 | 72.88 | UDP-N-acetylmuramoylalanine--D-glutamate ligase OS = Streptococcus pneumoniae (strain CGSP14) GN = murD PE = 3 SV = 1 - [MURD_STRPS] | Intracellular |
| B2IPC3 | 41.47 | 10 | 299 | 72.75 | GTPase Era OS = Streptococcus pneumoniae (strain CGSP14) GN = era PE = 3 SV = 1 - [ERA_STRPS] | Intracellular |

TABLE 5-continued

Proteins identified in MV$_L$ from serotype 3. The accession numbers refer to SwissProt on the date of filing.

| Accession # | Coverage | # Peptides | #AAs | Score | Description | Localization |
|---|---|---|---|---|---|---|
| B2IRX7 | 40.79 | 13 | 353 | 72.1 | Methionine import ATP-binding protein MetN OS = *Streptococcus pneumoniae* (strain CGSP14) GN = metN PE = 3 SV = 1 - [B2IRX7_STRPS] | Intracellular |
| B2INU1 | 50.65 | 9 | 306 | 70.6 | Bifunctional protein FolD OS = *Streptococcus pneumoniae* (strain CGSP14) GN = folD PE = 3 SV = 1 - [B2INU1_STRPS] | Lipid anchored |
| B2ILW4 | 36.11 | 6 | 324 | 69.62 | Enoyl-(Acyl-carrier-protein) reductase OS = *Streptococcus pneumoniae* (strain CGSP14) GN = fabK PE = 4 SV = 1 - [B2ILW4_STRPS] | Intracellular |
| B2IS45 | 40.35 | 3 | 114 | 69.56 | 50S ribosomal protein L22 OS = *Streptococcus pneumoniae* (strain CGSP14) GN = rplV PE = 3 SV = 1 - [RL22_STRPS] | Intracellular |
| B2IPZ1 | 30.21 | 13 | 652 | 67.59 | DNA ligase OS = *Streptococcus pneumoniae* (strain CGSP14) GN = ligA PE = 3 SV = 1 - [DNLJ_STRPS] | Intracellular |
| B2IMZ3 | 34.66 | 12 | 603 | 66.96 | ABC transporter, ATP-binding/permease protein OS = *Streptococcus pneumoniae* (strain CGSP14) GN = SPCG_2040 PE = 4 SV = 1 - [B2IMZ3_STRPS] | Multi-transmembrane |
| B2IS63 | 54.72 | 6 | 212 | 66.76 | Adenylate kinase OS = *Streptococcus pneumoniae* (strain CGSP14) GN = adk PE = 3 SV = 1 - [KAD_STRPS] | Intracellular |
| B2INV5 | 53.01 | 6 | 83 | 65.46 | 30S ribosomal protein S20 OS = *Streptococcus pneumoniae* (strain CGSP14) GN = rpsT PE = 3 SV = 1 - [B2INV5_STRPS] | Intracellular |
| B2IRK2 | 38.07 | 10 | 373 | 65.45 | tRNA-specific 2-thiouridylase MnmA OS = *Streptococcus pneumoniae* (strain CGSP14) GN = mnmA PE = 3 SV = 2 - [MNMA_STRPS] | Intracellular |
| B2IRB7 | 27.22 | 2 | 158 | 65.21 | Uncharacterized protein OS = *Streptococcus pneumoniae* (strain CGSP14) GN = SPCG_1584 PE = 4 SV = 1 - [B2IRB7_STRPS] | N-terminally anchored (No CS) |
| B2INE6 | 56.27 | 10 | 311 | 64.68 | Dihydroorotate dehydrogenase OS = *Streptococcus pneumoniae* (strain CGSP14) GN = pyrD PE = 3 SV = 1 - [B2INE6_STRPS] | Intracellular |
| B2IMB0 | 27.41 | 15 | 777 | 64.13 | Type I restriction-modification system, R subunit OS = *Streptococcus pneumoniae* (strain CGSP14) GN = hsdR PE = 4 SV = 1 - [B2IMB0_STRPS] | Intracellular |
| B2ISQ4 | 20.27 | 11 | 750 | 63.95 | Penicillin-binding protein 2X OS = *Streptococcus pneumoniae* (strain CGSP14) GN = pbp2X PE = 4 SV = 1 - [B2ISQ4_STRPS] | N-terminally anchored (No CS) |
| B2IPQ3 | 27.88 | 12 | 556 | 63.73 | Formate--tetrahydrofolate ligase OS = *Streptococcus pneumoniae* (strain CGSP14) GN = fhs PE = 3 SV = 1 - [FTHS_STRPS] | Intracellular |
| B2IMU7 | 41.84 | 5 | 141 | 63.38 | 50S ribosomal protein L11 OS = *Streptococcus pneumoniae* (strain CGSP14) GN = rplK PE = 3 SV = 1 - [RL11_STRPS] | Intracellular |
| B2ISY0 | 38 | 4 | 100 | 62.82 | UPF0154 protein SPCG_1855 OS = *Streptococcus pneumoniae* (strain CGSP14) GN = SPCG_1855 PE = 3 SV = 1 - [B2ISY0_STRPS] | N-terminally anchored (No CS) |
| B2IQP4 | 29.49 | 9 | 434 | 62.33 | Peptidase, U32 family OS = *Streptococcus pneumoniae* (strain CGSP14) GN = SPCG_1416 PE = 4 SV = 1 - [B2IQP4_STRPS] | Intracellular |
| B2IR79 | 57.14 | 11 | 259 | 62.31 | Uncharacterized protein OS = *Streptococcus pneumoniae* (strain CGSP14) GN = SPCG_1546 PE = 4 SV = 1 - [B2IR79_STRPS] | N-terminally anchored (No CS) |

TABLE 5-continued

Proteins identified in MV$_L$ from serotype 3. The accession numbers refer to SwissProt on the date of filing.

| Accession # | Coverage | # Peptides | #AAs | Score | Description | Localization |
|---|---|---|---|---|---|---|
| B2ILW2 | 21.6 | 8 | 324 | 62.19 | 3-oxoacyl-[acyl-carrier-protein] synthase 3 OS = *Streptococcus pneumoniae* (strain CGSP14) GN = fabH PE = 3 SV = 1 - [FABH_STRPS] | Intracellular |
| B2IPZ9 | 43.28 | 9 | 305 | 61.07 | Riboflavin biosynthesis protein OS = *Streptococcus pneumoniae* (strain CGSP14) GN = mreA PE = 3 SV = 1 - [B2IPZ9_STRPS] | Intracellular |
| B2IN32 | 29.98 | 13 | 587 | 60.72 | Aspartate--tRNA ligase OS = *Streptococcus pneumoniae* (strain CGSP14) GN = aspS PE = 3 SV = 1 - [SYD_STRPS] | Intracellular |
| B2IRR9 | 42.46 | 7 | 179 | 60.72 | Cell division protein SepF OS = *Streptococcus pneumoniae* (strain CGSP14) GN = sepF PE = 3 SV = 1 - [SEPF_STRPS] | Intracellular |
| B2IN19 | 28.12 | 13 | 690 | 60.07 | Cation-transporting ATPase, EI-E2 family OS = *Streptococcus pneumoniae* (strain CGSP14) GN = ctpC PE = 3 SV = 1 - [B2IN19_STRPS] | Intracellular |
| B2IQY8 | 36.71 | 9 | 444 | 59.95 | UDP-N-acetylmuramate--L-alanine ligase OS = *Streptococcus pneumoniae* (strain CGSP14) GN = murC PE = 3 SV = 1 - [MURC_STRPS] | Intracellular |
| B2IS26 | 33.86 | 8 | 189 | 59.81 | Uncharacterized protein OS = *Streptococcus pneumoniae* (strain CGSP14) GN = SPCG_0204 PE = 4 SV = 1 - [B2IS26_STRPS] | Lipid anchored |
| B2INY7 | 45.25 | 8 | 263 | 59.27 | ABC transporter, ATP-binding protein OS = *Streptococcus pneumoniae* (strain CGSP14) GN = SPCG_0812 PE = 4 SV = 1 - [B2INY7_STRPS] | Intracellular |
| B2ILR6 | 14.66 | 6 | 464 | 58.78 | Mid-cell-anchored protein Z OS = *Streptococcus pneumoniae* (strain CGSP14) GN = mapZ PE = 3 SV = 1 - [B2ILR6_STRPS] | N-terminally anchored (No CS) |
| B2ILX8 | 36.68 | 10 | 488 | 58.59 | Glutamyl-tRNA(Gln) amidotransferase subunit A OS = *Streptococcus pneumoniae* (strain CGSP14) GN = gatA PE = 3 SV = 1 - [GATA_STRPS] | Intracellular |
| B2IMN3 | 35.26 | 7 | 380 | 58.5 | Queuine tRNA-ribosyltransferase OS = *Streptococcus pneumoniae* (strain CGSP14) GN = tgt PE = 3 SV = 1 - [TGT_STRPS] | Intracellular |
| B2IN17 | 21.09 | 12 | 825 | 58.4 | Penicillin-binding protein 1B OS = *Streptococcus pneumoniae* (strain CGSP14) GN = pbp1B PE = 4 SV = 1 - [B2IN17_STRPS] | Intracellular/TMH start AFTER 60 |
| B2IR27 | 45.45 | 8 | 330 | 57.61 | Phosphate acyltransferase OS = *Streptococcus pneumoniae* (strain CGSP14) GN = plsX PE = 3 SV = 1 - [PLSX_STRPS] | Intracellular |
| B2INF7 | 73.21 | 6 | 112 | 56.77 | ATP cone domain-containing protein OS = *Streptococcus pneumoniae* (strain CGSP14) GN = SPCG_0728 PE = 4 SV = 1 - [B2INF7_STRPS] | Intracellular |
| B2IMZ8 | 20.78 | 9 | 563 | 56.13 | Arginine--tRNA ligase OS = *Streptococcus pneumoniae* (strain CGSP14) GN = argS PE = 3 SV = 1 - [SYR_STRPS] | Intracellular |
| B2ILU5 | 35.6 | 10 | 427 | 55.96 | Trigger factor OS = *Streptococcus pneumoniae* (strain CGSP14) GN = tig PE = 3 SV = 1 - [TIG_STRPS] | Intracellular |
| B2INK8 | 56.55 | 9 | 336 | 55.86 | tRNA-dihydrouridine synthase OS = *Streptococcus pneumoniae* (strain CGSP14) GN = SPCG_2157 PE = 3 SV = 1 - [B2INK8_STRPS] | Intracellular |

TABLE 5-continued

Proteins identified in MV$_L$ from serotype 3. The accession numbers refer to SwissProt on the date of filing.

| Accession # | Coverage | # Peptides | #AAs | Score | Description | Localization |
|---|---|---|---|---|---|---|
| B2IM90 | 37.14 | 11 | 560 | 55.51 | ABC transporter, ATP-binding protein OS = *Streptococcus pneumoniae* (strain CGSP14) GN = SPCG_0465 PE = 4 SV = 1 - [B2IM90_STRPS] | Intracellular |
| B2IQA4 | 37.72 | 12 | 448 | 54.94 | Glutamate dehydrogenase OS = *Streptococcus pneumoniae* (strain CGSP14) GN = gdhA PE = 3 SV = 1 - [B2IQA4_STRPS] | Intracellular |
| B2IPP0 | 30.1 | 8 | 495 | 54.8 | Glucose-6-phosphate 1-dehydrogenase OS = *Streptococcus pneumoniae* (strain CGSP14) GN = zwf PE = 3 SV = 1 - [B2IPP0_STRPS] | Intracellular |
| B2IPZ5 | 24.33 | 13 | 633 | 54.29 | ABC transporter, ATP-binding protein OS = *Streptococcus pneumoniae* (strain CGSP14) GN = SPCG_1167 PE = 4 SV = 1 - [B2IPZ5_STRPS] | Intracellular |
| B2IS10 | 23.73 | 8 | 649 | 54.27 | DNA mismatch repair protein MutL OS = *Streptococcus pneumoniae* (strain CGSP14) GN = mutL PE = 3 SV = 1 - [MUTL_STRPS] | Intracellular |
| B2IN96 | 47.62 | 10 | 378 | 54.14 | Lactate oxidase OS = *Streptococcus pneumoniae* (strain CGSP14) GN = lctO PE = 4 SV = 1 - [B2IN96_STRPS] | Intracellular |
| B2IND6 | 51.69 | 6 | 236 | 53.89 | Branched-chain amino acid ABC transporter, ATP-binding protein OS = *Streptococcus pneumoniae* (strain CGSP14) GN = SPCG_0703 PE = 4 SV = 1 - [B2IND6_STRPS] | Intracellular |
| B2IS98 | 58.85 | 9 | 209 | 53.7 | Probable nicotinate-nucleotide adenylyltransferase OS = *Streptococcus pneumoniae* (strain CGSP14) GN = nadD PE = 3 SV = 1 - [B2IS98_STRPS] | Intracellular |
| B2IPN8 | 43.01 | 8 | 272 | 53.21 | Cof family protein OS = *Streptococcus pneumoniae* (strain CGSP14) GN = SPCG_1058 PE = 4 SV = 1 - [B2IPN8_STRPS] | Intracellular |
| B2INN8 | 51.27 | 10 | 275 | 52.83 | Energy-coupling factor transporter ATP-binding protein EcfA OS = *Streptococcus pneumoniae* (strain CGSP14) GN = ecfA PE = 3 SV = 1 - [B2INN8_STRPS] | N-terminally anchored (No CS) |
| B2ISR0 | 23.55 | 8 | 535 | 52.43 | Glucan 1,6-alpha-glucosidase OS = *Streptococcus pneumoniae* (strain CGSP14) GN = dexB PE = 4 SV = 1 - [B2ISR0_STRPS] | Intracellular |
| B2IRF6 | 52.19 | 8 | 228 | 52.22 | Potassium uptake protein, Trk family OS = *Streptococcus pneumoniae* (strain CGSP14) GN = trkA PE = 4 SV = 1 - [B2IRF6_STRPS] | N-terminally anchored (with CS) |
| B2IM43 | 17.16 | 7 | 443 | 51.63 | CBS domain protein OS = *Streptococcus pneumoniae* (strain CGSP14) GN = SPCG_1928 PE = 4 SV = 1 - [B2IM43_STRPS] | Multi-transmembrane |
| B2ILX2 | 40 | 6 | 255 | 51.58 | Acetyl-coenzyme A carboxylase carboxyl transferase subunit alpha OS = *Streptococcus pneumoniae* (strain CGSP14) GN = accA PE = 3 SV = 1 - [ACCA_STRPS] | Intracellular |
| B2ISA0 | 34.78 | 10 | 368 | 51.32 | GTP-binding protein OS = *Streptococcus pneumoniae* (strain CGSP14) GN = SPCG_1723 PE = 4 SV = 1 - [B2ISA0_STRPS] | Intracellular |
| B2IPB9 | 23.19 | 10 | 677 | 50.7 | Endo-beta-N-acetylglucosaminidase OS = *Streptococcus pneumoniae* (strain CGSP14) GN = lytB PE = 4 SV = 1 - [B2IPB9_STRPS] | Secretory (released) (with CS) |

TABLE 5-continued

Proteins identified in MV$_L$ from serotype 3. The accession numbers refer to SwissProt on the date of filing.

| Accession # | Coverage | # Peptides | #AAs | Score | Description | Localization |
|---|---|---|---|---|---|---|
| B2IQW9 | 61.87 | 6 | 139 | 50.69 | ATP synthase epsilon chain OS = *Streptococcus pneumoniae* (strain CGSP14) GN = atpC PE = 3 SV = 1 - [ATPE_STRPS] | Intracellular |
| B2IPN9 | 24.94 | 7 | 429 | 50.34 | Signal recognition particle receptor FtsY OS = *Streptococcus pneumoniae* (strain CGSP14) GN = ftsY PE = 3 SV = 1 - [B2IPN9_STRPS] | Intracellular |
| B2IRI7 | 17.95 | 9 | 713 | 49.57 | Uncharacterized protein OS = *Streptococcus pneumoniae* (strain CGSP14) GN = SPCG_0106 PE = 4 SV = 1 - [B2IRI7_STRPS] | Multi-transmembrane |
| B2IQH3 | 24.39 | 7 | 488 | 49.39 | Chlorohydrolase OS = *Streptococcus pneumoniae* (strain CGSP14) GN = trzA PE = 4 SV = 1 - [B2IQH3_STRPS] | Intracellular |
| B2IRD2 | 21.59 | 7 | 264 | 48.68 | Acyltransferase family protein OS = *Streptococcus pneumoniae* (strain CGSP14) GN = SPCG_1599 PE = 4 SV = 1 - [B2IRD2_STRPS] | Multi-transmembrane |
| B2IR63 | 31.14 | 7 | 395 | 48.62 | Aspartate aminotransferase OS = *Streptococcus pneumoniae* (strain CGSP14) GN = aspB PE = 3 SV = 1 - [B2IR63_STRPS] | Intracellular |
| B2INK4 | 23.36 | 10 | 608 | 48.46 | Uncharacterized protein OS = *Streptococcus pneumoniae* (strain CGSP14) GN = SPCG_2153 PE = 4 SV = 1 - [B2INK4_STRPS] | N-terminally anchored (No CS) |
| B2INI8 | 28.14 | 7 | 501 | 48.06 | Zinc ABC transporter, zinc-binding lipoprotein OS = *Streptococcus pneumoniae* (strain CGSP14) GN = SPCG_2137 PE = 3 SV = 1 - [B2INI8_STRPS] | Lipid anchored |
| B2IPU4 | 40.71 | 7 | 253 | 47.82 | Lactose phosphotransferase system repressor OS = *Streptococcus pneumoniae* (strain CGSP14) GN = lacR PE = 4 SV = 1 - [B2IPU4_STRPS] | Intracellular |
| B2INN7 | 41.94 | 8 | 279 | 47.56 | Energy-coupling factor transporter ATP-binding protein EcfA OS = *Streptococcus pneumoniae* (strain CGSP14) GN = ecfA PE = 3 SV = 1 - [B2INN7_STRPS] | N-terminally anchored (No CS) |
| B2IS50 | 52.46 | 7 | 122 | 47.46 | 50S ribosomal protein L14 OS = *Streptococcus pneumoniae* (strain CGSP14) GN = rplN PE = 3 SV = 1 - [RL14_STRPS] | Intracellular |
| B2IRI6 | 32.63 | 3 | 95 | 47.46 | Bacteriocin, putative OS = *Streptococcus pneumoniae* (strain CGSP14) GN = SPCG_0105 PE = 4 SV = 1 - [B2IRI6_STRPS] | N-terminally anchored (with CS) |
| B2IPJ1 | 50 | 9 | 264 | 47.22 | Iron-compound ABC transporter, ATP-binding protein OS = *Streptococcus pneumoniae* (strain CGSP14) GN = SPCG_1013 PE = 4 SV = 1 - [B2IPJ1_STRPS] | Intracellular |
| B2IPR3 | 40.89 | 7 | 247 | 47.21 | Uncharacterized protein OS = *Streptococcus pneumoniae* (strain CGSP14) GN = SPCG_1083 PE = 4 SV = 1 - [B2IPR3_STRPS] | N-terminally anchored (with CS) |
| B2IR24 | 28.28 | 9 | 389 | 47.15 | Uncharacterized protein OS = *Streptococcus pneumoniae* (strain CGSP14) GN = SPCG_0036 PE = 3 SV = 1 - [B2IR24_STRPS] | Intracellular |
| B2ISX7 | 60.12 | 8 | 173 | 47.03 | Phosphoesterase OS = *Streptococcus pneumoniae* (strain CGSP14) GN = SPCG_1852 PE = 3 SV = 1 - [B2ISX7_STRPS] | Intracellular |
| B2IM86 | 29.62 | 8 | 449 | 46.75 | Potassium uptake protein, Trk family OS = *Streptococcus pneumoniae* (strain CGSP14) GN = trkA PE = 4 SV = 1 - [B2IM86_STRPS] | N-terminally anchored (with CS) |

TABLE 5-continued

Proteins identified in MV$_L$ from serotype 3. The accession numbers refer to SwissProt on the date of filing.

| Accession # | Coverage | # Peptides | #AAs | Score | Description | Localization |
|---|---|---|---|---|---|---|
| B2IPT8 | 33.13 | 9 | 326 | 46.7 | Tagatose 1,6-diphosphate aldolase OS = *Streptococcus pneumoniae* (strain CGSP14) GN = lacD PE = 3 SV = 1 - [B2IPT8_STRPS] | Intracellular |
| B2ILZ5 | 39.81 | 10 | 540 | 46.59 | 60 kDa chaperonin OS = *Streptococcus pneumoniae* (strain CGSP14) GN = groL PE = 3 SV = 1 - [CH60_STRPS] | Intracellular |
| B2ILX7 | 34.58 | 8 | 480 | 46.43 | Aspartyl/glutamyl-tRNA(Asn/Gln) amidotransferase subunit B OS = *Streptococcus pneumoniae* (strain CGSP14) GN = gatB PE = 3 SV = 1 - [GATB_STRPS] | Intracellular |
| B2IMQ9 | 16.96 | 8 | 737 | 45.59 | Polyribonucleotide nucleotidyltransferase OS = *Streptococcus pneumoniae* (strain CGSP14) GN = pnp PE = 3 SV = 2 - [PNP_STRPS] | Intracellular |
| B2IQN3 | 45.45 | 5 | 66 | 44.91 | 30S ribosomal protein S21 OS = *Streptococcus pneumoniae* (strain CGSP14) GN = rpsU PE = 3 SV = 1 - [B2IQN3_STRPS] | Intracellular |
| B2IR90 | 38.37 | 2 | 172 | 44.68 | Non-heme iron-containing ferritin OS = *Streptococcus pneumoniae* (strain CGSP14) GN = SPCG_1557 PE = 3 SV = 1 - [B2IR90_STRPS] | Intracellular |
| B2IMS2 | 42.66 | 7 | 293 | 44.59 | Fructose-bisphosphate aldolase OS = *Streptococcus pneumoniae* (strain CGSP14) GN = fba PE = 3 SV = 1 - [B2IMS2_STRPS] | Intracellular |
| B2IRX2 | 10.53 | 5 | 399 | 44.06 | Uncharacterized protein OS = *Streptococcus pneumoniae* (strain CGSP14) GN = SPCG_1689 PE = 4 SV = 1 - [B2IRX2_STRPS] | Multi-transmembrane |
| B2ISH7 | 20.98 | 10 | 815 | 43.34 | Formate acetyltransferase, putative OS = *Streptococcus pneumoniae* (strain CGSP14) GN = pflF PE = 4 SV = 1 - [B2ISH7_STRPS] | Intracellular |
| B2ISG1 | 26.84 | 7 | 190 | 43.06 | Uncharacterized protein OS = *Streptococcus pneumoniae* (strain CGSP14) GN = SPCG_1779 PE = 4 SV = 1 - [B2ISG1_STRPS] | Multi-transmembrane |
| B2IMY2 | 73.21 | 7 | 56 | 42.86 | Uncharacterized protein OS = *Streptococcus pneumoniae* (strain CGSP14) GN = SPCG_0626 PE = 4 SV = 1 - [B2IMY2_STRPS] | Secretory (released) (with CS) |
| B2IM36 | 15.5 | 8 | 671 | 42.81 | Uncharacterized protein OS = *Streptococcus pneumoniae* (strain CGSP14) GN = SPCG_1921 PE = 4 SV = 1 - [B2IM36_STRPS] | Multi-transmembrane |
| B2IM12 | 26.96 | 8 | 471 | 42.77 | Pneumolysin OS = *Streptococcus pneumoniae* (strain CGSP14) GN = ply PE = 4 SV = 1 - [B2IM12_STRPS] | Intracellular |
| B2INM4 | 34.62 | 6 | 182 | 42.71 | Ribosomal subunit interface protein OS = *Streptococcus pneumoniae* (strain CGSP14) GN = SPCG_2173 PE = 4 SV = 1 - [B2INM4_STRPS] | Intracellular |
| B2IPW4 | 27.34 | 9 | 567 | 42.61 | Dihydrolipoyl dehydrogenase OS = *Streptococcus pneumoniae* (strain CGSP14) GN = acoL PE = 4 SV = 1 - [B2IPW4_STRPS] | Intracellular |
| B2IQ29 | 38.89 | 6 | 180 | 42.56 | Hypoxanthine-guanine phosphoribosyltransferase OS = *Streptococcus pneumoniae* (strain CGSP14) GN = hgt PE = 4 SV = 1 - [B2IQZ9_STRPS] | Intracellular |
| B2IS21 | 19.23 | 6 | 234 | 42.44 | Uncharacterized protein OS = *Streptococcus pneumoniae* (strain CGSP14) GN = SPCG_0199 PE = 4 SV = 1 - [B2IS21_STRPS] | Multi-transmembrane |
| B2IPB4 | 18.18 | 3 | 66 | 42.39 | 50S ribosomal protein L35 OS = *Streptococcus pneumoniae* (strain CGSP14) GN = rpmI PE = 3 SV = 1 - [RL35_STRPS] | Intracellular |

TABLE 5-continued

Proteins identified in MV$_L$ from serotype 3. The accession numbers refer to SwissProt on the date of filing.

| Accession # | Coverage | # Peptides | #AAs | Score | Description | Localization |
|---|---|---|---|---|---|---|
| B2IM29 | 23.68 | 5 | 418 | 42.24 | Putative competence-damage inducible protein OS = Streptococcus pneumoniae (strain CGSP14) GN = cinA PE = 3 SV = 1 - [CINA_STRPS] | Intracellular |
| B2IR86 | 66.5 | 11 | 197 | 41.89 | Probable GTP-binding protein EngB OS = Streptococcus pneumoniae (strain CGSP14) GN = engB PE = 3 SV = 1 - [ENGB_STRPS] | Intracellular |
| B2IPS2 | 46.7 | 4 | 212 | 41.29 | Uridine kinase OS = Streptococcus pneumoniae (strain CGSP14) GN = udk PE = 3 SV = 1 - [URK_STRPS] | Intracellular |
| B2INP0 | 22.46 | 5 | 276 | 41.12 | Uncharacterized protein OS = Streptococcus pneumoniae (strain CGSP14) GN = SPCG_2189 PE = 4 SV = 1 - [B2INP0_STRPS] | Intracellular/TMH start AFTER 60 |
| B2ILX1 | 42.71 | 7 | 288 | 41.03 | Acetyl-coenzyme A carboxylase carboxyl transferase subunit beta OS = Streptococcus pneumoniae (strain CGSP14) GN = accD PE = 3 SV = 1 - [B2ILX1_STRPS] | Intracellular |
| B2IMY9 | 31.48 | 10 | 486 | 40.7 | Glutamate--tRNA ligase OS = Streptococcus pneumoniae (strain CGSP14) GN = gltX PE = 3 SV = 1 - [SYE_STRPS] | Intracellular |
| B2ISL4 | 51.11 | 9 | 270 | 40.64 | Cof family protein OS = Streptococcus pneumoniae (strain CGSP14) GN = SPCG_0299 PE = 4 SV = 1 - [B2ISL4_STRPS] | Intracellular |
| B2IQH7 | 42.21 | 5 | 289 | 40.55 | Homoserine kinase OS = Streptococcus pneumoniae (strain CGSP14) GN = thrB PE = 3 SV = 1 - [KHSE_STRPS] | Intracellular |
| B2IS89 | 36.54 | 7 | 208 | 40.54 | Guanylate kinase OS = Streptococcus pneumoniae (strain CGSP14) GN = gmk PE = 3 SV = 1 - [B2IS89_STRPS] | Intracellular |
| B2IRQ3 | 18.92 | 7 | 650 | 40.16 | Endopeptidase O OS = Streptococcus pneumoniae (strain CGSP14) GN = pepO PE = 4 SV = 1 - [B2IRQ3_STRPS] | Intracellular |
| B2IR80 | 26.03 | 6 | 292 | 39.76 | Uncharacterized protein OS = Streptococcus pneumoniae (strain CGSP14) GN = SPCG_1547 PE = 4 SV = 1 - [B2IR80_STRPS] | Multi-transmembrane |
| B2INZ2 | 20.82 | 6 | 413 | 39.4 | D-alanyl-D-alanine carboxypeptidase OS = Streptococcus pneumoniae (strain CGSP14) GN = dacA PE = 3 SV = 1 - [B2INZ2_STRPS] | N-terminally anchored (with CS) |
| B2IR93 | 45.95 | 6 | 259 | 39.26 | Triosephosphate isomerase OS = Streptococcus pneumoniae (strain CGSP14) GN = tpiA PE = 3 SV = 1 - [B2IR93_STRPS] | Intracellular |
| B2IP56 | 34.48 | 8 | 290 | 39.23 | Uncharacterized protein OS = Streptococcus pneumoniae (strain CGSP14) GN = SPCG_0875 PE = 4 SV = 1 - [B2IP56_STRPS] | Lipid anchored |
| B2IPZ7 | 46.59 | 6 | 279 | 39.17 | DegV family protein OS = Streptococcus pneumoniae (strain CGSP14) GN = SPCG_1169 PE = 4 SV = 1 - [B2IPZ7_STRPS] | Intracellular |
| B2INK5 | 19.52 | 8 | 502 | 39.03 | Glycerol kinase OS = Streptococcus pneumoniae (strain CGSP14) GN = glpK PE = 3 SV = 1 - [GLPK_STRPS] | Intracellular |
| B2INM2 | 32.67 | 7 | 150 | 38.84 | 50S ribosomal protein L9 OS = Streptococcus pneumoniae (strain CGSP14) GN = rplI PE = 3 SV = 1 - [RL9_STRPS] | Intracellular |
| B2IPH6 | 21.17 | 4 | 359 | 38.78 | Peptide chain release factor 1 OS = Streptococcus pneumoniae (strain CGSP14) GN = prfA PE = 3 SV = 1 - [RF1_STRPS] | Intracellular |

TABLE 5-continued

Proteins identified in MV$_L$ from serotype 3. The accession numbers refer to SwissProt on the date of filing.

| Accession # | Coverage | # Peptides | #AAs | Score | Description | Localization |
|---|---|---|---|---|---|---|
| B2ING0 | 44.21 | 3 | 95 | 38.52 | 30S ribosomal protein S16 OS = Streptococcus pneumoniae (strain CGSP14) GN = rpsP PE = 3 SV = 1 - [RS16_STRPS] | Intracellular |
| B2IQZ0 | 33.07 | 7 | 378 | 38.34 | DNA polymerase III subunit beta OS = Streptococcus pneumoniae (strain CGSP14) GN = dnaN PE = 4 SV = 1 - [B2IQZ0_STRPS] | Intracellular |
| B2IR11 | 29.29 | 8 | 420 | 37.79 | DNA repair protein radA OS = Streptococcus pneumoniae (strain CGSP14) GN = radA PE = 3 SV = 1 - [B2IR11_STRPS] | Intracellular |
| B2ISK0 | 7.86 | 8 | 1463 | 37.3 | DNA polymerase III PolC-type OS = Streptococcus pneumoniae (strain CGSP14) GN = polC PE = 3 SV = 1 - [B2ISK0_STRPS] | Intracellular |
| B2IMD8 | 40.15 | 8 | 264 | 37.04 | Uncharacterized protein OS = Streptococcus pneumoniae (strain CGSP14) GN = SPCG_0513 PE = 4 SV = 1 - [B2IMD8_STRPS] | Intracellular |
| B2IP06 | 33.66 | 7 | 303 | 36.91 | Tagatose-6-phosphate kinase OS = Streptococcus pneumoniae (strain CGSP14) GN = fruB PE = 3 SV = 1 - [B2IP06_STRPS] | Intracellular |
| B2IPT6 | 46.2 | 5 | 171 | 36.86 | Galactose-6-phosphate isomerase subunit LacB OS = Streptococcus pneumoniae (strain CGSP14) GN = lacB PE = 3 SV = 1 - [LACB_STRPS] | Intracellular |
| B2IMT1 | 28.33 | 7 | 406 | 36.74 | Beta-lactam resistance factor OS = Streptococcus pneumoniae (strain CGSP14) GN = murM PE = 4 SV = 1 - [B2IMT1_STRPS] | Intracellular |
| B2IN52 | 24.87 | 8 | 567 | 36.72 | Dihydroxy-acid dehydratase OS = Streptococcus pneumoniae (strain CGSP14) GN = ilvD PE = 3 SV = 1 - [ILVD_STRPS] | Intracellular |
| B2IRH4 | 23.13 | 5 | 320 | 36.59 | Uncharacterized protein OS = Streptococcus pneumoniae (strain CGSP14) GN = SPCG_0093 PE = 4 SV = 1 - [B2IRH4_STRPS] | N-terminally anchored (No CS) |
| B2IME1 | 27.51 | 7 | 378 | 36.3 | Transcription termination/antitermination protein NusA OS = Streptococcus pneumoniae (strain CGSP14) GN = nusA PE = 3 SV = 1 - [B2IME1_STRPS] | Intracellular |
| B2ISX2 | 51.67 | 9 | 240 | 36.23 | Pseudouridine synthase OS = Streptococcus pneumoniae (strain CGSP14) GN = rluB PE = 3 SV = 1 - [B2ISX2_STRPS] | Intracellular |
| B2IN61 | 77.55 | 6 | 49 | 35.89 | 50S ribosomal protein L33 OS = Streptococcus pneumoniae (strain CGSP14) GN = rpmG PE = 3 SV = 1 - [RL33_STRPS] | Intracellular |
| B2IQ98 | 60.64 | 4 | 94 | 35.66 | 50S ribosomal protein L31 type B OS = Streptococcus pneumoniae (strain CGSP14) GN = rpmE PE = 3 SV = 1 - [B2IQ98_STRPS] | Intracellular |
| B2IPY5 | 32.19 | 7 | 379 | 35.53 | Glycogen biosynthesis protein GlgD OS = Streptococcus pneumoniae (strain CGSP14) GN = glgD PE = 4 SV = 1 - [B2IPY5_STRPS] | Intracellular |
| B2IRA3 | 21.23 | 4 | 438 | 35.35 | Pyridine nucleotide-disulfide oxidoreductase OS = Streptococcus pneumoniae (strain CGSP14) GN = merA PE = 3 SV = 1 - [B2IRA3_STRPS] | Intracellular |
| B2IR65 | 48.8 | 6 | 209 | 35.25 | Uncharacterized protein OS = Streptococcus pneumoniae (strain CGSP14) GN = SPCG_1532 PE = 4 SV = 1 - [B2IR65_STRPS] | Intracellular |
| B2INN1 | 36.99 | 7 | 346 | 34.94 | Elongation factor Ts OS = Streptococcus pneumoniae (strain CGSP14) GN = tsf PE = 3 SV = 1 - [EFTS_STRPS] | Intracellular |

TABLE 5-continued

Proteins identified in MV$_L$ from serotype 3. The accession numbers refer to SwissProt on the date of filing.

| Accession # | Coverage | # Peptides | #AAs | Score | Description | Localization |
|---|---|---|---|---|---|---|
| B2IRV5 | 19.83 | 3 | 343 | 34.85 | Phospho-2-dehydro-3-deoxyheptonate aldolase OS = *Streptococcus pneumoniae* (strain CGSP14) GN = aroF PE = 3 SV = 1 - [B2IRV5_STRPS] | Intracellular |
| B2IN60 | 53.33 | 4 | 60 | 34.75 | 50S ribosomal protein L32 OS = *Streptococcus pneumoniae* (strain CGSP14) GN = rpmF PE = 3 SV = 1 - [RL32_STRPS] | Intracellular |
| B2IQ13 | 32.08 | 6 | 371 | 34.73 | Aminotransferase, class-V OS = *Streptococcus pneumoniae* (strain CGSP14) GN = SPCG_1185 PE = 3 SV = 1 - [B2IQ13_STRPS] | Intracellular |
| B2INQ1 | 36.11 | 5 | 180 | 34.11 | Transcriptional regulator, TetR family OS = *Streptococcus pneumoniae* (strain CGSP14) GN = SPCG_2200 PE = 4 SV = 1 - [B2INQ1_STRPS] | Intracellular |
| B2IP08 | 15.91 | 7 | 767 | 33.57 | SpoE family protein OS = *Streptococcus pneumoniae* (strain CGSP14) GN = ftsK PE = 3 SV = 1 - [B2IP08_STRPS] | Multi-transmembrane |
| B2IRW8 | 41.24 | 6 | 177 | 33.56 | Transcriptional repressor NrdR OS = *Streptococcus pneumoniae* (strain CGSP14) GN = nrdR PE = 3 SV = 1 - [B2IRW8_STRPS] | Intracellular |
| B2ISL9 | 57.61 | 6 | 184 | 33.49 | GTP cyclohydrolase 1 OS = *Streptococcus pneumoniae* (strain CGSP14) GN = folE PE = 3 SV = 1 - [GCH1_STRPS] | Intracellular |
| B2IQL2 | 25.35 | 4 | 217 | 32.6 | Phosphate-specific transport system accessory protein PhoU OS = *Streptococcus pneumoniae* (strain CGSP14) GN = SPCG_1384 PE = 3 SV = 1 - [B2IQL2_STRPS] | Intracellular |
| B2ILW1 | 39.58 | 4 | 144 | 32.47 | Transcriptional regulator, MarR family OS = *Streptococcus pneumoniae* (strain CGSP14) GN = SPCG_0414 PE = 4 SV = 1 - [B2ILW1_STRPS] | Intracellular |
| B2IS33 | 15.25 | 5 | 518 | 32.44 | Competence-induced protein Ccs4 OS = *Streptococcus pneumoniae* (strain CGSP14) GN = SPCG_0211 PE = 4 SV = 1 - [B2IS33_STRPS] | Multi-transmembrane |
| B2INX7 | 16.53 | 4 | 236 | 32.43 | Uncharacterized protein OS = *Streptococcus pneumoniae* (strain CGSP14) GN = SPCG_0802 PE = 4 SV = 1 - [B2INX7_STRPS] | Multi-transmembrane |
| B2INM3 | 14.16 | 7 | 657 | 32.29 | DHH subfamily 1 protein OS = *Streptococcus pneumoniae* (strain CGSP14) GN = SPCG_2172 PE = 4 SV = 1 - [B2INM3_STRPS] | Multi-transmembrane |
| B2INY8 | 22.62 | 6 | 420 | 32.18 | Uncharacterized protein OS = *Streptococcus pneumoniae* (strain CGSP14) GN = SPCG_0813 PE = 4 SV = 1 - [B2INY8_STRPS] | Intracellular |
| B2IN02 | 20.77 | 5 | 443 | 32.03 | Sensor histidine kinase PnpS OS = *Streptococcus pneumoniae* (strain CGSP14) GN = SPCG_2049 PE = 4 SV = 1 - [B2IN02_STRPS] | Multi-transmembrane |
| B2IMR8 | 13.73 | 5 | 459 | 31.87 | Transmembrane protein Vexp3 OS = *Streptococcus pneumoniae* (strain CGSP14) GN = SPCG_0562 PE = 3 SV = 1 - [B2IMR8_STRPS] | Multi-transmembrane |
| B2IP11 | 34.65 | 7 | 404 | 31.83 | Probable tRNA sulfurtransferase OS = *Streptococcus pneumoniae* (strain CGSP14) GN = thiI PE = 3 SV = 1 - [THII_STRPS] | Intracellular |
| B2INZ1 | 26.38 | 8 | 470 | 31.82 | FeS assembly protein SufB OS = *Streptococcus pneumoniae* (strain CGSP14) GN = SPCG_0816 PE = 4 SV = 1 - [B2INZ1_STRPS] | Intracellular |

TABLE 5-continued

Proteins identified in MV$_L$ from serotype 3. The accession numbers refer to SwissProt on the date of filing.

| Accession # | Coverage | # Peptides | #AAs | Score | Description | Localization |
|---|---|---|---|---|---|---|
| B2IQ37 | 41.27 | 5 | 252 | 31.78 | ABC transporter, ATP-binding protein OS = Streptococcus pneumoniae (strain CGSP14) GN = SPCG_1209 PE = 4 SV = 1 - [B2IQ37_STRPS] | Intracellular |
| B2IN78 | 31.83 | 6 | 399 | 31.49 | Cell division protein DivIB OS = Streptococcus pneumoniae (strain CGSP14) GN = divIB PE = 3 SV = 1 - [B2IN78_STRPS] | Intracellular/ TMH start AFTER 60 |
| B2IS71 | 21.69 | 5 | 249 | 31.41 | Phosphoglycerate mutase family protein OS = Streptococcus pneumoniae (strain CGSP14) GN = gpmB PE = 4 SV = 1 - [B2IS71_STRPS] | Intracellular |
| B2IQJ2 | 23.71 | 5 | 388 | 31.39 | Chorismate synthase OS = Streptococcus pneumoniae (strain CGSP14) GN = aroC PE = 3 SV = 1 - [AROC_STRPS] | Intracellular |
| B2IST9 | 13.89 | 7 | 583 | 31.29 | ABC transporter, ATP-binding/permease protein OS = Streptococcus pneumoniae (strain CGSP14) GN = SPCG_1814 PE = 4 SV = 1 - [B2IST9_STRPS] | Multi-transmembrane |
| B2IPQ2 | 32.05 | 6 | 234 | 30.92 | Uncharacterized protein OS = Streptococcus pneumoniae (strain CGSP14) GN = SPCG_1072 PE = 4 SV = 1 - [B2IPQ2_STRPS] | Intracellular |
| B2ISM0 | 18.89 | 3 | 270 | 30.69 | 7,8-dihydroneopterin aldolase OS = Streptococcus pneumoniae (strain CGSP14) GN = sulD PE = 3 SV = 1 - [B2ISM0_STRPS] | Intracellular |
| B2IMH1 | 16.74 | 6 | 472 | 30.67 | Cof family protein OS = Streptococcus pneumoniae (strain CGSP14) GN = SPCG_1962 PE = 4 SV = 1 - [B2IMH1_STRPS] | Intracellular |
| B2ISV2 | 17.09 | 5 | 392 | 30.34 | Galactokinase OS = Streptococcus pneumoniae (strain CGSP14) GN = galK PE = 3 SV = 1 - [B2ISV2_STRPS] | Intracellular |
| B2IR20 | 12.6 | 8 | 889 | 30.19 | DNA polymerase OS = Streptococcus pneumoniae (strain CGSP14) GN = polA PE = 3 SV = 1 - [B2IR20_STRPS] | Intracellular |
| B2IR50 | 26.4 | 6 | 481 | 30 | UDP-N-acetylmuramoyl-L-alanyl-D-glutamate--L-lysine ligase OS = Streptococcus pneumoniae (strain CGSP14) GN = murE PE = 3 SV = 1 - [B2IR50_STRPS] | Intracellular |
| B2ISI6 | 20.93 | 6 | 258 | 29.94 | Isoprenyl transferase OS = Streptococcus pneumoniae (strain CGSP14) GN = uppS PE = 3 SV = 1 - [B2ISI6_STRPS] | Intracellular |
| B2IMQ1 | 31.47 | 7 | 375 | 29.85 | Phenylalanine--tRNA ligase alpha subunit OS = Streptococcus pneumoniae (strain CGSP14) GN = pheS PE = 3 SV = 1 - [B2IMQ1_STRPS] | Intracellular |
| B2ISS1 | 20.39 | 6 | 407 | 29.77 | Tryptophan synthase beta chain OS = Streptococcus pneumoniae (strain CGSP14) GN = trpB PE = 3 SV = 1 - [TRPB_STRPS] | Intracellular |
| B2IMZ0 | 22.05 | 5 | 449 | 29.65 | Glucose-6-phosphate isomerase OS = Streptococcus pneumoniae (strain CGSP14) GN = pgi PE = 3 SV = 1 - [G6PI_STRPS] | Intracellular |
| B2IRD1 | 13.75 | 4 | 778 | 29.59 | Cation-transporting ATPase, E1-E2 family OS = Streptococcus pneumoniae (strain CGSP14) GN = ctpE PE = 3 SV = 1 - [B2IRD1_STRPS] | Multi-transmembrane |
| B2IQ17 | 51.09 | 5 | 229 | 29.49 | Glutamine amidotransferase, class I OS = Streptococcus pneumoniae (strain CGSP14) GN = SPCG_1189 PE = 4 SV = 1 - [B2IQ17_STRPS] | Intracellular |

TABLE 5-continued

Proteins identified in MV$_L$ from serotype 3. The accession numbers refer to SwissProt on the date of filing.

| Accession # | Coverage | # Peptides | #AAs | Score | Description | Localization |
|---|---|---|---|---|---|---|
| B2IPV5 | 30.5 | 5 | 200 | 29.44 | Uncharacterized protein OS = *Streptococcus pneumoniae* (strain CGSP14) GN = SPCG_1127 PE = 4 SV = 1 - [B2IPV5_STRPS] | Intracellular |
| B2ILW5 | 27.78 | 6 | 306 | 29.34 | Malonyl CoA-acyl carrier protein transacylase OS = *Streptococcus pneumoniae* (strain CGSP14) GN = fabD PE = 3 SV = 1 - [B2ILW5_STRPS] | Intracellular |
| B2IQI6 | 29.48 | 6 | 424 | 29.26 | Psr protein OS = *Streptococcus pneumoniae* (strain CGSP14) GN = SPCG_1358 PE = 4 SV = 1 - [B2IQI6_STRPS] | Intracellular/ TMH start AFTER 60 |
| B2IPB3 | 40.51 | 5 | 195 | 28.99 | Translation initiation factor IF-3 OS = *Streptococcus pneumoniae* (strain CGSP14) GN = infC PE = 3 SV = 1 - [B2IPB3_STRPS] | Intracellular |
| B2IM63 | 18.52 | 7 | 432 | 28.92 | Competence-induced protein Ccs50 OS = *Streptococcus pneumoniae* (strain CGSP14) GN = SPCG_1944 PE = 4 SV = 1 - [B2IM63_STRPS] | N-terminally anchored (No CS) |
| B2IP99 | 44.53 | 6 | 247 | 28.66 | Uridylate kinase OS = *Streptococcus pneumoniae* (strain CGSP14) GN = pyrH PE = 3 SV = 1 - [B2IP99_STRPS] | Intracellular |
| B2IPF5 | 10.79 | 5 | 834 | 28.65 | Uncharacterized protein OS = *Streptococcus pneumoniae* (strain CGSP14) GN = SPCG_0977 PE = 4 SV = 1 - [B2IPF5_STRPS] | N-terminally anchored (No CS) |
| B2IM26 | 26.1 | 6 | 318 | 28.61 | Autolysin OS = *Streptococcus pneumoniae* (strain CGSP14) GN = lytA PE = 4 SV = 1 - [B2IM26_STRPS] | Intracellular |
| B2INF6 | 43.1 | 5 | 239 | 28.52 | tRNA (guanine-N(1)-)-methyltransferase OS = *Streptococcus pneumoniae* (strain CGSP14) GN = trmD PE = 3 SV = 1 - [TRMD_STRPS] | Intracellular |
| B2ISI0 | 15.25 | 6 | 833 | 28.41 | Leucine--tRNA ligase OS = *Streptococcus pneumoniae* (strain CGSP14) GN = leuS PE = 3 SV = 1 - [SYL_STRPS] | Intracellular |
| B2IQH8 | 20.5 | 6 | 439 | 28.08 | Homoserine dehydrogenase OS = *Streptococcus pneumoniae* (strain CGSP14) GN = hom PE = 3 SV = 1 - [B2IQH8_STRPS] | Intracellular |
| B2INT8 | 57.89 | 3 | 76 | 27.91 | Uncharacterized protein OS = *Streptococcus pneumoniae* (strain CGSP14) GN = SPCG_0763 PE = 4 SV = 1 - [B2INT8_STRPS] | Intracellular |
| B2IMD9 | 15.64 | 2 | 211 | 27.64 | tRNA (guanine-N(7)-)-methyltransferase OS = *Streptococcus pneumoniae* (strain CGSP14) GN = trmB PE = 3 SV = 1 - [TRMB_STRPS] | Intracellular |
| B2IQS2 | 26.88 | 4 | 253 | 27.63 | SpoU rRNA methylase family protein OS = *Streptococcus pneumoniae* (strain CGSP14) GN = trmH PE = 3 SV = 1 - [B2IQS2_STRPS] | Intracellular |
| B2IR73 | 16.69 | 5 | 623 | 27.4 | ABC transporter, ATP-binding protein OS = *Streptococcus pneumoniae* (strain CGSP14) GN = SPCG_1540 PE = 4 SV = 1 - [B2IR73_STRPS] | Intracellular |
| B2IPP4 | 10.12 | 6 | 662 | 27.29 | UvrABC system protein B OS = *Streptococcus pneumoniae* (strain CGSP14) GN = uvrB PE = 3 SV = 1 - [UVRB_STRPS] | Intracellular |
| B2IQK6 | 26.91 | 4 | 301 | 27.27 | UDP-N-acetylenolpyruvoylglucosamine reductase OS = *Streptococcus pneumoniae* (strain CGSP14) GN = murB PE = 3 SV = 1 - [MURB_STRPS] | Intracellular |

TABLE 5-continued

Proteins identified in MV$_L$ from serotype 3. The accession numbers refer to SwissProt on the date of filing.

| Accession # | Coverage | # Peptides | #AAs | Score | Description | Localization |
|---|---|---|---|---|---|---|
| B2IP98 | 25.45 | 6 | 444 | 27.26 | Methylenetetrahydrofolate--tRNA-(uracil-5-)-methyltransferase TrmFO OS = Streptococcus pneumoniae (strain CGSP14) GN = trmFO PE = 3 SV = 2 - [TRMFO_STRPS] | Intracellular |
| B2IQK5 | 19.48 | 5 | 385 | 27.06 | Spermidine/putrescine import ATP-binding protein PotA OS = Streptococcus pneumoniae (strain CGSP14) GN = potA PE = 3 SV = 1 - [B2IQK5_STRPS] | Intracellular |
| B2INN3 | 30.61 | 7 | 392 | 26.86 | Secreted 45 kd protein OS = Streptococcus pneumoniae (strain CGSP14) GN = SPCG_2182 PE = 4 SV = 1 - [B2INN3_STRPS] | Secretory (released) (with CS) |
| B2IN20 | 40.78 | 4 | 103 | 26.71 | Uncharacterized protein OS = Streptococcus pneumoniae (strain CGSP14) GN = SPCG_2067 PE = 4 SV = 1 - [B2IN20_STRPS] | Intracellular |
| B2IPN6 | 8.14 | 6 | 1179 | 26.7 | Chromosome partition protein Smc OS = Streptococcus pneumoniae (strain CGSP14) GN = smc PE = 3 SV = 1 - [B2IPN6_STRPS] | Intracellular |
| B2IRW9 | 52.07 | 5 | 121 | 26.67 | Transcriptional regulator, GntR family OS = Streptococcus pneumoniae (strain CGSP14) GN = SPCG_1686 PE = 4 SV = 1 - [B2IRW9_STRPS] | Intracellular |
| B2IS84 | 13.47 | 2 | 438 | 26.55 | Ribosomal RNA small subunit methyltransferase B OS = Streptococcus pneumoniae (strain CGSP14) GN = sunL PE = 3 SV = 1 - [B2IS84_STRPS] | Intracellular |
| B2IMX9 | 19.88 | 7 | 332 | 26.49 | Pneumococcal surface protein, putative OS = Streptococcus pneumoniae (strain CGSP14) GN = SPCG_0623 PE = 4 SV = 1 - [B2IMX9_STRPS] | Lipid anchored |
| B2IPI5 | 8.69 | 4 | 541 | 26.36 | RNA methyltransferase, TrmA family OS = Streptococcus pneumoniae (strain CGSP14) GN = SPCG_1007 PE = 3 SV = 1 - [B2IPI5_STRPS] | Intracellular |
| B2IPS8 | 15.14 | 7 | 555 | 25.77 | DNA repair protein RecN OS = Streptococcus pneumoniae (strain CGSP14) GN = recN PE = 3 SV = 1 - [B2IPS8_STRPS] | Intracellular |
| B2INY5 | 17.06 | 6 | 551 | 25.65 | DNA polymerase III subunits gamma and tau OS = Streptococcus pneumoniae (strain CGSP14) GN = dnaX PE = 4 SV = 1 - [B2INY5_STRPS] | Intracellular |
| B2ISU0 | 10.1 | 4 | 594 | 25.61 | ABC transporter, ATP-binding/permease protein OS = Streptococcus pneumoniae (strain CGSP14) GN = SPCG_1815 PE = 4 SV = 1 - [B2ISU0_STRPS] | Multi-transmembrane |
| B2INU6 | 24.53 | 6 | 424 | 25.32 | Phosphopentomutase OS = Streptococcus pneumoniae (strain CGSP14) GN = deoB PE = 3 SV = 1 - [B2INU6_STRPS] | Intracellular |
| B2IM77 | 17.44 | 2 | 281 | 25.26 | Undecaprenyl-diphosphatase OS = Streptococcus pneumoniae (strain CGSP14) GN = uppP PE = 3 SV = 1 - [UPPP_STRPS] | Intracellular |
| B2IS76 | 21.11 | 5 | 398 | 25.26 | Hydroxymethylglutaryl-CoA synthase OS = Streptococcus pneumoniae (strain CGSP14) GN = mvaS PE = 4 SV = 1 - [B2IS76_STRPS] | Intracellular |
| B2IPD9 | 20.3 | 4 | 266 | 24.91 | Uncharacterized protein OS = Streptococcus pneumoniae (strain CGSP14) GN = SPCG_0961 PE = 4 SV = 1 - [B2IPD9_STRPS] | N-terminally anchored (No CS) |

TABLE 5-continued

Proteins identified in MV$_L$ from serotype 3. The accession numbers refer to SwissProt on the date of filing.

| Accession # | Coverage | # Peptides | #AAs | Score | Description | Localization |
|---|---|---|---|---|---|---|
| B2IP88 | 14.52 | 6 | 420 | 24.84 | Gamma-glutamyl phosphate reductase OS = *Streptococcus pneumoniae* (strain CGSP14) GN = proA PE = 3 SV = 1 - [PROA_STRPS] | Intracellular |
| B2IQU2 | 18.36 | 4 | 305 | 24.77 | Glycine--tRNA ligase alpha subunit OS = *Streptococcus pneumoniae* (strain CGSP14) GN = glyQ PE = 3 SV = 1 - [SYGA_STRPS] | Intracellular |
| B2INW0 | 25 | 5 | 220 | 24.67 | Deoxyribose-phosphate aldolase OS = *Streptococcus pneumoniae* (strain CGSP14) GN = deoC PE = 3 SV = 1 - [DEOC_STRPS] | Intracellular |
| B2IRB6 | 28.25 | 6 | 223 | 24.63 | Cytidylate kinase OS = *Streptococcus pneumoniae* (strain CGSP14) GN = cmk PE = 3 SV = 1 - [KCY_STRPS] | Intracellular |
| B2IP93 | 24.91 | 5 | 289 | 24.4 | Ribosomal RNA small subunit methyltransferase I OS = *Streptococcus pneumoniae* (strain CGSP14) GN = rsmI PE = 3 SV = 1 - [B2IP93_STRPS] | Intracellular |
| B2IPN4 | 29.88 | 5 | 328 | 24.28 | GMP reductase OS = *Streptococcus pneumoniae* (strain CGSP14) GN = guaC PE = 3 SV = 1 - [GUAC_STRPS] | Intracellular |
| B2INI7 | 24.9 | 5 | 257 | 24.1 | Fucose operon repressor, putative OS = *Streptococcus pneumoniae* (strain CGSP14) GN = fcsR PE = 4 SV = 1 - [B2INI7_STRPS] | Intracellular |
| B2IMP1 | 31.07 | 5 | 206 | 24.09 | Hydrolase, haloacid dehalogenase-like family OS = *Streptococcus pneumoniae* (strain CGSP14) GN = SPCG_2031 PE = 4 SV = 1 - [B2IMP1_STRPS] | Intracellular |
| B2IRV6 | 17.78 | 3 | 343 | 23.78 | Phospho-2-dehydro-3-deoxyheptonate aldolase OS = *Streptococcus pneumoniae* (strain CGSP14) GN = aroG PE = 3 SV = 1 - [B2IRV6_STRPS] | Intracellular |
| B2IQ68 | 27.02 | 5 | 359 | 23.7 | Carbamoyl-phosphate synthase small chain OS = *Streptococcus pneumoniae* (strain CGSP14) GN = carA PE = 3 SV = 1 - [B2IQ68_STRPS] | Intracellular |
| B2IMY1 | 17.2 | 3 | 279 | 23.45 | Thymidylate synthase OS = *Streptococcus pneumoniae* (strain CGSP14) GN = thyA PE = 3 SV = 1 - [B2IMY1_STRPS] | Intracellular |
| B2IM44 | 17.88 | 3 | 274 | 23.39 | DNA-entry nuclease OS = *Streptococcus pneumoniae* (strain CGSP14) GN = endA PE = 4 SV = 1 - [B2IM44_STRPS] | N-terminally anchored (No CS) |
| B2IRI8 | 22.54 | 3 | 213 | 23.34 | Amino acid ABC transporter, ATP-binding protein, putative OS = *Streptococcus pneumoniae* (strain CGSP14) GN = SPCG_0107 PE = 4 SV = 1 - [B2IRI8_STRPS] | Intracellular |
| B2IRQ1 | 5.51 | 2 | 653 | 23.17 | PTS system IIABC components OS = *Streptococcus pneumoniae* (strain CGSP14) GN = scrA PE = 4 SV = 1 - [B2IRQ1_STRPS] | Multi-transmembrane |
| B2IQR5 | 19.92 | 4 | 246 | 23.16 | CppA protein OS = *Streptococcus pneumoniae* (strain CGSP14) GN = cppA PE = 4 SV = 1 - [B2IQR5_STRPS] | Intracellular |
| B2ILR4 | 22.22 | 2 | 117 | 23.07 | Cell cycle protein GpsB OS = *Streptococcus pneumoniae* (strain CGSP14) GN = gpsB PE = 3 SV = 1 - [B2ILR4_STRPS] | Intracellular |
| B2IQN2 | 20.25 | 4 | 316 | 22.86 | HPr kinase/phosphorylase OS = *Streptococcus pneumoniae* (strain CGSP14) GN = hprK PE = 3 SV = 1 - [B2IQN2_STRPS] | Intracellular |

TABLE 5-continued

Proteins identified in MV$_L$ from serotype 3. The accession numbers refer to SwissProt on the date of filing.

| Accession # | Coverage | # Peptides | #AAs | Score | Description | Localization |
|---|---|---|---|---|---|---|
| B2IMA5 | 25 | 6 | 448 | 22.78 | Glutamine synthetase, type I OS = Streptococcus pneumoniae (strain CGSP14) GN = glnA PE = 3 SV = 1 - [B2IMA5_STRPS] | Intracellular |
| B2IQ75 | 33.87 | 4 | 186 | 22.38 | LemA protein OS = Streptococcus pneumoniae (strain CGSP14) GN = lemA PE = 4 SV = 1 - [B2IQ75_STRPS] | N-terminally anchored (No CS) |
| B2INX5 | 19.41 | 5 | 340 | 21.91 | Branched-chain-amino-acid aminotransferase OS = Streptococcus pneumoniae (strain CGSP14) GN = ilvE PE = 3 SV = 1 - [B2INX5_STRPS] | Intracellular |
| B2IMY7 | 43.48 | 4 | 207 | 21.8 | Uncharacterized protein OS = Streptococcus pneumoniae (strain CGSP14) GN = SPCG_0630 PE = 4 SV = 1 - [B2IMY7_STRPS] | Intracellular |
| B2IPY6 | 14.21 | 4 | 380 | 21.63 | Glucose-1-phosphate adenylyltransferase OS = Streptococcus pneumoniae (strain CGSP14) GN = glgC PE = 3 SV = 1 - [GLGC_STRPS] | Intracellular |
| B2IM69 | 20.91 | 4 | 416 | 21.42 | L-threonine dehydratase OS = Streptococcus pneumoniae (strain CGSP14) GN = ilvA PE = 3 SV = 1 - [B2IM69_STRPS] | Intracellular |
| B2INA8 | 35.36 | 5 | 263 | 21.29 | Phosphomethylpyrimidine kinase OS = Streptococcus pneumoniae (strain CGSP14) GN = thiD PE = 4 SV = 1 - [B2INA8_STRPS] | Intracellular |
| B2ISK9 | 13.48 | 3 | 267 | 21.26 | PTS system, mannose-specific IIC component OS = Streptococcus pneumoniae (strain CGSP14) GN = manM PE = 4 SV = 1 - [B2ISK9_STRPS] | Multi-transmembrane (Lipid modified N-termini) |
| B2IQ32 | 12.93 | 3 | 441 | 21.17 | Glycosyl transferase, group 1 OS = Streptococcus pneumoniae (strain CGSP14) GN = SPCG_1204 PE = 4 SV = 1 - [B2IQ32_STRPS] | Intracellular |
| B2IM58 | 8.12 | 3 | 308 | 20.91 | Membrane protein insertase YidC OS = Streptococcus pneumoniae (strain CGSP14) GN = yidC PE = 3 SV = 1 - [B2IM58_STRPS] | Multi-transmembrane |
| B2INR5 | 26.54 | 4 | 309 | 20.79 | Oxidoreductase, aldo/keto reductase family OS = Streptococcus pneumoniae (strain CGSP14) GN = SPCG_0740 PE = 4 SV = 1 - [B2INR5_STRPS] | Intracellular |
| B2INC9 | 36.22 | 3 | 196 | 20.35 | ATP-dependent Clp protease proteolytic subunit OS = Streptococcus pneumoniae (strain CGSP14) GN = clpP PE = 3 SV = 1 - [CLPP_STRPS] | Intracellular |
| B2IQ35 | 25.75 | 4 | 369 | 20.25 | RNA polymerase sigma factor SigA OS = Streptococcus pneumoniae (strain CGSP14) GN = rpoD PE = 3 SV = 1 - [B2IQ35_STRPS] | Intracellular |
| B2IMR7 | 20 | 3 | 215 | 20.15 | ABC transporter, ATP-binding protein Vexp2 OS = Streptococcus pneumoniae (strain CGSP14) GN = SPCG_0561 PE = 4 SV = 1 - [B2IMR7_STRPS] | Intracellular |

TABLE 6

Proteins identified in MP from serotype 3. The accession numbers refer to SwissProt on the date of filing.

| Accession # | Coverage | # Peptides | #AAs | Score | Description | Localization |
|---|---|---|---|---|---|---|
| B2IQV2 | 90.84 | 45 | 404 | 2064.28 | Elongation factor Tu OS = *Streptococcus pneumoniae* (strain CGSP14) GN = tuf PE = 3 SV = 1 - [B2IQV2_STRPS] | Intracellular |
| B2IRT9 | 69.68 | 49 | 442 | 1423.4 | Sugar ABC transporter, sugar-binding protein OS = *Streptococcus pneumoniae* (strain CGSP14) GN = SPCG_1656 PE = 4 SV = 1 - [B2IRT9_STRPS] | Lipid anchored |
| B2INY1 | 82.25 | 60 | 400 | 1396.37 | 30S ribosomal protein S1 OS = *Streptococcus pneumoniae* (strain CGSP14) GN = rpsA PE = 4 SV = 1 - [B2INY1_STRPS] | Intracellular |
| B2ISJ9 | 86.15 | 57 | 693 | 1352.29 | Elongation factor G OS = *Streptococcus pneumoniae* (strain CGSP14) GN = fusA PE = 3 SV = 1 - [EFG_STRPS] | Intracellular |
| B2IPX8 | 86.64 | 41 | 434 | 1214.93 | Enolase OS = *Streptococcus pneumoniae* (strain CGSP14) GN = eno PE = 3 SV = 1 - [ENO_STRPS] | Intracellular |
| B2INB2 | 75.63 | 49 | 591 | 1080.64 | Pyruvate oxidase OS = *Streptococcus pneumoniae* (strain CGSP14) GN = spxB PE = 3 SV = 1 - [B2INB2_STRPS] | Intracellular |
| B2IN25 | 76.44 | 47 | 450 | 1068.79 | Maltose/maltodextrin ABC transporter, maltose/maltodextrin-binding protein OS = *Streptococcus pneumoniae* (strain CGSP14) GN = SPCG_2072 PE = 4 SV = 1 - [B2IN25_STRPS] | Lipid anchored |
| B2INK4 | 76.15 | 51 | 608 | 829.85 | Uncharacterized protein OS = *Streptococcus pneumoniae* (strain CGSP14) GN = SPCG_2153 PE = 4 SV = 1 - [B2INK4_STRPS] | N-terminally anchored (No CS) |
| B2ISK8 | 52.48 | 17 | 303 | 715.49 | PTS system, mannose-specific IID component OS = *Streptococcus pneumoniae* (strain CGSP14) GN = manN PE = 4 SV = 1 - [B2ISK8_STRPS] | Multi-transmembrane |
| B2IR98 | 86.7 | 33 | 376 | 633.37 | Sugar ABC transporter, ATP-binding protein OS = *Streptococcus pneumoniae* (strain CGSP14) GN = SPCG_1565 PE = 3 SV = 1 - [B2IR98_STRPS] | Intracellular |
| B2IMI7 | 75.21 | 29 | 359 | 616.73 | Glyceraldehyde-3-phosphate dehydrogenase OS = *Streptococcus pneumoniae* (strain CGSP14) GN = gapA PE = 3 SV = 1 - [B2IMI7_STRPS] | Intracellular |
| B2ISL0 | 55.12 | 20 | 332 | 608.4 | PTS system, mannose-specific IIAB components OS = *Streptococcus pneumoniae* (strain CGSP14) GN = manL PE = 4 SV = 1 - [B2ISL0_STRPS] | Intracellular |
| B2IRH0 | 78.91 | 39 | 512 | 573.11 | ABC transporter, substrate-binding protein OS = *Streptococcus pneumoniae* (strain CGSP14) GN = SPCG_0089 PE = 4 SV = 1 - [B2IRH0_STRPS] | Lipid anchored |
| B2IS43 | 74.01 | 23 | 277 | 570.24 | 50S ribosomal protein L2 OS = *Streptococcus pneumoniae* (strain CGSP14) GN = rplB PE = 3 SV = 1 - [RL2_STRPS] | Intracellular |
| B2INK5 | 70.12 | 34 | 502 | 534.8 | Glycerol kinase OS = *Streptococcus pneumoniae* (strain CGSP14) GN = glpK PE = 3 SV = 1 - [GLPK_STRPS] | Intracellular |
| B2IRV7 | 73.6 | 55 | 837 | 530.96 | Protein translocase subunit SecA OS = *Streptococcus pneumoniae* (strain CGSP14) GN = secA PE = 3 SV = 1 - [B2IRV7_STRPS] | Intracellular |
| B2INW2 | 65.51 | 28 | 374 | 519.89 | Lipoprotein OS = *Streptococcus pneumoniae* (strain CGSP14) GN = SPCG_0787 PE = 4 SV = 1 - [B2INW2_STRPS] | Lipid anchored |

TABLE 6-continued

Proteins identified in MP from serotype 3. The accession numbers refer to SwissProt on the date of filing.

| Accession # | Coverage | # Peptides | #AAs | Score | Description | Localization |
|---|---|---|---|---|---|---|
| B2IPD4 | 58.15 | 28 | 313 | 480.11 | Foldase protein PrsA OS = *Streptococcus pneumoniae* (strain CGSP14) GN = prsA PE = 3 SV = 1 - [PRSA_STRPS] | Lipid anchored |
| B2IR00 | 59.97 | 38 | 652 | 462.58 | ATP-dependent zinc metalloprotease FtsH OS = *Streptococcus pneumoniae* (strain CGSP14) GN = ftsH PE = 3 SV = 1 - [B2IR00_STRPS] | Multi-transmembrane |
| B2IM39 | 54.12 | 57 | 1225 | 460.95 | DNA-directed RNA polymerase subunit beta' OS = *Streptococcus pneumoniae* (strain CGSP14) GN = rpoC PE = 3 SV = 1 - [RPOC_STRPS] | Intracellular |
| B2IM81 | 63.18 | 37 | 774 | 432.81 | Formate acetyltransferase OS = *Streptococcus pneumoniae* (strain CGSP14) GN = pfl PE = 4 SV = 1 - [B2IM81_STRPS] | Intracellular |
| B2IM49 | 72.73 | 25 | 330 | 394.5 | Aspartate--ammonia ligase OS = *Streptococcus pneumoniae* (strain CGSP14) GN = asnA PE = 3 SV = 1 - [ASNA_STRPS] | Intracellular |
| B2IN96 | 69.05 | 25 | 378 | 394.18 | Lactate oxidase OS = *Streptococcus pneumoniae* (strain CGSP14) GN = lctO PE = 4 SV = 1 - [B2IN96_STRPS] | Intracellular |
| B2IPT8 | 93.56 | 27 | 326 | 382.46 | Tagatose 1,6-diphosphate aldolase OS = *Streptococcus pneumoniae* (strain CGSP14) GN = lacD PE = 3 SV = 1 - [B2IPT8_STRPS] | Intracellular |
| B2INN2 | 73.36 | 26 | 259 | 380.63 | 30S ribosomal protein S2 OS = *Streptococcus pneumoniae* (strain CGSP14) GN = rpsB PE = 3 SV = 2 - [RS2_STRPS] | Intracellular |
| B2IQX0 | 86.32 | 28 | 468 | 375.02 | ATP synthase subunit beta OS = *Streptococcus pneumoniae* (strain CGSP14) GN = atpD PE = 3 SV = 1 - [ATPB_STRPS] | Intracellular |
| B2IMA2 | 85.18 | 25 | 398 | 374.17 | Phosphoglycerate kinase OS = *Streptococcus pneumoniae* (strain CGSP14) GN = pgk PE = 3 SV = 1 - [PGK_STRPS] | Intracellular |
| B2IS46 | 81.11 | 26 | 217 | 368.3 | 30S ribosomal protein S3 OS = *Streptococcus pneumoniae* (strain CGSP14) GN = rpsC PE = 3 SV = 1 - [RS3_STRPS] | Intracellular |
| B2ISZ0 | 64.49 | 31 | 659 | 336.33 | Oligopeptide ABC transporter, oligopeptide-binding protein AmiA OS = *Streptococcus pneumoniae* (strain CGSP14) GN = amiA PE = 4 SV = 1 - [B2ISZ0_STRPS] | Lipid anchored |
| B2ISG3 | 77.23 | 21 | 202 | 332.38 | General stress protein 24, putative OS = *Streptococcus pneumoniae* (strain CGSP14) GN = SPCG_1781 PE = 4 SV = 1 - [B2ISG3_STRPS] | Intracellular |
| B2IML8 | 69.46 | 25 | 406 | 332.33 | Acetate kinase OS = *Streptococcus pneumoniae* (strain CGSP14) GN = ackA PE = 3 SV = 1 - [B2IML8_STRPS] | Intracellular |
| B2IP54 | 71.66 | 27 | 501 | 328.6 | Pyruvate kinase OS = *Streptococcus pneumoniae* (strain CGSP14) GN = SPCG_0873 PE = 3 SV = 1 - [B2IP54_STRPS] | Intracellular |
| B2IN10 | 57.69 | 12 | 338 | 324.09 | Glycerol-3-phosphate dehydrogenase [NAD(P)+] OS = *Streptococcus pneumoniae* (strain CGSP14) GN = gpsA PE = 3 SV = 1 - [GPDA_STRPS] | Intracellular |
| B2IRR1 | 66.09 | 12 | 230 | 318.07 | 2,3-bisphosphoglycerate-dependent phosphoglycerate mutase OS = *Streptococcus pneumoniae* (strain CGSP14) GN = gpmA PE = 3 SV = 1 - [GPMA_STRPS] | Intracellular |

TABLE 6-continued

Proteins identified in MP from serotype 3. The accession numbers refer to SwissProt on the date of filing.

| Accession # | Coverage | # Peptides | #AAs | Score | Description | Localization |
|---|---|---|---|---|---|---|
| B2IRI6 | 36.84 | 5 | 95 | 310.42 | Bacteriocin, putative OS = *Streptococcus pneumoniae* (strain CGSP14) GN = SPCG_0105 PE = 4 SV = 1 - [B2IRI6_STRPS] | N-terminally anchored (with CS) |
| B2IQY1 | 57.35 | 26 | 551 | 302.6 | Uncharacterized protein OS = *Streptococcus pneumoniae* (strain CGSP14) GN = SPCG_1503 PE = 4 SV = 1 - [B2IQY1_STRPS] | Intracellular/ TMH start AFTER 60 |
| B2ISJ7 | 67.88 | 14 | 137 | 301.47 | 30S ribosomal protein S12 OS = *Streptococcus pneumoniae* (strain CGSP14) GN = rpsL PE = 3 SV = 1 - [RS12_STRPS] | Intracellular |
| B2IQX2 | 38.92 | 21 | 501 | 285.3 | ATP synthase subunit alpha OS = *Streptococcus pneumoniae* (strain CGSP14) GN = atpA PE = 3 SV = 1 - [ATPA_STRPS] | Intracellular |
| B2IP53 | 50.15 | 16 | 335 | 269.91 | ATP-dependent 6-phosphofructokinase OS = *Streptococcus pneumoniae* (strain CGSP14) GN = pfkA PE = 3 SV = 1 - [PFKA_STRPS] | Intracellular |
| B2IR47 | 51.69 | 27 | 652 | 263.77 | Oligopeptide ABC transporter, oligopeptide-binding protein AliB OS = *Streptococcus pneumoniae* (strain CGSP14) GN = aliB PE = 4 SV = 1 - [B2IR47_STRPS] | Lipid anchored |
| B2ISZ6 | 50.36 | 17 | 419 | 260.6 | Sugar ABC transporter, sugar-binding protein OS = *Streptococcus pneumoniae* (strain CGSP14) GN = SPCG_1871 PE = 4 SV = 1 - [B2ISZ6_STRPS] | Lipid anchored |
| B2IMB5 | 52.72 | 24 | 607 | 254.75 | Chaperone protein DnaK OS = *Streptococcus pneumoniae* (strain CGSP14) GN = dnaK PE = 3 SV = 1 - [DNAK_STRPS] | Intracellular |
| B2INT1 | 42.12 | 26 | 584 | 253.89 | Septation ring formation regulator EzrA OS = *Streptococcus pneumoniae* (strain CGSP14) GN = ezrA PE = 3 SV = 1 - [B2INT1_STRPS] | N-terminally anchored (No CS) |
| B2IM12 | 66.03 | 26 | 471 | 237.78 | Pneumolysin OS = *Streptococcus pneumoniae* (strain CGSP14) GN = ply PE = 4 SV = 1 - [B2IM12_STRPS] | Intracellular |
| B2IS47 | 55.47 | 11 | 137 | 228.66 | 50S ribosomal protein L16 OS = *Streptococcus pneumoniae* (strain CGSP14) GN = rplP PE = 3 SV = 1 - [RL16_STRPS] | Intracellular |
| B2IRM9 | 68.48 | 18 | 276 | 218.21 | ABC transporter, substrate-binding protein OS = *Streptococcus pneumoniae* (strain CGSP14) GN = SPCG_0152 PE = 4 SV = 1 - [B2IRM9_STRPS] | Lipid anchored |
| B2IRG4 | 64.53 | 23 | 203 | 217.88 | 30S ribosomal protein S4 OS = *Streptococcus pneumoniae* (strain CGSP14) GN = rpsD PE = 3 SV = 1 - [RS4_STRPS] | Intracellular |
| B2IS57 | 86.59 | 19 | 164 | 213.33 | 30S ribosomal protein S5 OS = *Streptococcus pneumoniae* (strain CGSP14) GN = rpsE PE = 3 SV = 1 - [B2IS57_STRPS] | Intracellular |
| B2IM40 | 44.9 | 29 | 824 | 208.41 | DNA-directed RNA polymerase subunit beta OS = *Streptococcus pneumoniae* (strain CGSP14) GN = rpoB PE = 3 SV = 1 - [B2IM40_STRPS] | Intracellular |
| B2ISM3 | 87.16 | 20 | 148 | 207.33 | 50S ribosomal protein L13 OS = *Streptococcus pneumoniae* (strain CGSP14) GN = rplM PE = 3 SV = 1 - [B2ISM3_STRPS] | Intracellular |
| B2IQ88 | 76.52 | 13 | 115 | 207.04 | 50S ribosomal protein L19 OS = *Streptococcus pneumoniae* (strain CGSP14) GN = rplS PE = 3 SV = 1 - [RL19_STRPS] | Intracellular |

TABLE 6-continued

Proteins identified in MP from serotype 3. The accession numbers refer to SwissProt on the date of filing.

| Accession # | Coverage | # Peptides | #AAs | Score | Description | Localization |
|---|---|---|---|---|---|---|
| B2ISD1 | 80.77 | 12 | 104 | 201.22 | Thioredoxin OS = *Streptococcus pneumoniae* (strain CGSP14) GN = trxA PE = 3 SV = 1 - [B2ISD1_STRPS] | Intracellular |
| B2IS40 | 62.98 | 15 | 208 | 197.25 | 50S ribosomal protein L3 OS = *Streptococcus pneumoniae* (strain CGSP14) GN = rplC PE = 3 SV = 1 - [RL3_STRPS] | Intracellular |
| B2IMJ9 | 41.57 | 28 | 890 | 195.17 | Aldehyde-alcohol dehydrogenase OS = *Streptococcus pneumoniae* (strain CGSP14) GN = adhE PE = 3 SV = 1 - [B2IMJ9_STRPS] | Intracellular |
| B2IPW4 | 45.86 | 24 | 567 | 191.95 | Dihydrolipoyl dehydrogenase OS = *Streptococcus pneumoniae* (strain CGSP14) GN = acoL PE = 4 SV = 1 - [B2IPW4_STRPS] | Intracellular |
| B2IP07 | 28.31 | 14 | 650 | 190.79 | PTS system, fructose specific IIABC components OS = *Streptococcus pneumoniae* (strain CGSP14) GN = fruA PE = 4 SV = 1 - [B2IP07_STRPS] | Multi-transmembrane |
| B2IS55 | 84.27 | 13 | 178 | 180.96 | 50S ribosomal protein L6 OS = *Streptococcus pneumoniae* (strain CGSP14) GN = rplF PE = 3 SV = 1 - [RL6_STRPS] | Intracellular |
| B2IME4 | 33.44 | 20 | 930 | 180.14 | Translation initiation factor IF-2 OS = *Streptococcus pneumoniae* (strain CGSP14) GN = infB PE = 3 SV = 1 - [IF2_STRPS] | Intracellular |
| B2ISW0 | 53.72 | 12 | 242 | 178.66 | Choline transporter OS = *Streptococcus pneumoniae* (strain CGSP14) GN = SPCG_1835 PE = 4 SV = 1 - [B2ISW0_STRPS] | Intracellular |
| B2IS66 | 43.31 | 8 | 127 | 176.98 | 30S ribosomal protein S11 OS = *Streptococcus pneumoniae* (strain CGSP14) GN = rpsK PE = 3 SV = 1 - [RS11_STRPS] | Intracellular |
| B2IPR1 | 43.98 | 13 | 332 | 173.61 | L-lactate dehydrogenase OS = *Streptococcus pneumoniae* (strain CGSP14) GN = ldh PE = 3 SV = 1 - [B2IPR1_STRPS] | Intracellular |
| B2IRS1 | 44.15 | 15 | 419 | 169.63 | Cell division protein FtsZ OS = *Streptococcus pneumoniae* (strain CGSP14) GN = ftsZ PE = 3 SV = 1 - [B2IRS1_STRPS] | Intracellular |
| B2IPP2 | 36.89 | 22 | 721 | 166.14 | Amino acid ABC transporter, amino acid-binding protein/permease protein OS = *Streptococcus pneumoniae* (strain CGSP14) GN = SPCG_1062 PE = 3 SV = 1 - [B2IPP2_STRPS] | Multi-transmembrane |
| B2ILZ5 | 43.89 | 21 | 540 | 165.77 | 60 kDa chaperonin OS = *Streptococcus pneumoniae* (strain CGSP14) GN = groL PE = 3 SV = 1 - [CH60_STRPS] | Intracellular |
| B2IS41 | 65.22 | 16 | 207 | 162.59 | 50S ribosomal protein L4 OS = *Streptococcus pneumoniae* (strain CGSP14) GN = rplD PE = 3 SV = 1 - [RL4_STRPS] | Intracellular |
| B2ILW6 | 75.31 | 15 | 243 | 162.56 | 3-ketoacyl-(Acyl-carrier-protein) reductase OS = *Streptococcus pneumoniae* (strain CGSP14) GN = fabG PE = 4 SV = 1 - [B2ILW6_STRPS] | Intracellular |
| B2ISY9 | 34.54 | 14 | 498 | 161.94 | Oligopeptide ABC transporter, permease protein AmiC OS = *Streptococcus pneumoniae* (strain CGSP14) GN = amiC PE = 3 SV = 1 - [B2ISY9_STRPS] | Multi-transmembrane |
| B2ISY6 | 58.31 | 18 | 331 | 161.56 | Oligopeptide ABC transporter, ATP-binding protein AmiF OS = *Streptococcus pneumoniae* (strain CGSP14) GN = amiF PE = 3 SV = 1 - [B2ISY6_STRPS] | Intracellular |

TABLE 6-continued

Proteins identified in MP from serotype 3. The accession numbers refer to SwissProt on the date of filing.

| Accession # | Coverage | # Peptides | #AAs | Score | Description | Localization |
|---|---|---|---|---|---|---|
| B2IS52 | 77.22 | 13 | 180 | 159.07 | 50S ribosomal protein L5 OS = *Streptococcus pneumoniae* (strain CGSP14) GN = rplE PE = 3 SV = 1 - [RL5_STRPS] | Intracellular |
| B2ILW7 | 50.24 | 10 | 414 | 153.03 | 3-oxoacyl-[acyl-carrier-protein] synthase 2 OS = *Streptococcus pneumoniae* (strain CGSP14) GN = fabF PE = 3 SV = 1 - [B2ILW7_STRPS] | Intracellular |
| B2ISY7 | 46.76 | 16 | 355 | 151.21 | Oligopeptide ABC transporter, ATP-binding protein AmiE OS = *Streptococcus pneumoniae* (strain CGSP14) GN = amiE PE = 3 SV = 1 - [B2ISY7_STRPS] | Intracellular |
| B2ILU5 | 34.89 | 13 | 427 | 150.71 | Trigger factor OS = *Streptococcus pneumoniae* (strain CGSP14) GN = tig PE = 3 SV = 1 - [TIG_STRPS] | Intracellular |
| B2IMU8 | 55.46 | 15 | 229 | 148.33 | 50S ribosomal protein L1 OS = *Streptococcus pneumoniae* (strain CGSP14) GN = rplA PE = 3 SV = 1 - [RL1_STRPS] | Intracellular |
| B2IS44 | 56.99 | 10 | 93 | 148.01 | 30S ribosomal protein S19 OS = *Streptococcus pneumoniae* (strain CGSP14) GN = rpsS PE = 3 SV = 1 - [RS19_STRPS] | Intracellular |
| B2IQT6 | 47.49 | 18 | 459 | 146.83 | NADH oxidase OS = *Streptococcus pneumoniae* (strain CGSP14) GN = nox PE = 4 SV = 1 - [B2IQT6_STRPS] | Intracellular |
| B2INP5 | 40.65 | 15 | 492 | 145.57 | Inosine-5'-monophosphate dehydrogenase OS = *Streptococcus pneumoniae* (strain CGSP14) GN = imdH PE = 3 SV = 1 - [B2INP5_STRPS] | Intracellular |
| B2INF2 | 51.27 | 20 | 513 | 140.36 | ABC transporter, ATP-binding protein OS = *Streptococcus pneumoniae* (strain CGSP14) GN = SPCG_0719 PE = 4 SV = 1 - [B2INF2_STRPS] | Intracellular |
| B2IRS2 | 50.33 | 12 | 457 | 140.22 | Cell division protein FtsA OS = *Streptococcus pneumoniae* (strain CGSP14) GN = ftsZ PE = 3 SV = 1 - [B2IRS2_STRPS] | Intracellular |
| B2IPY5 | 51.98 | 15 | 379 | 138.63 | Glycogen biosynthesis protein GlgD OS = *Streptococcus pneumoniae* (strain CGSP14) GN = glgD PE = 4 SV = 1 - [B2IPY5_STRPS] | Intracellular |
| B2IQH2 | 47.59 | 12 | 187 | 137.62 | 50S ribosomal protein L10 OS = *Streptococcus pneumoniae* (strain CGSP14) GN = rplJ PE = 3 SV = 1 - [B2IQH2_STRPS] | Intracellular |
| B2IPM7 | 29.64 | 14 | 577 | 137.31 | Phosphoenolpyruvate-protein phosphotransferase OS = *Streptococcus pneumoniae* (strain CGSP14) GN = SPCG_1121 PE = 3 SV = 1 - [B2IPM7_STRPS] | Intracellular |
| B2ISJ8 | 57.69 | 11 | 156 | 133.5 | 30S ribosomal protein S7 OS = *Streptococcus pneumoniae* (strain CGSP14) GN = rpsG PE = 3 SV = 1 - [RS7_STRPS] | Intracellular |
| B2IS54 | 74.24 | 10 | 132 | 133.28 | 30S ribosomal protein S8 OS = *Streptococcus pneumoniae* (strain CGSP14) GN = rpsH PE = 3 SV = 1 - [RS8_STRPS] | Intracellular |
| B2INZ1 | 46.38 | 17 | 470 | 132.61 | FeS assembly protein SufB OS = *Streptococcus pneumoniae* (strain CGSP14) GN = SPCG_0816 PE = 4 SV = 1 - [B2INZ1_STRPS] | Intracellular |
| B2IS53 | 62.92 | 10 | 89 | 131.91 | 30S ribosomal protein S14 OS = *Streptococcus pneumoniae* (strain CGSP14) GN = rpsN PE = 3 SV = 1 - [RS14_STRPS] | Intracellular |

TABLE 6-continued

Proteins identified in MP from serotype 3. The accession numbers refer to SwissProt on the date of filing.

| Accession # | Coverage | # Peptides | #AAs | Score | Description | Localization |
|---|---|---|---|---|---|---|
| B2IS59 | 63.7 | 9 | 146 | 131.45 | 50S ribosomal protein L15 OS = Streptococcus pneumoniae (strain CGSP14) GN = rplO PE = 3 SV = 1 - [RL15_STRPS] | Intracellular |
| B2INH5 | 50.5 | 17 | 299 | 127.85 | SPFH domain/Band 7 family OS = Streptococcus pneumoniae (strain CGSP14) GN = SPCG_2124 PE = 4 SV = 1 - [B2INH5_STRPS] | N-terminally anchored (No CS) |
| B2IRE3 | 73.42 | 12 | 158 | 127.54 | PTS system, IIB component OS = Streptococcus pneumoniae (strain CGSP14) GN = SPCG_0062 PE = 4 SV = 1 - [B2IRE3_STRPS] | Intracellular |
| B2IN11 | 64.88 | 14 | 299 | 125.53 | UTP--glucose-1-phosphate uridylyltransferase OS = Streptococcus pneumoniae (strain CGSP14) GN = galU PE = 3 SV = 1 [B2IN11_STRPS] | Secretory (released) (with CS) |
| B2ISI9 | 43.76 | 23 | 617 | 125.33 | Proline--tRNA ligase OS = Streptococcus pneumoniae (strain CGSP14) GN = proS PE = 3 SV = 1 - [SYP_STRPS] | Intracellular |
| B2IPB5 | 60.5 | 12 | 119 | 125.17 | 50S ribosomal protein L20 OS = Streptococcus pneumoniae (strain CGSP14) GN = rplT PE = 3 SV = 1 - [RL20_STRPS] | Intracellular |
| B2IMN9 | 40.47 | 11 | 425 | 125.01 | Uncharacterized protein OS = Streptococcus pneumoniae (strain CGSP14) GN = SPCG_2034 PE = 4 SV = 1 - [B2IMN9_STRPS] | Intracellular |
| B2IS90 | 47.86 | 20 | 537 | 123.3 | Ribonuclease Y OS = Streptococcus pneumoniae (strain CGSP14) GN = rny PE = 3 SV = 1 - [B2IS90_STRPS] | Intracellular |
| B2IPB4 | 36.36 | 6 | 66 | 122.81 | 50S ribosomal protein L35 OS = Streptococcus pneumoniae (strain CGSP14) GN = rpmI PE = 3 SV = 1 - [RL35_STRPS] | Intracellular |
| B2IQW2 | 62.61 | 5 | 115 | 121.34 | Bacterocin transport accessory protein OS = Streptococcus pneumoniae (strain CGSP14) GN = bta PE = 4 SV = 1 - [B2IQW2_STRPS] | Intracellular |
| B2INS1 | 30.9 | 21 | 848 | 120 | Aminopeptidase N OS = Streptococcus pneumoniae (strain CGSP14) GN = pepN PE = 4 SV = 1 - [B2INS1_STRPS] | Intracellular |
| B2IPP1 | 53.66 | 9 | 246 | 116.21 | Amino acid ABC transporter, ATP-binding protein OS = Streptococcus pneumoniae (strain CGSP14) GN = SPCG_1061 PE = 4 SV = 1 - [B2IPP1_STRPS] | Intracellular |
| B2IMN0 | 34.94 | 8 | 352 | 116.08 | Alcohol dehydrogenase, zinc-containing OS = Streptococcus pneumoniae (strain CGSP14) GN = adh PE = 3 SV = 1 - [B2IMN0_STRPS] | Intracellular |
| B2IRN0 | 53.52 | 14 | 284 | 114.19 | Lipoprotein OS = Streptococcus pneumoniae (strain CGSP14) GN = SPCG_0153 PE = 3 SV = 1 - [B2IRN0_STRPS] | Lipid anchored |
| B2IQZ2 | 48.66 | 14 | 374 | 110.45 | Ribosome-binding ATPase YchF OS = Streptococcus pneumoniae (strain CGSP14) GN = ychF PE = 3 SV = 1 - [B2IQZ2_STRPS] | Intracellular |
| B2IQI0 | 41.57 | 13 | 344 | 105.33 | Uncharacterized protein OS = Streptococcus pneumoniae (strain CGSP14) GN = SPCG_1352 PE = 4 SV = 1 - [B2IQI0_STRPS] | Multi-transmembrane |
| B2IS49 | 60.47 | 7 | 86 | 105.08 | 30S ribosomal protein S17 OS = Streptococcus pneumoniae (strain CGSP14) GN = rpsQ PE = 3 SV = 1 - [RS17_STRPS] | Intracellular |

TABLE 6-continued

Proteins identified in MP from serotype 3. The accession numbers refer to SwissProt on the date of filing.

| Accession # | Coverage | # Peptides | #AAs | Score | Description | Localization |
|---|---|---|---|---|---|---|
| B2IR07 | 35.97 | 15 | 442 | 104.04 | Adenylosuccinate synthetase OS = *Streptococcus pneumoniae* (strain CGSP14) GN = purA PE = 3 SV = 1 - [B2IR07_STRPS] | Intracellular |
| B2IMU7 | 42.55 | 6 | 141 | 103.8 | 50S ribosomal protein L11 OS = *Streptococcus pneumoniae* (strain CGSP14) GN = rplK PE = 3 SV = 1 - [RL11_STRPS] | Intracellular |
| B2ISV9 | 21.53 | 9 | 511 | 103.52 | Choline transporter OS = *Streptococcus pneumoniae* (strain CGSP14) GN = SPCG_1834 PE = 3 SV = 1 - [B2ISV9_STRPS] | Multi-transmembrane |
| B2IQV9 | 40.56 | 16 | 572 | 103.11 | Phosphoglucomutase OS = *Streptococcus pneumoniae* (strain CGSP14) GN = pgm PE = 3 SV = 1 - [B2IQV9_STRPS] | Intracellular |
| B2IR17 | 52.51 | 12 | 339 | 101.9 | Ribose-phosphate pyrophosphokinase OS = *Streptococcus pneumoniae* (strain CGSP14) GN = prsA PE = 3 SV = 1 - [B2IR17_STRPS] | Intracellular |
| B2IRQ3 | 37.38 | 18 | 650 | 101.35 | Endopeptidase O OS = *Streptococcus pneumoniae* (strain CGSP14) GN = pepO PE = 4 SV = 1 - [B2IRQ3_STRPS] | Intracellular |
| B2IS63 | 54.72 | 6 | 212 | 100 | Adenylate kinase OS = *Streptococcus pneumoniae* (strain CGSP14) GN = adk PE = 3 SV = 1 - [KAD_STRPS] | Intracellular |
| B2IMK3 | 38.15 | 13 | 658 | 99.61 | Transketolase OS = *Streptococcus pneumoniae* (strain CGSP14) GN = tktA PE = 3 SV = 1 - [B2IMK3_STRPS] | Intracellular |
| B2IMS2 | 55.97 | 12 | 293 | 98.56 | Fructose-bisphosphate aldolase OS = *Streptococcus pneumoniae* (strain CGSP14) GN = fba PE = 3 SV = 1 - [B2IMS2_STRPS] | Intracellular |
| B2IMH3 | 55.78 | 12 | 346 | 96.72 | Catabolite control protein A OS = *Streptococcus pneumoniae* (strain CGSP14) GN = ccpA PE = 4 SV = 1 - [B2IMH3_STRPS] | Intracellular |
| B2IPY8 | 48.31 | 15 | 474 | 96.35 | Glyceraldehyde-3-phosphate dehydrogenase, NADP-dependent OS = *Streptococcus pneumoniae* (strain CGSP14) GN = gapN PE = 3 SV = 1 - [B2IPY8_STRPS] | Intracellular |
| B2ILY5 | 30.81 | 10 | 555 | 96.12 | Uncharacterized protein OS = *Streptococcus pneumoniae* (strain CGSP14) GN = SPCG_0438 PE = 4 SV = 1 - [B2ILY5_STRPS] | Intracellular |
| B2IS42 | 95.92 | 11 | 98 | 95.91 | 50S ribosomal protein L23 OS = *Streptococcus pneumoniae* (strain CGSP14) GN = rplW PE = 3 SV = 1 - [RL23_STRPS] | Intracellular |
| B2IM28 | 43.56 | 13 | 388 | 95.69 | Protein RecA OS = *Streptococcus pneumoniae* (strain CGSP14) GN = recA PE = 3 SV = 1 - [RECA_STRPS] | Intracellular |
| B2IRR6 | 27.44 | 10 | 266 | 95.52 | Cell division protein DivIVA OS = *Streptococcus pneumoniae* (strain CGSP14) GN = SPCG_1633 PE = 4 SV = 1 - [B2IRR6_STRPS] | Intracellular |
| B2IS68 | 64.06 | 8 | 128 | 93.87 | 50S ribosomal protein L17 OS = *Streptococcus pneumoniae* (strain CGSP14) GN = rplQ PE = 3 SV = 1 - [RL17_STRPS] | Intracellular |
| B2IPR2 | 22.47 | 13 | 841 | 93.61 | DNA gyrase subunit A OS = *Streptococcus pneumoniae* (strain CGSP14) GN = gyrA PE = 3 SV = 1 - [B2IPR2_STRPS] | Intracellular |
| B2IM73 | 29.94 | 12 | 521 | 93.46 | Amino acid ABC transporter, amino acid-binding protein/permease protein OS = *Streptococcus pneumoniae* (strain CGSP14) GN = glnH PE = 3 SV = 1 - [B2IM73_STRPS] | Multi-transmembrane |

TABLE 6-continued

Proteins identified in MP from serotype 3. The accession numbers refer to SwissProt on the date of filing.

| Accession # | Coverage | # Peptides | #AAs | Score | Description | Localization |
|---|---|---|---|---|---|---|
| B2INV5 | 59.04 | 7 | 83 | 93.23 | 30S ribosomal protein S20 OS = *Streptococcus pneumoniae* (strain CGSP14) GN = rpsT PE = 3 SV = 1 - [B2INV5_STRPS] | Intracellular |
| B2IRH9 | 39.61 | 21 | 616 | 93.09 | Capsular polysaccharide biosynthesis protein, putative OS = *Streptococcus pneumoniae* (strain CGSP14) GN = SPCG_0098 PE = 4 SV = 1 - [B2IRH9_STRPS] | Multi-transmembrane |
| B2INY7 | 55.13 | 9 | 263 | 92.69 | ABC transporter, ATP-binding protein OS = *Streptococcus pneumoniae* (strain CGSP14) GN = SPCG_0812 PE = 4 SV = 1 - [B2INY7_STRPS] | Intracellular |
| B2INW3 | 45.21 | 14 | 511 | 92.64 | Sugar ABC transporter, ATP-binding protein OS = *Streptococcus pneumoniae* (strain CGSP14) GN = SPCG_0788 PE = 4 SV = 1 - [B2INW3_STRPS] | Intracellular |
| B2IQU4 | 57.5 | 9 | 280 | 89.47 | Oxidoreductase, aldo/keto reductase family OS = *Streptococcus pneumoniae* (strain CGSP14) GN = SPCG_1466 PE = 4 SV = 1 - [B2IQU4_STRPS] | Intracellular |
| B2ILR7 | 36.8 | 13 | 481 | 87.34 | 6-phosphogluconate dehydrogenase, decarboxylating OS = *Streptococcus pneumoniae* (strain CGSP14) GN = gnd PE = 3 SV = 1 - [B2ILR7_STRPS] | Intracellular |
| B2IRW4 | 23.85 | 14 | 436 | 87.08 | GTPase Der OS = *Streptococcus pneumoniae* (strain CGSP14) GN = der PE = 3 SV = 1 - [DER_STRPS] | Intracellular |
| B2IQW3 | 46.76 | 10 | 278 | 86.59 | Amino acid ABC transporter, amino acid-binding protein OS = *Streptococcus pneumoniae* (strain CGSP14) GN = SPCG_1485 PE = 4 SV = 1 - [B2IQW3_STRPS] | Lipid anchored |
| B2IP17 | 33.14 | 8 | 341 | 85.78 | Iron-compound ABC transporter, iron compound-binding protein OS = *Streptococcus pneumoniae* (strain CGSP14) GN = SPCG_1009 PE = 4 SV = 1 - [B2IPI7_STRPS] | Lipid anchored |
| B2IS65 | 58.68 | 12 | 121 | 85.63 | 30S ribosomal protein S13 OS = *Streptococcus pneumoniae* (strain CGSP14) GN = rpsM PE = 3 SV = 1 - [RS13_STRPS] | Intracellular |
| B2ISM4 | 59.23 | 8 | 130 | 85.44 | 30S ribosomal protein S9 OS = *Streptococcus pneumoniae* (strain CGSP14) GN = rpsI PE = 3 SV = 1 - [RS9_STRPS] | Intracellular |
| B2INT7 | 37.9 | 17 | 752 | 85.35 | ATP-dependent Clp protease, ATP-binding subunit ClpE OS = *Streptococcus pneumoniae* (strain CGSP14) GN = clpE PE = 3 SV = 1 - [B2INT7_STRPS] | Intracellular |
| B2IMU6 | 41.18 | 8 | 238 | 85.34 | Uncharacterized protein OS = *Streptococcus pneumoniae* (strain CGSP14) GN = SPCG_0590 PE = 4 SV = 1 - [B2IMU6_STRPS] | Lipid anchored |
| B2IQR1 | 39.42 | 15 | 520 | 84.59 | GMP synthase [glutamine-hydrolyzing] OS = *Streptococcus pneumoniae* (strain CGSP14) GN = guaA PE = 3 SV = 1 - [GUAA_STRPS] | Intracellular |
| B2IPT6 | 68.42 | 8 | 171 | 84.01 | Galactose-6-phosphate isomerase subunit LacB OS = *Streptococcus pneumoniae* (strain CGSP14) GN = lacB PE = 3 SV = 1 - [LACB_STRPS] | Intracellular |
| B2INL3 | 30.25 | 17 | 810 | 83.74 | ATP-dependent Clp protease, ATP-binding subunit OS = *Streptococcus pneumoniae* (strain CGSP14) GN = SPCG_2162 PE = 3 SV = 1 - [B2INL3_STRPS] | Intracellular |

TABLE 6-continued

Proteins identified in MP from serotype 3. The accession numbers refer to SwissProt on the date of filing.

| Accession # | Coverage | # Peptides | #AAs | Score | Description | Localization |
|---|---|---|---|---|---|---|
| B2IS51 | 78.22 | 10 | 101 | 83.43 | 50S ribosomal protein L24 OS = *Streptococcus pneumoniae* (strain CGSP14) GN = rplX PE = 3 SV = 1 - [RL24_STRPS] | Intracellular |
| B2INN1 | 42.77 | 10 | 346 | 83.3 | Elongation factor Ts OS = *Streptococcus pneumoniae* (strain CGSP14) GN = tsf PE = 3 SV = 1 - [EFTS_STRPS] | Intracellular |
| B2IS56 | 67.18 | 10 | 131 | 82.77 | 50S ribosomal protein L18 OS = *Streptococcus pneumoniae* (strain CGSP14) GN = rplR PE = 3 SV = 1 - [B2IS56_STRPS] | Intracellular |
| B2ISX8 | 27.68 | 8 | 336 | 82.74 | Non-canonical purine NTP pyrophosphatase OS = *Streptococcus pneumoniae* (strain CGSP14) GN = SPCG_1853 PE = 3 SV = 1 - [B2ISX8_STRPS] | Intracellular |
| B2INT0 | 24.07 | 12 | 648 | 81.85 | DNA gyrase subunit B OS = *Streptococcus pneumoniae* (strain CGSP14) GN = gyrB PE = 3 SV = 1 - [B2INT0_STRPS] | Intracellular |
| B2IN71 | 31.13 | 15 | 620 | 81.8 | Elongation factor Tu family protein OS = *Streptococcus pneumoniae* (strain CGSP14) GN = SPCG_0638 PE = 4 SV = 1 - [B2IN71_STRPS] | Intracellular |
| B2IPU8 | 19.19 | 9 | 719 | 79.81 | Ribonucleoside-diphosphate reductase OS = *Streptococcus pneumoniae* (strain CGSP14) GN = nrdE PE = 3 SV = 1 - [B2IPU8_STRPS] | Intracellular |
| B2INM4 | 49.45 | 9 | 182 | 79.8 | Ribosomal subunit interface protein OS = *Streptococcus pneumoniae* (strain CGSP14) GN = SPCG_2173 PE = 4 SV = 1 - [B2INM4_STRPS] | Intracellular |
| B2ISV2 | 28.57 | 7 | 392 | 79.49 | Galactokinase OS = *Streptococcus pneumoniae* (strain CGSP14) GN = galK PE = 3 SV = 1 - [B2ISV2_STRPS] | Intracellular |
| B2IMZ0 | 45.21 | 9 | 449 | 77.7 | Glucose-6-phosphate isomerase OS = *Streptococcus pneumoniae* (strain CGSP14) GN = pgi PE = 3 SV = 1 - [G6PI_STRPS] | Intracellular |
| B2IRD4 | 61.8 | 6 | 89 | 77.46 | 30S ribosomal protein S15 OS = *Streptococcus pneumoniae* (strain CGSP14) GN = rpsO PE = 3 SV = 1 - [RS15_STRPS] | Intracellular |
| B2IR65 | 69.38 | 11 | 209 | 76.49 | Uncharacterized protein OS = *Streptococcus pneumoniae* (strain CGSP14) GN = SPCG_1532 PE = 4 SV = 1 - [B2IR65_STRPS] | Intracellular |
| B2IR90 | 43.02 | 4 | 172 | 76.3 | Non-heme iron-containing ferritin OS = *Streptococcus pneumoniae* (strain CGSP14) GN = SPCG_1557 PE = 3 SV = 1 - [B2IR90_STRPS] | Intracellular |
| B2IPY6 | 28.16 | 9 | 380 | 75.91 | Glucose-1-phosphate adenylyltransferase OS = *Streptococcus pneumoniae* (strain CGSP14) GN = glgC PE = 3 SV = 1 - [GLGC_STRPS] | Intracellular |
| B2IN68 | 38.1 | 7 | 126 | 75.25 | Uncharacterized protein OS = *Streptococcus pneumoniae* (strain CGSP14) GN = SPCG_0635 PE = 4 SV = 1 - [B2IN68_STRPS] | N-terminally anchored (No CS) |
| B2IR60 | 97.92 | 8 | 96 | 74.99 | 30S ribosomal protein S6 OS = *Streptococcus pneumoniae* (strain CGSP14) GN = rpsF PE = 3 SV = 1 - [RS6_STRPS] | Intracellular |
| B2IQ02 | 48.45 | 7 | 97 | 74.43 | 50S ribosomal protein L27 OS = *Streptococcus pneumoniae* (strain CGSP14) GN = rpmA PE = 3 SV = 1 - [RL27_STRPS] | Intracellular |

TABLE 6-continued

Proteins identified in MP from serotype 3. The accession numbers refer to SwissProt on the date of filing.

| Accession # | Coverage | # Peptides | #AAs | Score | Description | Localization |
|---|---|---|---|---|---|---|
| B2IM41 | 40.05 | 10 | 377 | 74.15 | Uncharacterized protein OS = *Streptococcus pneumoniae* (strain CGSP14) GN = SPCG_1926 PE = 3 SV = 1 - [B2IM41_STRPS] | Intracellular |
| B2IR71 | 16.41 | 12 | 914 | 73.99 | Cation-transporting ATPase, E1-E2 family OS = *Streptococcus pneumoniae* (strain CGSP14) GN = pacL PE = 3 SV = 1 - [B2IR71_STRPS] | Multi-transmembrane |
| B2IQV3 | 35.99 | 6 | 289 | 72.94 | Glycerol uptake facilitator protein, putative OS = *Streptococcus pneumoniae* (strain CGSP14) GN = glpF PE = 3 SV = 1 - [B2IQV3_STRPS] | Multi-transmembrane |
| B2ILW5 | 35.95 | 9 | 306 | 72.85 | Malonyl CoA-acyl carrier protein transacylase OS = *Streptococcus pneumoniae* (strain CGSP14) GN = fabD PE = 3 SV = 1 - [B2ILW5_STRPS] | Intracellular |
| B2IRQ6 | 42.81 | 10 | 313 | 71.49 | Manganese ABC transporter, manganese-binding adhesion liprotein OS = *Streptococcus pneumoniae* (strain CGSP14) GN = SPCG_1623 PE = 3 SV = 1 - [B2IRQ6_STRPS] | Lipid anchored |
| B2IQX4 | 60.98 | 9 | 164 | 71.29 | ATP synthase subunit b OS = *Streptococcus pneumoniae* (strain CGSP14) GN = atpF PE = 3 SV = 1 - [ATPF_STRPS] | N-terminally anchored (No CS) |
| B2IPT0 | 26.59 | 10 | 628 | 71.03 | Elongation factor 4 OS = *Streptococcus pneumoniae* (strain CGSP14) GN = lepA PE = 3 SV = 1 - [B2IPT0_STRPS] | Intracellular |
| B2ISJ1 | 27.74 | 11 | 602 | 69.46 | Glutamine--fructose-6-phosphate aminotransferase [isomerizing] OS = *Streptococcus pneumoniae* (strain CGSP14) GN = glmS PE = 3 SV = 1 - [B2ISJ1_STRPS] | Intracellular |
| B2IQU1 | 23.75 | 13 | 678 | 68.47 | Glycine--tRNA ligase beta subunit OS = *Streptococcus pneumoniae* (strain CGSP14) GN = glyS PE = 3 SV = 1 - [SYGB_STRPS] | Intracellular |
| B2INH0 | 41.42 | 11 | 338 | 68.3 | Ornithine carbamoyltransferase OS = *Streptococcus pneumoniae* (strain CGSP14) GN = arcB PE = 3 SV = 1 - [OTC_STRPS] | Intracellular |
| B2IQL4 | 61.42 | 12 | 267 | 68.04 | Phosphate import ATP-binding protein PstB OS = *Streptococcus pneumoniae* (strain CGSP14) GN = pstB PE = 3 SV = 1 - [B2IQL4_STRPS] | Intracellular |
| B2ING9 | 37.9 | 10 | 409 | 65.94 | Arginine deiminase OS = *Streptococcus pneumoniae* (strain CGSP14) GN = arcA PE = 3 SV = 1 - [ARCA_STRPS] | Intracellular |
| B2IR87 | 27.8 | 9 | 410 | 65.69 | ATP-dependent Clp protease ATP-binding subunit ClpX OS = *Streptococcus pneumoniae* (strain CGSP14) GN = clpX PE = 3 SV = 1 - [CLPX_STRPS] | Intracellular |
| B2IPY4 | 19.29 | 7 | 477 | 64.75 | Glycogen synthase OS = *Streptococcus pneumoniae* (strain CGSP14) GN = glgA PE = 3 SV = 1 - [GLGA_STRPS] | Intracellular |
| B2ISY0 | 36 | 4 | 100 | 63.86 | UPF0154 protein SPCG_1855 OS = *Streptococcus pneumoniae* (strain CGSP14) GN = SPCG_1855 PE = 3 SV = 1 - [B2ISY0_STRPS] | N-terminally anchored (No CS) |
| B2IQL1 | 28.04 | 6 | 271 | 63.33 | Amino acid ABC transporter, amino acid-binding protein OS = *Streptococcus pneumoniae* (strain CGSP14) GN = SPCG_1383 PE = 4 SV = 1 - [B2IQL1_STRPS] | Lipid anchored |

TABLE 6-continued

Proteins identified in MP from serotype 3. The accession numbers refer to SwissProt on the date of filing.

| Accession # | Coverage | # Peptides | #AAs | Score | Description | Localization |
|---|---|---|---|---|---|---|
| B2IN60 | 55 | 5 | 60 | 63.27 | 50S ribosomal protein L32 OS = Streptococcus pneumoniae (strain CGSP14) GN = rpmF PE = 3 SV = 1 - [RL32_STRPS] | Intracellular |
| B2IQK0 | 22.48 | 15 | 872 | 63.2 | Alanine--tRNA ligase OS = Streptococcus pneumoniae (strain CGSP14) GN = alaS PE = 3 SV = 1 - [SYA_STRPS] | Intracellular |
| B2INE4 | 30.43 | 8 | 447 | 62.91 | DEAD-box ATP-dependent RNA helicase CshB OS = Streptococcus pneumoniae (strain CGSP14) GN = rheB PE = 3 SV = 1 - [B2INE4_STRPS] | Intracellular |
| B2IS50 | 59.84 | 8 | 122 | 62.57 | 50S ribosomal protein L14 OS = Streptococcus pneumoniae (strain CGSP14) GN = rplN PE = 3 SV = 1 - [RL14_STRPS] | Intracellular |
| B2IND2 | 34.2 | 8 | 386 | 62.51 | Branched-chain amino acid ABC transporter, amino acid-binding protein OS = Streptococcus pneumoniae (strain CGSP14) GN = SPCG_0699 PE = 4 SV = 1 - [B2IND2_STRPS] | Lipid anchored |
| B2IRC1 | 40.12 | 8 | 339 | 61.9 | UDP-glucose 4-epimerase OS = Streptococcus pneumoniae (strain CGSP14) GN = galE PE = 4 SV = 1 - [B2IRC1_STRPS] | Intracellular |
| B2IR96 | 77.27 | 7 | 176 | 61.33 | Adenine phosphoribosyltransferase OS = Streptococcus pneumoniae (strain CGSP14) GN = apt PE = 3 SV = 1 - [B2IR96_STRPS] | Intracellular |
| B2IM46 | 42.61 | 9 | 345 | 61.11 | Uncharacterized protein OS = Streptococcus pneumoniae (strain CGSP14) GN = SPCG_1931 PE = 4 SV = 1 - [B2IM46_STRPS] | N-terminally anchored (No CS) |
| B2IMG8 | 28.22 | 8 | 404 | 61 | Aspartate aminotransferase OS = Streptococcus pneumoniae (strain CGSP14) GN = aspC PE = 4 SV = 1 - [B2IMG8_STRPS] | Intracellular |
| B2IQN0 | 59.06 | 5 | 127 | 60.7 | Uncharacterized protein OS = Streptococcus pneumoniae (strain CGSP14) GN = SPCG_1399 PE = 4 SV = 1 - [B2IQN0_STRPS] | N-terminally anchored (No CS) |
| B2IMQ9 | 22.52 | 11 | 737 | 60.06 | Polyribonucleotide nucleotidyltransferase OS = Streptococcus pneumoniae (strain CGSP14) GN = pnp PE = 3 SV = 2 - [PNP_STRPS] | Intracellular |
| B2IQ40 | 24.39 | 14 | 898 | 59.69 | Phosphoenolpyruvate carboxylase OS = Streptococcus pneumoniae (strain CGSP14) GN = ppc PE = 3 SV = 1 - [B2IQ40_STRPS] | Intracellular |
| B2IND9 | 60.43 | 10 | 230 | 59.42 | Cell division ABC transporter, ATP-binding protein FtsE OS = Streptococcus pneumoniae (strain CGSP14) GN = ftsE PE = 4 SV = 1 - [B2IND9_STRPS] | Intracellular |
| B2IQU5 | 27.92 | 10 | 480 | 59.4 | Peptidoglycan N-acetylglucosamine deacetylase A OS = Streptococcus pneumoniae (strain CGSP14) GN = pgdA PE = 4 SV = 1 - [B2IQU5_STRPS] | N-terminally anchored (No CS) |
| B2IQ23 | 39.06 | 8 | 425 | 59.39 | Uncharacterized protein OS = Streptococcus pneumoniae (strain CGSP14) GN = SPCG_1195 PE = 4 SV = 1 - [B2IQ23_STRPS] | Intracellular |
| B2INH1 | 22.54 | 6 | 315 | 59 | Carbamate kinase OS = Streptococcus pneumoniae (strain CGSP14) GN = arcC PE = 3 SV = 1 - [B2INH1_STRPS] | Secretory (released) (with CS) |
| B2IRI7 | 20.76 | 11 | 713 | 58.73 | Uncharacterized protein OS = Streptococcus pneumoniae (strain CGSP14) GN = SPCG_0106 PE = 4 SV = 1 - [B2IRI7_STRPS] | Multi-transmembrane |

TABLE 6-continued

Proteins identified in MP from serotype 3. The accession numbers refer to SwissProt on the date of filing.

| Accession # | Coverage | # Peptides | #AAs | Score | Description | Localization |
|---|---|---|---|---|---|---|
| B2IMP1 | 37.86 | 6 | 206 | 56.51 | Hydrolase, haloacid dehalogenase-like family OS = Streptococcus pneumoniae (strain CGSP14) GN = SPCG_2031 PE = 4 SV = 1 - [B2IMP1_STRPS] | Intracellular |
| B2IQH6 | 45.83 | 13 | 312 | 56.05 | Bifunctional methionine sulfoxide reductase A/B protein OS = Streptococcus pneumoniae (strain CGSP14) GN = msrA PE = 3 SV = 1 - [B2IQH6_STRPS] | N-terminally anchored (No CS) |
| B2IMB6 | 28.84 | 8 | 378 | 56.02 | Chaperone protein DnaJ OS = Streptococcus pneumoniae (strain CGSP14) GN = dnaJ PE = 3 SV = 1 - [B2IMB6_STRPS] | Intracellular |
| B2ISI8 | 32.46 | 7 | 419 | 55.7 | Zinc metalloprotease OS = Streptococcus pneumoniae (strain CGSP14) GN = eep PE = 3 SV = 1 - [B2ISI8_STRPS] | Multi-transmembrane |
| B2IR93 | 26.64 | 4 | 259 | 55.23 | Triosephosphate isomerase OS = Streptococcus pneumoniae (strain CGSP14) GN = tpiA PE = 3 SV = 1 - [B2IR93_STRPS] | Intracellular |
| B2ILX0 | 37.58 | 11 | 455 | 54.82 | Acetyl-CoA carboxylase OS = Streptococcus pneumoniae (strain CGSP14) GN = accC PE = 4 SV = 1 - [B2ILX0_STRPS] | Intracellular |
| B2IS39 | 65.69 | 6 | 102 | 54.76 | 30S ribosomal protein S10 OS = Streptococcus pneumoniae (strain CGSP14) GN = rpsJ PE = 3 SV = 1 - [RS10_STRPS] | Intracellular |
| B2IQ29 | 53.89 | 9 | 180 | 54.16 | Hypoxanthine-guanine phosphoribosyltransferase OS = Streptococcus pneumoniae (strain CGSP14) GN = hgt PE = 4 SV = 1 - [B2IQZ9_STRPS] | Intracellular |
| B2IMZ6 | 14.35 | 10 | 857 | 54.16 | DNA mismatch repair protein MutS OS = Streptococcus pneumoniae (strain CGSP14) GN = hexA PE = 3 SV = 1 - [B2IMZ6_STRPS] | Intracellular |
| B2IR84 | 36.49 | 7 | 296 | 53.72 | Nucleotide-binding protein SPCG_1551 OS = Streptococcus pneumoniae (strain CGSP14) GN = SPCG_1551 PE = 3 SV = 1 - [Y1551_STRPS] | Intracellular |
| B2ISX0 | 31.78 | 8 | 321 | 53.7 | Iron-compound ABC transporter, iron-compound-binding protein OS = Streptococcus pneumoniae (strain CGSP14) GN = SPCG_1845 PE = 4 SV = 1 - [B2ISX0_STRPS] | Lipid anchored |
| B2ILX6 | 56.45 | 6 | 186 | 52.99 | Elongation factor P OS = Streptococcus pneumoniae (strain CGSP14) GN = efp PE = 3 SV = 1 - [EFP_STRPS] | Intracellular |
| B2IMZ8 | 23.45 | 9 | 563 | 52.53 | Arginine--tRNA ligase OS = Streptococcus pneumoniae (strain CGSP14) GN = argS PE = 3 SV = 1 - [SYR_STRPS] | Intracellular |
| B2INY8 | 20.48 | 9 | 420 | 52.28 | Uncharacterized protein OS = Streptococcus pneumoniae (strain CGSP14) GN = SPCG_0813 PE = 4 SV = 1 - [B2INY8_STRPS] | Intracellular |
| B2IRA3 | 23.52 | 7 | 438 | 52.2 | Pyridine nucleotide-disulfide oxidoreductase OS = Streptococcus pneumoniae (strain CGSP14) GN = merA PE = 3 SV = 1 - [B2IRA3_STRPS] | Intracellular |
| B2IPW2 | 16.67 | 6 | 330 | 51.71 | Acetoin dehydrogenase, E1 component, beta subunit, putative OS = Streptococcus pneumoniae (strain CGSP14) GN = acoB PE = 4 SV = 1 - [B2IPW2_STRPS] | Intracellular |

TABLE 6-continued

Proteins identified in MP from serotype 3. The accession numbers refer to SwissProt on the date of filing.

| Accession # | Coverage | # Peptides | #AAs | Score | Description | Localization |
|---|---|---|---|---|---|---|
| B2IRU1 | 40.52 | 9 | 232 | 51.05 | Putative N-acetylmannosamine-6-phosphate 2-epimerase OS = Streptococcus pneumoniae (strain CGSP14) GN = nanE PE = 3 SV = 1 - [B2IRU1_STRPS] | Intracellular |
| B2ISY2 | 5.67 | 4 | 705 | 50.76 | Trehalose PTS system, IIABC components OS = Streptococcus pneumoniae (strain CGSP14) GN = treP PE = 4 SV = 1 - [B2ISY2_STRPS] | Multi-transmembrane |
| B2IRX3 | 29.29 | 10 | 297 | 50.56 | ABC transporter, ATP-binding protein OS = Streptococcus pneumoniae (strain CGSP14) GN = SPCG_1690 PE = 4 SV = 1 - [B2IRX3_STRPS] | Intracellular |
| B2IQY9 | 24.72 | 10 | 453 | 50.5 | Chromosomal replication initiator protein DnaA OS = Streptococcus pneumoniae (strain CGSP14) GN = dnaA PE = 3 SV = 1 - [DNAA_STRPS] | Intracellular |
| B2IMI1 | 36.61 | 4 | 183 | 50.13 | Transcription termination/antitermination protein NusG OS = Streptococcus pneumoniae (strain CGSP14) GN = nusG PE = 3 SV = 1 - [B2IMI1_STRPS] | Intracellular |
| B2ING0 | 66.32 | 5 | 95 | 49.96 | 30S ribosomal protein S16 OS = Streptococcus pneumoniae (strain CGSP14) GN = rpsP PE = 3 SV = 1 - [RS16_STRPS] | Intracellular |
| B2INE1 | 11.85 | 6 | 726 | 48.69 | PTS system, IIABC components OS = Streptococcus pneumoniae (strain CGSP14) GN = ptsG PE = 4 SV = 1 - [B2INE1_STRPS] | Multi-transmembrane |
| B2IMN6 | 33 | 9 | 494 | 48.52 | Threonine synthase OS = Streptococcus pneumoniae (strain CGSP14) GN = thrC PE = 4 SV = 1 - [B2IMN6_STRPS] | Intracellular |
| B2ILR1 | 12.8 | 8 | 719 | 47.81 | Penicillin-binding protein 1A OS = Streptococcus pneumoniae (strain CGSP14) GN = pbp1A PE = 4 SV = 1 - [B2ILR1_STRPS] | N-terminally anchored (No CS) |
| B2IR57 | 22.53 | 8 | 466 | 47.14 | Cof family protein/peptidyl-prolyl cis-trans isomerase, cyclophilin type OS = Streptococcus pneumoniae (strain CGSP14) GN = SPCG_1524 PE = 4 SV = 1 - [B2IR57_STRPS] | Intracellular |
| B2IRQ1 | 10.57 | 5 | 653 | 46.37 | PTS system IIABC components OS = Streptococcus pneumoniae (strain CGSP14) GN = scrA PE = 4 SV = 1 - [B2IRQ1_STRPS] | Multi-transmembrane |
| B2IRE5 | 23.91 | 5 | 276 | 46.36 | PTS system, IID component OS = Streptococcus pneumoniae (strain CGSP14) GN = SPCG_0064 PE = 4 SV = 1 - [B2IRE5_STRPS] | Multi-transmembrane |
| B2IRX0 | 47.08 | 8 | 240 | 46.21 | ABC transporter, ATP-binding protein OS = Streptococcus pneumoniae (strain CGSP14) GN = SPCG_1687 PE = 4 SV = 1 - [B2IRX0_STRPS] | Intracellular |
| B2IRI9 | 40.73 | 7 | 302 | 45.81 | Amino acid ABC transporter, periplasmic amino acid-binding protein, putative OS = Streptococcus pneumoniae (strain CGSP14) GN = SPCG_0108 PE = 4 SV = 1 - [B2IRI9_STRPS] | Lipid anchored |
| B2IQL3 | 29.76 | 6 | 252 | 45.8 | Phosphate import ATP-binding protein PstB OS = Streptococcus pneumoniae (strain CGSP14) GN = pstB PE = 3 SV = 1 - [B2IQL3_STRPS] | Intracellular |

TABLE 6-continued

Proteins identified in MP from serotype 3. The accession numbers refer to SwissProt on the date of filing.

| Accession # | Coverage | # Peptides | #AAs | Score | Description | Localization |
|---|---|---|---|---|---|---|
| B2IQ98 | 60.64 | 5 | 94 | 45.67 | 50S ribosomal protein L31 type B OS = Streptococcus pneumoniae (strain CGSP14) GN = rpmE PE = 3 SV = 1 - [B2IQ98_STRPS] | Intracellular |
| B2IRE7 | 15.8 | 6 | 386 | 44.99 | Sugar isomerase domain protein AgaS OS = Streptococcus pneumoniae (strain CGSP14) GN = agaS PE = 4 SV = 1 - [B2IRE7_STRPS] | Intracellular |
| B2IMZ5 | 21.99 | 9 | 564 | 44.92 | ABC transporter, ATP-binding/permease protein OS = Streptococcus pneumoniae (strain CGSP14) GN = SPCG_2042 PE = 4 SV = 1 - [B2IMZ5_STRPS] | Multi-transmembrane |
| B2IRQ7 | 56.4 | 7 | 172 | 44.31 | Probable thiol peroxidase OS = Streptococcus pneumoniae (strain CGSP14) GN = tpx PE = 3 SV = 1 - [B2IRQ7_STRPS] | Intracellular |
| B2ILX8 | 33.61 | 8 | 488 | 43.22 | Glutamyl-tRNA(Gln) amidotransferase subunit A OS = Streptococcus pneumoniae (strain CGSP14) GN = gatA PE = 3 SV = 1 - [GATA_STRPS] | Intracellular |
| B2IM45 | 29.04 | 8 | 427 | 43.07 | UDP-N-acetylglucosamine 1-carboxyvinyltransferase OS = Streptococcus pneumoniae (strain CGSP14) GN = murA PE = 3 SV = 1 - [B2IM45_STRPS] | Intracellular |
| B2IM60 | 25 | 6 | 416 | 43.06 | Diaminopimelate decarboxylase OS = Streptococcus pneumoniae (strain CGSP14) GN = lysA PE = 3 SV = 1 - [B2IM60_STRPS] | Intracellular |
| B2IRA1 | 21.95 | 9 | 524 | 42.94 | DEAD-box ATP-dependent RNA helicase CshA OS = Streptococcus pneumoniae (strain CGSP14) GN = cshA PE = 3 SV = 1 - [B2IRA1_STRPS] | Intracellular |
| B2IR78 | 17.33 | 6 | 450 | 42.72 | Phosphoglucosamine mutase OS = Streptococcus pneumoniae (strain CGSP14) GN = glmM PE = 3 SV = 1 - [GLMM_STRPS] | Intracellular |
| B2IST7 | 22.06 | 7 | 417 | 42.6 | Capsular polysaccharide biosynthesis protein, putative OS = Streptococcus pneumoniae (strain CGSP14) GN = SPCG_1812 PE = 3 SV = 1 - [B2IST7_STRPS] | Intracellular |
| B2INT8 | 57.89 | 2 | 76 | 41.48 | Uncharacterized protein OS = Streptococcus pneumoniae (strain CGSP14) GN = SPCG_0763 PE = 4 SV = 1 - [B2INT8_STRPS] | Intracellular |
| B2IQ61 | 25.95 | 6 | 289 | 41.38 | Choline kinase OS = Streptococcus pneumoniae (strain CGSP14) GN = pck PE = 4 SV = 1 - [B2IQ61_STRPS] | Intracellular |
| B2ILR6 | 14.66 | 5 | 464 | 41.32 | Mid-cell-anchored protein Z OS = Streptococcus pneumoniae (strain CGSP14) GN = mapZ PE = 3 SV = 1 - [B2ILR6_STRPS] | Multi-transmembrane |
| B2ILR4 | 29.91 | 3 | 117 | 40.9 | Cell cycle protein GpsB OS = Streptococcus pneumoniae (strain CGSP14) GN = gpsB PE = 3 SV = 1 - [B2ILR4_STRPS] | Intracellular |
| B2IQ25 | 28.88 | 8 | 419 | 40.5 | UDP-N-acetylglucosamine 1-carboxyvinyltransferase OS = Streptococcus pneumoniae (strain CGSP14) GN = murZ PE = 3 SV = 1 - [B2IQ25_STRPS] | Intracellular |
| B2IQH8 | 27.11 | 8 | 439 | 40.48 | Homoserine dehydrogenase OS = Streptococcus pneumoniae (strain CGSP14) GN = hom PE = 3 SV = 1 - [B2IQH8_STRPS] | Intracellular |
| B2IN58 | 28.96 | 6 | 335 | 40.08 | Uncharacterized protein OS = Streptococcus pneumoniae (strain CGSP14) GN = SPCG_2101 PE = 4 SV = 1 - [B2IN58_STRPS] | Multi-transmembrane |

TABLE 6-continued

Proteins identified in MP from serotype 3. The accession numbers refer to SwissProt on the date of filing.

| Accession # | Coverage | # Peptides | #AAs | Score | Description | Localization |
|---|---|---|---|---|---|---|
| B2IRK5 | 20.21 | 7 | 559 | 40.01 | Ribonuclease J OS = *Streptococcus pneumoniae* (strain CGSP14) GN = rnj PE = 3 SV = 1 - [B2IRK5_STRPS] | Intracellular |
| B2INR2 | 26.51 | 10 | 679 | 39.94 | Methionine--tRNA ligase OS = *Streptococcus pneumoniae* (strain CGSP14) GN = metG PE = 3 SV = 1 - [B2INR2_STRPS] | Intracellular |
| B2IQ29 | 30.5 | 8 | 436 | 39.93 | GTPase Obg OS = *Streptococcus pneumoniae* (strain CGSP14) GN = obg PE = 3 SV = 1 - [OBG_STRPS] | Intracellular |
| B2IMY2 | 73.21 | 7 | 56 | 39.82 | Uncharacterized protein OS = *Streptococcus pneumoniae* (strain CGSP14) GN = SPCG_0626 PE = 4 SV = 1 - [B2IMY2_STRPS] | Secretory (released) (with CS) |
| B2IPW3 | 33.6 | 8 | 375 | 39.59 | Dihydrolipoamide acetyltransferase OS = *Streptococcus pneumoniae* (strain CGSP14) GN = acoC PE = 3 SV = 1 - [B2IPW3_STRPS] | Intracellular |
| B2IRI8 | 38.5 | 6 | 213 | 39.57 | Amino acid ABC transporter, ATP-binding protein, putative OS = *Streptococcus pneumoniae* (strain CGSP14) GN = SPCG_0107 PE = 4 SV = 1 - [B2IRI8_STRPS] | Intracellular |
| B2ISR0 | 13.08 | 6 | 535 | 39.53 | Glucan 1,6-alpha-glucosidase OS = *Streptococcus pneumoniae* (strain CGSP14) GN = dexB PE = 4 SV = 1 - [B2ISR0_STRPS] | Intracellular |
| B2IM72 | 56.91 | 6 | 246 | 39.3 | Amino acid ABC transporter, ATP-binding protein OS = *Streptococcus pneumoniae* (strain CGSP14) GN = glnQ PE = 4 SV = 1 - [B2IM72_STRPS] | Intracellular |
| B2IS45 | 48.25 | 3 | 114 | 39.27 | 50S ribosomal protein L22 OS = *Streptococcus pneumoniae* (strain CGSP14) GN = rplV PE = 3 SV = 1 - [RL22_STRPS] | Intracellular |
| B2IM26 | 26.1 | 5 | 318 | 39.16 | Autolysin OS = *Streptococcus pneumoniae* (strain CGSP14) GN = lytA PE = 4 SV = 1 - [B2IM26_STRPS] | Intracellular |
| B2IM71 | 46.48 | 4 | 71 | 38.4 | Uncharacterized protein OS = *Streptococcus pneumoniae* (strain CGSP14) GN = SPCG_0446 PE = 4 SV = 1 - [B2IM71_STRPS] | Intracellular |
| B2INE0 | 30.09 | 8 | 329 | 38.01 | Cell division protein FtsX OS = *Streptococcus pneumoniae* (strain CGSP14) GN = ftsX PE = 3 SV = 1 - [B2INE0_STRPS] | Multi-transmembrane |
| B2IQ19 | 15.99 | 8 | 763 | 37.52 | DNA helicase OS = *Streptococcus pneumoniae* (strain CGSP14) GN = pcrA PE = 3 SV = 1 - [B2IQ19_STRPS] | Intracellular |
| B2IRN7 | 21.52 | 6 | 660 | 37.25 | Threonine--tRNA ligase OS = *Streptococcus pneumoniae* (strain CGSP14) GN = thrS PE = 3 SV = 1 - [B2IRN7_STRPS] | Intracellular |
| B2IS67 | 24.44 | 7 | 311 | 36.89 | DNA-directed RNA polymerase subunit alpha OS = *Streptococcus pneumoniae* (strain CGSP14) GN = rpoA PE = 3 SV = 1 - [B2IS67_STRPS] | Intracellular |
| B2IQA4 | 21.65 | 8 | 448 | 36.16 | Glutamate dehydrogenase OS = *Streptococcus pneumoniae* (strain CGSP14) GN = gdhA PE = 3 SV = 1 - [B2IQA4_STRPS] | Intracellular |
| B2INE5 | 20.96 | 6 | 396 | 36.08 | S-adenosylmethionine synthase OS = *Streptococcus pneumoniae* (strain CGSP14) GN = metK PE = 3 SV = 1 - [METK_STRPS] | Intracellular |
| B2IQN3 | 51.52 | 4 | 66 | 35.91 | 30S ribosomal protein S21 OS = *Streptococcus pneumoniae* (strain CGSP14) GN = rpsU PE = 3 SV = 1 - [B2IQN3_STRPS] | Intracellular |

TABLE 6-continued

Proteins identified in MP from serotype 3. The accession numbers refer to SwissProt on the date of filing.

| Accession # | Coverage | # Peptides | #AAs | Score | Description | Localization |
|---|---|---|---|---|---|---|
| B2IRK4 | 18.21 | 8 | 637 | 35.62 | tRNA uridine 5-carboxymethylaminomethyl modification enzyme MnmG OS = Streptococcus pneumoniae (strain CGSP14) GN = mnmG PE = 3 SV = 1 - [B2IRK4_STRPS] | Intracellular |
| B2IR76 | 14.89 | 4 | 282 | 35.33 | DegV family protein OS = Streptococcus pneumoniae (strain CGSP14) GN = SPCG_1543 PE = 4 SV = 1 - [B2IR76_STRPS] | Intracellular |
| B2IRT0 | 25.85 | 4 | 294 | 35.15 | ROK family protein OS = Streptococcus pneumoniae (strain CGSP14) GN = SPCG_1647 PE = 4 SV = 1 - [B2IRT0_STRPS] | Intracellular |
| B2IR21 | 58.62 | 7 | 145 | 35.06 | Uncharacterized protein OS = Streptococcus pneumoniae (strain CGSP14) GN = SPCG_0033 PE = 4 SV = 1 - [B2IR21_STRPS] | Intracellular |
| B2IPF4 | 25.4 | 8 | 311 | 35.02 | Adhesion lipoprotein OS = Streptococcus pneumoniae (strain CGSP14) GN = lmb PE = 3 SV = 1 - [B2IPF4_STRPS] | Lipid anchored |
| B2ILV9 | 26.21 | 6 | 454 | 34.9 | Aspartokinase OS = Streptococcus pneumoniae (strain CGSP14) GN = lysC PE = 3 SV = 1 - [B2ILV9_STRPS] | Intracellular |
| B2IPP0 | 17.37 | 7 | 495 | 34.88 | Glucose-6-phosphate 1-dehydrogenase OS = Streptococcus pneumoniae (strain CGSP14) GN = zwf PE = 3 SV = 1 - [B2IPP0_STRPS] | Intracellular |
| B2IRU0 | 8.43 | 5 | 510 | 34.78 | PTS system, IIBC components OS = Streptococcus pneumoniae (strain CGSP14) GN = SPCG_1657 PE = 4 SV = 1 - [B2IRU0_STRPS] | Multi-transmembrane |
| B2IQX1 | 34.93 | 7 | 292 | 34.34 | ATP synthase gamma chain OS = Streptococcus pneumoniae (strain CGSP14) GN = atpG PE = 3 SV = 1 - [ATPG_STRPS] | Intracellular |
| B2ISZ2 | 16.94 | 5 | 490 | 34.05 | Sucrose phosphorylase OS = Streptococcus pneumoniae (strain CGSP14) GN = SPCG_1867 PE = 4 SV = 1 - [B2ISZ2_STRPS] | Intracellular |
| B2IP00 | 28.21 | 6 | 397 | 33.73 | Serine protease OS = Streptococcus pneumoniae (strain CGSP14) GN = sphtra PE = 4 SV = 1 - [B2IP00_STRPS] | N-terminally anchored (No CS) |
| B2INW0 | 31.82 | 5 | 220 | 33.64 | Deoxyribose-phosphate aldolase OS = Streptococcus pneumoniae (strain CGSP14) GN = deoC PE = 3 SV = 1 - [DEOC_STRPS] | Intracellular |
| B2IM98 | 15.7 | 6 | 535 | 33.16 | CTP synthase OS = Streptococcus pneumoniae (strain CGSP14) GN = pyrG PE = 3 SV = 1 - [B2IM98_STRPS] | Intracellular |
| B2IMU0 | 11.8 | 4 | 466 | 33.1 | Dipeptidase OS = Streptococcus pneumoniae (strain CGSP14) GN = pepV PE = 4 SV = 1 - [B2IMU0_STRPS] | Intracellular |
| B2IPU4 | 37.15 | 5 | 253 | 33.02 | Lactose phosphotransferase system repressor OS = Streptococcus pneumoniae (strain CGSP14) GN = lacR PE = 4 SV = 1 - [B2IPU4_STRPS] | Intracellular |
| B2IRR9 | 38.55 | 5 | 179 | 32.57 | Cell division protein SepF OS = Streptococcus pneumoniae (strain CGSP14) GN = sepF PE = 3 SV = 1 - [SEPF_STRPS] | Intracellular |
| B2IQJ5 | 27.56 | 5 | 225 | 32.43 | 3-dehydroquinate dehydratase OS = Streptococcus pneumoniae (strain CGSP14) GN = aroD PE = 3 SV = 1 - [AROD_STRPS] | Intracellular |

TABLE 6-continued

Proteins identified in MP from serotype 3. The accession numbers refer to SwissProt on the date of filing.

| Accession # | Coverage | # Peptides | #AAs | Score | Description | Localization |
|---|---|---|---|---|---|---|
| B2INC8 | 38.43 | 7 | 216 | 32.37 | Uracil phosphoribosyltransferase OS = *Streptococcus pneumoniae* (strain CGSP14) GN = upp PE = 3 SV = 1 - [B2INC8_STRPS] | Intracellular |
| B2INU6 | 33.73 | 8 | 424 | 32.09 | Phosphopentomutase OS = *Streptococcus pneumoniae* (strain CGSP14) GN = deoB PE = 3 SV = 1 - [B2INU6_STRPS] | Intracellular |
| B2IME1 | 24.87 | 6 | 378 | 32.06 | Transcription termination/antitermination protein NusA OS = *Streptococcus pneumoniae* (strain CGSP14) GN = nusA PE = 3 SV = 1 - [B2IME1_STRPS] | Intracellular |
| B2INN5 | 22.79 | 4 | 272 | 31.93 | Cell shape-determining protein MreC OS = *Streptococcus pneumoniae* (strain CGSP14) GN = mreC PE = 3 SV = 1 - [B2INN5_STRPS] | N-terminally anchored (No CS) |
| B2IN76 | 12.22 | 6 | 450 | 31.55 | UDP-N-acetylmuramoylalanine--D-glutamate ligase OS = *Streptococcus pneumoniae* (strain CGSP14) GN = murD PE = 3 SV = 1 - [MURD_STRPS] | Intracellular |
| B2INF3 | 16.1 | 4 | 267 | 31.17 | Peptidyl-prolyl cis-trans isomerase OS = *Streptococcus pneumoniae* (strain CGSP14) GN = ppiA PE = 3 SV = 1 - [B2INF3_STRPS] | Lipid anchored |
| B2IQ22 | 31.82 | 6 | 286 | 30.97 | Methionine aminopeptidase OS = *Streptococcus pneumoniae* (strain CGSP14) GN = map PE = 1 SV = 1 - [B2IQ22_STRPS] | Intracellular |
| B2IS48 | 70.59 | 5 | 68 | 30.8 | 50S ribosomal protein L29 OS = *Streptococcus pneumoniae* (strain CGSP14) GN = rpmC PE = 3 SV = 1 - [RL29_STRPS] | Intracellular |
| B2IS10 | 19.57 | 6 | 649 | 30.36 | DNA mismatch repair protein MutL OS = *Streptococcus pneumoniae* (strain CGSP14) GN = mutL PE = 3 SV = 1 - [MUTL_STRPS] | Intracellular |
| B2IM44 | 29.93 | 6 | 274 | 30.16 | DNA-entry nuclease OS = *Streptococcus pneumoniae* (strain CGSP14) GN = endA PE = 4 SV = 1 - [B2IM44_STRPS] | N-terminally anchored (No CS) |
| B2INF7 | 54.46 | 5 | 112 | 29.66 | ATP cone domain-containing protein OS = *Streptococcus pneumoniae* (strain CGSP14) GN = SPCG_0728 PE = 4 SV = 1 - [B2INF7_STRPS] | Intracellular |
| B2IS34 | 13.3 | 7 | 737 | 29.66 | Anaerobic ribonucleoside triphosphate reductase OS = *Streptococcus pneumoniae* (strain CGSP14) GN = SPCG_0212 PE = 4 SV = 1 - [B2IS34_STRPS] | Intracellular |
| B2IN20 | 40.78 | 3 | 103 | 29.58 | Uncharacterized protein OS = *Streptococcus pneumoniae* (strain CGSP14) GN = SPCG_2067 PE = 4 SV = 1 - [B2IN20_STRPS] | Intracellular |
| B2IMB7 | 38.95 | 4 | 95 | 29.51 | Uncharacterized protein OS = *Streptococcus pneumoniae* (strain CGSP14) GN = SPCG_0492 PE = 4 SV = 1 - [B2IMB7_STRPS] | Intracellular |
| B2IMY9 | 20.58 | 6 | 486 | 29.3 | Glutamate--tRNA ligase OS = *Streptococcus pneumoniae* (strain CGSP14) GN = gltX PE = 3 SV = 1 - [SYE_STRPS] | Intracellular |
| B2IQ75 | 46.77 | 5 | 186 | 29.27 | LemA protein OS = *Streptococcus pneumoniae* (strain CGSP14) GN = lemA PE = 4 SV = 1 - [B2IQ75_STRPS] | N-terminally anchored (No CS) |
| B2IPN9 | 20.75 | 6 | 429 | 29.19 | Signal recognition particle receptor FtsY OS = *Streptococcus pneumoniae* (strain CGSP14) GN = ftsY PE = 3 SV = 1 - [B2IPN9_STRPS] | Intracellular |

TABLE 6-continued

Proteins identified in MP from serotype 3. The accession numbers refer to SwissProt on the date of filing.

| Accession # | Coverage | # Peptides | #AAs | Score | Description | Localization |
|---|---|---|---|---|---|---|
| B2INM2 | 45.33 | 7 | 150 | 28.94 | 50S ribosomal protein L9 OS = *Streptococcus pneumoniae* (strain CGSP14) GN = rplI PE = 3 SV = 1 - [RL9_STRPS] | Intracellular |
| B2IR80 | 20.89 | 5 | 292 | 28.84 | Uncharacterized protein OS = *Streptococcus pneumoniae* (strain CGSP14) GN = SPCG_1547 PE = 4 SV = 1 - [B2IR80_STRPS] | Multi-transmembrane |
| B2IPW9 | 32.16 | 8 | 283 | 28.64 | Ribosome biogenesis GTPase A OS = *Streptococcus pneumoniae* (strain CGSP14) GN = SPCG_1141 PE = 3 SV = 1 - [B2IPW9_STRPS] | Intracellular |
| B2IN61 | 75.51 | 4 | 49 | 28.27 | 50S ribosomal protein L33 OS = *Streptococcus pneumoniae* (strain CGSP14) GN = rpmG PE = 3 SV = 1 - [RL33_STRPS] | Intracellular |
| B2IM15 | 25.95 | 5 | 158 | 28.26 | Uncharacterized protein OS = *Streptococcus pneumoniae* (strain CGSP14) GN = SPCG_1901 PE = 4 SV = 1 - [B2IM15_STRPS] | Multi-transmembrane |
| B2IPZ5 | 13.9 | 7 | 633 | 28.19 | ABC transporter, ATP-binding protein OS = *Streptococcus pneumoniae* (strain CGSP14) GN = SPCG_1167 PE = 4 SV = 1 - [B2IPZ5_STRPS] | Intracellular |
| B2IMA9 | 20.94 | 6 | 487 | 28.12 | Type I restriction-modification system, M subunit OS = *Streptococcus pneumoniae* (strain CGSP14) GN = hsdM PE = 4 SV = 1 - [B2IMA9_STRPS] | Intracellular |
| B2IQ67 | 11.63 | 7 | 1058 | 28.04 | Carbamoyl-phosphate synthase large chain OS = *Streptococcus pneumoniae* (strain CGSP14) GN = carB PE = 3 SV = 1 - [CARB_STRPS] | Intracellular |
| B2IMV8 | 16.5 | 4 | 491 | 28.03 | PTS system, IIC component, putative OS = *Streptococcus pneumoniae* (strain CGSP14) GN = SPCG_0602 PE = 4 SV = 1 - [B2IMV8_STRPS] | Multi-transmembrane |
| B2INP6 | 15.54 | 4 | 341 | 28 | Tryptophan--tRNA ligase OS = *Streptococcus pneumoniae* (strain CGSP14) GN = trpS PE = 3 SV = 1 - [B2INP6_STRPS] | Intracellular |
| B2INU9 | 26.02 | 4 | 269 | 27.83 | Purine nucleoside phosphorylase OS = *Streptococcus pneumoniae* (strain CGSP14) GN = pnp PE = 3 SV = 1 - [B2INU9_STRPS] | Intracellular |
| B2IMS9 | 20.8 | 7 | 553 | 27.26 | Ribonuclease J OS = *Streptococcus pneumoniae* (strain CGSP14) GN = rnj PE = 3 SV = 1 - [B2IMS9_STRPS] | Intracellular |
| B2ILY3 | 41.94 | 4 | 62 | 27.17 | 50S ribosomal protein L28 OS = *Streptococcus pneumoniae* (strain CGSP14) GN = rpmB PE = 3 SV = 1 - [RL28_STRPS] | Intracellular |
| B2IRW8 | 34.46 | 5 | 177 | 26.92 | Transcriptional repressor NrdR OS = *Streptococcus pneumoniae* (strain CGSP14) GN = nrdR PE = 3 SV = 1 - [B2IRW8_STRPS] | Intracellular |
| B2IMH1 | 20.97 | 7 | 472 | 26.92 | Cof family protein OS = *Streptococcus pneumoniae* (strain CGSP14) GN = SPCG_1962 PE = 4 SV = 1 - [B2IMH1_STRPS] | Intracellular |
| B2IPM6 | 13.79 | 2 | 87 | 26.87 | Phosphocarrier protein HPr OS = *Streptococcus pneumoniae* (strain CGSP14) GN = SPCG_1120 PE = 4 SV = 1 - [B2IPM6_STRPS] | Intracellular |
| B2IRB7 | 27.22 | 2 | 158 | 26.84 | Uncharacterized protein OS = *Streptococcus pneumoniae* (strain CGSP14) GN = SPCG_1584 PE = 4 SV = 1 - [B2IRB7_STRPS] | N-terminally anchored (No CS) |

TABLE 6-continued

Proteins identified in MP from serotype 3. The accession numbers refer to SwissProt on the date of filing.

| Accession # | Coverage | # Peptides | #AAs | Score | Description | Localization |
|---|---|---|---|---|---|---|
| B2ILW4 | 23.46 | 5 | 324 | 26.69 | Enoyl-(Acyl-carrier-protein) reductase OS = Streptococcus pneumoniae (strain CGSP14) GN = fabK PE = 4 SV = 1 - [B2ILW4_STRPS] | Intracellular |
| B2IN41 | 16.32 | 7 | 429 | 26.52 | Histidine--tRNA ligase OS = Streptococcus pneumoniae (strain CGSP14) GN = hisS PE = 3 SV = 1 - [SYH_STRPS] | Intracellular |
| B2IQU2 | 16.07 | 3 | 305 | 26.2 | Glycine--tRNA ligase alpha subunit OS = Streptococcus pneumoniae (strain CGSP14) GN = glyQ PE = 3 SV = 1 - [SYGA_STRPS] | Intracellular |
| B2IPW1 | 23.91 | 4 | 322 | 26.19 | Acetoin dehydrogenase, E1 component, alpha subunit, putative OS = Streptococcus pneumoniae (strain CGSP14) GN = acoA PE = 4 SV = 1 - [B2IPW1_STRPS] | Intracellular |
| B2ISG1 | 25.79 | 5 | 190 | 26.04 | Uncharacterized protein OS = Streptococcus pneumoniae (strain CGSP14) GN = SPCG_1779 PE = 4 SV = 1 - [B2ISG1_STRPS] | Multi-transmembrane |
| B2IPZ7 | 19.35 | 4 | 279 | 25.42 | DegV family protein OS = Streptococcus pneumoniae (strain CGSP14) GN = SPCG_1169 PE = 4 SV = 1 - [B2IPZ7_STRPS] | Intracellular |
| B2ISK9 | 13.48 | 4 | 267 | 25.25 | PTS system, mannose-specific IIC component OS = Streptococcus pneumoniae (strain CGSP14) GN = manM PE = 4 SV = 1 - [B2ISK9_STRPS] | Multi-transmembrane (Lipid modified N-termini) |
| B2IS70 | 20.32 | 5 | 433 | 25.16 | UPF0210 protein SPCG_0246 OS = Streptococcus pneumoniae (strain CGSP14) GN = SPCG_0246 PE = 3 SV = 1 - [B2IS70_STRPS] | Intracellular |
| B2INL6 | 15.22 | 4 | 335 | 24.97 | ABC transporter, substrate-binding protein, putative OS = Streptococcus pneumoniae (strain CGSP14) GN = SPCG_2165 PE = 4 SV = 1 - [B2INL6_STRPS] | Lipid anchored |
| B2IPF2 | 46.6 | 4 | 191 | 24.92 | Thioredoxin family protein OS = Streptococcus pneumoniae (strain CGSP14) GN = SPCG_0974 PE = 4 SV = 1 - [B2IPF2_STRPS] | Lipid anchored |
| B2INJ2 | 24.59 | 7 | 427 | 24.82 | DltD protein OS = Streptococcus pneumoniae (strain CGSP14) GN = dltD PE = 4 SV = 1 - [B2INJ2_STRPS] | N-terminally anchored (No CS) |
| B2IPH6 | 13.65 | 3 | 359 | 24.36 | Peptide chain release factor 1 OS = Streptococcus pneumoniae (strain CGSP14) GN = prfA PE = 3 SV = 1 - [RF1_STRPS] | Intracellular |
| B2ILY0 | 20.43 | 4 | 514 | 24.35 | Peptide chain release factor 3 OS = Streptococcus pneumoniae (strain CGSP14) GN = prfC PE = 3 SV = 1 - [RF3_STRPS] | Intracellular |
| B2ILV5 | 20.88 | 4 | 182 | 24.04 | Alkyl hydroperoxide reductase AhpD OS = Streptococcus pneumoniae (strain CGSP14) GN = mip PE = 3 SV = 1 - [B2ILV5_STRPS] | Intracellular |
| B2IRX2 | 21.8 | 4 | 399 | 23.82 | Uncharacterized protein OS = Streptococcus pneumoniae (strain CGSP14) GN = SPCG_1689 PE = 4 SV = 1 - [B2IRX2_STRPS] | Multi-transmembrane |
| B2IM58 | 11.36 | 4 | 308 | 23.79 | Membrane protein insertase YidC OS = Streptococcus pneumoniae (strain CGSP14) GN = yidC PE = 3 SV = 1 - [B2IM58_STRPS] | Multi-transmembrane |
| B2IR27 | 23.03 | 4 | 330 | 23.79 | Phosphate acyltransferase OS = Streptococcus pneumoniae (strain CGSP14) GN = plsX PE = 3 SV = 1 - [PLSX_STRPS] | Intracellular |

TABLE 6-continued

Proteins identified in MP from serotype 3. The accession numbers refer to SwissProt on the date of filing.

| Accession # | Coverage | # Peptides | #AAs | Score | Description | Localization |
|---|---|---|---|---|---|---|
| B2IQL7 | 22.95 | 4 | 292 | 23.74 | Phosphate ABC transporter, phosphate-binding protein, putative OS = Streptococcus pneumoniae (strain CGSP14) GN = SPCG_1389 PE = 4 SV = 1 - [B2IQL7_STRPS] | Lipid anchored |
| B2IR86 | 41.62 | 7 | 197 | 23.54 | Probable GTP-binding protein EngB OS = Streptococcus pneumoniae (strain CGSP14) GN = engB PE = 3 SV = 1 - [ENGB_STRPS] | Intracellular |
| B2IP77 | 21 | 5 | 419 | 23.53 | Uncharacterized protein OS = Streptococcus pneumoniae (strain CGSP14) GN = SPCG_0896 PE = 4 SV = 1 - [B2IP77_STRPS] | Intracellular |
| B2ISL2 | 23.6 | 5 | 339 | 23.5 | Alcohol dehydrogenase OS = Streptococcus pneumoniae (strain CGSP14) GN = adhP PE = 3 SV = 1 - [B2ISL2_STRPS] | Intracellular |
| B2IPR3 | 21.05 | 5 | 247 | 23.35 | Uncharacterized protein OS = Streptococcus pneumoniae (strain CGSP14) GN = SPCG_1083 PE = 4 SV = 1 - [B2IPR3_STRPS] | N-terminally anchored (with CS) |
| B2IR97 | 25 | 6 | 252 | 23.12 | Methyltransferase, putative OS = Streptococcus pneumoniae (strain CGSP14) GN = SPCG_1564 PE = 4 SV = 1 - [B2IR97_STRPS] | Intracellular |
| B2IS98 | 24.4 | 4 | 209 | 22.81 | Probable nicotinate-nucleotide adenylyltransferase OS = Streptococcus pneumoniae (strain CGSP14) GN = nadD PE = 3 SV = 1 - [B2IS98_STRPS] | Intracellular |
| B2IQS3 | 22.11 | 4 | 303 | 22.58 | Thioredoxin reductase OS = Streptococcus pneumoniae (strain CGSP14) GN = trxB PE = 3 SV = 1 - [B2IQS3_STRPS] | Intracellular |
| B2IPW5 | 31.61 | 6 | 329 | 22.56 | Lipoate-protein ligase, putative OS = Streptococcus pneumoniae (strain CGSP14) GN = SPCG_1137 PE = 4 SV = 1 - [B2IPW5_STRPS] | Intracellular |
| B2IMB4 | 30.77 | 5 | 182 | 22.24 | Protein GrpE OS = Streptococcus pneumoniae (strain CGSP14) GN = grpE PE = 3 SV = 1 - [B2IMB4_STRPS] | Intracellular |
| B2ILY4 | 43.8 | 3 | 121 | 22.23 | Uncharacterized protein OS = Streptococcus pneumoniae (strain CGSP14) GN = asp23 PE = 4 SV = 1 - [B2ILY4_STRPS] | Intracellular |
| B2IPH3 | 18.37 | 7 | 479 | 22.18 | tRNA modification GTPase MnmE OS = Streptococcus pneumoniae (strain CGSP14) GN = thdF PE = 3 SV = 1 - [B2IPH3_STRPS] | Intracellular |
| B2INP7 | 17.59 | 6 | 540 | 22.16 | ABC transporter, ATP-binding protein OS = Streptococcus pneumoniae (strain CGSP14) GN = SPCG_2196 PE = 4 SV = 1 - [B2INP7_STRPS] | Intracellular |
| B2IP74 | 14.66 | 5 | 491 | 21.9 | Lysine decarboxylase OS = Streptococcus pneumoniae (strain CGSP14) GN = cad PE = 4 SV = 1 - [B2IP74_STRPS] | Intracellular |
| B2ISG4 | 52.24 | 2 | 67 | 21.88 | Uncharacterized protein OS = Streptococcus pneumoniae (strain CGSP14) GN = SPCG_1782 PE = 3 SV = 1 - [B2ISG4_STRPS] | Intracellular |
| B2ISY1 | 17.74 | 7 | 541 | 21.79 | Dextran glucosidase DexS, putative OS = Streptococcus pneumoniae (strain CGSP14) GN = dexS PE = 4 SV = 1 - [B2ISY1_STRPS] | Intracellular |
| B2IMA5 | 15.4 | 5 | 448 | 21.67 | Glutamine synthetase, type I OS = Streptococcus pneumoniae (strain CGSP14) GN = glnA PE = 3 SV = 1 - [B2IMA5_STRPS] | Intracellular |

TABLE 6-continued

Proteins identified in MP from serotype 3. The accession numbers refer to SwissProt on the date of filing.

| Accession # | Coverage | # Peptides | #AAs | Score | Description | Localization |
|---|---|---|---|---|---|---|
| B2IN77 | 24.72 | 6 | 352 | 21.61 | UDP-N-acetylglucosamine--N-acetylmuramyl-(pentapeptide) pyrophosphoryl-undecaprenol N-acetylglucosamine transferase OS = Streptococcus pneumoniae (strain CGSP14) GN = murG PE = 3 SV = 1 - [MURG_STRPS] | Intracellular |
| B2IQ12 | 25.39 | 5 | 319 | 21.48 | Ribose-phosphate pyrophosphokinase OS = Streptococcus pneumoniae (strain CGSP14) GN = prs PE = 3 SV = 1 - [B2IQ12_STRPS] | Intracellular |
| B2ISL4 | 16.3 | 4 | 270 | 21.32 | Cof family protein OS = Streptococcus pneumoniae (strain CGSP14) GN = SPCG_0299 PE = 4 SV = 1 - [B2ISL4_STRPS] | Intracellular |
| B2IQ78 | 13.38 | 5 | 523 | 21.2 | Signal recognition particle protein OS = Streptococcus pneumoniae (strain CGSP14) GN = ffh PE = 3 SV = 1 - [B2IQ78_STRPS] | Intracellular |
| B2IS71 | 21.69 | 5 | 249 | 21.06 | Phosphoglycerate mutase family protein OS = Streptococcus pneumoniae (strain CGSP14) GN = gpmB PE = 4 SV = 1 - [B2IS71_STRPS] | Intracellular |
| B2IM30 | 15.38 | 5 | 338 | 20.64 | Transcriptional regulator, putative OS = Streptococcus pneumoniae (strain CGSP14) GN = lytR PE = 4 SV = 1 - [B2IM30_STRPS] | Secretory (released) (with CS) |
| B2IQN9 | 10.91 | 4 | 486 | 20.01 | Nicotinate phosphoribosyltransferase OS = Streptococcus pneumoniae (strain CGSP14) GN = SPCG_1408 PE = 3 SV = 1 - [B2IQN9_STRPS] | Intracellular |

Example 2: Microparticles (MPs) Confer Serotype-Independent Protective Immunity For each immunization experiment male C57BL/6 wild-type mice ca 5 weeks old were used. Before immunization, mice were anesthetized by inhalation of isofluorane (Abbott) and then intranasally administered with 50 µl/mouse of microparticles (MP) combined with the adjuvant aluminium hydroxide (Sigma Aldrich, 10 mg/ml in PBS) or the adjuvant alone for the control groups. Immunization was repeated again after two weeks from the first immunization following the same conditions described above. After 4 weeks of immunization, mice were infected by intranasal administration of 50 µl/mouse of 5×10$^6$ CFU, for S. pneumoniae type 1 infection experiments (FIG. 7), or 10$^6$ CFU, for S. pneumoniae type 3 infection experiments (FIG. 11).

All mice were anesthetized by inhalation of isofluorane prior to challenge with bacteria. After the infection, clinical symptoms of the mice were monitored multiple times per day (in accordance with the ethical permit). Blood samples (5 µl/mouse) were taken every day of infection and level of bacteremia was assessed by plating serial dilutions of blood samples onto blood-agar plates. Mice that reached humane end-points were anesthetized by inhalation of isofluorane and intranasal administered with 100 µl/mouse of the fluorescent marker Bacterisense 645 (Perkin Elmer) 30 minutes before the sacrifice. Prior to sacrifice, mice were anesthetized again (isofluorane inhalation). After sacrifice, mice were placed in the IVIS Spectrum Imaging System to detect the fluorescent signal of the bacterial infection. After the IVIS imaging, lungs and spleens were collected for further analysis. Bacterial amount in the lungs was assessed by CFU count of bacteria after plating serial dilutions of lung homogenates onto blood-agar plates.

Figure 7B:
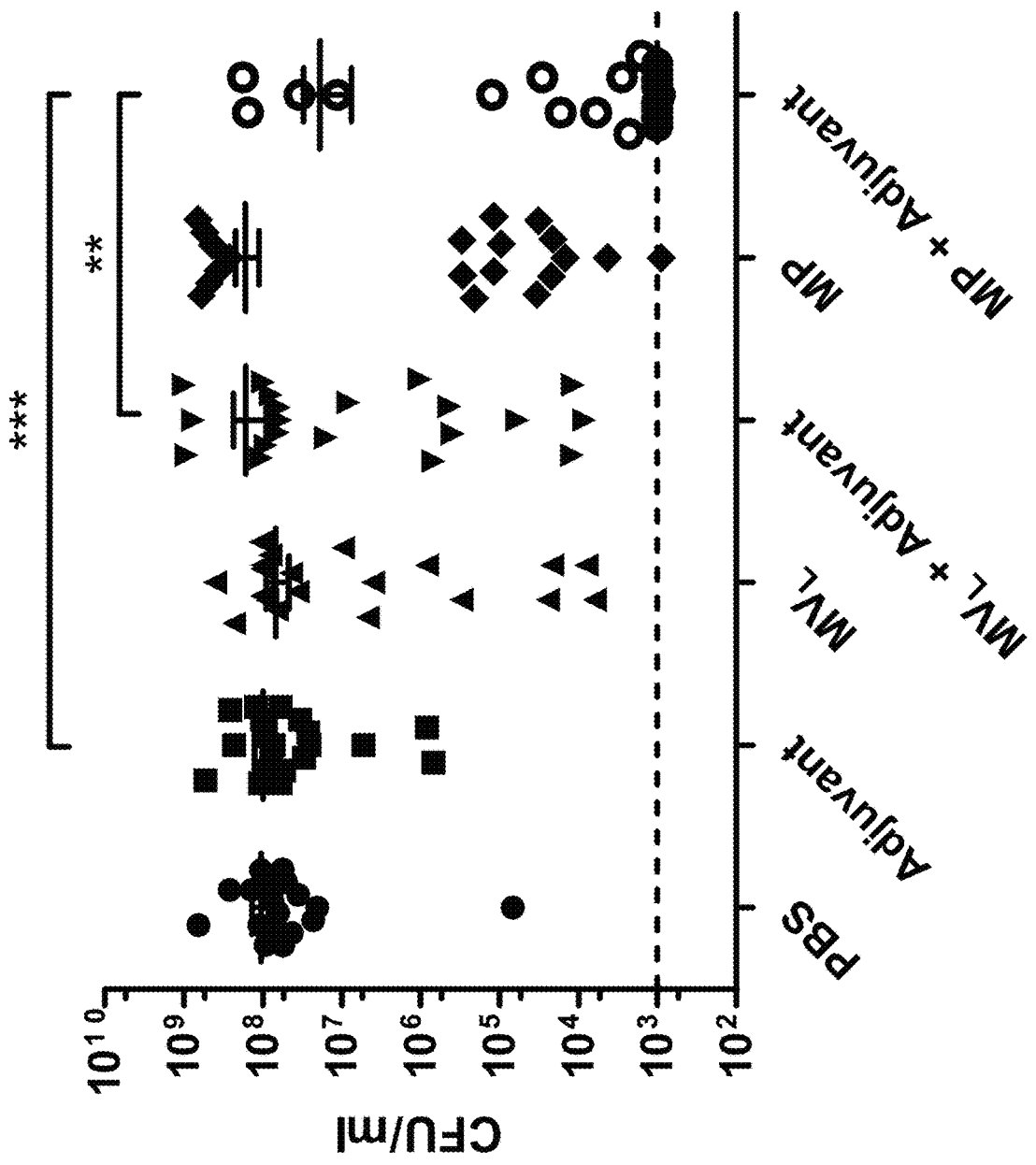

Intranasal immunization with microparticles (MP) from a serotype 4 S. pneumoniae increased survival after a challenge with serotype 1 S. pneumoniae (FIG. 7A). The increase in survival was significant also in comparison to immunization with MV$_L$. The immunization greatly reduced the bacterial load in the lungs of the mice surviving the challenge with serotype 1 S. pneumoniae (FIG. 7B). Furthermore, mice immunized with serotype 3 MP and then challenged with serotype 3 bacteria showed 100% protection in the pneumonia model, higher than immunization with the currently available vaccine PCV13, which only conferred a protection of 75% in the model. Moreover, protection against pneumococcal infection was absent in mice lacking B cells, suggesting the involvement of an adaptive immune response with anti-pneumococcal antibodies (FIG. 11).

Figure 9B:
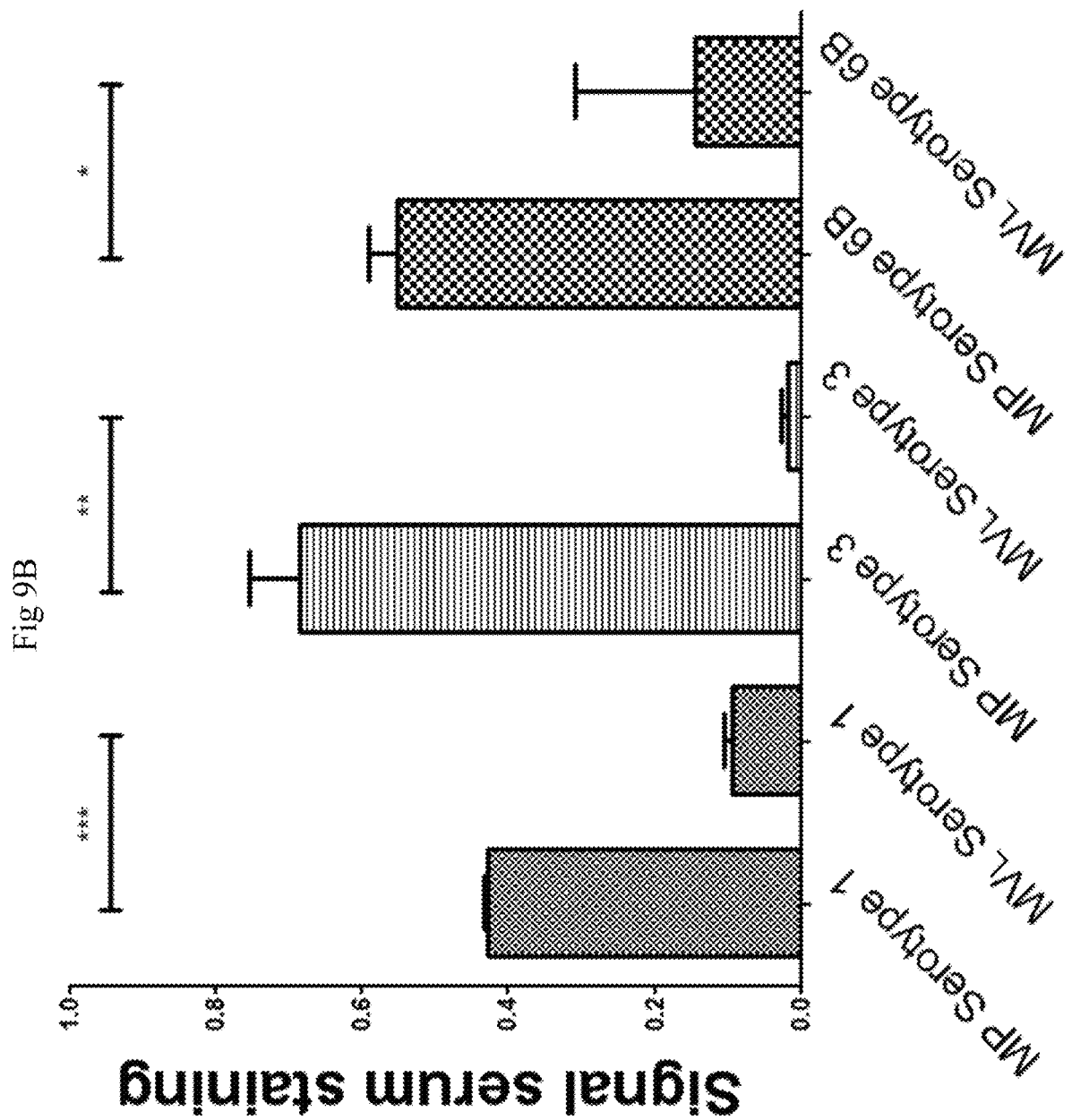

Example 3: Serotype-Independent Binding and Opsonophagocitic Activity of Antibodies Raised Against Pneumococcal Membrane Particles Antibodies raised against the inventive MP from serotype 4 as antigen were reactive against Streptococcus pneumoniae of other serotypes, such as 1, 6B and 3 (FIG. 9). In other words, the MP were able to elicit production of serotype-independent antibodies, much more so than MV$_L$ (FIG. 9B).

The production of anti-MP antibodies in mice was more efficient (in particular at time point 2 weeks) when the antigen was administered together with an adjuvant. However, satisfactory results were obtainable even without an adjuvant (FIG. 8). Moreover, antibodies in sera were able to bind both the encapsulated T4 (TIGR4) and the unencapsulated isogenic mutant T4R to the same extent, indicating that the antibody response was capsule-independent.

Importantly, the anti-MP antibodies showed opsonophagocitic activity, increasing adhesion of bacteria and killing of internalized bacteria by RAW murine macrophages (FIG. 10).

Materials and Methods

Bacterial strains and growth conditions. In this study six strains of Streptococcus pneumoniae were used: TIGR4 or T4 (serotype 4) (22), its isogenic mutants lacking the cytotoxin pneumolysin (T4Δply) (23), the autolysin LytA (T4ΔlytA) (3), or the capsule (T4R) (24), ATCC 6301 (serotype 1) and 1-33 (serotype 3). Bacteria were grown in C+Y medium pH 7.9-8.0 (for serotype 4) or THY medium (for serotype 1 and 3) at 37° C. A spectrophotometer (Genesys 20, Thermo Spectronic) was used to follow the growth by monitoring the optical density (OD) at 600 nm.

Isolation and purification of membrane vesicles ($MV_L$) and microparticles (MP). For isolation of $MV_L$ from a liquid culture, pneumococcal strains (TIGR4, T4Δply or T4ΔlytA) were grown at 37° C. in C+Y medium, pH 7.9-8.0 until $OD_{600\ nm}$=0.9. The culture was then centrifuged (17,000×g for 30 minutes at 4° C.) to remove bacterial cells from the supernatant. The cell-free supernatant was filtered through a 0.22 μm filter (Sarstedt) and centrifuged (120,000×g for 2 hours at 4° C.) to sediment the vesicles. Pellets were washed twice in phosphate-buffered saline (PBS) and resuspended in PBS.

For isolation of microparticles (MP) from bacteria grown on plates, the pneumococcal strains were streaked on blood agar plates and incubated overnight at 37° C. with 5% $CO_2$. Bacteria were harvested from plates, resuspended in PBS and MP were pelleted following the same procedure as mentioned above.

Crude $MV_L$/MP preparations were further purified by density gradient centrifugation using Optiprep™ Density Gradient Medium (Sigma). Pelleted particle fractions were adjusted to 50% (w/v) Optiprep™ in a total volume of 2 ml and overlayed with one fraction of 30% (w/v) Optiprep™ (9 ml) followed by a fraction of 5% (w/v) Optiprep™ (3 ml). Gradients were centrifuged at 250,000×g for 3 hours at 4° C. and the first 4 ml on top, containing the particles, were collected. After 3 washes with PBS (250,000×g for 2 hours at 4C), pellets were recovered in PBS and stored at −80° C.

Electron microscopy. To visualize $MV_L$ and MP on bacteria, S. pneumoniae T4R was grown in C+Y medium until $OD_{600}$=0.4 at 37° C. Bacteria were harvested by centrifugation for 10 min at 4,000×g, 4° C. and pellets were suspended in 100 μl PBS. Glow discharged carbon coated grids (Oxford Instruments, UK) were incubated for 1 min with a drop of bacterial solution or purified $MV_L$/MP preparation and negatively stained with 2% uranyl acetate in water (7 times for 10 sec). Specimens were examined on a FEI CM120 microscope operated at 80 kV. Images were collected with a side mounted camera MegaView III (Olympus Soft Imaging solutions).

Atomic force microscopy. 5 μl of MP samples isolated from S. pneumoniae were placed onto freshly cleaved mica (Goodfellow Cambridge Ltd., Cambridge, United Kingdom). The specimens on the mica were blot dried and placed into a desiccator for at least 2 h. Imaging was performed on a Nanoscope IIIa (Digital Instruments, Santa Barbara) Atomic Force Microscope using Tapping Mode with standard silicon cantilevers oscillating at resonant frequency (270 to 305 kHz). Images were collected at a scan rate of 0.8-1.5 Hz, depending on sample number and the size of the scan. The final images were fitted in both axes and presented in a surface plot of the height mode.

SDS-PAGE and western blotting. The total amount of proteins in purified $MV_L$ or MP, lysates of A549 cells or dendritic cells stimulated with $MV_L$ or MP were quantified with Pierce™ BCA Protein Assay Kit (Life Technologies). Samples containing equal amounts of total protein were resolved by SDS-PAGE using 4-12% Bis-Tris gels (Life Technologies) and transferred to PVDF membranes. Membranes were then blocked with 5% skim milk in PBS containing 0.1% Tween-20 and incubated with antibodies as indicated. For detection of pneumolysin a mouse monoclonal antibody (Abcam, final dilution 1:500) was used. Polyclonal GAPDH (1:2,000) and LytA (1:2,000) (3) antisera raised in rabbits were used. Rabbit polyclonal antibodies against PspC (1:1,000), RrgB (1:1,000), PsaA (1:25,000), PhtD (1:25,000) and mouse polyclonal antibodies against SrtA (1:500) were kindly provided by Novartis Vaccines and Diagnostics. As loading control for A549 cells and dendritic cell lysates, a mouse monoclonal R-actin antibody (Santa Cruz) was used as primary antibody. Anti-mouse IgG or anti-rabbit IgG conjugated to horseradish peroxidase (GE Healhcare) were used as secondary antibodies (final dilution 1:10,000). Blots were developed with Amersham™ ECL Plus Western blotting detection system (GE Healthcare Life Sciences), using a ChemiDoc™ XRS+ (Bio-Rad Laboratories).

Tandem mass spectrometry. Proteins in $MV_L$ or MP samples were reduced, alkylated and in-solution digested by trypsin according to a standard operating procedure. Thereafter the samples were purified by Pierce C18 Spin Columns (Thermo Scientific), dried and resolved in 0.1% formic acid. The resulting peptides were separated in reversed-phase on a C18-column and electrosprayed on-line to a Q Exactive Plus mass spectrometer (Thermo Finnigan). Tandem mass spectrometry was performed applying HCD.

Database searches were made using the Sequest algorithm towards a FASTA database including proteins from Streptococcus pneumoniae TIGR4. The search criteria for protein identification were set to at least two matching peptides of 95% confidence level per protein. Only proteins with a Sequest score above 20 were considered for analysis, to avoid the possibility of false positives.

Subcellular localizations of proteins were predicted using the algorithm of website Locate P located at the following URL: www.cmbi.ru.nl/locatep-db/cgi-bin/locatepdb.py (11).

Hemolysis assay. Purified $MV_L$ or MP were incubated in 96-well plates with blood from buffy coats (diluted 1:50 in PBS containing 1 mM dithiothreitol (DTT)) for 1 hour at 37° C. After 50 minutes 1% Triton X-100 in PBS was added to the positive control wells in order to lyse all the erythrocytes. Plates were then spun at 400×g for 15 minutes at 4° C.; supernatant was transferred to an optical plate and the optical density was measured at 540 nm.

A549 cell toxicity assay. A459 lung epithelial cells were grown and maintained at 37° C., with 5% $CO_2$ in RPMI medium (Gibco) supplemented with 10% (v/v) Fetal bovine serum (FBS) (HyClone). To assess $MV_L$ or MP associated cytotoxic effects, 0.6×10⁶ A549 cells were seeded in 6-well plates and incubated overnight at 37° C. Cells were then washed with PBS and incubated for 24 hours with medium containing $MV_L$ or MP at indicated concentrations. Washed cells were labelled with Fixable Viability Dye eFluor® 780 (1:50,000, eBioscience) for 30 minutes at 4° C. in the dark, in presence or absence of 0.02% NP40 (Sigma) as positive control, and fixed with 4% paraformaldehyde (PFA) for 30 minutes at room temperature. Next, cells were gently scraped into PBS containing 1% FBS and analyzed in a Gallios™ Flow Cytometer (Beckman Coulter).

A549 cell uptake assay. To assess $MV_L$ and MP uptake by A549 cells via immunoblotting, $0.6\times10^6$ A549 cells were seeded in 6-well plates and incubated overnight at 37° C. Cells were then washed with PBS and incubated for 24 hours with medium containing the particles at indicated concentrations. After washing, cells were lysed in RIPA buffer containing 1× protease inhibitor cocktail (Roche). Cell lysates were analyzed by SDS-PAGE and western blotting.

Immunofluorescence microscopy. A549 cells ($6.25\times10^4$) were seeded in 24-well plates with coverslips on the bottom of the wells, and incubated at 37° C. overnight. Cells were then washed, fixed with 4% PFA for 30 minutes and permeabilized with 1% Triton X-100 in PBS for 5 minutes. $MV_L$ or MP were detected with mouse monoclonal anti-Ply (1:200) and polyclonal rabbit antibodies to LytA (1:200). Respective antigens were visualized with Alexa Fluor® 488-conjugated goat-anti mouse IgG antibody (Life Technologies) and Alexa Fluor® 350-conjugated goat-anti rabbit IgG (Life Technologies) (1:1,000).

Actin cytoskeleton was stained with Alexa Fluor® 594 Phalloidin (Life Technologies, 1:40 dilution) for 1 hour and coverslips were mounted with Vectashield (Vector Laboratories, Inc.) on microscope slides. Images were acquired with a DeltaVision microscope equipped with a 60x-objective. Quick projection images of approximately 20 z-stacks were taken. Orthogonal views were used to visualize the cell monolayer from the x, y, and z axes.

After growth, pneumococci (serotypes 1, 3 and 6B) have been stained using the sera from the immunized mice as primary antibody (dilution 1:100 in PBS 1% BSA) and Alexa Fluor 488 goat anti mouse (dilution 1:500 in PBS 1% BSA) as secondary antibody.

Imaging has been performed with high-resolution Delta Vision Elite System using 100x objective (1000×total magnification). FITC Laser intensity 50%, exposure time 0,025 ms (FIGS. 13-15).

Quantification of the Signal Detected on the Bacteria after Immunofluorescence Staining Using the functions Image>Adjust>Threshold and Analyze>Measure of ImageJ, the area covered by the bacteria and the area covered by the signal detected on the bacteria after staining with sera were selected, defined and measured. The final signal ratio was calculated by dividing the area of the signal (detected using the sera) by the total area of the bacteria.

Isolation and differentiation of human monocyte-derived dendritic cells. Dendritic cells were isolated using RosetteSep™ Human Monocyte Enrichment Cocktail (Stemcell Technologies) according to the manufacturer's instructions. In brief, blood from buffy coats from healthy donors was incubated for 20 minutes with RosetteSep™ Human Monocyte Enrichment Cocktail (Stemcell Technologies), layered on top of Ficoll-Paque™ Plus (GE Healthcare) and centrifuged at 1200×g for 20 minutes without acceleration or brake. The monocyte containing layer was recovered, cells washed 7 times with PBS and passed through a 100 µm cell strainer. Monocytes were then differentiated for 6 days in RPMI containing 10% FBS supplemented with 37.5 ng/ml of Granulocyte macrophage colony-stimulating factor (GM-CSF) (Peprotech) and 37.5 ng/ml of Interleukin 4 (IL-4) (Peprotech), changing the medium after 4 days. For experiments, cells were resuspended in RPMI containing 10% FBS.

Toxicity and apoptosis assay of dendritic cells. $6\times10^5$ cells were seeded in 96-well plates and incubated with RPMI containing 10% FBS and $MV_L$ or MP at indicated concentrations, or with T4R in a multiplicity of infection (MOI) of 20, as positive control, for 24 hours. Gentamicin (100 µg/ml, Sigma) was added after 1 hour of incubation to stop bacteria from growing in samples stimulated with T4R. Before staining, cells were washed once in PBS and once in Annexin V Binding Buffer (BD Pharmingen). Staining was performed with Fixable Viability Dye eFluor® 780 (1:50,000, eBioscience) and FITC Annexin V (1:20, BD Pharmingen) for 30 minutes at 4° C., followed by two washes with Annexin buffer. Labelled cells were fixed in 4% PFA for 30 minutes, resuspended in PBS containing 1% FBS and analyzed in a Gallios™ Flow Cytometer (Beckman Coulter).

Activation assay of dendritic cells. $6\times10^5$ cells were seeded in 96-well plates and incubated in RPMI containing 10% FBS with $MV_L$ or MP at indicated concentrations, or with 1 µg/ml lipopolysaccharide (LPS) (Sigma) as positive control, for 24 hours. Cells were stained with Phycoerythrin (PE) Mouse Anti-Human CD86 (BD Pharmingen) and PE-Cy™5 Mouse Anti-Human HLA-DR (BD Pharmingen) for 20 minutes at 4° C., washed twice with PBS and resuspended in PBS 1% FBS. Labelled cells were analyzed in a Gallios™ Flow Cytometer (Beckman Coulter).

Uptake assay with dendritic cells. $10^6$ cells were seeded in 96-well plates and incubated with RPMI containing 10% FBS, in presence or absence of the inhibitors cytochalasin D (0.5 µg/ml, Sigma) and wortmannin (0.5 µg/ml, Sigma) (C/W), or methyl-R-cyclodextrin (MSCD) (10 µM, Sigma), for 30 minutes. Cells were then incubated with particles at indicated concentration for 1 hour and lysed in RIPA buffer containing 1× protease inhibitor cocktail (Roche). Cell lysates were analyzed by SDS-PAGE and western blotting.

Quantification of cytokines. Different cytokines were assessed (IL-6, IL-8, IL-10 and TNF) in cell-free supernatants of $10^5$ dendritic cells by Enzyme-Linked Immunosorbent Assay (ELISA), using commercially available BD OptEIA™ kits from BD Biosciences. Cells were incubated with particles at indicated concentrations, or with T4R or LPS (as previously described), for 24 hours.

Opsonophagocytosis assay with RAW cells. RAW 264.7 murine macrophages were grown and maintained at 37° C., with 5% $CO_2$ in RPMI medium (Gibco) supplemented with 10% (v/v) Fetal bovine serum (FBS) (HyClone).To assess the opsonophagocytosis activity of antibodies in immunized mice sera $2\times10^5$ RAW 264.7 cells were seeded in 24-well plates and incubated overnight at 37° C. Serotype 1 bacteria were incubated for 30 minutes at 37° C. with 5% $CO_2$ with 20% serum from mice immunized with MP+adjuvant, or with adjuvant alone as negative control. RAW cells were then washed with PBS and incubated for 1.5 hours with $2.5\times10^7$/well of pre-treated bacteria. Cells were washed three times with PBS to remove unattached bacteria. To measure total uptake of bacteria, cells were incubated with a 50/50 solution of 2% saponin (Sigma) and trypsin-EDTA (Gibco) for 15 minutes at 37° C., to lyse eukaryotic cells, and total bacteria were plated for enumeration. To evaluate phagocytosis 300 µg/ml of Gentamicin (Sigma) and 0.12 mg/ml of Penicillin G (Sigma) were added to separate wells and incubated 15 minutes at 37° C., to kill extracellular bacteria. Cells were then washed three times with PBS and incubated with a 50/50 solution of 2% saponin and trypsin-EDTA for 15 minutes at 37° C. to lyse eukaryotic cells. To evaluate killing of bacteria inside macrophages separate wells were treated with antibiotics (as for phagocytosis), washed three times with PBS and then incubated for 1 hour at 37° C. with medium. Cells were then washed three times with PBS and incubated with a 50/50 solution of 2% saponin and trypsin-EDTA for 15 minutes at 37° C. to lyse eukaryotic cells.

Mouse IgG ELISA assay. To detect MV- and MP-specific mouse IgG in sera of immunized mice optical plates (Sarstedt) were coated with 1 µg/ml of MP in 0.1 M Sodium Carbonate buffer pH 9.5, overnight at 4° C. Wells were then washed three times with PBS containing 0.05% Tween-20 and incubated with PBS with 10% FBS, for 1 hours at room temperature. After three washes wells were incubated with mice sera diluted 1:500 in PBS with 10% FBS, for 2 hours at room temperature. Wells were then washed three times and incubated with anti-mouse IgG-HRP (GE Healthcare) diluted 1:500 in PBS 10% FBS, for 2 hours at room temperature. After three washes wells were then incubated with TMB substrate (BD Bioscience) for 10 minutes and the reaction was stopped with 1 M $H_3PO_4$. Absorbance at 450 nm was then measured with a plate reader.

To detect pneumo-specific mouse IgG in sera of immunized mice, bacteria were grown on blood agar plates overnight at 37° C., resuspended in PBS and heat-inactivated for 2 hours at 60° C. After diluting the bacteria to $OD_{600}$ 0.6, optical plates (Sarstedt) were coated with 100 µl of bacteria in 0.1 M Sodium Carbonate buffer pH 9.5, overnight at 4° C. Wells were then washed three times with PBS and incubated with PBS with 2.5% skim milk, for 2 hours at room temperature. After three washes wells were incubated with mice sera diluted 1:500 in PBS, for 1 hour at room temperature. Wells were then washed three times and incubated with anti-mouse IgG-HRP (GE Healthcare) diluted 1:500 in PBS, for 1 hour at room temperature. After three washes well were then incubated with TMB substrate (BD Bioscience) for 10 minutes and the reaction was stopped with 1 M $H_3PO_4$. Absorbance at 450 nm was then measured with a plate reader.

Statistical analysis. For multiple comparisons the non-parametric ANOVA test was used to assess the presence of the differences between the groups, then the Dunn's test was used to make pairwise comparisons; for two groups comparison the non-parametric two tailed Wilcoxon's rank sum test (also known as Mann-Whitney test) was used. Statistically significant data was defined as *P<0.05, P<0.01, *P<0.001, ****=P<0.0001.

REFERENCES

1. Olaya-Abril A, Prados-Rosales R, McConnell M J, Martin-Pena R, Gonzalez-Reyes J A, Jimenez-Munguia I, et al. Characterization of protective extracellular membrane-derived vesicles produced by Streptococcus pneumoniae. Journal of proteomics. 2014; 106:46-60.
2. Mitchell T J, Dalziel C E. The biology of pneumolysin. Subcell Biochem. 2014; 80:145-60.
3. Mellroth P, Daniels R, Eberhardt A, Ronnlund D, Blom H, Widengren J, et al. LytA, major autolysin of Streptococcus pneumoniae, requires access to nascent peptidoglycan. J Biol Chem. 2012; 287(14):11018-29.
4. Bergmann S, Hammerschmidt S. Versatility of pneumococcal surface proteins. Microbiology. 2006; 152(Pt 2):295-303.
5. Iannelli F, Oggioni M R, Pozzi G. Allelic variation in the highly polymorphic locus pspC of Streptococcus pneumoniae. Gene. 2002; 284(1-2):63-71.
6. Barocchi M A, Ries J, Zogaj X, Hemsley C, Albiger B, Kanth A, et al. A pneumococcal pilus influences virulence and host inflammatory responses. Proc Natl Acad Sci USA. 2006; 103(8):2857-62.
7. Nelson A L, Ries J, Bagnoli F, Dahlberg S, Falker S, Rounioja S, et al. RrgA is a pilus-associated adhesin in Streptococcus pneumoniae. Mol Microbiol. 2007; 66(2): 329-40.
8. Iovino F, Hammarlof D L, Garriss G, Brovall S, Nannapaneni P, Henriques-Normark B. Pneumococcal meningitis is promoted by single cocci expressing pilus adhesin RrgA. J Clin Invest. 2016; 126(8):2821-6.
9. Bersch B, Bougault C, Roux L, Favier A, Vernet T, Durmort C. New insights into histidine triad proteins: solution structure of a Streptococcus pneumoniae PhtD domain and zinc transfer to AdcAII. PloS one. 2013; 8(11): e81168.
10. Kilian M, Mestecky J, Schrohenloher R E. Pathogenic species of the genus Haemophilus and Streptococcus pneumoniae produce immunoglobulin A1 protease. Infection and immunity. 1979; 26(1):143-9.
11. Zhou M, Boekhorst J, Francke C, Siezen R J. LocateP: genome-scale subcellular-location predictor for bacterial proteins. BMC Bioinformatics. 2008; 9:173.
12. Gosink K K, Mann E R, Guglielmo C, Tuomanen EI, Masure H R. Role of novel choline binding proteins in virulence of Streptococcus pneumoniae. Infection and immunity. 2000; 68(10):5690-5.
13. Singh A K, Pluvinage B, Higgins M A, Dalia A B, Woodiga S A, Flynn M, et al. Unravelling the multiple functions of the architecturally intricate Streptococcus pneumoniae beta-galactosidase, BgaA. PLoS Pathog. 2014; 10(9):e1004364.
14. Terrasse R, Amoroso A, Vernet T, Di Guilmi A M. Streptococcus pneumoniae GAPDH Is Released by Cell Lysis and Interacts with Peptidoglycan. PloS one. 2015; 10(4):e0125377.
15. Johnston J W, Myers L E, Ochs M M, Benjamin W H, Jr., Briles D E, Hollingshead S K. Lipoprotein PsaA in virulence of Streptococcus pneumoniae: surface accessibility and role in protection from superoxide. Infection and immunity. 2004; 72(10):5858-67.
16. Paterson G K, Mitchell T J. The role of Streptococcus pneumoniae sortase A in colonisation and pathogenesis. Microbes Infect. 2006; 8(1):145-53.
17. Brooks-Walter A, Briles D E, Hollingshead S K. The pspC gene of Streptococcus pneumoniae encodes a polymorphic protein, PspC, which elicits cross-reactive antibodies to PspA and provides immunity to pneumococcal bacteremia. Infection and immunity. 1999; 67(12):6533-42.
18. Thay B, Wai S N, Oscarsson J. Staphylococcus aureus alpha-toxin-dependent induction of host cell death by membrane-derived vesicles. PloS one. 2013; 8(1):e54661.
19. Gurung M, Moon D C, Choi C W, Lee J H, Bae Y C, Kim J, et al. Staphylococcus aureus produces membrane-derived vesicles that induce host cell death. PloS one. 2011; 6(11):e27958.
20. Ellis T N, Leiman S A, Kuehn M J. Naturally produced outer membrane vesicles from Pseudomonas aeruginosa elicit a potent innate immune response via combined sensing of both lipopolysaccharide and protein components. Infection and immunity. 2010; 78(9):3822-31.

21. Bielig H, Rompikuntal P K, Dongre M, Zurek B, Lindmark B, Ramstedt M, et al. NOD-like receptor activation by outer membrane vesicles from *Vibrio cholerae* non-01 non-0139 strains is modulated by the quorum-sensing regulator HapR. Infection and immunity. 2011; 79(4):1418-27.

22. Tettelin H, Nelson K E, Paulsen I T, Eisen J A, Read T D, Peterson S, et al. Complete genome sequence of a virulent isolate of *Streptococcus pneumoniae*. Science. 2001; 293(5529):498-506.

23. Littmann M, Albiger B, Frentzen A, Normark S, Henriques-Normark B, Plant L. *Streptococcus pneumoniae* evades human dendritic cell surveillance by pneumolysin expression. EMBO Mol Med. 2009; 1(4):211-22.

24. Fernebro J, Andersson I, Sublett J, Morfeldt E, Novak R, Tuomanen E, et al. Capsular expression in *Streptococcus pneumoniae* negatively affects spontaneous and antibiotic-induced lysis and contributes to antibiotic tolerance. The Journal of infectious diseases. 2004; 189(2):328-38.

The invention claimed is:

1. A method for inducing protective immunity against *Streptococcus pneumoniae* in a subject, comprising administering to the subject a composition comprising a *Streptococcus pneumoniae* membrane vesicle microparticle (MP), wherein said MP comprises:
   i. the protein Ply at the level of ≥0.070 µg/µg total protein in the MP;
   ii. the protein LytA at the level of ≥0.070 µg/µg total protein in the MP;
   iii. the protein PspC at the level of ≥0.130 µg/µg total protein in the MP;
   or
   iv. the protein RrgB at the level of ≥0.020 µg/µg total protein in the MP.

2. The method according to claim 1, wherein the immunity is protective against a condition selected from pneumococcal sinusitis, pneumococcal otitis, pneumococcal pneumonia, and invasive pneumococcal disease including but not limited to pneumococcal sepsis and pneumococcal meningitis.

3. The method according to claim 1, wherein the composition is a liquid and comprises MPs in an amount of at least 1 µg/ml.

4. The method according to claim 1, wherein said MP comprises:
   i. the protein Ply at the level of ≥0.070 µg/µg total protein in the MP;
   ii. the protein LytA at the level of ≥0.070 µg/µg total protein in the MP;
   iii. the protein PspC at the level of ≥0.130 µg/µg total protein in the MP; and
   iv. the protein RrgB at the level of ≥0.020 µg/µg total protein in the MP.

5. The method according to claim 1, wherein the MP is 5-300 nm in diameter.

6. The method according to claim 1, wherein the MP is 10-125 nm in diameter.

7. The method according to claim 1, wherein the composition elicits antibodies against *Streptococcus pneumoniae* serotype 3 when administered to a mammalian host.

8. The method according to claim 1, wherein the composition elicits serotype independent antibodies against *Streptococcus pneumoniae* when administered to a mammalian host.

9. The method according to claim 1, wherein the composition is administered intranasally.

10. The method according to claim 1, wherein the composition further comprises an adjuvant.

11. The method according to claim 10, wherein the adjuvant comprises aluminium hydroxide.

12. The method according to claim 2, wherein the immunity is protective against invasive pneumococcal disease.

13. The method according to claim 1, wherein the MP comprises a capsular polysaccharide of a capsular serotype of *Streptococcus pneumoniae* at a level of ≥0.001 µg/µg total protein in the MP.

14. The method according to claim 1, wherein said MP comprises the protein Ply at the level of ≥0.070 µg/µg total protein in the MP.

15. The method according to claim 1, wherein said MP comprises the protein LytA at the level of ≥0.070 µg/µg total protein in the MP.

16. The method according to claim 1, wherein said MP comprises the protein PspC at the level of ≥0.130 µg/µg total protein in the MP.

17. The method according to claim 1, wherein said MP comprises the protein RrgB at the level of ≥0.020 µg/µg total protein in the MP.

18. The method according to claim 1, wherein said MP comprises the protein Ply at the level of ≥0.35 µg/µg total protein in the MP.

19. The method according to claim 1, wherein said MP comprises the protein LytA at the level of ≥0.20 µg/µg total protein in the MP.

20. The method according to claim 1, wherein said MP comprises the protein PspC at the level of ≥0.3 µg/µg total protein in the MP.

21. The method according to claim 1, wherein said MP comprises the protein RrgB at the level of ≥0.028 µg/µg total protein in the MP.

* * * * *

SEQUENCE LISTING

<160> NUMBER OF SEQ ID NOS: 18

<210> SEQ ID NO 1
<211> LENGTH: 471
<212> TYPE: PRT
<213> ORGANISM: Streptococcus pneumoniae

<400> SEQUENCE: 1

```
Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
    210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Gly Gly Asp Pro Ser Ser Gly Ala Arg Val Val Thr
    290                 295                 300
```

```
Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
            340                 345                 350

Thr Lys Val Thr Ala Tyr Arg Asn Gly Asp Leu Leu Leu Asp His Ser
        355                 360                 365

Gly Ala Tyr Val Ala Gln Tyr Tyr Ile Thr Trp Asn Glu Leu Ser Tyr
    370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
            420                 425                 430

Trp Glu Trp Trp Arg Thr Val Tyr Glu Lys Thr Asp Leu Pro Leu Val
        435                 440                 445

Arg Lys Arg Thr Ile Ser Ile Trp Gly Thr Thr Leu Tyr Pro Gln Val
    450                 455                 460

Glu Asp Lys Val Glu Asn Asp
465                 470

<210> SEQ ID NO 2
<211> LENGTH: 318
<212> TYPE: PRT
<213> ORGANISM: Streptococcus pneumoniae

<400> SEQUENCE: 2

Met Glu Ile Asn Val Ser Lys Leu Arg Thr Asp Leu Pro Gln Val Gly
1               5                   10                  15

Val Gln Pro Tyr Arg Gln Val His Ala His Ser Thr Gly Asn Pro His
                20                  25                  30

Ser Thr Val Gln Asn Glu Ala Asp Tyr His Trp Arg Lys Asp Pro Glu
            35                  40                  45

Leu Gly Phe Phe Ser His Ile Val Gly Asn Gly Cys Ile Met Gln Val
        50                  55                  60

Gly Pro Val Asp Asn Gly Ala Trp Asp Val Gly Gly Trp Asn Ala
65                  70                  75                  80

Glu Thr Tyr Ala Ala Val Glu Leu Ile Glu Ser His Ser Thr Lys Glu
                85                  90                  95

Glu Phe Met Thr Asp Tyr Arg Leu Tyr Ile Glu Leu Leu Arg Asn Leu
                100                 105                 110

Ala Asp Glu Ala Gly Leu Pro Lys Thr Leu Asp Thr Gly Ser Leu Ala
            115                 120                 125

Gly Ile Lys Thr His Glu Tyr Cys Thr Asn Asn Gln Pro Asn Asn His
        130                 135                 140

Ser Asp His Val Asp Pro Tyr Pro Tyr Leu Ala Lys Trp Gly Ile Ser
145                 150                 155                 160

Arg Glu Gln Phe Lys His Asp Ile Glu Asn Gly Leu Thr Ile Glu Thr
                165                 170                 175

Gly Trp Gln Lys Asn Asp Thr Gly Tyr Trp Tyr Val His Ser Asp Gly
                180                 185                 190

Ser Tyr Pro Lys Asp Lys Phe Glu Lys Ile Asn Gly Thr Trp Tyr Tyr
```

```
            195                 200                 205
Phe Asp Ser Ser Gly Tyr Met Leu Ala Asp Arg Trp Arg Lys His Thr
210                 215                 220

Asp Gly Asn Trp Tyr Trp Phe Asp Asn Ser Gly Glu Met Ala Thr Gly
225                 230                 235                 240

Trp Lys Lys Ile Ala Asp Lys Trp Tyr Tyr Phe Asn Glu Glu Gly Ala
                245                 250                 255

Met Lys Thr Gly Trp Val Lys Tyr Lys Asp Thr Trp Tyr Tyr Leu Asp
                260                 265                 270

Ala Lys Glu Gly Ala Met Val Ser Asn Ala Phe Ile Gln Ser Ala Asp
                275                 280                 285

Gly Thr Gly Trp Tyr Tyr Leu Lys Pro Asp Gly Thr Leu Ala Asp Lys
                290                 295                 300

Pro Glu Phe Thr Val Glu Pro Asp Gly Leu Ile Thr Val Lys
305                 310                 315

<210> SEQ ID NO 3
<211> LENGTH: 929
<212> TYPE: PRT
<213> ORGANISM: Streptococcus pneumoniae

<400> SEQUENCE: 3

Met Phe Ala Ser Lys Ser Glu Arg Lys Val His Tyr Ser Ile Arg Lys
1               5                   10                  15

Phe Ser Ile Gly Val Ala Ser Val Ala Val Ala Ser Leu Phe Leu Gly
                20                  25                  30

Gly Val Val His Ala Glu Gly Val Arg Ser Gly Asn Asn Leu Thr Val
                35                  40                  45

Thr Ser Ser Gly Gln Asp Ile Ser Lys Lys Tyr Ala Asp Glu Val Glu
50                  55                  60

Ser His Leu Glu Ser Ile Leu Lys Asp Val Lys Asn Leu Lys Lys
65                  70                  75                  80

Val Gln His Thr Gln Asn Val Gly Leu Ile Thr Lys Leu Ser Glu Ile
                85                  90                  95

Lys Lys Lys Tyr Leu Tyr Asp Leu Lys Val Asn Val Leu Ser Glu Ala
                100                 105                 110

Glu Leu Thr Ser Lys Thr Lys Glu Thr Lys Glu Lys Leu Thr Ala Thr
                115                 120                 125

Phe Glu Gln Phe Lys Lys Asp Thr Leu Pro Thr Glu Pro Glu Lys Lys
130                 135                 140

Val Ala Glu Ala Gln Lys Val Glu Glu Ala Lys Lys Lys Ala Glu
145                 150                 155                 160

Asp Gln Lys Glu Lys Asp Arg Arg Asn Tyr Pro Thr Ile Thr Tyr Lys
                165                 170                 175

Thr Leu Glu Leu Glu Ile Ala Glu Ser Asp Val Glu Val Lys Lys Ala
                180                 185                 190

Glu Leu Glu Leu Val Lys Val Lys Ala Lys Glu Ser Gln Asp Glu Glu
                195                 200                 205

Lys Ile Lys Gln Ala Glu Ala Glu Val Glu Ser Lys Gln Ala Glu Ala
                210                 215                 220

Thr Arg Leu Lys Lys Ile Lys Thr Asp Arg Glu Glu Ala Lys Arg Lys
225                 230                 235                 240

Ala Asp Ala Lys Leu Lys Glu Ala Val Glu Lys Asn Val Ala Thr Ser
                245                 250                 255
```

-continued

Glu Gln Asp Lys Pro Lys Arg Arg Ala Lys Arg Gly Val Ser Gly Glu
                260                 265                 270

Leu Ala Thr Pro Asp Lys Glu Asn Asp Ala Lys Ser Ser Asp Ser
            275                 280                 285

Ser Val Gly Glu Glu Thr Leu Pro Ser Pro Ser Leu Asn Met Ala Asn
    290                 295                 300

Glu Ser Gln Thr Glu His Arg Lys Asp Val Asp Glu Tyr Ile Lys Lys
305                 310                 315                 320

Met Leu Ser Glu Ile Gln Leu Asp Arg Arg Lys His Thr Gln Asn Val
                325                 330                 335

Asn Leu Asn Ile Lys Leu Ser Ala Ile Lys Thr Lys Tyr Leu Tyr Glu
            340                 345                 350

Leu Ser Val Leu Lys Glu Asn Ser Lys Lys Glu Glu Leu Thr Ser Lys
            355                 360                 365

Thr Lys Ala Glu Leu Thr Ala Ala Phe Glu Gln Phe Lys Lys Asp Thr
370                 375                 380

Leu Lys Pro Glu Lys Lys Val Ala Glu Ala Lys Lys Val Glu Glu
385                 390                 395                 400

Ala Lys Lys Lys Ala Lys Asp Gln Lys Glu Glu Asp Arg Arg Asn Tyr
                405                 410                 415

Pro Thr Asn Thr Tyr Lys Thr Leu Glu Leu Glu Ile Ala Glu Ser Asp
            420                 425                 430

Val Lys Val Lys Glu Ala Glu Leu Glu Leu Val Lys Glu Glu Ala Asn
            435                 440                 445

Glu Ser Arg Asn Glu Glu Lys Ile Lys Gln Ala Lys Glu Lys Val Glu
            450                 455                 460

Ser Lys Lys Ala Glu Ala Thr Arg Leu Glu Lys Ile Lys Thr Asp Arg
465                 470                 475                 480

Lys Lys Ala Glu Glu Ala Lys Arg Lys Ala Glu Ser Glu Lys
                485                 490                 495

Lys Ala Ala Glu Ala Lys Gln Lys Val Asp Ala Glu Glu Tyr Ala Leu
                500                 505                 510

Glu Ala Lys Ile Ala Glu Leu Glu Tyr Glu Val Gln Arg Leu Glu Lys
            515                 520                 525

Glu Leu Lys Glu Ile Asp Glu Ser Asp Ser Glu Asp Tyr Leu Lys Glu
            530                 535                 540

Gly Leu Arg Ala Pro Leu Gln Ser Lys Leu Asp Thr Lys Lys Ala Lys
545                 550                 555                 560

Leu Ser Lys Leu Glu Glu Leu Ser Asp Lys Ile Asp Glu Leu Asp Ala
                565                 570                 575

Glu Ile Ala Lys Leu Glu Val Gln Leu Lys Asp Ala Glu Gly Asn Asn
            580                 585                 590

Asn Val Glu Ala Tyr Phe Lys Glu Gly Leu Glu Lys Thr Thr Ala Glu
            595                 600                 605

Lys Lys Ala Glu Leu Glu Lys Ala Glu Ala Asp Leu Lys Lys Ala Val
610                 615                 620

Asp Glu Pro Glu Thr Pro Ala Pro Ala Pro Gln Pro Ala Pro Ala Pro
625                 630                 635                 640

Glu Lys Pro Ala Glu Lys Pro Ala Pro Ala Pro Glu Lys Pro Ala Pro
                645                 650                 655

Ala Pro Glu Lys Pro Ala Pro Ala Pro Glu Lys Pro Ala Pro Ala Pro
            660                 665                 670

Glu Lys Pro Ala Pro Ala Pro Glu Lys Pro Ala Pro Thr Pro Glu Thr

```
                    675                 680                 685

Pro Lys Thr Gly Trp Lys Gln Glu Asn Gly Met Trp Tyr Phe Tyr Asn
    690                 695                 700

Thr Asp Gly Ser Met Ala Thr Gly Trp Leu Gln Asn Asn Gly Ser Trp
705                 710                 715                 720

Tyr Tyr Leu Asn Ser Asn Gly Ala Met Ala Thr Gly Trp Leu Gln Asn
                725                 730                 735

Asn Gly Ser Trp Tyr Tyr Leu Asn Ser Asn Gly Ala Met Ala Thr Gly
            740                 745                 750

Trp Leu Gln Tyr Asn Gly Ser Trp Tyr Tyr Leu Asn Ala Asn Gly Asp
        755                 760                 765

Met Ala Thr Gly Trp Leu Gln Tyr Asn Gly Ser Trp Tyr Tyr Leu Asn
    770                 775                 780

Ala Asn Gly Asp Met Ala Thr Gly Trp Phe Gln Tyr Asn Gly Ser Trp
785                 790                 795                 800

Tyr Tyr Leu Asn Ala Asn Gly Asp Met Ala Thr Gly Trp Phe Gln Tyr
                805                 810                 815

Asn Gly Ser Trp Tyr Tyr Leu Asn Ala Asn Gly Asp Met Ala Thr Gly
            820                 825                 830

Trp Leu Gln Tyr Asn Gly Ser Trp Tyr Tyr Leu Asn Ser Asn Gly Ala
        835                 840                 845

Met Val Thr Gly Trp Leu Gln Asn Asn Gly Ser Trp Tyr Tyr Leu Asn
    850                 855                 860

Ala Asn Gly Ser Met Ala Thr Asp Trp Val Lys Asp Gly Asp Thr Trp
865                 870                 875                 880

Tyr Tyr Leu Glu Ala Ser Gly Ala Met Lys Ala Ser Gln Trp Phe Lys
                885                 890                 895

Val Ser Asp Asn Trp Tyr Val Asn Gly Ser Gly Ala Leu Ala Val
            900                 905                 910

Asn Thr Thr Val Asp Ser Tyr Arg Val Asn Pro Asn Gly Glu Trp Val
        915                 920                 925

Asn
```

<210> SEQ ID NO 4
<211> LENGTH: 579
<212> TYPE: PRT
<213> ORGANISM: Streptococcus pneumoniae

<400> SEQUENCE: 4

```
Met Phe Ala Ser Lys Ser Glu Arg Lys Val His Tyr Ser Ile Arg Lys
1               5                   10                  15

Phe Ser Ile Gly Val Ala Ser Val Val Val Ala Ser Leu Val Met Gly
            20                  25                  30

Ser Val His Ala Thr Glu Asn Glu Gly Ser Thr Gln Ala Ala Thr
        35                  40                  45

Phe Ser Asn Met Ala Asn Lys Ser Gln Thr Gln Gly Glu Ile Asn
    50                  55                  60

Ile Glu Arg Asp Lys Ala Lys Thr Ala Val Ser Glu Tyr Lys Glu Lys
65                  70                  75                  80

Lys Val Ser Glu Ile Tyr Thr Lys Leu Glu Arg Asp Arg His Lys Asp
                85                  90                  95

Thr Val Asp Leu Val Asn Lys Leu Gln Glu Ile Lys Asn Glu Tyr Leu
            100                 105                 110

Asn Lys Ile Val Gln Ser Thr Ser Lys Thr Glu Ile Gln Gly Leu Ile
```

```
              115                 120                 125
Thr Thr Ser Arg Ser Lys Leu Asp Glu Ala Val Ser Lys Tyr Lys Lys
    130                 135                 140

Ala Pro Ser Ser Ser Ser Ser Gly Ser Ser Thr Lys Pro Glu Ala
145                 150                 155                 160

Ser Asp Thr Ala Lys Pro Asn Lys Pro Thr Glu Leu Glu Lys Lys Val
                165                 170                 175

Ala Glu Ala Glu Lys Lys Val Glu Ala Lys Lys Ala Lys Asp
                180                 185                 190

Gln Lys Glu Glu Asp Tyr Arg Asn Tyr Pro Thr Ile Thr Tyr Lys Thr
                195                 200                 205

Leu Glu Leu Glu Ile Ala Glu Ser Asp Val Glu Val Lys Lys Ala Glu
                210                 215                 220

Leu Glu Leu Val Lys Glu Ala Lys Glu Pro Arg Asn Glu Glu Lys
225                 230                 235                 240

Val Lys Gln Ala Lys Ala Lys Val Glu Ser Glu Glu Thr Glu Ala Thr
                245                 250                 255

Arg Leu Glu Lys Ile Lys Thr Asp Arg Lys Lys Ala Glu Glu Glu Ala
                260                 265                 270

Lys Arg Lys Ala Ala Glu Glu Asp Lys Val Lys Glu Lys Pro Ala Glu
                275                 280                 285

Gln Pro Lys Pro Ala Pro Ala Pro Gln Pro Glu Lys Pro Ala Pro Lys
290                 295                 300

Pro Glu Asn Pro Ala Pro Lys Pro Glu Asn Pro Ala Pro Lys Pro Glu
305                 310                 315                 320

Lys Pro Ala Glu Gln Gln Ala Glu Glu Asp Tyr Ala Arg Arg Ser Glu
                325                 330                 335

Glu Glu Tyr Asn Arg Leu Thr Gln Gln Pro Pro Lys Thr Glu Lys
                340                 345                 350

Pro Ala Gln Pro Ser Thr Pro Lys Thr Gly Trp Lys Gln Glu Asn Gly
                355                 360                 365

Met Trp Tyr Phe Tyr Asn Thr Asp Gly Ser Met Ala Thr Gly Trp Leu
    370                 375                 380

Gln Asn Asn Gly Ser Trp Tyr Tyr Leu Asn Ser Asn Gly Ala Met Ala
385                 390                 395                 400

Thr Gly Trp Leu Gln Asn Asn Gly Ser Trp Tyr Tyr Leu Asn Ala Asn
                405                 410                 415

Gly Ser Met Ala Thr Gly Trp Leu Gln Asn Asn Gly Ser Trp Tyr Tyr
                420                 425                 430

Leu Asn Ala Asn Gly Ser Met Ala Thr Gly Trp Leu Gln Tyr Asn Gly
                435                 440                 445

Ser Trp Tyr Tyr Leu Asn Ala Asn Gly Asp Met Ala Thr Gly Trp Leu
    450                 455                 460

Gln Tyr Asn Gly Ser Trp Tyr Tyr Leu Asn Ala Asn Gly Asp Met Ala
465                 470                 475                 480

Thr Gly Trp Leu Gln Tyr Asn Gly Ser Trp Tyr Tyr Leu Asn Ala Asn
                485                 490                 495

Gly Asp Met Ala Thr Gly Trp Leu Gln Tyr Asn Gly Ser Trp Tyr Tyr
                500                 505                 510

Leu Asn Ala Asn Gly Asp Met Ala Thr Gly Trp Val Lys Asp Gly Asp
                515                 520                 525

Thr Trp Tyr Tyr Leu Glu Ala Ser Gly Ala Met Lys Ala Ser Gln Trp
                530                 535                 540
```

```
Phe Lys Val Ser Asp Lys Trp Tyr Tyr Val Asn Gly Ser Gly Ala Leu
545                 550                 555                 560

Ala Val Asn Thr Thr Val Asp Gly Tyr Gly Val Asn Ala Asn Gly Glu
                565                 570                 575

Trp Val Asn

<210> SEQ ID NO 5
<211> LENGTH: 693
<212> TYPE: PRT
<213> ORGANISM: Streptococcus pneumoniae

<400> SEQUENCE: 5

Met Phe Ala Ser Lys Ser Glu Arg Lys Val His Tyr Ser Ile Arg Lys
1               5                   10                  15

Phe Ser Val Gly Val Ala Ser Val Val Ala Ser Leu Val Met Gly
            20                  25                  30

Ser Val Val His Ala Thr Glu Asn Glu Gly Ala Thr Gln Val Pro Thr
            35                  40                  45

Ser Ser Asn Arg Ala Asn Glu Ser Gln Ala Glu Gln Gly Glu Gln Pro
    50                  55                  60

Lys Lys Leu Asp Ser Glu Arg Asp Lys Ala Arg Lys Glu Val Glu Glu
65                  70                  75                  80

Tyr Val Lys Lys Ile Val Gly Glu Ser Tyr Ala Lys Ser Thr Lys Lys
                85                  90                  95

Arg His Thr Ile Thr Val Ala Leu Val Asn Glu Leu Asn Asn Ile Lys
            100                 105                 110

Asn Glu Tyr Leu Asn Lys Ile Val Glu Ser Thr Ser Glu Ser Gln Leu
        115                 120                 125

Gln Ile Leu Met Met Glu Ser Arg Ser Lys Val Asp Glu Ala Val Ser
    130                 135                 140

Lys Phe Glu Lys Asp Ser Ser Ser Ser Ser Ser Asp Ser Ser Thr
145                 150                 155                 160

Lys Pro Glu Ala Ser Asp Thr Ala Lys Pro Asn Lys Pro Thr Glu Pro
                165                 170                 175

Gly Glu Lys Val Ala Glu Ala Lys Lys Val Glu Glu Ala Glu Lys
            180                 185                 190

Lys Ala Lys Asp Gln Lys Glu Glu Asp Arg Arg Asn Tyr Pro Thr Ile
        195                 200                 205

Thr Tyr Lys Thr Leu Glu Leu Glu Ile Ala Glu Ser Asp Val Glu Val
    210                 215                 220

Lys Lys Ala Glu Leu Glu Leu Val Lys Val Lys Ala Asn Glu Pro Arg
225                 230                 235                 240

Asp Glu Gln Lys Ile Lys Gln Ala Glu Ala Glu Val Glu Ser Lys Gln
                245                 250                 255

Ala Glu Ala Thr Arg Leu Lys Lys Ile Lys Thr Asp Arg Glu Glu Ala
            260                 265                 270

Glu Glu Glu Ala Lys Arg Arg Ala Asp Ala Lys Glu Gln Gly Lys Pro
        275                 280                 285

Lys Gly Arg Ala Lys Arg Gly Val Pro Gly Glu Leu Ala Thr Pro Asp
    290                 295                 300

Lys Lys Glu Asn Asp Ala Lys Ser Ser Asp Ser Ser Val Gly Glu Glu
305                 310                 315                 320

Thr Leu Pro Ser Pro Ser Leu Lys Pro Glu Lys Lys Val Ala Glu Ala
                325                 330                 335
```

Glu Lys Lys Val Glu Ala Lys Lys Ala Glu Asp Gln Lys Glu
            340                 345                 350

Glu Asp Arg Arg Asn Tyr Pro Thr Ile Thr Tyr Lys Thr Leu Glu Leu
            355                 360                 365

Glu Ile Ala Glu Ser Asp Val Glu Val Lys Lys Ala Glu Leu Glu Leu
370                 375                 380

Val Lys Glu Glu Ala Lys Glu Pro Arg Asn Glu Glu Lys Val Lys Gln
385                 390                 395                 400

Ala Lys Ala Glu Val Glu Ser Lys Lys Ala Glu Ala Thr Arg Leu Glu
            405                 410                 415

Lys Ile Lys Thr Asp Arg Lys Lys Ala Glu Glu Ala Lys Arg Lys
            420                 425                 430

Ala Ala Glu Glu Asp Lys Val Lys Glu Lys Pro Ala Glu Gln Pro Gln
            435                 440                 445

Pro Ala Pro Ala Pro Lys Ala Glu Lys Pro Ala Pro Ala Pro Lys Pro
    450                 455                 460

Glu Asn Pro Ala Glu Gln Pro Lys Ala Glu Lys Pro Ala Asp Gln Gln
465                 470                 475                 480

Ala Glu Glu Asp Tyr Ala Arg Arg Ser Glu Glu Glu Tyr Asn Arg Leu
            485                 490                 495

Thr Gln Gln Gln Pro Pro Lys Thr Glu Lys Pro Ala Gln Pro Ser Thr
            500                 505                 510

Pro Lys Thr Gly Trp Lys Gln Glu Asn Gly Met Trp Tyr Phe Tyr Asn
    515                 520                 525

Thr Asp Gly Ser Met Ala Thr Gly Trp Leu Gln Asn Asn Gly Ser Trp
    530                 535                 540

Tyr Tyr Leu Asn Ser Asn Gly Ala Met Ala Thr Gly Trp Leu Gln Asn
545                 550                 555                 560

Asn Gly Ser Trp Tyr Tyr Leu Asn Ala Asn Gly Ser Met Ala Thr Gly
            565                 570                 575

Trp Leu Gln Asn Asn Gly Ser Trp Tyr Tyr Leu Asn Ala Asn Gly Ser
            580                 585                 590

Met Ala Thr Gly Trp Leu Gln Tyr Asn Gly Ser Trp Tyr Tyr Leu Asn
    595                 600                 605

Ala Asn Gly Asp Met Ala Thr Gly Trp Leu Gln Tyr Asn Gly Ser Trp
    610                 615                 620

Tyr Tyr Leu Asn Ala Asn Gly Asp Met Ala Thr Gly Trp Val Lys Asp
625                 630                 635                 640

Gly Asp Thr Trp Tyr Tyr Leu Glu Ala Ser Gly Ala Met Lys Ala Ser
            645                 650                 655

Gln Trp Phe Lys Val Ser Asp Lys Trp Tyr Tyr Val Asn Gly Ser Gly
            660                 665                 670

Ala Leu Ala Val Asn Thr Thr Val Asp Gly Tyr Gly Val Asn Ala Asn
            675                 680                 685

Gly Glu Trp Val Asn
    690

<210> SEQ ID NO 6
<211> LENGTH: 701
<212> TYPE: PRT
<213> ORGANISM: Streptococcus pneumoniae

<400> SEQUENCE: 6

Met Phe Ala Ser Lys Ser Glu Arg Lys Val His Tyr Ser Ile Arg Lys

-continued

```
1               5               10              15
Phe Ser Ile Gly Val Ala Ser Val Ala Ser Leu Val Met Gly
            20              25              30
Ser Val Val His Ala Thr Glu Asn Glu Gly Ser Thr Gln Ala Ala Thr
            35              40              45
Ser Ser Asn Met Ala Lys Thr Glu His Arg Lys Ala Ala Lys Gln Val
50              55              60
Val Asp Glu Tyr Ile Glu Lys Met Leu Arg Glu Ile Gln Leu Asp Arg
65              70              75              80
Arg Lys His Thr Gln Asn Val Ala Leu Asn Ile Lys Leu Ser Ala Ile
            85              90              95
Lys Thr Lys Tyr Leu Arg Glu Leu Asn Val Leu Glu Glu Lys Ser Lys
            100             105             110
Asp Glu Leu Pro Ser Glu Ile Lys Ala Lys Leu Asp Ala Ala Phe Glu
            115             120             125
Lys Phe Lys Lys Asp Thr Leu Lys Pro Gly Glu Lys Val Ala Glu Ala
            130             135             140
Lys Lys Lys Val Glu Glu Ala Lys Lys Ala Glu Asp Gln Lys Glu
145             150             155             160
Glu Asp Arg Arg Asn Tyr Pro Thr Asn Thr Tyr Lys Thr Leu Glu Leu
            165             170             175
Glu Ile Ala Glu Phe Asp Val Lys Val Lys Glu Ala Glu Leu Glu Leu
            180             185             190
Val Lys Glu Glu Ala Lys Glu Ser Arg Asn Glu Gly Thr Ile Lys Gln
            195             200             205
Ala Lys Glu Lys Val Glu Ser Lys Lys Ala Glu Ala Thr Arg Leu Glu
            210             215             220
Asn Ile Lys Thr Asp Arg Lys Lys Ala Glu Glu Ala Lys Arg Lys
225             230             235             240
Ala Asp Ala Lys Leu Lys Glu Ala Asn Val Ala Thr Ser Asp Gln Gly
            245             250             255
Lys Pro Lys Gly Arg Ala Lys Arg Gly Val Pro Gly Glu Leu Ala Thr
            260             265             270
Pro Asp Lys Lys Glu Asn Asp Ala Lys Ser Ser Asp Ser Ser Val Gly
            275             280             285
Glu Glu Thr Leu Pro Ser Ser Ser Leu Lys Ser Gly Lys Lys Val Ala
            290             295             300
Glu Ala Glu Lys Lys Val Glu Glu Ala Glu Lys Lys Ala Lys Asp Gln
305             310             315             320
Lys Glu Glu Asp Arg Arg Asn Tyr Pro Thr Asn Thr Tyr Lys Thr Leu
            325             330             335
Asp Leu Glu Ile Ala Glu Ser Asp Val Lys Val Lys Glu Ala Glu Leu
            340             345             350
Glu Leu Val Lys Glu Glu Ala Lys Glu Pro Arg Asp Glu Glu Lys Ile
            355             360             365
Lys Gln Ala Lys Ala Lys Val Glu Ser Lys Lys Ala Glu Ala Thr Arg
            370             375             380
Leu Glu Asn Ile Lys Thr Asp Arg Lys Lys Ala Glu Glu Glu Ala Lys
385             390             395             400
Arg Lys Ala Ala Glu Glu Asp Lys Val Lys Glu Lys Pro Ala Glu Gln
            405             410             415
Pro Gln Pro Ala Pro Ala Thr Gln Pro Glu Lys Pro Ala Pro Lys Pro
            420             425             430
```

```
Glu Lys Pro Ala Glu Gln Pro Lys Ala Glu Thr Asp Asp Gln Gln
            435                 440                 445

Ala Glu Glu Asp Tyr Ala Arg Arg Ser Glu Glu Tyr Asn Arg Leu
450                 455                 460

Thr Gln Gln Pro Pro Lys Thr Glu Lys Pro Ala Gln Pro Ser Thr
465                 470                 475                 480

Pro Lys Thr Gly Trp Lys Gln Glu Asn Gly Met Trp Tyr Phe Tyr Asn
                485                 490                 495

Thr Asp Gly Ser Met Ala Thr Gly Trp Leu Gln Asn Asn Gly Ser Trp
            500                 505                 510

Tyr Tyr Leu Asn Ala Asn Gly Ala Met Ala Thr Gly Trp Leu Gln Asn
            515                 520                 525

Asn Gly Ser Trp Tyr Tyr Leu Asn Ala Asn Gly Ser Met Ala Thr Gly
            530                 535                 540

Trp Leu Gln Asn Asn Gly Ser Trp Tyr Tyr Leu Asn Ala Asn Gly Ala
545                 550                 555                 560

Met Ala Thr Gly Trp Leu Gln Tyr Asn Gly Ser Trp Tyr Tyr Leu Asn
            565                 570                 575

Ser Asn Gly Ala Met Ala Thr Gly Trp Leu Gln Tyr Asn Gly Ser Trp
            580                 585                 590

Tyr Tyr Leu Asn Ala Asn Gly Asp Met Ala Thr Gly Trp Leu Gln Asn
            595                 600                 605

Asn Gly Ser Trp Tyr Tyr Leu Asn Ala Asn Gly Asp Met Ala Thr Gly
            610                 615                 620

Trp Leu Gln Tyr Asn Gly Ser Trp Tyr Tyr Leu Asn Ala Asn Gly Asp
625                 630                 635                 640

Met Ala Thr Gly Trp Val Lys Asp Gly Asp Thr Trp Tyr Tyr Leu Glu
            645                 650                 655

Ala Ser Gly Ala Met Lys Ala Ser Gln Trp Phe Lys Val Ser Asp Lys
            660                 665                 670

Trp Tyr Tyr Val Asn Gly Ser Gly Ala Leu Ala Val Asn Thr Thr Val
            675                 680                 685

Asp Gly Tyr Gly Val Asn Ala Asn Gly Glu Trp Val Asn
            690                 695                 700

<210> SEQ ID NO 7
<211> LENGTH: 693
<212> TYPE: PRT
<213> ORGANISM: Streptococcus pneumoniae

<400> SEQUENCE: 7

Met Phe Ala Ser Lys Ser Glu Arg Lys Val His Tyr Ser Ile Arg Lys
1               5                   10                  15

Phe Ser Val Gly Val Ala Ser Val Val Ala Ser Leu Val Met Gly
                20                  25                  30

Ser Val Val His Ala Thr Glu Asn Glu Gly Ala Thr Gln Val Pro Thr
            35                  40                  45

Ser Ser Asn Arg Ala Asn Glu Ser Gln Ala Glu Gln Gly Glu Gln Pro
        50                  55                  60

Lys Lys Leu Asp Ser Glu Arg Asp Lys Ala Lys Glu Val Glu Glu
65                  70                  75                  80

Tyr Val Lys Lys Ile Val Gly Glu Ser Tyr Ala Lys Ser Thr Lys Lys
                85                  90                  95

Arg His Thr Ile Thr Val Ala Leu Val Asn Glu Leu Asn Asn Ile Lys
```

```
                100              105              110
Asn Glu Tyr Leu Asn Lys Ile Val Glu Ser Thr Ser Glu Ser Gln Leu
            115                  120                  125
Gln Ile Leu Met Met Glu Ser Arg Ser Lys Val Asp Glu Ala Val Ser
            130                  135                  140
Lys Phe Glu Lys Asp Ser Ser Ser Ser Ser Ser Asp Ser Ser Thr
145                  150                  155                  160
Lys Pro Glu Ala Ser Asp Thr Ala Lys Pro Asn Lys Pro Thr Glu Pro
                165                  170                  175
Gly Glu Lys Val Ala Glu Ala Lys Lys Val Glu Glu Ala Glu Lys
                180                  185                  190
Lys Ala Lys Asp Gln Lys Glu Glu Asp Arg Arg Asn Tyr Pro Thr Ile
            195                  200                  205
Thr Tyr Lys Thr Leu Glu Leu Glu Ile Ala Glu Ser Asp Val Glu Val
            210                  215                  220
Lys Lys Ala Glu Leu Glu Leu Val Lys Val Lys Ala Asn Glu Pro Arg
225                  230                  235                  240
Asp Glu Gln Lys Ile Lys Gln Ala Glu Ala Glu Val Glu Ser Lys Gln
                245                  250                  255
Ala Glu Ala Thr Arg Leu Lys Lys Ile Lys Thr Asp Arg Glu Glu Ala
                260                  265                  270
Glu Glu Glu Ala Lys Arg Arg Ala Asp Ala Lys Glu Gln Gly Lys Pro
                275                  280                  285
Lys Gly Arg Ala Lys Arg Gly Val Pro Gly Glu Leu Ala Thr Pro Asp
                290                  295                  300
Lys Lys Glu Asn Asp Ala Lys Ser Ser Asp Ser Ser Val Gly Glu Glu
305                  310                  315                  320
Thr Leu Pro Ser Pro Ser Leu Lys Pro Glu Lys Val Ala Glu Ala
                325                  330                  335
Glu Lys Lys Val Glu Glu Ala Lys Lys Lys Ala Glu Asp Gln Lys Glu
                340                  345                  350
Glu Asp Arg Arg Asn Tyr Pro Thr Asn Thr Tyr Lys Thr Leu Glu Leu
                355                  360                  365
Glu Ile Ala Glu Ser Asp Val Glu Val Lys Lys Ala Glu Leu Glu Leu
                370                  375                  380
Val Lys Glu Glu Ala Lys Glu Pro Arg Asn Glu Glu Lys Val Lys Gln
385                  390                  395                  400
Ala Lys Ala Glu Val Glu Ser Lys Lys Ala Glu Ala Thr Arg Leu Glu
                405                  410                  415
Lys Ile Lys Thr Asp Arg Lys Lys Ala Glu Glu Glu Ala Lys Arg Lys
                420                  425                  430
Ala Ala Glu Asp Lys Val Lys Glu Lys Pro Ala Glu Gln Pro Gln
            435                  440                  445
Pro Ala Pro Ala Pro Lys Ala Glu Lys Pro Ala Pro Ala Pro Lys Pro
            450                  455                  460
Glu Asn Pro Ala Glu Gln Pro Lys Ala Glu Lys Pro Ala Asp Gln Gln
465                  470                  475                  480
Ala Glu Glu Asp Tyr Ala Arg Arg Ser Glu Glu Tyr Asn Arg Leu
                485                  490                  495
Thr Gln Gln Gln Pro Pro Lys Thr Glu Lys Pro Ala Gln Pro Ser Thr
                500                  505                  510
Pro Lys Thr Gly Trp Lys Gln Glu Asn Gly Met Trp Tyr Phe Tyr Asn
            515                  520                  525
```

-continued

Thr Asp Gly Ser Met Ala Thr Gly Trp Leu Gln Asn Gly Ser Trp
        530                 535                 540

Tyr Tyr Leu Asn Ser Asn Gly Ala Met Ala Thr Gly Trp Leu Gln Asn
545                 550                 555                 560

Asn Gly Ser Trp Tyr Tyr Leu Asn Ala Asn Gly Ser Met Ala Thr Gly
            565                 570                 575

Trp Leu Gln Asn Asn Gly Ser Trp Tyr Tyr Leu Asn Ala Asn Gly Ser
        580                 585                 590

Met Ala Thr Gly Trp Leu Gln Tyr Asn Gly Ser Trp Tyr Tyr Leu Asn
            595                 600                 605

Ala Asn Gly Ser Met Ala Thr Gly Trp Leu Gln Tyr Asn Gly Ser Trp
        610                 615                 620

Tyr Tyr Leu Asn Ala Asn Gly Asp Met Ala Thr Gly Trp Val Lys Asp
625                 630                 635                 640

Gly Asp Thr Trp Tyr Tyr Leu Glu Ala Ser Gly Ala Met Lys Ala Ser
            645                 650                 655

Gln Trp Phe Lys Val Ser Asp Lys Trp Tyr Tyr Val Asn Gly Ser Gly
        660                 665                 670

Ala Leu Ala Val Asn Thr Thr Val Asp Gly Tyr Gly Val Asn Ala Asn
            675                 680                 685

Gly Glu Trp Val Asn
    690

<210> SEQ ID NO 8
<211> LENGTH: 866
<212> TYPE: PRT
<213> ORGANISM: Streptococcus pneumoniae

<400> SEQUENCE: 8

Met Phe Ala Ser Lys Ser Glu Arg Lys Val His Tyr Ser Ile Arg Lys
1               5                   10                  15

Phe Ser Ile Gly Val Ala Ser Val Val Ala Ser Leu Phe Leu Gly
                20                  25                  30

Gly Val Val His Ala Glu Glu Val Arg Arg Gly Asn Asn Leu Thr Val
            35                  40                  45

Thr Ser Ser Gly Asp Glu Val Glu Ser His Tyr Gln Ser Ile Leu Glu
    50                  55                  60

Lys Val Arg Lys Ser Leu Glu Lys Asp Arg His Thr Gln Asn Val Asp
65                  70                  75                  80

Leu Ile Lys Lys Leu Gln Asp Ile Lys Arg Thr Tyr Leu Tyr Asn Leu
                85                  90                  95

Lys Glu Lys Pro Glu Ala Glu Leu Thr Ser Lys Thr Lys Glu Leu
                100                 105                 110

Asp Ala Ala Phe Glu Lys Phe Lys Lys Glu Pro Glu Leu Thr Lys Lys
            115                 120                 125

Leu Ala Glu Ala Glu Lys Lys Ala Lys Asp Gln Lys Glu Glu Asp His
        130                 135                 140

Arg Asn Tyr Pro Thr Asn Thr Tyr Lys Thr Ile Glu Leu Glu Ile Ala
145                 150                 155                 160

Glu Ala Glu Val Gly Val Ala Lys Ala Leu Glu Leu Ala Gln Ala
                165                 170                 175

Gln Val Gln Ile Pro Gln Asp Thr Glu Lys Ile Asn Ala Ala Lys Ala
            180                 185                 190

Lys Val Glu Ala Ala Lys Ser Asn Val Lys Lys Leu Glu Lys Ile Lys

-continued

```
            195                 200                 205
Ser Asp Ile Glu Lys Thr Tyr Leu Tyr Lys Leu Asp Asn Ser Thr Lys
210                 215                 220
Glu Thr Pro Lys Pro Arg Val Arg Arg Asn Ser Pro Glu Ile Lys Ala
225                 230                 235                 240
Lys Gly Arg Val Lys Asn Tyr Lys Glu Ala Asn Ile Glu Leu Ser Lys
                    245                 250                 255
Tyr Met Thr Asp Leu Tyr Lys Leu Asp Asn Ser Thr Lys Glu Thr Pro
                260                 265                 270
Lys Ser Arg Val Arg Arg Asn Ser Pro Gln Val Gly Asp Ser Arg Glu
            275                 280                 285
Leu Lys Glu Thr Ile Asp Lys Ala Lys Lys Thr Leu Ser Thr Tyr Met
290                 295                 300
Val Thr Arg Leu Thr Lys Leu Asp Pro Ser Val Phe Trp Phe Ala Asp
305                 310                 315                 320
Leu Leu Met Asp Ala Lys Lys Val Val Glu Glu Tyr Lys Thr Lys Leu
                    325                 330                 335
Glu Asp Ala Ser Asp Gln Lys Ser Val Glu Asp Leu Arg Lys Glu Ala
                340                 345                 350
Glu Gly Lys Ile Glu Ser Leu Ile Val Thr His Gln Asn Arg Glu Lys
            355                 360                 365
Glu Asn Gln Pro Ala Pro Gln Pro Gly Gly Ala Gly Gly Ser Met
370                 375                 380
Val Val Pro Pro Val Thr Gln Thr Pro Pro Ser Thr Ser Gln Ser Pro
385                 390                 395                 400
Gly Gln Lys Ala Thr Glu Ala Glu Lys Lys Leu Gln Asp Leu Ile
                    405                 410                 415
Arg Gln Phe Gln Glu Ala Leu Asn Lys Leu Asp Asp Glu Thr Lys Thr
                420                 425                 430
Val Pro Asp Gly Gly Lys Leu Thr Gly Glu Ala Trp Lys Ala Tyr Asn
            435                 440                 445
Glu Thr Arg Thr Tyr Ala Lys Glu Val Val Asp Lys Ser Lys Lys Leu
450                 455                 460
Leu Ser Gln Thr Ala Val Thr Met Asp Glu Leu Ala Met Gln Leu Thr
465                 470                 475                 480
Lys Leu Asn Asp Ala Met Ser Lys Leu Lys Glu Ala Lys Ala Lys Leu
                    485                 490                 495
Val Pro Glu Val Lys Pro Gln Pro Glu Asn Pro Glu Pro Lys Pro Gln
                500                 505                 510
Pro Glu Gly Glu Lys Pro Ser Val Pro Asp Ile Asn Gln Glu Lys Glu
            515                 520                 525
Lys Ala Lys Leu Ala Ile Ala Thr Tyr Met Ser Lys Ile Leu Asp Asp
530                 535                 540
Ile Lys Lys His His Leu Lys Lys Glu Lys His His Gln Ile Val Ala
545                 550                 555                 560
Leu Ile Lys Asp Leu Asp Lys Leu Lys Gln Ala Leu Ser Glu Ile
                    565                 570                 575
Asp Asn Val Asn Thr Lys Val Glu Ile Glu Asn Thr Val His Lys Val
                580                 585                 590
Phe Ala Ala Met Asp Thr Val Val Thr Asn Ser Lys Lys Ala Leu Ile
            595                 600                 605
Gln Asn Thr Pro Gln Val Pro Glu Ala Pro Lys Ser Pro Glu Val Pro
610                 615                 620
```

```
Lys Val Ser Asp Thr Pro Lys Ala Pro Asp Thr Pro Gln Val Pro Glu
625                 630                 635                 640

Ala Pro Lys Ala Pro Asp Thr Pro Gln Ile Pro Glu Ala Pro Ala Pro
            645                 650                 655

Glu Thr Pro Ala Pro Ala Pro Glu Ala Pro Lys Thr Gly Trp Lys Gln
            660                 665                 670

Glu Asn Gly Met Trp Tyr Phe Tyr Asn Thr Asp Gly Ser Met Ala Thr
            675                 680                 685

Gly Trp Leu Glu Tyr Asn Gly Ser Trp Tyr Tyr Leu Asn Ala Asn Gly
            690                 695                 700

Ala Met Ala Thr Gly Trp Leu Glu Tyr Asn Gly Ser Trp Tyr Tyr Leu
705                 710                 715                 720

Asn Thr Asn Gly Ala Met Glu Thr Gly Trp Leu Glu Tyr Asn Gly Ser
            725                 730                 735

Trp Tyr Tyr Leu Asn Thr Asn Gly Ala Met Glu Thr Gly Trp Leu Glu
            740                 745                 750

Tyr Asn Gly Ser Trp Tyr Tyr Leu Asn Thr Asn Gly Ala Met Glu Thr
            755                 760                 765

Gly Trp Leu Glu Tyr Asn Gly Ser Trp Tyr Tyr Leu Asn Thr Asn Gly
            770                 775                 780

Ala Met Glu Thr Gly Trp Leu Glu Tyr Asn Gly Ser Trp Tyr Tyr Leu
785                 790                 795                 800

Asn Ala Asn Gly Ser Met Ala Thr Gly Trp Leu Lys Asp Gly Asp Thr
            805                 810                 815

Trp Tyr Tyr Leu Glu Ala Ser Gly Ala Met Lys Glu Ser Gln Trp Phe
            820                 825                 830

Lys Val Ser Asp Lys Trp Tyr Tyr Val Asn Gly Ser Gly Ala Leu Ala
            835                 840                 845

Val Asn Thr Thr Val Asp Gly Tyr Gly Val Asn Ala Asn Gly Lys Trp
            850                 855                 860

Val Asn
865

<210> SEQ ID NO 9
<211> LENGTH: 869
<212> TYPE: PRT
<213> ORGANISM: Streptococcus pneumoniae

<400> SEQUENCE: 9

Met Phe Ala Ser Lys Ser Glu Arg Lys Val His Tyr Ser Ile Arg Lys
1               5                   10                  15

Phe Ser Ile Gly Val Ala Ser Val Val Ala Ser Leu Val Met Gly
            20                  25                  30

Ser Val Val His Ala Thr Glu Asn Glu Gly Ile Thr Gln Val Pro Thr
            35                  40                  45

Ser Tyr Asn Lys Ala Asn Glu Ser Gln Thr Glu His Arg Lys Ala Ala
            50                  55                  60

Lys Gln Val Asp Glu Asp Ile Lys Lys Met Leu Ser Glu Ile Gln Glu
65                  70                  75                  80

Tyr Ile Lys Lys Met Leu Ser Glu Ile Gln Leu Asp Lys Arg Lys Asp
                85                  90                  95

Thr Gln Asn Arg Thr Leu Asn Arg Lys Leu Ser Ala Ile Gln Thr Lys
            100                 105                 110

Tyr Leu Tyr Glu Leu Arg Val Leu Lys Glu Lys Ser Lys Lys Glu Glu
```

-continued

```
            115                 120                 125
Leu Thr Ser Lys Thr Lys Lys Glu Leu Asp Ala Ala Phe Glu Lys Phe
        130                 135                 140
Lys Lys Glu Pro Glu Leu Thr Lys Lys Leu Ala Glu Ala Lys Gln Lys
145                 150                 155                 160
Ala Lys Ala Gln Lys Glu Glu Asp Phe Arg Asn Tyr Pro Thr Asn Thr
                165                 170                 175
Tyr Lys Thr Leu Glu Leu Glu Ile Ala Glu Phe Asp Val Lys Val Lys
            180                 185                 190
Glu Ala Asp Leu Glu Leu Val Lys Glu Ala Lys Pro Arg Asn Glu
        195                 200                 205
Glu Lys Ile Lys Gln Ala Lys Ala Lys Val Glu Ser Lys Lys Ala Glu
    210                 215                 220
Ala Thr Arg Leu Glu Glu Ile Lys Thr Glu Arg Lys Arg Ala Glu Glu
225                 230                 235                 240
Glu Ala Lys Arg Lys Ala Gly Glu Ser Glu Glu Lys Ala Ala Glu Ala
                245                 250                 255
Asn Gln Lys Val Asp Thr Lys Glu Gln Gly Lys Pro Lys Arg Arg Ala
            260                 265                 270
Lys Arg Gly Val Ser Gly Glu Leu Ala Thr Pro Asp Lys Lys Glu Asn
        275                 280                 285
Asp Ala Lys Ser Ser Asp Ser Ser Val Gly Glu Glu Thr Leu Pro Ser
290                 295                 300
Pro Ser Leu Asn Met Ala Asn Glu Ser Gln Thr Glu His Arg Lys Asp
305                 310                 315                 320
Val Asp Glu Tyr Ile Lys Lys Met Leu Ser Gly Ile Gln Leu Asp Arg
                325                 330                 335
Arg Lys Gln Thr Gln Asn Val Asn Leu Asn Ile Lys Leu Ser Ala Ile
            340                 345                 350
Lys Thr Lys Tyr Leu Tyr Glu Leu Ser Val Leu Lys Glu Asn Ser Lys
        355                 360                 365
Lys Glu Glu Leu Thr Ser Lys Thr Lys Ala Glu Leu Thr Ala Ala Phe
    370                 375                 380
Glu Gln Phe Lys Lys Asp Thr Leu Lys Pro Glu Lys Lys Val Ala Glu
385                 390                 395                 400
Ala Glu Lys Lys Val Glu Glu Ala Lys Lys Lys Ala Lys Asp Gln Lys
                405                 410                 415
Glu Glu Asp Arg Arg Asn Tyr Pro Thr Asn Thr Tyr Lys Thr Leu Glu
            420                 425                 430
Leu Glu Ile Ala Glu Ser Asp Val Lys Val Lys Glu Ala Glu Leu Glu
        435                 440                 445
Leu Val Lys Glu Glu Ala Asn Glu Ser Arg Asn Glu Lys Ile Lys
    450                 455                 460
Gln Ala Lys Glu Lys Val Glu Ser Lys Lys Ala Glu Ala Thr Arg Leu
465                 470                 475                 480
Glu Lys Ile Lys Thr Asp Arg Lys Lys Ala Glu Glu Ala Lys Arg
                485                 490                 495
Lys Ala Glu Glu Ser Glu Lys Lys Ala Ala Glu Ala Lys Gln Lys Val
            500                 505                 510
Asp Ala Glu Glu Tyr Ala Leu Glu Ala Lys Ile Ala Glu Leu Glu Tyr
        515                 520                 525
Glu Val Gln Arg Leu Glu Lys Glu Leu Lys Glu Ile Asp Glu Ser Asp
    530                 535                 540
```

Ser Glu Asp Tyr Leu Lys Gly Leu Arg Ala Pro Leu Gln Ser Lys
545                 550                 555                 560

Leu Asp Thr Lys Lys Ala Lys Leu Ser Lys Leu Glu Glu Leu Ser Asp
                565                 570                 575

Lys Ile Asp Glu Leu Asp Val Asn Cys Asn Leu Arg Ser Gln Leu Lys
                580                 585                 590

Asp Ala Glu Gly Asn Asn Asn Val Glu Ala Tyr Phe Lys Glu Gly Leu
            595                 600                 605

Glu Lys Thr Thr Ala Glu Lys Ala Glu Leu Glu Lys Ala Glu Ala
        610                 615                 620

Asp Leu Lys Lys Ala Val Asp Glu Pro Glu Thr Pro Ala Pro Ala Pro
625                 630                 635                 640

Gln Pro Ala Pro Ala Pro Glu Lys Pro Ala Glu Lys Gln Ala Pro Ala
                645                 650                 655

Ser Ser Pro Glu Lys Pro Ala Pro Ala Pro Glu Lys Pro Gly Pro Ala
            660                 665                 670

Pro Glu Lys Pro Ala Pro Ala Pro Glu Lys Pro Ala Pro Thr Pro Glu
        675                 680                 685

Thr Pro Lys Thr Gly Trp Lys Gln Glu Asn Gly Met Trp Tyr Phe Tyr
690                 695                 700

Asn Thr Asp Gly Ser Met Ala Thr Gly Trp Leu Gln Asn Asn Gly Ser
705                 710                 715                 720

Trp Tyr Tyr Leu Asn Ser Asn Gly Ala Met Ala Thr Gly Trp Leu Gln
                725                 730                 735

Asn Asn Gly Ser Trp Tyr Tyr Leu Asn Ser Asn Gly Ala Met Ala Thr
            740                 745                 750

Gly Trp Leu Gln Tyr Asn Gly Ser Trp Tyr Tyr Leu Asn Ala Asn Gly
        755                 760                 765

Asp Met Ala Thr Gly Trp Leu Gln Tyr Asn Gly Ser Trp Tyr Tyr Leu
770                 775                 780

Asn Ala Asn Gly Asp Met Ala Thr Gly Trp Leu Gln Tyr Asn Gly Ser
785                 790                 795                 800

Trp Tyr Tyr Leu Asn Ala Asn Gly Asp Met Ala Thr Gly Trp Val Lys
                805                 810                 815

Asp Gly Asp Thr Trp Tyr Tyr Leu Glu Ala Ser Gly Ala Met Lys Ala
            820                 825                 830

Arg Trp Phe Lys Val Ser Asp Lys Trp Tyr Tyr Val Asn Gly Ser Gly
        835                 840                 845

Ala Leu Ala Val Asn Thr Thr Val Asp Ser Tyr Arg Val Asn Ala Asn
850                 855                 860

Gly Glu Trp Val Asn
865

<210> SEQ ID NO 10
<211> LENGTH: 681
<212> TYPE: PRT
<213> ORGANISM: Streptococcus pneumoniae

<400> SEQUENCE: 10

Met Phe Ala Ser Lys Ser Glu Arg Lys Val His Tyr Ser Ile Arg Lys
1               5                   10                  15

Phe Ser Ile Gly Val Ala Ser Val Ala Val Ala Ser Leu Phe Leu Gly
                20                  25                  30

Gly Val Ala His Ala Glu Gly Val Arg Ile Gly Asn Asn Ser Thr Val

```
              35                  40                  45
Thr Ser Ser Gly Asp Glu Val Glu Ser His Leu Gln Ser Ile Leu Lys
 50                  55                  60

Asp Val Asn Lys Asn Leu Lys Lys Val Gln His Thr Gln Asn Val Gly
 65                  70                  75                  80

Leu Leu Thr Lys Leu Ser Glu Ile Lys Arg Lys Tyr Leu Tyr Glu Leu
                     85                  90                  95

Lys Val Asn Gly Leu Glu Glu Lys Ser Lys Ala Glu Leu Thr Ser Lys
                    100                 105                 110

Thr Lys Lys Glu Leu Thr Ala Ala Phe Glu Gln Phe Lys Lys Asp Thr
                115                 120                 125

Leu Ser Thr Glu Leu Glu Lys Val Ala Glu Ala Gln Lys Lys Val
                130                 135                 140

Ala Glu Ala Glu Lys Lys Ala Lys Ala Gln Lys Glu Glu Asp His Arg
145                 150                 155                 160

Asn Tyr Pro Thr Asn Thr Tyr Lys Thr Leu Glu Leu Glu Ile Ala Glu
                    165                 170                 175

Ser Asp Val Glu Val Lys Lys Ala Glu Leu Glu Leu Leu Lys Glu Glu
                180                 185                 190

Ala Lys Glu Ser Arg Asp Glu Gly Thr Ile Lys Gln Ala Glu Ala Lys
                195                 200                 205

Val Glu Ser Lys Lys Ala Glu Ala Thr Lys Leu Glu Lys Ile Lys Thr
                210                 215                 220

Asp Arg Glu Lys Ala Glu Glu Ala Lys Arg Arg Ala Asp Ala Lys
225                 230                 235                 240

Leu Gln Glu Ala Asn Val Ala Thr Ser Gly Gln Asp Lys Ser Lys Arg
                    245                 250                 255

Arg Ala Lys Arg Ala Val Pro Gly Glu Pro Ala Thr Pro Asp Lys Lys
                260                 265                 270

Glu Asn Asp Ala Lys Ser Ser Asp Ser Ser Val Gly Glu Glu Thr Leu
                275                 280                 285

Pro Ser Pro Ser Leu Lys Pro Glu Lys Lys Val Ala Glu Ala Glu Lys
290                 295                 300

Lys Val Glu Glu Ala Glu Lys Ala Lys Asp Gln Lys Glu Glu Asp
305                 310                 315                 320

Arg Arg Asn Tyr Pro Thr Asn Thr Tyr Lys Thr Leu Glu Leu Glu Ile
                325                 330                 335

Ala Glu Ser Asp Val Lys Val Lys Glu Ala Glu Leu Glu Leu Val Lys
                340                 345                 350

Glu Glu Val Asn Glu Pro Arg Asn Glu Glu Lys Val Lys Gln Ala Lys
                355                 360                 365

Ala Glu Val Glu Ser Lys Lys Ala Glu Ala Thr Arg Leu Glu Lys Ile
                370                 375                 380

Lys Thr Asp Arg Lys Lys Ala Glu Glu Ala Lys Arg Lys Ala Ala Glu
385                 390                 395                 400

Glu Asp Lys Val Lys Glu Lys Pro Ala Pro Ala Gln Pro Ala Pro
                    405                 410                 415

Ala Pro Gln Pro Glu Lys Pro Ala Glu Glu Thr Pro Ala Pro Ala Pro
                420                 425                 430

Lys Pro Glu Lys Pro Thr Glu Gln Pro Lys Ala Glu Lys Pro Asp Asp
                435                 440                 445

Gln Gln Ala Glu Glu Asp Tyr Ala Arg Arg Ser Glu Glu Glu Tyr Asn
450                 455                 460
```

Arg Leu Thr Gln Gln Pro Pro Lys Pro Glu Gln Pro Ala Pro Ala
465                 470                 475                 480

Pro Lys Ile Gly Trp Lys Gln Glu Asn Gly Met Trp Tyr Phe Tyr Asn
            485                 490                 495

Thr Asp Gly Ser Met Ala Thr Gly Trp Leu Gln Asn Asn Gly Ser Trp
            500                 505                 510

Tyr Tyr Leu Asn Ala Asn Gly Ala Met Ala Thr Gly Trp Leu Gln Asn
            515                 520                 525

Asn Gly Ser Trp Tyr Tyr Leu Asn Ala Asn Gly Ser Met Ala Thr Gly
            530                 535                 540

Trp Leu Gln Tyr Asn Gly Ser Trp Tyr Tyr Leu Asn Ser Asn Gly Ala
545                 550                 555                 560

Met Ala Thr Gly Trp Leu Gln Asn Asn Gly Ser Trp Tyr Tyr Leu Asn
            565                 570                 575

Ala Asn Gly Ser Met Ala Thr Gly Trp Leu Gln Tyr Asn Gly Ser Trp
            580                 585                 590

Tyr Tyr Leu Asn Ser Asn Gly Ala Met Val Thr Gly Trp Leu Gln Asn
            595                 600                 605

Asn Gly Ser Trp Tyr Tyr Leu Asn Ala Asn Gly Ser Met Ala Thr Asp
            610                 615                 620

Trp Val Lys Asp Gly Asp Thr Trp Tyr Tyr Leu Glu Ala Ser Gly Ala
625                 630                 635                 640

Met Lys Ala Ser Gln Trp Phe Lys Val Ser Asp Lys Trp Tyr Tyr Val
            645                 650                 655

Asn Gly Ser Gly Ala Leu Ala Val Asn Thr Thr Val Asp Ser Tyr Arg
            660                 665                 670

Val Asn Ala Asn Gly Glu Trp Val Asn
            675                 680

<210> SEQ ID NO 11
<211> LENGTH: 769
<212> TYPE: PRT
<213> ORGANISM: Streptococcus pneumoniae

<400> SEQUENCE: 11

Met Phe Lys Ser Asn Tyr Glu Arg Lys Met Cys Tyr Ser Ile Arg Lys
1               5                   10                  15

Phe Ser Ile Gly Val Ala Ser Val Ala Val Ala Ser Leu Val Met Gly
            20                  25                  30

Ser Val Val His Ala Thr Glu Asn Glu Gly Thr Thr Gln Ala Pro Thr
            35                  40                  45

Ser Ser Asn Arg Gly Asn Glu Ser Gln Ala Glu Gln Arg Arg Glu Leu
        50                  55                  60

Asp Leu Glu Arg Asp Lys Val Lys Lys Glu Val Arg Glu Tyr Lys Glu
65                  70                  75                  80

Lys Lys Val Lys Glu Leu Tyr Ser Lys Ser Thr Lys Ser Arg His Lys
            85                  90                  95

Lys Thr Val Asp Ile Val Asn Lys Leu Gln Asn Ile Asn Asn Glu Tyr
            100                 105                 110

Leu Asn Lys Ile Ile Gln Ser Thr Ser Thr Tyr Glu Glu Leu Gln Lys
            115                 120                 125

Leu Met Met Glu Ser Gln Ser Glu Val Asp Lys Ala Val Ser Glu Phe
        130                 135                 140

Glu Lys Asp Leu Ser Ser Ser Ser Ser Ser Gly Ser Ser Thr Glu Pro

```
                145                 150                 155                 160
        Glu Ala Ser Asp Thr Ala Lys Pro Asn Lys Pro Thr Glu Leu Glu Lys
                        165                 170                 175
        Lys Val Ala Glu Ala Gln Gln Lys Val Glu Ala Glu Lys Lys Ala
                    180                 185                 190
        Lys Asp Gln Lys Glu Glu Asp Tyr Arg Asn Tyr Pro Thr Ile Thr Tyr
                        195                 200                 205
        Lys Thr Leu Glu Leu Glu Ile Ala Glu Phe Asp Val Lys Val Lys Glu
                    210                 215                 220
        Ala Glu Leu Glu Leu Val Lys Val Lys Ala Lys Glu Ser Arg Asp Glu
        225                 230                 235                 240
        Lys Lys Ile Lys Gln Ala Glu Ala Glu Val Glu Ser Lys Gln Ala Glu
                        245                 250                 255
        Ala Thr Arg Leu Lys Lys Ile Lys Thr Asp Arg Lys Lys Ala Glu Glu
                    260                 265                 270
        Glu Ala Lys Leu Lys Glu Ala Val Glu Lys Asn Ala Ala Thr Ser Glu
                    275                 280                 285
        Gln Gly Lys Pro Lys Arg Arg Val Lys Arg Ala Leu Gly Glu Gln
                290                 295                 300
        Ala Thr Pro Asp Lys Lys Asp Tyr Phe Glu Lys Asp Phe Arg Pro Ala
        305                 310                 315                 320
        Phe Asn Lys Asn Arg Gln Met Val Ala Ile Gln Glu Ser Leu Asn Lys
                        325                 330                 335
        Leu Asp Gly Glu Thr Lys Thr Val Pro Asp Gly Ala Lys Leu Thr Gly
                    340                 345                 350
        Glu Ala Gly Asn Ala Tyr Asn Glu Val Arg Asp Tyr Ala Ile Lys Val
                    355                 360                 365
        Val Ser Glu Asn Lys Lys Leu Leu Ser Gln Thr Ala Val Thr Met Asp
                270                 375                 380
        Glu Leu Ala Met Gln Leu Thr Lys Leu Asn Asp Ala Met Ser Lys Leu
        385                 390                 395                 400
        Arg Glu Ala Lys Ala Lys Leu Val Pro Glu Val Lys Pro Gln Pro Glu
                        405                 410                 415
        Asn Pro Glu His Gln Arg Pro Thr Thr Pro Ala Pro Asp Thr Lys Pro
                    420                 425                 430
        Ile Pro Gln Pro Glu Gly Lys Lys Pro Ser Val Pro Asp Ile Asn Gln
                    435                 440                 445
        Glu Lys Glu Lys Ala Lys Leu Ala Val Ala Thr Tyr Met Ser Lys Ile
                450                 455                 460
        Leu Asp Asp Ile Gln Lys His His Leu Gln Lys Glu Lys His Arg Gln
        465                 470                 475                 480
        Ile Val Ala Leu Ile Lys Glu Leu Asp Glu Phe Lys Lys Gln Ala Leu
                        485                 490                 495
        Ser Glu Ile Asp Asn Val Asn Thr Lys Val Glu Ile Glu Asn Thr Val
                    500                 505                 510
        His Lys Ile Phe Ala Asp Met Asp Ala Val Val Thr Lys Phe Lys Lys
                    515                 520                 525
        Gly Leu Thr Gln Asp Thr Pro Lys Glu Pro Asp Asn Lys Lys Pro Ser
                530                 535                 540
        Ala Pro Lys Pro Gly Met Gln Pro Ser Pro Gln Pro Glu Gly Lys Lys
        545                 550                 555                 560
        Pro Ser Val Pro Ala Gln Pro Gly Thr Glu Asp Lys Lys Pro Ser Ala
                        565                 570                 575
```

-continued

```
Pro Lys Pro Gly Met Gln Pro Ser Pro Gln Pro Glu Gly Lys Lys Pro
            580                 585                 590

Ser Val Pro Ala Gln Pro Gly Thr Glu Asp Lys Lys Pro Ser Ala Pro
        595                 600                 605

Lys Pro Asp Met Gln Pro Ser Pro Gln Pro Glu Gly Lys Lys Pro Ser
610                 615                 620

Val Pro Ala Gln Pro Gly Thr Glu Asp Lys Lys Pro Ser Ala Pro Lys
625                 630                 635                 640

Pro Gly Met Gln Pro Ser Pro Gln Pro Glu Gly Lys Lys Pro Ser Val
            645                 650                 655

Pro Ala Gln Pro Gly Thr Glu Asp Lys Lys Pro Ser Ala Pro Lys Pro
        660                 665                 670

Asp Met Gln Pro Ser Pro Gln Pro Glu Gly Lys Lys Pro Ser Val Pro
            675                 680                 685

Ala Gln Pro Gly Thr Glu Asp Lys Lys Pro Ser Ala Pro Lys Pro Asp
        690                 695                 700

Met Gln Pro Ser Pro Gln Pro Glu Gly Lys Lys Pro Ser Val Pro Glu
705                 710                 715                 720

Ile Asn Gln Glu Lys Gly Lys Ala Lys Leu Ala Val Ala Thr Glu Lys
                725                 730                 735

Lys Leu Pro Ser Thr Gly Val Ala Ser Asn Leu Val Leu Glu Ile Ile
            740                 745                 750

Gly Leu Leu Gly Leu Ile Gly Thr Ser Phe Ile Ala Met Lys Arg Arg
            755                 760                 765

Lys
```

<210> SEQ ID NO 12
<211> LENGTH: 503
<212> TYPE: PRT
<213> ORGANISM: Streptococcus pneumoniae

<400> SEQUENCE: 12

```
Met Phe Ala Ser Lys Ser Glu Arg Lys Val His Tyr Ser Ile Arg Lys
1               5                   10                  15

Phe Ser Ile Gly Val Ala Ser Val Ala Val Ala Ser Leu Val Met Gly
            20                  25                  30

Ser Val Val His Ala Thr Glu Asn Glu Gly Ser Thr Gln Ala Ala Thr
        35                  40                  45

Ser Ser Asn Met Ala Asn Lys Ser Gln Thr Glu Gln Gly Glu Ile Asn
    50                  55                  60

Ile Glu Arg Asp Lys Ala Lys Thr Ala Val Ser Glu Tyr Lys Glu Lys
65                  70                  75                  80

Lys Val Ser Glu Ile Tyr Thr Lys Leu Glu Arg Asp Arg His Lys Asp
                85                  90                  95

Thr Val Asp Leu Val Asn Lys Leu Gln Glu Ile Lys Asn Glu Tyr Leu
            100                 105                 110

Asn Lys Ile Val Glu Ser Thr Ser Thr Ile Glu Ile Gln Gly Leu Ile
        115                 120                 125

Thr Thr Ser Arg Ser Lys Leu Asp Glu Ala Val Ser Lys Tyr Lys Lys
    130                 135                 140

Ala Pro Ser Ser Ser Ser Ser Gly Ser Ser Thr Lys Pro Glu Thr
145                 150                 155                 160

Pro Gln Pro Glu Thr Ser Lys Pro Glu Val Lys Pro Glu Pro Glu Thr
                165                 170                 175
```

Pro Lys Pro Glu Val Lys Pro Glu Pro Glu Thr Pro Lys Pro Glu Val
            180                 185                 190

Lys Pro Glu Pro Glu Thr Pro Lys Pro Glu Val Lys Pro Glu Leu Glu
        195                 200                 205

Thr Pro Lys Pro Glu Val Lys Pro Glu Pro Glu Thr Pro Lys Pro Glu
    210                 215                 220

Val Lys Pro Glu Pro Glu Thr Pro Lys Pro Glu Val Lys Pro Glu Pro
225                 230                 235                 240

Glu Thr Pro Lys Pro Glu Val Lys Pro Glu Leu Glu Thr Pro Lys Pro
                245                 250                 255

Glu Val Lys Pro Glu Leu Glu Thr Pro Lys Pro Glu Val Lys Pro Glu
            260                 265                 270

Pro Glu Thr Pro Lys Pro Glu Val Lys Pro Glu Leu Glu Thr Pro Lys
        275                 280                 285

Pro Glu Val Lys Pro Glu Pro Glu Thr Pro Lys Pro Glu Val Lys Pro
    290                 295                 300

Glu Leu Glu Thr Pro Lys Pro Glu Val Lys Pro Glu Pro Glu Thr Pro
305                 310                 315                 320

Lys Pro Glu Val Lys Pro Glu Leu Glu Thr Pro Lys Pro Glu Val Lys
                325                 330                 335

Pro Glu Pro Glu Thr Pro Lys Pro Glu Val Lys Pro Glu Pro Glu Thr
            340                 345                 350

Pro Lys Pro Glu Val Lys Pro Glu Pro Glu Thr Pro Lys Pro Glu Val
        355                 360                 365

Lys Pro Glu Pro Glu Thr Pro Lys Pro Glu Val Lys Pro Glu Pro Glu
    370                 375                 380

Thr Pro Lys Pro Glu Val Lys Pro Glu Pro Glu Thr Pro Lys Pro Glu
385                 390                 395                 400

Val Lys Pro Glu Pro Glu Thr Pro Lys Pro Glu Val Lys Pro Glu Pro
                405                 410                 415

Glu Thr Pro Lys Pro Glu Val Lys Pro Asp Asn Ser Lys Pro Gln Ala
            420                 425                 430

Asp Asp Lys Lys Pro Ser Thr Pro Asn Asn Leu Ser Lys Asp Lys Gln
        435                 440                 445

Ser Ser Asn Gln Ala Ser Thr Asn Glu Asn Lys Lys Gln Gly Pro Ala
    450                 455                 460

Thr Asn Lys Pro Lys Lys Ser Leu Pro Ser Thr Gly Ser Ile Ser Asn
465                 470                 475                 480

Leu Ala Leu Glu Ile Ala Gly Leu Leu Thr Leu Ala Gly Ala Thr Ile
                485                 490                 495

Leu Ala Lys Lys Arg Met Lys
            500

<210> SEQ ID NO 13
<211> LENGTH: 612
<212> TYPE: PRT
<213> ORGANISM: Streptococcus pneumoniae

<400> SEQUENCE: 13

Met Phe Ala Ser Lys Asn Glu Arg Lys Val His Tyr Ser Ile Arg Lys
1               5                   10                  15

Phe Ser Ile Gly Val Ala Ser Val Ala Val Ala Ser Leu Phe Met Gly
            20                  25                  30

Ser Val Val His Ala Thr Glu Lys Glu Val Thr Thr Gln Val Ala Thr

```
                35                  40                  45
Ser Ser Asn Lys Ala Asn Lys Ser Gln Thr Glu His Met Lys Ala Ala
 50                  55                  60
Lys Gln Val Asp Glu Tyr Ile Glu Lys Met Leu Ser Glu Ile Gln Leu
 65                  70                  75                  80
Asp Arg Arg Lys His Thr Gln Asn Val Gly Leu Leu Thr Lys Leu Gly
                 85                  90                  95
Ala Ile Lys Thr Glu Tyr Leu Arg Gly Leu Ser Val Ser Lys Glu Lys
                100                 105                 110
Ser Thr Ala Glu Leu Pro Ser Glu Ile Lys Glu Lys Leu Thr Ala Ala
                115                 120                 125
Phe Glu Gln Phe Lys Lys Asp Thr Leu Lys Ser Gly Lys Lys Val Ala
                130                 135                 140
Glu Ala Gln Lys Lys Ala Lys Asp Gln Lys Glu Ala Lys Gln Glu Ile
145                 150                 155                 160
Glu Ala Leu Ile Val Lys His Lys Gly Arg Glu Ile Asp Leu Asp Arg
                165                 170                 175
Lys Lys Ala Lys Ala Ala Val Thr Glu His Leu Lys Lys Leu Leu Asn
                180                 185                 190
Asp Ile Glu Lys Asn Leu Lys Lys Glu Gln His Thr His Thr Val Glu
                195                 200                 205
Leu Ile Lys Asn Leu Lys Asp Ile Glu Lys Thr Tyr Leu His Lys Leu
                210                 215                 220
Asp Glu Ser Thr Gln Lys Ala Gln Leu Gln Lys Leu Ile Ala Glu Ser
225                 230                 235                 240
Gln Ser Lys Leu Asp Glu Ala Phe Ser Lys Phe Lys Asn Gly Leu Ser
                245                 250                 255
Ser Ser Ser Asn Ser Gly Ser Ser Thr Lys Pro Glu Thr Pro Gln Pro
                260                 265                 270
Glu Thr Pro Lys Pro Glu Val Lys Pro Glu Leu Glu Thr Pro Lys Pro
                275                 280                 285
Glu Val Lys Pro Glu Pro Glu Thr Pro Lys Pro Glu Val Lys Pro Glu
                290                 295                 300
Leu Glu Thr Pro Lys Pro Glu Val Lys Pro Glu Pro Glu Thr Pro Lys
305                 310                 315                 320
Pro Glu Val Lys Pro Glu Leu Glu Thr Pro Lys Pro Glu Val Lys Pro
                325                 330                 335
Glu Leu Glu Thr Pro Lys Pro Glu Val Lys Pro Glu Pro Glu Thr Pro
                340                 345                 350
Lys Pro Glu Val Lys Pro Glu Leu Glu Thr Pro Lys Pro Glu Val Lys
                355                 360                 365
Pro Glu Leu Glu Thr Pro Lys Pro Glu Val Lys Pro Glu Leu Glu Thr
                370                 375                 380
Pro Lys Pro Glu Val Lys Pro Glu Leu Glu Thr Pro Lys Pro Glu Val
385                 390                 395                 400
Lys Pro Glu Leu Glu Thr Pro Lys Pro Glu Val Lys Pro Glu Leu Glu
                405                 410                 415
Thr Pro Lys Pro Glu Val Lys Pro Glu Leu Glu Thr Pro Lys Pro Glu
                420                 425                 430
Val Lys Pro Glu Leu Glu Thr Pro Lys Pro Glu Val Lys Pro Glu Pro
                435                 440                 445
Glu Thr Pro Lys Pro Glu Val Lys Pro Glu Pro Glu Thr Pro Lys Pro
                450                 455                 460
```

Glu Val Lys Pro Glu Leu Glu Thr Pro Lys Pro Val Lys Pro Glu
465                 470                 475                 480

Leu Glu Thr Pro Lys Pro Glu Val Lys Pro Glu Leu Glu Thr Pro Lys
                485                 490                 495

Pro Glu Val Lys Pro Glu Pro Glu Thr Pro Lys Pro Val Lys Pro
            500                 505                 510

Glu Leu Glu Thr Pro Lys Pro Glu Val Lys Pro Glu Pro Glu Ile Pro
                515                 520                 525

Lys Pro Glu Val Lys Pro Asp Asn Ser Lys Pro Gln Ala Asp Asp Lys
            530                 535                 540

Lys Pro Ser Thr Pro Asn Asn Leu Ser Lys Asp Lys Gln Ser Ser Asn
545                 550                 555                 560

Gln Ala Ser Thr Asn Glu Asn Lys Lys Gln Gly Pro Ala Thr Asn Lys
                565                 570                 575

Pro Lys Lys Ser Leu Pro Ser Thr Gly Ser Ile Ser Asn Leu Ala Leu
            580                 585                 590

Glu Ile Ala Gly Leu Leu Thr Leu Ala Gly Ala Thr Ile Leu Ala Lys
                595                 600                 605

Lys Arg Met Lys
        610

<210> SEQ ID NO 14
<211> LENGTH: 635
<212> TYPE: PRT
<213> ORGANISM: Streptococcus pneumoniae

<400> SEQUENCE: 14

Met Asn Lys Lys Met Ile Leu Thr Ser Leu Ala Ser Val Ala Ile
1               5                   10                  15

Leu Gly Ala Gly Phe Val Ala Ser Gln Pro Thr Phe Val Arg Ala Glu
                20                  25                  30

Glu Ser Pro Val Ala Ser Gln Ser Lys Ala Glu Lys Asp Tyr Asp Ala
            35                  40                  45

Ala Val Lys Lys Ser Glu Ala Ala Lys Lys Ala Tyr Glu Glu Ala Lys
50                  55                  60

Lys Ala Leu Glu Glu Ala Lys Val Ala Gln Lys Lys Tyr Glu Asp Asp
65                  70                  75                  80

Gln Lys Lys Thr Glu Glu Lys Ala Glu Leu Glu Lys Glu Ala Ser Glu
                85                  90                  95

Ala Ile Ala Lys Ala Thr Glu Glu Val Gln Gln Ala Tyr Leu Ala Tyr
            100                 105                 110

Gln Arg Ala Ser Asn Lys Ala Glu Ala Ala Lys Met Ile Glu Glu Ala
        115                 120                 125

Gln Arg Arg Glu Asn Glu Ala Arg Ala Lys Phe Thr Thr Ile Arg Thr
    130                 135                 140

Thr Met Val Val Pro Glu Pro Glu Gln Leu Ala Glu Thr Lys Lys Lys
145                 150                 155                 160

Ala Glu Glu Ala Lys Ala Lys Glu Pro Lys Leu Ala Lys Lys Ala Ala
                165                 170                 175

Glu Ala Lys Ala Lys Leu Glu Glu Ala Glu Lys Lys Ala Thr Glu Ala
            180                 185                 190

Lys Gln Lys Val Asp Ala Glu Glu Val Ala Pro Gln Ala Lys Ile Ala
        195                 200                 205

Glu Leu Glu Asn Gln Val His Arg Leu Glu Gln Glu Leu Lys Glu Ile

```
            210                 215                 220
Asp Glu Ser Glu Ser Glu Asp Tyr Ala Lys Glu Gly Phe Arg Ala Pro
225                 230                 235                 240

Leu Gln Ser Lys Leu Asp Ala Lys Lys Ala Lys Leu Ser Lys Leu Glu
                245                 250                 255

Glu Leu Ser Asp Lys Ile Asp Glu Leu Asp Ala Glu Ile Ala Lys Leu
                260                 265                 270

Glu Asp Gln Leu Lys Ala Ala Glu Glu Asn Asn Asn Val Glu Asp Tyr
                275                 280                 285

Phe Lys Glu Gly Leu Glu Lys Thr Ile Ala Ala Lys Lys Ala Glu Leu
                290                 295                 300

Glu Lys Thr Glu Ala Asp Leu Lys Lys Ala Val Asn Glu Pro Glu Lys
305                 310                 315                 320

Ser Ala Glu Glu Pro Ser Gln Pro Glu Lys Pro Ala Glu Glu Ala Pro
                325                 330                 335

Ala Pro Glu Gln Pro Thr Glu Pro Thr Gln Pro Glu Lys Pro Ala Glu
                340                 345                 350

Glu Thr Pro Ala Pro Lys Pro Glu Lys Pro Ala Glu Gln Pro Lys Ala
                355                 360                 365

Glu Lys Thr Asp Asp Gln Gln Ala Glu Glu Asp Tyr Ala Arg Arg Ser
                370                 375                 380

Glu Glu Glu Tyr Asn Arg Leu Thr Gln Gln Pro Pro Lys Ala Glu
385                 390                 395                 400

Lys Pro Ala Pro Ala Pro Gln Pro Glu Gln Pro Ala Pro Ala Pro Lys
                405                 410                 415

Thr Gly Trp Lys Gln Glu Asn Gly Met Trp Tyr Phe Tyr Asn Thr Asp
                420                 425                 430

Gly Ser Met Ala Thr Gly Trp Leu Gln Asn Asn Gly Ser Trp Tyr Tyr
                435                 440                 445

Leu Asn Ser Asn Gly Ala Met Ala Thr Gly Trp Leu Gln Tyr Asn Gly
                450                 455                 460

Ser Trp Tyr Tyr Leu Asn Ala Asn Gly Ala Met Ala Thr Gly Trp Ala
465                 470                 475                 480

Lys Val Asn Gly Ser Trp Tyr Tyr Leu Asn Ala Asn Gly Ser Met Ala
                485                 490                 495

Thr Gly Trp Val Lys Asp Gly Asp Thr Trp Tyr Tyr Leu Glu Ala Ser
                500                 505                 510

Gly Ala Met Lys Ala Ser Gln Trp Phe Lys Val Ser Asp Lys Trp Tyr
                515                 520                 525

Tyr Val Asn Ser Asn Gly Ala Met Ala Thr Gly Trp Leu Gln Tyr Asn
                530                 535                 540

Gly Ser Trp Tyr Tyr Leu Asn Ala Asn Gly Ala Met Ala Thr Gly Trp
545                 550                 555                 560

Ala Lys Val Asn Gly Ser Trp Tyr Tyr Leu Asn Ala Asn Gly Ser Met
                565                 570                 575

Ala Thr Gly Trp Val Lys Asp Gly Asp Thr Trp Tyr Tyr Leu Glu Ala
                580                 585                 590

Ser Gly Ala Met Lys Ala Ser Gln Trp Phe Lys Val Ser Asp Lys Trp
                595                 600                 605

Tyr Tyr Val Asn Gly Ser Gly Ser Leu Ala Val Asn Thr Thr Val Asp
                610                 615                 620

Gly Tyr Thr Val Asn Glu Asn Gly Glu Trp Val
625                 630                 635
```

<210> SEQ ID NO 15
<211> LENGTH: 665
<212> TYPE: PRT
<213> ORGANISM: Streptococcus pneumoniae

<400> SEQUENCE: 15

```
Met Lys Ser Ile Asn Lys Phe Leu Thr Met Leu Ala Ala Leu Leu Leu
1               5                   10                  15

Thr Ala Ser Ser Leu Phe Ser Ala Ala Thr Val Phe Ala Ala Gly Thr
            20                  25                  30

Thr Thr Thr Ser Val Thr Val His Lys Leu Leu Ala Thr Asp Gly Asp
        35                  40                  45

Met Asp Lys Ile Ala Asn Glu Leu Glu Thr Gly Asn Tyr Ala Gly Asn
50                  55                  60

Lys Val Gly Val Leu Pro Ala Asn Ala Lys Glu Ile Ala Gly Val Met
65                  70                  75                  80

Phe Val Trp Thr Asn Thr Asn Asn Glu Ile Ile Asp Glu Asn Gly Gln
                85                  90                  95

Thr Leu Gly Val Asn Ile Asp Pro Gln Thr Phe Lys Leu Ser Gly Ala
            100                 105                 110

Met Pro Ala Thr Ala Met Lys Lys Leu Thr Glu Ala Glu Gly Ala Lys
        115                 120                 125

Phe Asn Thr Ala Asn Leu Pro Ala Ala Lys Tyr Lys Ile Tyr Glu Ile
130                 135                 140

His Ser Leu Ser Thr Tyr Val Gly Glu Asp Gly Ala Thr Leu Thr Gly
145                 150                 155                 160

Ser Lys Ala Val Pro Ile Glu Ile Glu Leu Pro Leu Asn Asp Val Val
                165                 170                 175

Asp Ala His Val Tyr Pro Lys Asn Thr Glu Ala Lys Pro Lys Ile Asp
            180                 185                 190

Lys Asp Phe Lys Gly Lys Ala Asn Pro Asp Thr Pro Arg Val Asp Lys
        195                 200                 205

Asp Thr Pro Val Asn His Gln Val Gly Asp Val Val Glu Tyr Glu Ile
210                 215                 220

Val Thr Lys Ile Pro Ala Leu Ala Asn Tyr Ala Thr Ala Asn Trp Ser
225                 230                 235                 240

Asp Arg Met Thr Glu Gly Leu Ala Phe Asn Lys Gly Thr Val Lys Val
                245                 250                 255

Thr Val Asp Asp Val Ala Leu Glu Ala Gly Asp Tyr Ala Leu Thr Glu
            260                 265                 270

Val Ala Thr Gly Phe Asp Leu Lys Leu Thr Asp Ala Gly Leu Ala Lys
        275                 280                 285

Val Asn Asp Gln Asn Ala Glu Lys Thr Val Lys Ile Thr Tyr Ser Ala
290                 295                 300

Thr Leu Asn Asp Lys Ala Ile Val Glu Val Pro Glu Ser Asn Asp Val
305                 310                 315                 320

Thr Phe Asn Tyr Gly Asn Asn Pro Asp His Gly Asn Thr Pro Lys Pro
                325                 330                 335

Asn Lys Pro Asn Glu Asn Gly Asp Leu Thr Leu Thr Lys Thr Trp Val
            340                 345                 350

Asp Ala Thr Gly Ala Pro Ile Pro Ala Gly Ala Glu Ala Thr Phe Asp
        355                 360                 365

Leu Val Asn Ala Gln Thr Gly Lys Val Val Gln Thr Val Thr Leu Thr
```

```
            370             375             380
Thr Asp Lys Asn Thr Val Thr Val Asn Gly Leu Asp Lys Asn Thr Glu
385                 390                 395                 400

Tyr Lys Phe Val Glu Arg Ser Ile Lys Gly Tyr Ser Ala Asp Tyr Gln
                405                 410                 415

Glu Ile Thr Thr Ala Gly Glu Ile Ala Val Lys Asn Trp Lys Asp Glu
            420                 425                 430

Asn Pro Lys Pro Leu Asp Pro Thr Glu Pro Lys Val Val Thr Tyr Gly
                435                 440                 445

Lys Lys Phe Val Lys Val Asn Asp Lys Asp Asn Arg Leu Ala Gly Ala
            450                 455                 460

Glu Phe Val Ile Ala Asn Ala Asp Asn Ala Gly Gln Tyr Leu Ala Arg
465                 470                 475                 480

Lys Ala Asp Lys Val Ser Gln Glu Glu Lys Gln Leu Val Val Thr Thr
                485                 490                 495

Lys Asp Ala Leu Asp Arg Ala Val Ala Ala Tyr Asn Ala Leu Thr Ala
                500                 505                 510

Gln Gln Gln Thr Gln Gln Glu Lys Glu Lys Val Asp Lys Ala Gln Ala
                515                 520                 525

Ala Tyr Asn Ala Ala Val Ile Ala Ala Asn Asn Ala Phe Glu Trp Val
                535                 540
            530

Ala Asp Lys Asp Asn Glu Asn Val Val Lys Leu Val Ser Asp Ala Gln
545                 550                 555                 560

Gly Arg Phe Glu Ile Thr Gly Leu Leu Ala Gly Thr Tyr Tyr Leu Glu
                565                 570                 575

Glu Thr Lys Gln Pro Ala Gly Tyr Ala Leu Leu Thr Ser Arg Gln Lys
                580                 585                 590

Phe Glu Val Thr Ala Thr Ser Tyr Ser Ala Thr Gly Gln Gly Ile Glu
                595                 600                 605

Tyr Thr Ala Gly Ser Gly Lys Asp Asp Ala Thr Lys Val Val Asn Lys
                610                 615                 620

Lys Ile Thr Ile Pro Gln Thr Gly Gly Ile Gly Thr Ile Phe Ala
625                 630                 635                 640

Val Ala Gly Ala Ala Ile Met Gly Ile Ala Val Tyr Ala Tyr Val Lys
                645                 650                 655

Asn Asn Lys Asp Glu Asp Gln Leu Ala
                660                 665

<210> SEQ ID NO 16
<211> LENGTH: 839
<212> TYPE: PRT
<213> ORGANISM: Streptococcus pneumoniae

<400> SEQUENCE: 16

Met Lys Ile Asn Lys Lys Tyr Leu Ala Gly Ser Val Ala Val Leu Ala
1               5                   10                  15

Leu Ser Val Cys Ser Tyr Glu Leu Gly Arg His Gln Ala Gly Gln Val
                20                  25                  30

Lys Lys Glu Ser Asn Arg Val Ser Tyr Ile Asp Gly Asp Gln Ala Gly
            35                  40                  45

Gln Lys Ala Glu Asn Leu Thr Pro Asp Glu Val Ser Lys Arg Glu Gly
        50                  55                  60

Ile Asn Ala Glu Gln Ile Val Ile Lys Ile Thr Asp Gln Gly Tyr Val
65                  70                  75                  80
```

```
Thr Ser His Gly Asp His Tyr His Tyr Tyr Asn Gly Lys Val Pro Tyr
             85                  90                  95

Asp Ala Ile Ile Ser Glu Glu Leu Leu Met Lys Asp Pro Asn Tyr Gln
            100                 105                 110

Leu Lys Asp Ser Asp Ile Val Asn Glu Ile Lys Gly Gly Tyr Val Ile
            115                 120                 125

Lys Val Asp Gly Lys Tyr Tyr Val Tyr Leu Lys Asp Ala Ala His Ala
            130                 135                 140

Asp Asn Ile Arg Thr Lys Glu Glu Ile Lys Arg Gln Lys Gln Glu His
145                 150                 155                 160

Ser His Asn His Gly Gly Ser Asn Asp Gln Ala Val Val Ala Ala
                165                 170                 175

Arg Ala Gln Gly Arg Tyr Thr Thr Asp Asp Gly Tyr Ile Phe Asn Ala
            180                 185                 190

Ser Asp Ile Ile Glu Asp Thr Gly Asp Ala Tyr Ile Val Pro His Gly
            195                 200                 205

Asp His Tyr His Tyr Ile Pro Lys Asn Glu Leu Ser Ala Ser Glu Leu
            210                 215                 220

Ala Ala Ala Glu Ala Tyr Trp Asn Gly Lys Gln Gly Ser Arg Pro Ser
225                 230                 235                 240

Ser Ser Ser Ser Tyr Asn Ala Asn Pro Ala Gln Pro Arg Leu Ser Glu
                245                 250                 255

Asn His Asn Leu Thr Val Thr Pro Thr Tyr His Gln Asn Gln Gly Glu
            260                 265                 270

Asn Ile Ser Ser Leu Leu Arg Glu Leu Tyr Ala Lys Pro Leu Ser Glu
            275                 280                 285

Arg His Val Glu Ser Asp Gly Leu Ile Phe Asp Pro Ala Gln Ile Thr
            290                 295                 300

Ser Arg Thr Ala Arg Gly Val Ala Val Pro His Gly Asn His Tyr His
305                 310                 315                 320

Phe Ile Pro Tyr Glu Gln Met Ser Glu Leu Glu Lys Arg Ile Ala Arg
            325                 330                 335

Ile Ile Pro Leu Arg Tyr Arg Ser Asn His Trp Val Pro Asp Ser Arg
            340                 345                 350

Pro Glu Gln Pro Ser Pro Gln Ser Thr Pro Glu Pro Ser Pro Ser Pro
            355                 360                 365

Gln Pro Ala Pro Asn Pro Gln Pro Ala Pro Ser Asn Pro Ile Asp Glu
            370                 375                 380

Lys Leu Val Lys Glu Ala Val Arg Lys Val Gly Asp Gly Tyr Val Phe
385                 390                 395                 400

Glu Glu Asn Gly Val Ser Arg Tyr Ile Pro Ala Lys Asp Leu Ser Ala
                405                 410                 415

Glu Thr Ala Ala Gly Ile Asp Ser Lys Leu Ala Lys Gln Glu Ser Leu
            420                 425                 430

Ser His Lys Leu Gly Ala Lys Lys Thr Asp Leu Pro Ser Ser Asp Arg
            435                 440                 445

Glu Phe Tyr Asn Lys Ala Tyr Asp Leu Leu Ala Arg Ile His Gln Asp
            450                 455                 460

Leu Leu Asp Asn Lys Gly Arg Gln Val Asp Phe Glu Ala Leu Asp Asn
465                 470                 475                 480

Leu Leu Glu Arg Leu Lys Asp Val Pro Ser Asp Lys Val Lys Leu Val
            485                 490                 495

Asp Asp Ile Leu Ala Phe Leu Ala Pro Ile Arg His Pro Glu Arg Leu
```

```
            500                 505                 510
Gly Lys Pro Asn Ala Gln Ile Thr Tyr Thr Asp Asp Glu Ile Gln Val
        515                 520                 525

Ala Lys Leu Ala Gly Lys Tyr Thr Glu Asp Gly Tyr Ile Phe Asp
        530                 535                 540

Pro Arg Asp Ile Thr Ser Asp Glu Gly Asp Ala Tyr Val Thr Pro His
545                 550                 555                 560

Met Thr His Ser His Trp Ile Lys Lys Asp Ser Leu Ser Glu Ala Glu
                565                 570                 575

Arg Ala Ala Ala Gln Ala Tyr Ala Lys Glu Lys Gly Leu Thr Pro Pro
                580                 585                 590

Ser Thr Asp His Gln Asp Ser Gly Asn Thr Glu Ala Lys Gly Ala Glu
                595                 600                 605

Ala Ile Tyr Asn Arg Val Lys Ala Ala Lys Lys Val Pro Leu Asp Arg
                610                 615                 620

Met Pro Tyr Asn Leu Gln Tyr Thr Val Glu Val Lys Asn Gly Ser Leu
625                 630                 635                 640

Ile Ile Pro His Tyr Asp His Tyr His Asn Ile Lys Phe Glu Trp Phe
                645                 650                 655

Asp Glu Gly Leu Tyr Glu Ala Pro Lys Gly Tyr Thr Leu Glu Asp Leu
                660                 665                 670

Leu Ala Thr Val Lys Tyr Tyr Val Glu His Pro Asn Glu Arg Pro His
                675                 680                 685

Ser Asp Asn Gly Phe Gly Asn Ala Ser Asp His Val Arg Lys Asn Lys
        690                 695                 700

Val Asp Gln Asp Ser Lys Pro Asp Glu Asp Lys Glu His Asp Glu Val
705                 710                 715                 720

Ser Glu Pro Thr His Pro Glu Ser Asp Glu Lys Glu Asn His Ala Gly
                725                 730                 735

Leu Asn Pro Ser Ala Asp Asn Leu Tyr Lys Pro Ser Thr Asp Thr Glu
                740                 745                 750

Glu Thr Glu Glu Glu Ala Glu Asp Thr Thr Asp Glu Ala Glu Ile Pro
                755                 760                 765

Gln Val Glu Asn Ser Val Ile Asn Ala Lys Ile Ala Asp Ala Glu Ala
        770                 775                 780

Leu Leu Glu Lys Val Thr Asp Pro Ser Ile Arg Gln Asn Ala Met Glu
785                 790                 795                 800

Thr Leu Thr Gly Leu Lys Ser Ser Leu Leu Gly Thr Lys Asp Asn
                805                 810                 815

Asn Thr Ile Ser Ala Glu Val Asp Ser Leu Leu Ala Leu Leu Lys Glu
                820                 825                 830

Ser Gln Pro Ala Pro Ile Gln
        835

<210> SEQ ID NO 17
<211> LENGTH: 893
<212> TYPE: PRT
<213> ORGANISM: Streptococcus pneumoniae

<400> SEQUENCE: 17

Met Leu Asn Arg Glu Thr His Met Lys Lys Val Arg Lys Ile Phe Gln
1                   5                   10                  15

Lys Ala Val Ala Gly Leu Cys Cys Ile Ser Gln Leu Thr Ala Phe Ser
                20                  25                  30
```

```
Ser Ile Val Ala Leu Ala Glu Thr Pro Glu Thr Ser Pro Ala Ile Gly
         35                  40                  45

Lys Val Val Ile Lys Glu Thr Gly Glu Gly Ala Leu Leu Gly Asp
 50                  55                  60

Ala Val Phe Glu Leu Lys Asn Asn Thr Asp Gly Thr Thr Val Ser Gln
 65                  70                  75                  80

Arg Thr Glu Ala Gln Thr Gly Glu Ala Ile Phe Ser Asn Ile Lys Pro
                 85                  90                  95

Gly Thr Tyr Thr Leu Thr Glu Ala Gln Pro Pro Val Gly Tyr Lys Pro
             100                 105                 110

Ser Thr Lys Gln Trp Thr Val Glu Val Glu Lys Asn Gly Arg Thr Thr
         115                 120                 125

Val Gln Gly Glu Gln Val Glu Asn Arg Glu Glu Ala Leu Ser Asp Gln
 130                 135                 140

Tyr Pro Gln Thr Gly Thr Tyr Pro Asp Val Gln Thr Pro Tyr Gln Ile
 145                 150                 155                 160

Ile Lys Val Asp Gly Ser Glu Lys Asn Gly Gln His Lys Ala Leu Asn
                 165                 170                 175

Pro Asn Pro Tyr Glu Arg Val Ile Pro Glu Gly Thr Leu Ser Lys Arg
             180                 185                 190

Ile Tyr Gln Val Asn Asn Leu Asp Asp Asn Gln Tyr Gly Ile Glu Leu
         195                 200                 205

Thr Val Ser Gly Lys Thr Val Tyr Glu Gln Lys Asp Lys Ser Val Pro
 210                 215                 220

Leu Asp Val Val Ile Leu Leu Asp Asn Ser Asn Ser Met Ser Asn Ile
 225                 230                 235                 240

Arg Asn Lys Asn Ala Arg Arg Ala Glu Arg Ala Gly Glu Ala Thr Arg
                 245                 250                 255

Ser Leu Ile Asp Lys Ile Thr Ser Asp Ser Glu Asn Arg Val Ala Leu
             260                 265                 270

Val Thr Tyr Ala Ser Thr Ile Phe Asp Gly Thr Glu Phe Thr Val Glu
         275                 280                 285

Lys Gly Val Ala Asp Lys Asn Gly Lys Arg Leu Asn Asp Ser Leu Phe
 290                 295                 300

Trp Asn Tyr Asp Gln Thr Ser Phe Thr Thr Asn Thr Lys Asp Tyr Ser
 305                 310                 315                 320

Tyr Leu Lys Leu Thr Asn Asp Lys Asn Asp Ile Val Glu Leu Lys Asn
                 325                 330                 335

Lys Val Pro Thr Glu Ala Glu Asp His Asp Gly Asn Arg Leu Met Tyr
             340                 345                 350

Gln Phe Gly Ala Thr Phe Thr Gln Lys Ala Leu Met Lys Ala Asp Glu
         355                 360                 365

Ile Leu Thr Gln Gln Ala Arg Gln Asn Ser Gln Lys Val Ile Phe His
 370                 375                 380

Ile Thr Asp Gly Val Pro Thr Met Ser Tyr Pro Ile Asn Phe Asn His
 385                 390                 395                 400

Ala Thr Phe Ala Pro Ser Tyr Gln Asn Gln Leu Asn Ala Phe Phe Ser
                 405                 410                 415

Lys Ser Pro Asn Lys Asp Gly Ile Leu Leu Ser Asp Phe Ile Thr Gln
             420                 425                 430

Ala Thr Ser Gly Glu His Thr Ile Val Arg Gly Asp Gly Gln Ser Tyr
         435                 440                 445

Gln Met Phe Thr Asp Lys Thr Val Tyr Glu Lys Gly Ala Pro Ala Ala
```

```
            450                 455                 460
Phe Pro Val Lys Pro Glu Lys Tyr Ser Glu Met Lys Ala Ala Gly Tyr
465                 470                 475                 480

Ala Val Ile Gly Asp Pro Ile Asn Gly Gly Tyr Ile Trp Leu Asn Trp
            485                 490                 495

Arg Glu Ser Ile Leu Ala Tyr Pro Phe Asn Ser Asn Thr Ala Lys Ile
                500                 505                 510

Thr Asn His Gly Asp Pro Thr Arg Trp Tyr Tyr Asn Gly Asn Ile Ala
            515                 520                 525

Pro Asp Gly Tyr Asp Val Phe Thr Val Gly Ile Gly Ile Asn Gly Asp
        530                 535                 540

Pro Gly Thr Asp Glu Ala Thr Ala Thr Ser Phe Met Gln Ser Ile Ser
545                 550                 555                 560

Ser Lys Pro Glu Asn Tyr Thr Asn Val Thr Asp Thr Thr Lys Ile Leu
                565                 570                 575

Glu Gln Leu Asn Arg Tyr Phe His Thr Ile Val Thr Glu Lys Lys Ser
            580                 585                 590

Ile Glu Asn Gly Thr Ile Thr Asp Pro Met Gly Glu Leu Ile Asp Leu
        595                 600                 605

Gln Leu Gly Thr Asp Gly Arg Phe Asp Pro Ala Asp Tyr Thr Leu Thr
    610                 615                 620

Ala Asn Asp Gly Ser Arg Leu Glu Asn Gly Gln Ala Val Gly Gly Pro
625                 630                 635                 640

Gln Asn Asp Gly Gly Leu Leu Lys Asn Ala Lys Val Leu Tyr Asp Thr
                645                 650                 655

Thr Glu Lys Arg Ile Arg Val Thr Gly Leu Tyr Leu Gly Thr Asp Glu
            660                 665                 670

Lys Val Thr Leu Thr Tyr Asn Val Arg Leu Asn Asp Glu Phe Val Ser
        675                 680                 685

Asn Lys Phe Tyr Asp Thr Asn Gly Arg Thr Thr Leu His Pro Lys Glu
            690                 695                 700

Val Glu Gln Asn Thr Val Arg Asp Phe Pro Ile Pro Lys Ile Arg Asp
705                 710                 715                 720

Val Arg Lys Tyr Pro Glu Ile Thr Ile Ser Lys Glu Lys Lys Leu Gly
                725                 730                 735

Asp Ile Glu Phe Ile Lys Val Asn Lys Asn Asp Lys Lys Pro Leu Arg
            740                 745                 750

Gly Ala Val Phe Ser Leu Gln Lys Gln His Pro Asp Tyr Pro Asp Ile
        755                 760                 765

Tyr Gly Ala Ile Asp Gln Asn Gly Thr Tyr Gln Asn Val Arg Thr Gly
    770                 775                 780

Glu Asp Gly Lys Leu Thr Phe Lys Asn Leu Ser Asp Gly Lys Tyr Arg
785                 790                 795                 800

Leu Phe Glu Asn Ser Glu Pro Ala Gly Tyr Lys Pro Val Gln Asn Lys
                805                 810                 815

Pro Ile Val Ala Phe Gln Ile Val Asn Gly Glu Val Arg Asp Val Thr
            820                 825                 830

Ser Ile Val Pro Gln Asp Ile Pro Ala Gly Tyr Glu Phe Thr Asn Asp
        835                 840                 845

Lys His Tyr Ile Thr Asn Glu Pro Ile Pro Lys Arg Glu Tyr Pro
    850                 855                 860

Arg Thr Gly Gly Ile Gly Met Leu Pro Phe Tyr Leu Ile Gly Cys Met
865                 870                 875                 880
```

```
Met Met Gly Gly Val Leu Leu Tyr Thr Arg Lys His Pro
            885                 890
```

<210> SEQ ID NO 18
<211> LENGTH: 2004
<212> TYPE: PRT
<213> ORGANISM: Streptococcus pneumoniae

<400> SEQUENCE: 18

```
Met Glu Lys Tyr Phe Gly Glu Lys Gln Glu Arg Phe Ser Phe Arg Lys
1               5                   10                  15

Leu Ser Val Gly Leu Val Ser Ala Thr Ile Ser Ser Leu Phe Phe Met
            20                  25                  30

Ser Val Leu Ala Ser Ser Val Asp Ala Gln Glu Thr Ala Gly Val
        35                  40                  45

His Tyr Lys Tyr Val Ala Asp Ser Glu Leu Ser Ser Glu Lys Lys
    50                  55                  60

Gln Leu Val Tyr Asp Ile Pro Thr Tyr Val Glu Asn Asp Asp Glu Thr
65                  70                  75                  80

Tyr Tyr Leu Val Tyr Lys Leu Asn Ser Gln Asn Gln Leu Ala Glu Leu
                85                  90                  95

Pro Asn Thr Gly Ser Lys Asn Glu Arg Gln Ala Leu Val Ala Gly Ala
            100                 105                 110

Ser Leu Ala Ala Met Gly Ile Leu Ile Phe Ala Val Ser Lys Lys Lys
        115                 120                 125

Val Lys Asn Lys Thr Val Leu His Leu Val Leu Val Ala Gly Ile Gly
    130                 135                 140

Asn Gly Val Leu Val Ser Val His Ala Leu Glu Asn His Leu Leu Leu
145                 150                 155                 160

Asn Tyr Asn Thr Asp Tyr Glu Leu Thr Ser Gly Lys Leu Pro Leu
                165                 170                 175

Pro Lys Glu Ile Ser Gly Tyr Thr Tyr Ile Gly Tyr Ile Lys Glu Gly
            180                 185                 190

Lys Thr Thr Ser Glu Ser Glu Val Ser Asn Gln Lys Ser Ser Val Ala
        195                 200                 205

Thr Pro Thr Lys Gln Gln Lys Val Asp Tyr Asn Val Thr Pro Asn Phe
    210                 215                 220

Val Asp His Pro Ser Thr Val Gln Ala Ile Gln Glu Gln Thr Pro Val
225                 230                 235                 240

Ser Ser Thr Lys Pro Thr Glu Val Gln Val Glu Lys Pro Phe Ser
                245                 250                 255

Thr Glu Leu Ile Asn Pro Arg Lys Glu Glu Lys Gln Ser Ser Asp Ser
            260                 265                 270

Gln Glu Gln Leu Ala Glu His Lys Asn Leu Glu Thr Lys Lys Glu Glu
        275                 280                 285

Lys Ile Ser Pro Lys Glu Lys Thr Gly Val Asn Thr Leu Asn Pro Gln
    290                 295                 300

Asp Glu Val Leu Ser Gly Gln Leu Asn Lys Pro Glu Leu Leu Tyr Arg
305                 310                 315                 320

Glu Glu Thr Met Glu Thr Lys Ile Asp Phe Gln Glu Glu Ile Gln Glu
                325                 330                 335

Asn Pro Asp Leu Ala Glu Gly Thr Val Arg Val Lys Gln Glu Gly Lys
            340                 345                 350

Leu Gly Lys Lys Val Glu Ile Val Arg Ile Phe Ser Val Asn Lys Glu
```

-continued

```
                355                 360                 365
Glu Val Ser Arg Glu Ile Val Ser Thr Ser Thr Thr Ala Pro Ser Pro
370                 375                 380
Arg Ile Val Glu Lys Gly Thr Lys Lys Thr Gln Val Ile Lys Glu Gln
385                 390                 395                 400
Pro Glu Thr Gly Val Glu His Lys Asp Val Gln Ser Gly Ala Ile Val
                405                 410                 415
Glu Pro Ala Ile Gln Pro Glu Leu Pro Glu Ala Val Val Ser Asp Lys
            420                 425                 430
Gly Glu Pro Glu Val Gln Pro Thr Leu Pro Glu Ala Val Val Thr Asp
        435                 440                 445
Lys Gly Glu Thr Glu Val Gln Pro Glu Ser Pro Asp Thr Val Val Ser
450                 455                 460
Asp Lys Gly Glu Pro Glu Gln Val Ala Pro Leu Pro Glu Tyr Lys Gly
465                 470                 475                 480
Asn Ile Glu Gln Val Lys Pro Glu Thr Pro Val Glu Lys Thr Lys Glu
                485                 490                 495
Gln Gly Pro Glu Lys Thr Glu Val Pro Val Lys Pro Thr Glu Glu
            500                 505                 510
Thr Pro Val Asn Pro Asn Glu Gly Thr Thr Glu Gly Thr Ser Ile Gln
        515                 520                 525
Glu Ala Glu Asn Pro Val Gln Pro Ala Glu Gly Ser Thr Thr Asn Ser
530                 535                 540
Glu Lys Val Ser Pro Asp Thr Ser Ser Lys Asn Thr Gly Glu Val Ser
545                 550                 555                 560
Ser Asn Pro Ser Asp Ser Thr Thr Ser Val Gly Glu Ser Asn Lys Pro
                565                 570                 575
Glu His Asn Asp Ser Lys Asn Glu Asn Ser Glu Lys Thr Val Glu Glu
            580                 585                 590
Val Pro Val Asn Pro Asn Glu Gly Thr Val Glu Gly Thr Ser Asn Gln
        595                 600                 605
Glu Thr Glu Lys Pro Val Gln Pro Ala Glu Gly Thr Gln Thr Asn Ser
610                 615                 620
Gly Lys Ile Ala Asn Glu Asn Thr Gly Glu Val Ser Asn Lys Pro Ser
625                 630                 635                 640
Asp Ser Lys Pro Pro Val Glu Glu Ser Asn Gln Pro Glu Lys Asn Gly
                645                 650                 655
Thr Ala Thr Lys Pro Glu Asn Ser Gly Asn Thr Thr Ser Glu Asn Gly
            660                 665                 670
Gln Thr Glu Pro Glu Pro Ser Asn Gly Asn Ser Thr Glu Asp Val Ser
        675                 680                 685
Thr Glu Ser Asn Thr Ser Asn Gly Asn Glu Glu Ile Lys Gln
690                 695                 700
Glu Asn Glu Leu Asp Pro Asp Lys Lys Val Glu Glu Pro Glu Lys Thr
705                 710                 715                 720
Leu Glu Leu Arg Asn Val Ser Asp Leu Glu Leu Tyr Ser Leu Ser Asn
                725                 730                 735
Gly Thr Tyr Lys Gln His Ile Ser Leu Glu Gln Val Pro Ser Asn Pro
            740                 745                 750
Asn Ser Tyr Phe Val Lys Val Lys Ser Ser Ser Phe Lys Asp Val Tyr
        755                 760                 765
Leu Pro Val Ala Ser Ile Ser Glu Glu Arg Lys Asn Asp Lys Ile Leu
770                 775                 780
```

-continued

Tyr Lys Ile Thr Ala Lys Val Glu Lys Leu Gln Gln Glu Ile Glu Ser
785                 790                 795                 800

Arg Tyr Lys Asp Asn Phe Thr Phe Tyr Leu Ala Lys Lys Gly Thr Glu
            805                 810                 815

Glu Thr Thr Asn Phe Thr Ser Phe Ser Asn Leu Val Lys Ala Ile Asn
        820                 825                 830

Gln Asn Pro Ser Gly Thr Tyr His Leu Ala Ala Ser Leu Asn Ala Asn
        835                 840                 845

Glu Val Glu Leu Gly Pro Asp Glu Arg Ser Tyr Ile Lys Asp Thr Phe
    850                 855                 860

Thr Gly Arg Leu Ile Gly Glu Lys Asp Gly Lys Asn Tyr Ala Ile Tyr
865                 870                 875                 880

Asn Leu Lys Lys Pro Leu Phe Glu Asn Leu Ser Gly Ala Thr Val Glu
            885                 890                 895

Lys Leu Ser Leu Lys Asn Val Ala Ile Ser Gly Lys Asp Asp Ile Gly
        900                 905                 910

Ser Leu Ala Asn Glu Ala Gln Asn Asn Thr Lys Ile Lys Gln Val His
        915                 920                 925

Val Asp Gly Val Leu Ala Gly Glu Arg Gly Ile Gly Gly Leu Leu Ala
    930                 935                 940

Lys Ala Glu Gln Ser Ser Ile Thr Glu Ser Ser Phe Lys Gly Arg Ile
945                 950                 955                 960

Ile Asn Thr Tyr Glu Thr Thr Ala Ala Tyr Asn Ile Gly Gly Met Val
            965                 970                 975

Gly His Leu Thr Gly Asp Lys Ala Leu Leu Thr Lys Ser Lys Ala Thr
        980                 985                 990

Val Ala Ile Ser Ser Asn Thr Asn Thr Ser Asp Gln Thr Val Gly Gly
        995                 1000                1005

Leu Ala Gly Leu Val Asp Arg Asp Ala Gln Ile Gln Asp Ser Tyr
    1010                1015                1020

Ala Glu Gly Asp Ile Asn Asn Val Lys His Phe Gly Arg Val Ala
    1025                1030                1035

Gly Val Ala Gly Asn Leu Trp Asp Arg Thr Ser Gly Asp Val Arg
    1040                1045                1050

His Ala Gly Ser Leu Thr Asn Val Leu Ser Asp Val Asn Val Thr
    1055                1060                1065

Asn Gly Asn Ala Ile Thr Gly Tyr His Tyr Asn Glu Met Lys Val
    1070                1075                1080

Lys Asp Thr Phe Ser Ser Lys Ala Asn Arg Val Tyr Asn Val Thr
    1085                1090                1095

Leu Val Lys Asp Glu Val Ser Lys Glu Ser Phe Glu Glu Arg
    1100                1105                1110

Gly Thr Met Leu Asp Ala Ser Gln Ile Ala Ser Lys Lys Ala Glu
    1115                1120                1125

Ile Asn Pro Leu Ile Leu Pro Thr Val Glu Pro Leu Ser Thr Ser
    1130                1135                1140

Gly Lys Lys Asp Ser Asp Phe Ser Lys Val Ala Tyr Tyr Gln Ala
    1145                1150                1155

Lys Arg Asn Leu Thr Tyr Lys Asn Ile Glu Lys Leu Leu Pro Phe
    1160                1165                1170

Tyr Asn Lys Ala Thr Ile Val Lys Tyr Gly Asn Leu Val Asn Glu
    1175                1180                1185

-continued

```
Asn Ser Leu Leu Tyr Gln Lys Glu Leu Leu Ser Ala Val Met Met
    1190            1195            1200

Lys Asp Asn Gln Val Ile Thr Asp Ile Val Ser Asn Lys Gln Thr
    1205            1210            1215

Ala Asn Lys Leu Leu Leu His Tyr Lys Asp Asp Leu Ser Glu Lys
    1220            1225            1230

Leu Asp Leu Lys Tyr Gln Asn Asp Phe Ala Lys Leu Ala Glu Tyr
    1235            1240            1245

Ser Leu Gly Asn Thr Gly Leu Leu Tyr Thr Pro Asn Gln Phe Leu
    1250            1255            1260

Tyr Asp Gln Thr Ser Ile Ile Lys Gln Val Leu Pro Asp Leu Gln
    1265            1270            1275

Lys Val Asp Tyr His Ser Glu Ala Ile Arg Lys Thr Leu Gly Ile
    1280            1285            1290

Ser Pro Asn Val Lys Gln Thr Glu Leu Tyr Leu Glu Asp Gln Phe
    1295            1300            1305

Ala Lys Thr Lys Gln Gln Leu Glu Asp Ser Leu Lys Lys Leu Leu
    1310            1315            1320

Ser Ala Asp Ala Gly Leu Ala Ser Ala Asn Pro Val Thr Glu Gly
    1325            1330            1335

Tyr Leu Val Asp Lys Ile Lys Arg Asn Lys Glu Ala Leu Leu Leu
    1340            1345            1350

Gly Leu Thr Tyr Leu Glu Arg Trp Tyr Asn Phe Ser Tyr Gly Gln
    1355            1360            1365

Val Asn Val Lys Asp Leu Val Leu Tyr His Leu Asp Phe Phe Gly
    1370            1375            1380

Lys Gly Asn Ala Ser Pro Leu Asp Thr Leu Ile Glu Leu Gly Lys
    1385            1390            1395

Ser Gly Phe Asn Asn Leu Leu Ala Lys Asn Asn Val Asp Thr Tyr
    1400            1405            1410

Gly Ile Ser Leu Ala Ser Gln His Gly Thr Thr Asp Leu Phe Ser
    1415            1420            1425

Thr Leu Glu His Tyr Arg Lys Val Phe Leu Pro Asn Thr Ser Asn
    1430            1435            1440

Asn Asp Trp Phe Lys Ser Glu Thr Lys Ala Tyr Ile Val Glu Glu
    1445            1450            1455

Lys Ser Thr Ile Glu Glu Val Lys Thr Lys Gln Gly Leu Ala Gly
    1460            1465            1470

Thr Lys Tyr Ser Ile Gly Val Tyr Asp Arg Ile Thr Ser Ala Thr
    1475            1480            1485

Trp Lys Tyr Arg Asn Met Val Leu Pro Leu Leu Thr Leu Pro Glu
    1490            1495            1500

Arg Ser Val Phe Val Ile Ser Thr Met Ser Ser Leu Gly Phe Gly
    1505            1510            1515

Ala Tyr Asp Arg Tyr Arg Ser Ser Asp His Lys Ala Gly Lys Ala
    1520            1525            1530

Leu Asn Asp Phe Val Glu Glu Asn Ala Arg Glu Thr Ala Lys Arg
    1535            1540            1545

Gln Arg Asp His Tyr Asp Tyr Trp Tyr Arg Ile Leu Asp Asp Asn
    1550            1555            1560

Ala Arg Glu Lys Leu Tyr Arg Asn Ile Leu Leu Tyr Asp Ala Tyr
    1565            1570            1575

Lys Phe Gly Asp Asp Asn Thr Val Gly Lys Ala Thr Glu Val Ala
```

```
            1580                1585                1590

Asp Phe Asp Asn Pro Asn Pro Ala Met Gln His Phe Phe Gly Pro
    1595                1600                1605

Val Gly Asn Lys Val Gly His Asn Gln His Gly Ala Tyr Ala Thr
    1610                1615                1620

Gly Asp Ala Val Tyr Tyr Met Gly Tyr Arg Met Leu Asp Lys Asp
    1625                1630                1635

Gly Ala Ile Thr Tyr Thr His Glu Met Thr His Asp Ser Asp Gln
    1640                1645                1650

Asp Ile Tyr Leu Gly Gly Tyr Gly Arg Arg Ser Gly Leu Gly Pro
    1655                1660                1665

Glu Phe Phe Ala Lys Gly Leu Leu Gln Ala Pro Asp His Pro Asp
    1670                1675                1680

Asp Ala Thr Ile Thr Ile Asn Ser Ile Leu Lys His Ser Lys Ser
    1685                1690                1695

Asp Ser Thr Glu Ser Arg Arg Leu Gln Val Leu Asp Pro Thr Thr
    1700                1705                1710

Arg Phe Asn Asn Ala Asp Asp Leu Lys Gln Tyr Val His Asn Met
    1715                1720                1725

Phe Asp Val Val Tyr Met Leu Glu Tyr Leu Glu Gly Asn Ser Ile
    1730                1735                1740

Leu Lys Leu Asp Thr Asn Gln Lys Gln Gln Leu Leu Arg Lys Val
    1745                1750                1755

Thr Asn Glu Tyr His Pro Asp Pro Asp Gly Asn Lys Val Tyr Ala
    1760                1765                1770

Thr Asn Val Val Arg Asn Leu Thr Val Glu Glu Val Glu Arg Leu
    1775                1780                1785

Arg Ser Phe Asn Asp Leu Ile Asp Asn Asn Ile Leu Ser Ser Arg
    1790                1795                1800

Glu Tyr Ala Ser Gly Lys Tyr Glu Arg Asn Gly Tyr Phe Thr Ile
    1805                1810                1815

Lys Leu Phe Ala Pro Ile Tyr Ala Ala Leu Ser Asn Asp Ile Gly
    1820                1825                1830

Thr Pro Gly Asp Leu Met Gly Arg Arg Ile Ala Tyr Glu Leu Leu
    1835                1840                1845

Ala Ala Lys Gly Phe Lys Asp Gly Met Val Pro Tyr Ile Ser Asn
    1850                1855                1860

Gln Tyr Glu Glu Glu Ala Lys Gln Lys Gly Lys Thr Ile Asn Leu
    1865                1870                1875

Tyr Gly Lys Thr Arg Gly Leu Val Thr Asp Asp Leu Val Leu Glu
    1880                1885                1890

Lys Val Phe Asn Asn Gln Tyr His Thr Trp Ser Glu Phe Lys Lys
    1895                1900                1905

Ala Met Tyr Gln Glu Arg Gln Asp Gln Phe Asp Arg Leu Asn Lys
    1910                1915                1920

Val Thr Phe Asn Asp Thr Thr Gln Pro Trp Gln Thr Phe Ala Lys
    1925                1930                1935

Lys Thr Thr Ser Ser Val Asp Glu Leu Gln Lys Leu Met Asp Val
    1940                1945                1950

Ala Val Arg Lys Asp Ala Glu His Asn Tyr Tyr His Trp Asn Asn
    1955                1960                1965

Tyr Asn Pro Asp Ile Asp Ser Glu Val His Lys Leu Lys Arg Ala
    1970                1975                1980
```

```
Ile Phe Lys Ala Tyr Leu Asp Gln Thr Asn Asp Phe Arg Ser Ser
    1985                1990            1995
Ile Phe Glu Asn Lys Lys
    2000
```